US011060099B2

(12) United States Patent
Greenfield et al.

(10) Patent No.: US 11,060,099 B2
(45) Date of Patent: Jul. 13, 2021

(54) PRODUCTION OF FATTY ACID DERIVATIVES

(71) Applicant: Genomatica, Inc., San Diego, CA (US)

(72) Inventors: Derek L. Greenfield, South San Francisco, CA (US); Andreas W. Schirmer, South San Francisco, CA (US); Elizabeth J. Clarke, South San Francisco, CA (US); Eli S. Groban, South San Francisco, CA (US); Bernardo M. Da Costa, South San Francisco, CA (US); Zhihao Hu, South San Francisco, CA (US); Kevin Holden, South San Francisco, CA (US); Noah Helman, South San Francisco, CA (US)

(73) Assignee: Genomatica, Inc., San Diego, CA (US)

( * ) Notice: Subject to any disclaimer, the term of this patent is extended or adjusted under 35 U.S.C. 154(b) by 0 days.

(21) Appl. No.: 15/650,285

(22) Filed: Jul. 14, 2017

(65) Prior Publication Data

US 2018/0010137 A1 Jan. 11, 2018

Related U.S. Application Data

(62) Division of application No. 14/390,378, filed as application No. PCT/US2013/035037 on Apr. 2, 2013, now abandoned.

(60) Provisional application No. 61/619,324, filed on Apr. 2, 2012.

(51) Int. Cl.

| | |
|---|---|
| ***C12N 1/21*** | (2006.01) |
| ***C12P 7/64*** | (2006.01) |
| ***C07K 14/195*** | (2006.01) |
| ***C07K 14/245*** | (2006.01) |
| ***C12N 9/16*** | (2006.01) |
| ***C12N 15/70*** | (2006.01) |
| ***C12N 9/04*** | (2006.01) |
| ***C12N 9/02*** | (2006.01) |
| ***C12N 9/10*** | (2006.01) |
| ***C12N 9/12*** | (2006.01) |
| ***C12N 9/88*** | (2006.01) |
| ***C12N 9/90*** | (2006.01) |
| ***C12N 9/00*** | (2006.01) |
| ***C12P 7/04*** | (2006.01) |

(52) U.S. Cl.

CPC ............. *C12N 15/70* (2013.01); *C12N 9/001* (2013.01); *C12N 9/0006* (2013.01); *C12N 9/1029* (2013.01); *C12N 9/1288* (2013.01); *C12N 9/88* (2013.01); *C12N 9/90* (2013.01); *C12N 9/93* (2013.01); *C12P 7/04* (2013.01); *C12P 7/6409* (2013.01); *C12P 7/6436* (2013.01); *C12Y 101/011* (2013.01); *C12Y 103/0101* (2013.01); *C12Y 103/01009* (2013.01); *C12Y 203/0118* (2013.01); *C12Y 203/01039* (2013.01); *C12Y 203/01041* (2013.01); *C12Y 203/01179* (2013.01); *C12Y 207/08007* (2013.01); *C12Y 402/01059* (2013.01); *C12Y 503/03014* (2013.01); *C12Y 604/01002* (2013.01)

(58) Field of Classification Search

None

See application file for complete search history.

(56) References Cited

U.S. PATENT DOCUMENTS

| | | | |
|---|---|---|---|
| 5,000,000 | A | 3/1991 | Ingram et al. |
| 5,028,539 | A | 7/1991 | Ingram et al. |
| 5,424,202 | A | 6/1995 | Ingram et al. |
| 5,482,846 | A | 1/1996 | Ingram et al. |
| 5,602,030 | A | 2/1997 | Ingrahm et al. |
| 5,939,250 | A | 8/1999 | Short |
| 5,965,408 | A | 10/1999 | Short |
| 7,192,735 | B2 | 3/2007 | Lambalot et al. |
| 7,897,369 | B2 | 3/2011 | Schmidt-Dannert et al. |
| 8,097,439 | B2 | 1/2012 | Alibhai et al. |
| 2003/0101485 | A1 | 5/2003 | Jinqing et al. |
| 2009/0140696 | A1 | 6/2009 | Okuto |
| 2010/0105963 | A1 | 4/2010 | Hu |
| 2010/0170826 | A1 | 7/2010 | Friedman et al. |

(Continued)

FOREIGN PATENT DOCUMENTS

| | | | |
|---|---|---|---|
| CN | 1295130 | A | 5/2001 |
| CN | 101490241 | A | 7/2009 |

(Continued)

OTHER PUBLICATIONS

Peng et al., Metabolic flux analysis for a ppc mutant *Escherichia coli* based on 13C-labelling experiments together with enzyme activity assays and intracellular metabolite measurements, FEMS Microbiol. Lett., 2004, 235, 17-23.*

(Continued)

*Primary Examiner* — Robert B Mondesi
*Assistant Examiner* — Todd M Epstein
(74) *Attorney, Agent, or Firm* — Harness Dickey & Pierce P.L.C.

(57) ABSTRACT

The invention relates to compositions and methods, including polynucleotide sequences, amino acid sequences, recombinant host cells and recombinant host cell cultures engineered to produce fatty acid derivative compositions comprising fatty acids, fatty alcohols, fatty aldehydes, fatty esters, alkanes, terminal olefins, internal olefins or ketones. The fatty acid derivative composition is produced extracellularly with a higher titer, yield or productivity than the corresponding wild type or non-engineered host cell.

14 Claims, 18 Drawing Sheets

Specification includes a Sequence Listing.

(56) References Cited

U.S. PATENT DOCUMENTS

| | | | | |
|---|---|---|---|---|
| 2010/0242345 | A1* | 9/2010 | Keasling | C10L 1/026 44/388 |
| 2010/0274033 | A1 | 10/2010 | Sanchez-Riera et al. | |
| 2011/0111458 | A1 | 5/2011 | Masuda et al. | |
| 2011/0151526 | A1 | 6/2011 | Saunders et al. | |
| 2011/0162259 | A1 | 7/2011 | Gaertner | |
| 2011/0206630 | A1 | 8/2011 | Rude | |
| 2012/0116108 | A1* | 5/2012 | Basu | C12N 9/0071 554/230 |

FOREIGN PATENT DOCUMENTS

| | | | | |
|---|---|---|---|---|
| JP | 2010-507369 | A | 3/2010 | |
| JP | 2010-526805 | A | 8/2010 | |
| JP | 2012-504963 | A | 3/2012 | |
| WO | WO-91/16427 | | 10/1991 | |
| WO | WO-2007/136762 | A2 | 11/2007 | |
| WO | WO-2008/119082 | A2 | 10/2008 | |
| WO | WO-2008/130437 | | 10/2008 | |
| WO | WO-2008/147781 | | 12/2008 | |
| WO | WO-2009/002480 | | 12/2008 | |
| WO | WO-2009/085278 | | 7/2009 | |
| WO | WO-2009/140695 | A2 | 11/2009 | |
| WO | WO-2010/042664 | A1 | 4/2010 | |
| WO | WO-2010/062480 | A2 | 6/2010 | |
| WO | WO-2010/075483 | | 7/2010 | |
| WO | WO-2010/127318 | | 11/2010 | |
| WO | WO-2011/038134 | A1 | 3/2011 | |
| WO | WO-2012/009660 | | 1/2012 | |
| WO | WO-2012/009660 | A2 | 1/2012 | |
| WO | WO-2012019175 | A2 * | 2/2012 | C12N 1/22 |
| WO | WO-2013/019647 | | 2/2013 | |
| WO | WO-2013/152051 | | 10/2013 | |
| WO | WO-2013/152052 | | 10/2013 | |

OTHER PUBLICATIONS

Lennen et al., Engineering *Escherichia coli* to synthesize free fatty acids, Trends in Biotechnol., 2012, 30, 659-67.*
Liu et al., Fatty acid production in genetically modified cyanobacteria, Proc. Natl. Acad. Sci. USA, 2011, 108, 6800-6904.*
Lu et al., Overproduction of free fatty acids in *E. coli*: Implications for biodiesel production, Metabolic Eng., 2008, 10, 333-39.*
Mori et al., ASecE Mutation That Modulates SecY-SecE Translocase Assembly, Identified as a Specific Suppressor of SecY Defects, J. Bacteriol., 2003, 185, 948-56.*
Wang et al., The gene locus yijP contributes to *Escherichia coli* K1 invasion of brain microvascular endothelial cells, Infect. Immun., 1999, 67, 4751-56.*
Communication issued on EP Appl. 13715879.6, dated Jun. 1, 2016.
Communication issued on EP Application 13715879.6, dated May 12, 2017.
Gokarn et al., "Metabolic Analysis of *Escherichia coli* in the Presence and Absence of the Carboxylating Enzymes Phosphoenolpyruvate Carboxylase and Pyruvate Carboxylase," Applied and Environmental Microbiology, May 2000, pp. 1844-1850.
Notice of Reasons for Rejection issued on Japanese application 2015-504687, dated Jan. 19, 2017, English translation.
Wang et al., "The Gene Locus yijP Contributes to *Escherichia coli* K1 Invasion of Brain Microvascular Endothelial Cells," Infection and Immunity, Sep. 1999, pp. 4751-4756.
Examination Report issued on Indonesian Appl. P-00201406815, dated Dec. 29, 2017.
Heath et al., "Inhibition of .beta.-Ketoacyl-Acyl Carrier Protein Synthase III (FabH) by Acyl-Acyl Carrier Protein in *Escherichia coli*", J.Biol. Chem.271(18):10996-11000 (1996).
Office Action issued on Chinese Application 201380026304.9, dated Dec. 29, 2015, English translation provided.
Amann et al., "Tightly regulated tac promoter vectors useful for the expression of unfused and fused proteins in *Escherichia coli*," Gene, 69: 301-315 (1988).
Arkin et al. (1992) Proc. Natl. Acad. Sci. U.S.A. 89:7811-7815.
Arnold, "Protein engineering for unusual environments," Curr. Opin. Biotech. 4: 450-455 (1993).
Baldari et al., "A novel leader peptide which allows efficient secretion of a fragment of human interleukin 1 beta in *Saccharomyces cerevisiae*," EMBO J. 6(1): 229-234 (1987).
Bergler et al., "Protein EnvM is the NADH-dependent Enoyl-ACP Reductase (Fabl) of *Escherichia coli*," J. Biol. Chem., 269(8): 5943-5946 (1994).
Bowie et al. "Deciphering the Message in Protein Sequences: Tolerance to Amino Acid Substitutions," (1990) Science, 247:1306-1310.
Caldwell et al., "Randomization of Genes by PCR Mutagenesis," PCR Methods Applic. 2: 28-33 (1992).
Caviglia et al., "Rat Long Chain Acyl-CoA Synthetase 5, but Not 1, 2, 3, or 4, Complements *Escherichia coli* fadD," J. Biol. Chem. 279(12): 11163-11169 (2004).
Cronan et al., "FadR, transcriptional co-ordination of metabolic expediency," Mol. Microbiol. 29(4): 937-943 (1998).
Datsenko et al., "One-step Inactivation of Chromosomal Genes in *Escherichia coli* K-12 using PCR Products," Proc. Natl. Acad. Sci USA 97: 6640-6645 (2000).
Davis et al., "Overproduction of Acetyl-CoA Carboxylase Activity Increases the Rete of Fatty Acid Biosynthesis in *Escherichia coli*," J. Biol. Chem., 2000, vol. 275, pp. 28593-28598.
Delegrave et al., "Searching Sequence Space to Engineer Proteins: Exponential Ensemble Mutagenesis," Biotech. Res, 11: 1548-1552 (1993).
Exam Report issued on Malaysian Appl. PI 2014002773, dated Sep. 15, 2017.
Final Office Action on U.S. Appl. No. 14/390,378 dated Jan. 19, 2017.
GenBank, Accession No. 460041.1, 2011, WWWW.ncbi.nlm.nih.gov.
GenBank, Accession No. AAC74178.1, 2010, WWW.ncbi.nlm.nih.gov.
GenBank, Accession No. BAA16180, 2008, WWW.ncbi.nlm.nih.gov.
GenBank, Accession No. NP_350156.1, 2010, WWW.ncbi.nlm.nih.gov.
GenBank, Accession No. NP_416826.1, 2011, WWW.ncbi.nlm.nih.gov.
GenBank, Accession No. NP_460163.1, 2011, WWW.ncbi.nlm.nih.gov.
GenBank, Accession No. NP_460164.1, 2011, WWW.ncbi.nlm.nih.gov.
GenBank, Accession No. NP_460165.1, 2011, WWW.ncbi.nlm.nih.gov.
GenBank, Accession No. YP_001217283.2, 2010, WWW.ncbi.nlm.nih.gov.
Grosjean et al., "Preferential codon usage in prokaryotic genes: the optimal codon-anticodon interaction energy and the selective codon usage in efficiently expressed genes," Gene 18:199-209 (1982).
Heath et al., "Regulation of Fatty Acid Elongation and Initiation by Acyl-Acyl Carrier Protein in *Escherichia coli*", J.Biol.Chem. vol. 271(4): 1833-1836 (1996).
Heath, "The Enoly-[acyl-carrier-protein] Reductases Fabl and FabL from Bacillus subtilis," Journal of Biological Chemistry, vol. 275, No. 51, Sep. 27, 2000, pp. 40128-40133.
International Search Report and Written Opinion on PCT/US2013/035037, dated Oct. 31, 2013.
Kurjan et al., Struture of a Yeast Pheromone Gene (MFx): A Putative x-Factor precursor Contains Four Tandem Copies of Mature x-Factor, Cell, vol. 30, pp. 933-943 (1982).
Leung et al. "A Journal of Methods in Cell and Molecular Biology," Technique 1:(1): 11-15 (1989).
Liu et al., "Quantitative analysis and engineering of fatty acid biosynthesis in *E. coli*," Metabolic Eng. 2010, vol. 12, pp. 378-386.
Lucklow et al., "High level expression of nonfused foreign genes with Autographa californica nuclear polyhedrosis virus expression vectors," Virology 170(1): 31-39 (1989).
Maniatis et al., "Regulation of Inducible and Tissue-Specific Gene Expression," Science 236: 1237-1245 (1987).

(56) References Cited

OTHER PUBLICATIONS

Massengo-Tiasse et al., "Vibrio cholerae FabV Defines a New Class of Enoyl-Acyl Carrier Protein Reductase", J. Biol. Chem. 283(3): 1308-1316 (2008).
Needleman and Wunsch, "A General Method Applicable to the Search for Similarities in the Amino Acid Sequence of Two Proteins," J. Mol. Biol. 48:443-453 (1970).
Non-Final Office Action on U.S. Appl. No. 14/390,378 dated May 23, 2016.
Office Action issued on Chinese Application 201380026304.9, dated Apr. 1, 2017, English translation only.
Palmeros et al., "A family of removable cassets designed to obtain antiobiotic-resistance-free genomic modifications of *Escherichia coli* and other bacteria," Gene, vol. 247, pp. 255-264, 2000.
Reidhaar-Olson et al., "Combinatorial Cassette Mutagenesis as a Probe of the Informational Content of Protein Sequences," Science 241: 53-57 (1988).
Rosenberg, "Multiple Sequence Alignment Accuracy and Evolutionary Distance Estimation," BMC Bioinformatics 6: 278 (2005).
Sambrook et al., "Molecular Cloning: A Laboratory Manual," 1989, 2nd Ed., Cold Spring Harbor Laboratory Press, Cold Spring Harbor, NY.
Smith et al., "Production of Human Beta Interferon in Insect Cells Infected with a Vaculovirus Expression Vector," Mol. Cell Biol. 3(12): 2156-2165 (1983).
Smith et al., "Single-step purification of polypeptides expressed in *Escherichia coli* as fusions with glutathione S-transferase," Gene 67: 31-40 (1988).
Stemmer, "DNA shuffling by random fragmentation and reassembly: In vitro recombination for molecular evolution," Proc. Natl. Acad. Sci. USA. 91: 10747-10751 (1994).
Studier et al., "Use of T7 RNA Polymerase to Direct Expression of Cloned Genes," Methods in Enzymology, 185: 60-89 (1990).
Zha et al., "Improving cellular malonyl-CoA level in *Escherichia coli* via metabolic engineering," Metabolic eng., 2009, vol. 11, pp. 192-198.
Zhang et al.,j "Transcriptional Analysis of Essential Genes of the *Escherichia coli* Fatty Acid Biosynthesis Gene Cluster by Functional Replacement with the Analogous *Salmonella typhimurium* Gene Cluster," J. Bacteriol., 1998, 180, pp. 3295-3303.
Zhu et al., "Functions of the Clostridium acetobutylicium FabF and FabZ proteins in unsaturated fatty acid biosynthesis", BMC Microbiology 9:119 (2009).
Decision of Rejection issued on Japanese Application2 015-504687, dated Dec. 4, 2017.
Examination Report issue on Australian Application 2013243601, dated Oct. 5, 2017.
Flores et al., "Expression of PEP carboxylase from *Escherichia coli* complements the phenotypic effects of pyruvate carboxylase mutations in *Saccharomyces cerevisiae*," FEBS Letters 412, 1997, pp. 531-534.
Ku et al., "High-level expression of maize phosphoenolpyruvate carboxylase in transgenic rice plants," Nature Biotechnology, vol. 17, Jan. 1999, pp. 76-80.
Peng et al., "Metabolic flux analysis for a ppc mutant *Escherichia coli* based on C-labeling experiments together with enzyme activity assays and intracellular metabolite measurements," FEMS Microbiology Letters 233, 2004, pp. 17-23.
Bergler et al., "The enoyl-[acyl-carrier-protein] reductase (Fabl) of *Escherichia coli*, which catalyzes a key regulatory step in fatty acid biosynthesis, accepts NADH and NADPH as cofactors and is inhibited by palmitoyl-CoA", Eur. J. Biochem. 242, 1996, 689-694.
First Examination Report on IN Patent Application No. 9107/DELNP/2014 dated Aug. 28, 2019, 7 pages.
Goeddel, Gene Expression Technology: Methods in Enzymology, vol. 185, Academic Press, San Diego, Calif. (1990).
International Preliminary Report on Patentability on PCT/US2013/035037, dated Oct. 7, 2014, 13 pages.
Office Action on CN Application No. 201380026304.9, dated Sep. 9, 2016, 9 pages (with translation).
Office Action on CN Application No. 201380026304.9, dated Oct. 26, 2018, 12 pages (with translation).
Office Action on ID Application No. P00201406815, dated Apr. 12, 2018, 3 pages (with translation).
Preliminary Office Action in BR Patent Application No. 112014024675.0 dated Sep. 2, 2019, 6 pages (translation).
Sanchez, Cesar, et al., "Cloning and characterization of a phosphopantetheinyl transferase from Streptomyces verticillus ATCC15003, the producer of the hybrid peptide-polyketide antitumor drug bleomycin," Chemistry & Biology, vol. 8, 2001, pp. 725-738.
Schultz et al., "Expression and secretion in yeast of a 400-kDa envelope glycoprotein derived from Epstein-Barr virus," Gene 54: 113-123 (1987).
Second Office Action in CA Patent Application No. 2,883,968 dated Apr. 23, 2019, 3 pages.
Studier et al., Gene Expression Technology: Methods in Enzymology 185, Academic Press, San Diego, CA, pp. 60-89 (1990).
Decision of Rejection in JP Patent No. 2018-072000 dated Jan. 8, 2020 (with English translation) (9 pages).
Fourth Office Action in CN Patent Application No. 201380026304.9, dated Jan. 5, 2018, (16 pages) (with English translation).
Office Action in CO Patent Application No. 14-240.053, dated May 12, 2016, (20 pages) (with English translation).
Office Action in CO Patent Application No. 14-240.053, dated Nov. 11, 2016, (14 pages) (with English translation).
Second Office Action in MX Patent Application No. MX/a/2014/011905, dated Dec. 3, 2018 (with English language comments; no Office Action translation available) (8 pages).
Substantive Examination Adverse Report in MY PI2014002773 dated Feb. 4, 2020 (2 pages).
Extended European Search Report in EP Patent Application No. 19211601.0 dated May 14, 2020 (9 pages).
Office Action in CA Patent Application No. 2883968 dated Apr. 28, 2020 (3 pages).
Notice of Reasons for Refusal in KR 10-2014-7030467 dated Mar. 2, 2020 (5 pages) (with English Translation).
Handke, P., et al., "Application and engineering of fatty acid biosynthesis in *Escherichia coli* for advanced fuels and Metabolic Engineering, 13: 28-37 (2011) chemicals,".
Quadri, L.E.N., et al., "Characterization of Sfp, a Bacillus subtilis Phosphopantetheinyl Transferase for Peptidyl Carrier Protein Domains in Peptide Synthetases," Biochemisty, 37: 1585-1595 (1998).
Office Action from corresponding Korean Application No. 10-2020-7015194 dated Apr. 15, 2021.

* cited by examiner

DAM1_377 with *C. glutamicum* Acc and BirA expression: Mal-CoA in log phase

DAM1-i377: Short-chain CoA levels in log phase, acc-panK coexpression

Duplicate plate screen at 32°C

PRODUCTION OF FATTY ACID DERIVATIVES

CROSS REFERENCE TO RELATED APPLICATIONS

This application is a divisional of U.S. application Ser. No. 14/390,378, filed Oct. 2, 2014, which is the National Phase of International Application No. PCT/US2013/035037 filed Apr. 2, 2013, which claims the benefit of U.S. Provisional Application No. 61/619,324, filed Apr. 2, 2012, which are hereby incorporated herein by reference in their entireties.

SEQUENCE LISTING

The instant application contains a Sequence Listing which has been submitted in ASCII format via EFS-Web and is hereby incorporated by reference in its entirety. Said ASCII copy, created on Apr. 2, 2013, is named LS00042PCT_SL.txt and is 143,098 bytes in size.

FIELD

The disclosure relates to recombinant host cells including strain modifications effective to improve titer, yield and/or productivity of fatty acid derivatives. The disclosure further relates to cell cultures including the recombinant host cells for the fermentative production of fatty acid derivatives and compositions thereof.

BACKGROUND

Fatty acid derivatives including fatty aldehydes, fatty alcohols, hydrocarbons (alkanes and olefins), fatty esters (e.g., waxes, fatty acid esters, or fatty esters), and ketones denote important categories of industrial chemicals and fuels. These molecules and their derivatives have numerous applications including, but not limited to, use as surfactants, lubricants, plasticizers, solvents, emulsifiers, emollients, thickeners, flavors, fragrances, and fuels. Crude petroleum is currently a primary source of raw materials for producing petrochemicals and fuels. The two main classes of raw materials derived from petroleum are short chain olefins (e.g., ethylene and propylene) and aromatics (e.g., benzene and xylene isomers). These raw materials are derived from longer chain hydrocarbons in crude petroleum by cracking it at considerable expense using a variety of methods, such as catalytic cracking, steam cracking, or catalytic reforming. These raw materials can be used to make petrochemicals such as monomers, solvents, detergents, and adhesives, which otherwise cannot be directly refined from crude petroleum. Petrochemicals, in turn, can be used to make specialty chemicals, such as plastics, resins, fibers, elastomers, pharmaceuticals, lubricants, gels, and the like. Particular specialty chemicals that can be produced from petrochemical raw materials include, but are not limited to, fatty acids, hydrocarbons, fatty aldehydes, fatty alcohols, esters, and ketones.

Hydrocarbons, for example, have many commercial uses. As such, shorter chain alkanes and alkenes are used in transportation fuels. Longer chain alkenes are used in plastics, lubricants, and synthetic lubricants. In addition, alkenes are used as a feedstock to produce alcohols, esters, plasticizers, surfactants, tertiary amines, enhanced oil recovery agents, fatty acids, thiols, alkenyl succinic anhydrides, epoxides, chlorinated alkanes, chlorinated alkenes, waxes, fuel additives, and drag flow reducers. Similarly, esters have many commercial uses. For example, biodiesel, an alternative fuel, is made of esters (e.g., fatty acid methyl ester, fatty acid ethyl esters, etc.). Some low molecular weight esters are volatile with a pleasant odor which makes them useful as fragrances or flavoring agents. In addition, esters are used as solvents for lacquers, paints, and varnishes. Furthermore, some naturally occurring substances, such as waxes, fats, and oils are also made of esters. Esters are further used as softening agents in resins and plastics, plasticizers, flame retardants, and additives in gasoline and oil. In addition, esters can be used in the manufacture of polymers, films, textiles, dyes, and pharmaceuticals.

Aldehydes are used to produce a large number of specialty chemicals. For example, aldehydes are used to produce polymers, resins (e.g., Bakelite), dyes, flavorings, plasticizers, perfumes, pharmaceuticals, and other chemicals, some of which may be used as solvents, preservatives, or disinfectants. In addition, certain natural and synthetic compounds, such as vitamins and compounds used as hormones are aldehydes. Furthermore, many sugars contain aldehyde groups. Fatty aldehydes can be converted to fatty alcohols by chemical or enzymatic reduction. Similarly, fatty alcohols have many commercial uses as well. The shorter chain fatty alcohols are used in the cosmetic and food industries as emulsifiers, emollients, and thickeners. Due to their amphiphilic nature, fatty alcohols behave as nonionic surfactants, which are useful in personal care and household products, such as, for example, detergents. In addition, fatty alcohols are used in waxes, gums, resins, pharmaceutical salves and lotions, lubricating oil additives, textile antistatic and finishing agents, plasticizers, cosmetics, industrial solvents, and solvents for fats. Fatty alcohols such as aliphatic alcohols include a chain of 8 to 22 carbon atoms. Fatty alcohols usually have an even number of carbon atoms and a single alcohol group (—OH) attached to the terminal carbon. Some are unsaturated and some are branched. They are widely used in industrial chemistry. Most fatty alcohols in nature are found as waxes which are esters with fatty acids and fatty alcohols. They are produced by bacteria, plants and animals. Currently, fatty alcohols are produced via catalytic hydrogenation of fatty acids produced from natural sources, such as coconut oil, palm oil, palm kernel oil, tallow and lard, or by chemical hydration of alpha-olefins produced from petrochemical feedstocks. Fatty alcohols derived from natural sources have varying chain lengths. The chain length of fatty alcohols is important and specific to particular applications. Dehydration of fatty alcohols to alpha-olefins can also be accomplished by chemical catalysis.

Due to the inherent challenges posed by exploring, extracting, transporting and refining petroleum for use in chemical- and fuel products, there is a need in the art for a an alternate source which can be produced economically and efficiently for the use of chemical- and fuel production. Moreover, the burning of petroleum-based fuels has become a serious hazard to the environment, especially in light of the ever increasing population inhabiting the planet. Thus, there is a need for a petroleum replacement that does not cause the type of environmental damage created by exploring, extracting, transporting and refining petroleum.

One option of producing renewable petroleum is by engineering host cells to produce renewable petroleum products. Biologically derived fuels and chemicals offer advantages over petroleum based fuels. Biologically derived chemicals such as hydrocarbons (e.g., alkanes, alkenes, or alkynes), fatty alcohols, esters, fatty acids, fatty aldehydes, and ketones are directly converted from biomass to the desired chemical product. However, in order for the use of biologically-derived fatty acid derivatives from fermentable sugars or biomass to be commercially viable as a source for production of renewable chemicals and fuels, the process must be optimized for efficient conversion and recovery of product. The development of biologically derived fuels and chemicals has been one focus of research and development in recent years. Still, there remains a considerable need for improvements in the relevant processes and products in order for biologically-derived fuels and chemicals to become a commercially viable option. Areas that need improvement include the energy efficiency of the production process and the final product yield. The current disclosure addresses this need.

SUMMARY

One aspect of the disclosure provides a recombinant host cell having a genetically engineered polynucleotide sequence, wherein the polynucleotide sequence codes for one or more polypeptides that have a specific enzymatic activity. The polynucleotide sequence is exogenous or endogenous to the host cell. As such, the disclosure provides a recombinant host cell having a genetically engineered polynucleotide sequence encoding one or more polypeptides, wherein the polypeptides have activity selected from the group including, but not limited to, 3-hydroxydecanoyl-[acp] dehydratase (E.C. 4.2.1.60) activity; β-ketoacyl-ACP synthase I (E.C. 2.3.1.41) activity; β-ketoacyl-ACP synthase II (E.C. 2.3.1.179) activity; [acp] S-malonyltransferase {malonyl-CoA-ACP transacylase} (E.C. 2.3.1.39) activity; 3-oxoacyl-{β-ketoacyl}-ACP reductase (E.C. 1.1.1.100) activity; β-ketoacyl-ACP synthase III (E.C. 2.3.1.180) activity; enoyl-ACP reductase (NADH) (E.C. 1.3.1.9) activity; enoyl-ACP reductase (NADPH) (E.C. 1.3.1.10) activity; 3-hydroxy-acyl-[acp] dehydratase (E.C. 4.2.1.59) activity; and trans-2, cis-3-decenoyl-ACP isomerase (E.C. 5.3.3.14) activity, wherein the recombinant host cell produce a fatty acid derivative composition at a higher titer, yield or productivity than a corresponding wild type host cell when cultured in a medium containing a carbon source under conditions effective to express the polynucleotide. In a related aspect, the recombinant host cell produces the fatty acid derivative composition at a higher titer, yield and/or productivity when the polypeptide is expressed in combination with at least one other polypeptide of the enzymatic activity. In another aspect, the recombinant host cell produces the fatty acid derivative composition at a higher titer, yield or productivity when the polypeptide is expressed in combination with at least five other polypeptides of the enzymatic activity. In yet another aspect, the recombinant host cell produces the fatty acid derivative composition at a higher titer, yield or productivity when expressed in combination with at least two or three or four or five or six or more polypeptides of the enzymatic activity. In another related aspect, the recombinant host cell includes one or more genetically engineered polynucleotide sequences that further code for a polypeptide that is an acyl carrier protein (ACP). ACP can be in expressed in combination with one or more of the polypeptides that code for any of the enzymatic activities, wherein the ACP further increases the titer, yield and/or productivity of the recombinant host cell when cultured under appropriate conditions. In yet another related aspect, a genetically engineered polynucleotide sequence further encodes a polypeptide that has accABCD activity (E.C. 6.4.1.2). accABCD can be in expressed in combination with one or more of the polypeptides that code for any of the enzymatic activities, wherein the accABCD further increases the titer, yield and/or productivity of the recombinant host cell when cultured under appropriate conditions.

Another aspect of the disclosure provides a recombinant host cell having a genetically engineered polynucleotide sequence encoding one or more polypeptides, wherein the polypeptides have enzymatic activity including, but not limited to, trans-2, cis-3-decenoyl-ACP isomerase activity (fabA or fabM); β-ketoacyl-ACP synthase I (fabB); malonyl-CoA-ACP transacylase (fabD); β-ketoacyl-ACP synthase I (fabF or fabB); β-ketoacyl-ACP reductase (fabG); β-ketoacyl-ACP synthase III (fabH); enoyl-ACP reductase (fabI or fabL or fabV or fabK); and 3-hydrox-acyl-[acp] dehydratase (fabA or fabZ); trans-2-enoyl-ACP reductase II (fabK). In a related aspect, the polypeptide is selected from fabA, fabB, fabD, fabF, fabG, fabH, fabI, fabL, fabV, fabZ, fabM, and fabK and or combinations thereof. In yet another related aspect, the polypeptide is selected from FabA from *Salmonella typhimurium* (NP_460041); FabB from *Escherichia coli* (NP_416826); FabD from *Salmonella typhimurium* (NP_460164); FabG from *Salmonella typhimurium* (NP_460165); FabH from *Salmonella typhimurium* (NP_460163); FabZ from *Salmonella typhimurium* (NP_459232); FabM from *Streptococcus mutans* (AAN59379); FabK from *Streptococcus pneumoniae* (AAF98273); FabV from *Vibrio cholera* (YP_001217283); FabF from *Clostridium acetobutylicum* (NP_350156); FabI from *Bacillus subtillis* subsp. *subtilis* str. 168 (NP_389054); FabL from *Bacillus subtillis* subsp. *subtilis* str. 168 (NP_388745); FabI from *Acinetobacter* sp. ADP1 (YP_047630); FabI from *Marinobacter aquaeoli* VT8 (YP_958813); FabI from *Rhodococcus opacus* B4 (YP_002784194); FabH from *Acinetobacter* sp. ADP1 (YP_046731); FabH from *Marinobacter aquaeoli* VT8 (YP_958649); and FabH from *Rhodococcus opacus* B4 (YP_00278448) or combinations thereof.

The disclosure further contemplates a recombinant host cell having a genetically engineered polynucleotide sequence encoding an ACP polypeptide, wherein the recombinant host cell produces a fatty acid derivative composition at a higher titer, yield or productivity than a corresponding wild type host cell when cultured in a medium containing a carbon source under conditions effective to express the ACP polypeptide. In a related aspect, the genetically engineered polynucleotide sequence further encodes a polypeptide that has phosphopantetheinyl transferase (E.C. 2.7.8.7) activity. Herein, the genetically engineered polynucleotide sequence includes a sfp gene coding encoding a phosphopantetheinyl transferase (E.C. 2.7.8.7). In a related aspect, a genetically engineered polynucleotide sequence further encodes a polypeptide that has accABCD activity (E.C. 6.4.1.2). ACP can be in expressed in combination with accABCD and/or a phosphopantetheinyl transferase, wherein the combination of any of the expressed polypeptides further leads to increases in the titer, yield and/or productivity of the recombinant host cell when cultured under appropriate conditions. In another related aspect, ACP is derived from the same organism as a terminal pathway enzyme expressed in the recombinant host cell, wherein the terminal enzyme cleaves any acyl-ACP species that is part of the fatty acid biosynthetic pathway. The ACP is exogenous or endogenous to the host cell.

The disclosure further encompasses a recombinant host cell including a genetically engineered polynucleotide sequence including a transposon, wherein insertion of the transposon into a yijP gene affects a second gene flanking the yijP gene, wherein the second gene codes for a polynucleotide that is up- or down regulated, and wherein the up- or down regulated polynucleotide codes for a polypeptide that affects production of a fatty acid derivative composition when the host cell is cultured in a medium containing a carbon source under conditions effective to express the polypeptide. The yijP gene can be flanked by genes on either side. In a related aspect, the insertion of the transposon into the yijP gene results in inactivation of the yijP gene or a polynucleotide thereof, which affects one or more of the genes flanking the yijP gene, wherein the flanking gene or genes code for a polypeptide that affects production of a fatty acid derivative composition when the host cell is cultured in a medium containing a carbon source under conditions effective to express the polypeptide. In one related aspect, the flanking gene includes polynucleotides including, but not limited to, ppc, yijO, frwD, pflC, pflD or argE.

Another aspect of the disclosure provides a recombinant host cell including a genetically engineered polynucleotide sequence encoding a phosphoenolpyruvate carboxylase (ppc) polypeptide, wherein the recombinant host cell produces a fatty acid derivative composition at a higher titer, yield or productivity than a corresponding wild type host cell when cultured in a medium containing a carbon source under conditions effective to express the ppc polypeptide.

Still, another aspect of the disclosure provides a cell culture that includes any of the recombinant host cells presented herein (supra). The recombinant host cell is cultured in a medium such that the recombinant host cell produces fatty acid derivative compositions according to the genetic engineering methods presented herein (supra). In a related aspect, the fatty acid derivative compositions produced by the recombinant host cells of the present disclosure include, but are not limited to, fatty acids, fatty esters, fatty alcohols, fatty aldehydes, alkanes, terminal olefins, internal olefins, and ketones. In another related aspect, the fatty acid derivative is a C6, C8, C10, C12, C13, C14, C15, C16, C17, or C18 fatty acid derivative. In yet another related aspect, the fatty acid derivative is a C10:1, C12:1, C14:1, C16:1, or C18:1 unsaturated fatty acid derivative. In a further related aspect, the fatty acid derivative composition comprises one or more of C8, C10, C12, C14, C16, and C18 fatty acid derivatives. The fatty acid derivative compositions produced by the cell cultures containing the recombinant host cells of the present disclosure include fatty acids, fatty aldehydes, fatty alcohols, fatty esters, alkanes, terminal olefins, internal olefins, and ketones. The disclosure further encompasses fatty acid derivative compositions that include fatty acid derivatives having a double bond at position 7 in the carbon chain between C7 and C8 from the reduced end of the fatty alcohol; fatty acid derivative compositions including unsaturated fatty acid derivatives; fatty acid derivative compositions including saturated fatty acid derivatives; and fatty acid derivative compositions including branched chain fatty acid derivatives.

The disclosure further contemplates a cell culture containing any of the recombinant host cells presented herein, wherein the recombinant host cells have a titer that is at least about 5% greater than the titer of the corresponding wild type host cells when cultured under the same conditions as the recombinant host cells. Herein, the recombinant host cells have a titer of from about 1 g/L to about 250 g/L, and more specifically from about 90 g/L to about 120 g/L. In a related aspect, the recombinant host cells have a yield that is at least about 10% to about 40%. In one aspect, the recombinant host cells have a yield of about 25%. Still encompassed herein is a cell culture containing any one of the recombinant host cells presented herein, wherein the productivity of the cell culture ranges from about 0.7 mg/L/hr to about 3 g/L/hr or higher.

Another aspect of the disclosure provides methods of making a recombinant host cell, including genetically engineering the recombinant host cell such that the cell expresses a polypeptide sequence that is encoded by one or more polynucleotide sequences under specific culture conditions, wherein the polynucleotide sequence codes for one or more polypeptides that have a specific enzymatic activity.

BRIEF DESCRIPTION OF THE DRAWINGS

The present disclosure is best understood when read in conjunction with the accompanying figures, which serve to illustrate the preferred embodiments. It is understood, however, that the disclosure is not limited to the specific embodiments disclosed in the figures.

(FIG. 12A) and 37° C. (FIG. 12B).

DETAILED DESCRIPTION

General Overview

Figure 1:
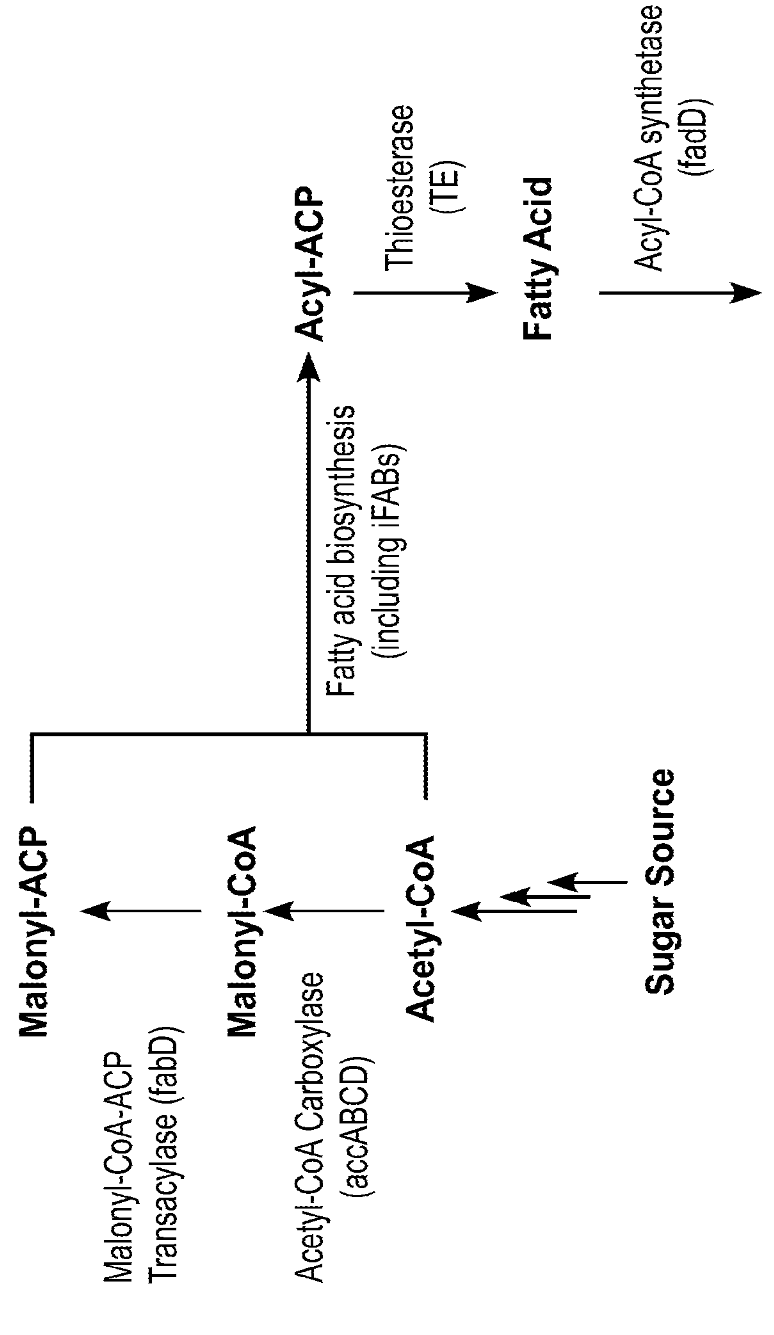
FIG. 1 presents an exemplary biosynthetic pathway for use in production of acyl CoA as a precursor to fatty acid derivatives in a recombinant microorganism. The cycle is initiated by condensation of malonyl-ACP and acetyl-CoA.

The disclosure is based, at least in part, on the discovery that modification of various aspects of the fatty acid biosynthetic pathway in a recombinant host cell facilitates enhanced production of fatty acid derivatives by the host cell. The disclosure relates to compositions of fatty acid derivatives having desired characteristics and methods for producing the same. Further, the disclosure relates to recombinant host cells (e.g., microorganisms), cultures of recombinant host cells, methods of making and using recombinant host cells, for example, use of cultured recombinant host cells in the fermentative production of fatty acid derivatives having desired characteristics.

More specifically, the production of a desired fatty acid derivative composition (e.g., acyl-CoA, fatty acids, fatty aldehydes, short and long chain alcohols, hydrocarbons, fatty alcohols, esters (e.g., waxes, fatty acid esters, or fatty esters), terminal olefins, internal olefins, and ketones is enhanced by modifying the expression of one or more genes involved in a biosynthetic pathway for fatty acid, fatty ester, alkane, alkene, olefin, or fatty alcohol, production, degradation and/or secretion. The disclosure provides recombinant host cells which have been engineered to provide enhanced fatty acid biosynthesis relative to non-engineered or native host cells (e.g., wild type host cells that function as control cells), which is accomplished, for example, through strain improvements. As such, the disclosure identifies polynucleotides useful in the recombinant host cells, methods, and compositions of the disclosure. It will be generally recognized that absolute sequence identity to such polynucleotides is not necessary. For example, changes in a particular polynucleotide sequence can be made and the encoded polypeptide screened for activity. Such changes typically comprise conservative mutations and silent mutations (e.g., codon optimization). Genetically engineered or modified polynucleotides and encoded variant polypeptides can be screened for a desired function, including but not limited to, increased catalytic activity, increased stability, or decreased inhibition (e.g., decreased feedback inhibition), using methods known in the art.

The disclosure identifies enzymatic activities involved in various steps (i.e., reactions) of the fatty acid biosynthetic pathways described herein according to Enzyme Classification (EC) number, and provides exemplary polypeptides (e.g.,enzymes) categorized by such EC numbers, and exemplary polynucleotides encoding such polypeptides. Such exemplary polypeptides and polynucleotides, which are identified herein by Accession Numbers and/or Sequence Identifier Numbers (SEQ ID NOs), are useful for engineering fatty acid pathways in parental host cells to obtain the recombinant host cells described herein. The polypeptides and polynucleotides described herein are exemplary and non-limiting. The sequences of homologues of exemplary polypeptides described herein are available to those of skill in the art through various databases (e.g., rhw Entrez databases provided by the National Center for Biotechnology Information (NCBI), the ExPasy databases provided by the Swiss Institute of Bioinformatics, the BRENDA database provided by the Technical University of Braunschweig, and the KEGG database provided by the Bioinformatics Center of Kyoto University and University of Tokyo, all which are available on the World Wide Web).

Definitions

As used in this specification and the appended claims, the singular forms "a," "an" and "the" include plural referents unless the context clearly dictates otherwise. Thus, for example, reference to "a recombinant host cell" includes two or more such recombinant host cells, reference to "a fatty alcohol" includes one or more fatty alcohols, or mixtures of fatty alcohols, reference to "a nucleic acid coding sequence" includes one or more nucleic acid coding sequences, reference to "an enzyme" includes one or more enzymes, and the like.

Accession Numbers: Sequence Accession numbers throughout this description were obtained from databases provided by the NCBI (National Center for Biotechnology Information) maintained by the National Institutes of Health, U.S.A. (which are identified herein as "NCBI Accession Numbers" or alternatively as "GenBank Accession Numbers"), and from the UniProt Knowledgebase (UniProtKB) and Swiss-Prot databases provided by the Swiss Institute of Bioinformatics (which are identified herein as "UniProtKB Accession Numbers").

Enzyme Classification (EC) Numbers: EC numbers are established by the Nomenclature Committee of the International Union of Biochemistry and Molecular Biology (IUBMB), description of which is available on the IUBMB Enzyme Nomenclature website on the World Wide Web. EC numbers classify enzymes according to the reaction they catalyze.

As used herein, the term "nucleotide" refers to a monomeric unit of a polynucleotide that consists of a heterocyclic base, a sugar, and one or more phosphate groups. The naturally occurring bases (guanine, (G), adenine, (A), cytosine, (C), thymine, (T), and uracil (U)) are typically derivatives of purine or pyrimidine, though it should be understood that naturally and non-naturally occurring base analogs are also included. The naturally occurring sugar is the pentose (five-carbon sugar) deoxyribose (which forms DNA) or ribose (which forms RNA), though it should be understood that naturally and non-naturally occurring sugar analogs are also included. Nucleic acids are typically linked via phosphate bonds to form nucleic acids or polynucleotides, though many other linkages are known in the art (e.g., phosphorothioates, boranophosphates, and the like).

As used herein, the term "polynucleotide" refers to a polymer of ribonucleotides (RNA) or deoxyribonucleotides (DNA), which can be single-stranded or double-stranded and which can contain non-natural or altered nucleotides. The terms "polynucleotide," "nucleic acid sequence," and "nucleotide sequence" are used interchangeably herein to refer to a polymeric form of nucleotides of any length, either RNA or DNA. These terms refer to the primary structure of the molecule, and thus include double- and single-stranded DNA, and double- and single-stranded RNA. The terms include, as equivalents, analogs of either RNA or DNA made from nucleotide analogs and modified polynucleotides such as, though not limited to methylated and/or capped polynucleotides. The polynucleotide can be in any form, including but not limited to, plasmid, viral, chromosomal, EST, cDNA, mRNA, and rRNA.

As used herein, the terms "polypeptide" and "protein" are used interchangeably to refer to a polymer of amino acid residues. The term "recombinant polypeptide" refers to a polypeptide that is produced by recombinant techniques, wherein generally DNA or RNA encoding the expressed protein is inserted into a suitable expression vector that is in turn used to transform a host cell to produce the polypeptide.

As used herein, the terms "homolog," and "homologous" refer to a polynucleotide or a polypeptide comprising a sequence that is at least about 50% identical to the corresponding polynucleotide or polypeptide sequence. Preferably homologous polynucleotides or polypeptides have polynucleotide sequences or amino acid sequences that have at least about 80%, 81%, 82%, 83%, 84%, 85%, 86%, 87%, 88%, 89%, 90%, 91%, 92%, 93%, 94%, 95%, 96%, 97%, 98% or at least about 99% homology to the corresponding amino acid sequence or polynucleotide sequence. As used herein the terms sequence "homology" and sequence "identity" are used interchangeably.

One of ordinary skill in the art is well aware of methods to determine homology between two or more sequences. Briefly, calculations of "homology" between two sequences can be performed as follows. The sequences are aligned for optimal comparison purposes (e.g., gaps can be introduced in one or both of a first and a second amino acid or nucleic acid sequence for optimal alignment and non-homologous sequences can be disregarded for comparison purposes). In a preferred embodiment, the length of a first sequence that is aligned for comparison purposes is at least about 30%, preferably at least about 40%, more preferably at least about 50%, even more preferably at least about 60%, and even more preferably at least about 70%, at least about 75%, at least about 80%, at least about 85%, at least about 90%, at least about 95%, or about 100% of the length of a second sequence. The amino acid residues or nucleotides at corresponding amino acid positions or nucleotide positions of the first and second sequences are then compared. When a position in the first sequence is occupied by the same amino acid residue or nucleotide as the corresponding position in the second sequence, then the molecules are identical at that position. The percent homology between the two sequences is a function of the number of identical positions shared by the sequences, taking into account the number of gaps and the length of each gap, that need to be introduced for optimal alignment of the two sequences.

The comparison of sequences and determination of percent homology between two sequences can be accomplished using a mathematical algorithm, such as BLAST (Altschul et al., J. Mol. Biol., 215(3): 403-410 (1990)). The percent homology between two amino acid sequences also can be determined using the Needleman and Wunsch algorithm that has been incorporated into the GAP program in the GCG software package, using either a Blossum 62 matrix or a PAM250 matrix, and a gap weight of 16, 14, 12, 10, 8, 6, or 4 and a length weight of 1, 2, 3, 4, 5, or 6 (Needleman and Wunsch, J. Mol. Biol., 48: 444-453 (1970)). The percent homology between two nucleotide sequences also can be determined using the GAP program in the GCG software package, using a NWSgapdna.CMP matrix and a gap weight of 40, 50, 60, 70, or 80 and a length weight of 1, 2, 3, 4, 5, or 6. One of ordinary skill in the art can perform initial homology calculations and adjust the algorithm parameters accordingly. A preferred set of parameters (and the one that should be used if a practitioner is uncertain about which parameters should be applied to determine if a molecule is within a homology limitation of the claims) are a Blossum 62 scoring matrix with a gap penalty of 12, a gap extend penalty of 4, and a frameshift gap penalty of 5. Additional methods of sequence alignment are known in the biotechnology arts (see, e.g., Rosenberg, BMC Bioinformatics, 6: 278 (2005); Altschul, et al., FEBS J., 272(20): 5101-5109 (2005)).

As used herein, the term "hybridizes under low stringency, medium stringency, high stringency, or very high stringency conditions" describes conditions for hybridization and washing. Guidance for performing hybridization reactions can be found in Current Protocols in Molecular Biology, John Wiley & Sons, N.Y. (1989), 6.3.1-6.3.6.

Aqueous and non-aqueous methods are described in that reference and either method can be used. Specific hybridization conditions referred to herein are as follows: 1) low stringency hybridization conditions—6× sodium chloride/sodium citrate (SSC) at about 45° C., followed by two washes in 0.2×SSC, 0.1% SDS at least at 50° C. (the temperature of the washes can be increased to 55° C. for low stringency conditions); 2) medium stringency hybridization conditions—6×SSC at about 45° C., followed by one or more washes in 0.2×SSC, 0.1% SDS at 60° C.; 3) high stringency hybridization conditions—6×SSC at about 45° C., followed by one or more washes in 0.2.×SSC, 0.1% SDS at 65° C.; and 4) very high stringency hybridization conditions—0.5M sodium phosphate, 7% SDS at 65° C., followed by one or more washes at 0.2×SSC, 1% SDS at 65° C. Very high stringency conditions (4) are the preferred conditions unless otherwise specified.

An "endogenous" polypeptide refers to a polypeptide encoded by the genome of the host cell (e.g., parental microbial cell) from which the recombinant cell is engineered or derived.

An "exogenous" polypeptide refers to a polypeptide which is not encoded by the genome of the parental microbial cell. A variant (i.e., mutant) polypeptide is an example of an exogenous polypeptide.

The term "heterologous" generally means derived from a different species or derived from a different organism. As used herein it refers to a nucleotide sequence or a polypeptide sequence that is not naturally present in a particular organism. Heterologous expression means that a protein or polypeptide is experimentally added to a cell that does not normally express that protein. As such, heterologous refers to the fact that a transferred protein was initially derived from a different cell type or a different species then the recipient. For example, a polynucleotide sequence endogenous to a plant cell can be introduced into a bacterial host cell by recombinant methods, and the plant polynucleotide is then a heterologous polynucleotide in a recombinant bacterial host cell.

As used herein, the term "fragment" of a polypeptide refers to a shorter portion of a full-length polypeptide or protein ranging in size from four amino acid residues to the entire amino acid sequence minus one amino acid residue. In certain embodiments of the disclosure, a fragment refers to the entire amino acid sequence of a domain of a polypeptide or protein (e.g., a substrate binding domain or a catalytic domain).

As used herein, the term "mutagenesis" refers to a process by which the genetic information of an organism is changed in a stable manner. Mutagenesis of a protein coding nucleic acid sequence produces a mutant protein. Mutagenesis also refers to changes in non-coding nucleic acid sequences that result in modified protein activity.

As used herein, the term "gene" refers to nucleic acid sequences encoding either an RNA product or a protein product, as well as operably-linked nucleic acid sequences affecting the expression of the RNA or protein (e.g., such sequences include but are not limited to promoter or enhancer sequences) or operably-linked nucleic acid sequences encoding sequences that affect the expression of the RNA or protein (e.g., such sequences include but are not limited to ribosome binding sites or translational control sequences).

Expression control sequences are known in the art and include, for example, promoters, enhancers, polyadenylation signals, transcription terminators, internal ribosome entry sites (IRES), and the like, that provide for the expression of the polynucleotide sequence in a host cell. Expression control sequences interact specifically with cellular proteins involved in transcription (Maniatis et al., Science, 236: 1237-1245 (1987)). Exemplary expression control sequences are described in, for example, Goeddel, Gene Expression Technology: Methods in Enzymology, Vol. 185, Academic Press, San Diego, Calif. (1990).

In the methods of the disclosure, an expression control sequence is operably linked to a polynucleotide sequence. By "operably linked" is meant that a polynucleotide sequence and an expression control sequence(s) are connected in such a way as to permit gene expression when the appropriate molecules (e.g., transcriptional activator proteins) are bound to the expression control sequence(s). Operably linked promoters are located upstream of the selected polynucleotide sequence in terms of the direction of transcription and translation. Operably linked enhancers can be located upstream, within, or downstream of the selected polynucleotide.

As used herein, the term "vector" refers to a nucleic acid molecule capable of transporting another nucleic acid, i.e., a polynucleotide sequence, to which it has been linked. One type of useful vector is an episome (i.e., a nucleic acid capable of extra-chromosomal replication). Useful vectors are those capable of autonomous replication and/or expression of nucleic acids to which they are linked. Vectors capable of directing the expression of genes to which they are operatively linked are referred to herein as "expression vectors." In general, expression vectors of utility in recombinant DNA techniques are often in the form of "plasmids," which refer generally to circular double stranded DNA loops that, in their vector form, are not bound to the chromosome. The terms "plasmid" and "vector" are used interchangeably herein, in as much as a plasmid is the most commonly used form of vector. However, also included are such other forms of expression vectors that serve equivalent functions and that become known in the art subsequently hereto. In some embodiments, a recombinant vector further comprises a promoter operably linked to the polynucleotide sequence. In some embodiments, the promoter is a developmentally-regulated, an organelle-specific, a tissue-specific, an inducible, a constitutive, or a cell-specific promoter. The recombinant vector typically comprises at least one sequence including (a) an expression control sequence operatively coupled to the polynucleotide sequence; (b) a selection marker operatively coupled to the polynucleotide sequence; (c) a marker sequence operatively coupled to the polynucleotide sequence; (d) a purification moiety operatively coupled to the polynucleotide sequence; (e) a secretion sequence operatively coupled to the polynucleotide sequence; and (f) a targeting sequence operatively coupled to the polynucleotide sequence. In certain embodiments, the nucleotide sequence is stably incorporated into the genomic DNA of the host cell, and the expression of the nucleotide sequence is under the control of a regulated promoter region. The expression vectors described herein include a polynucleotide sequence described herein in a form suitable for expression of the polynucleotide sequence in a host cell. It will be appreciated by those skilled in the art that the design of the expression vector can depend on such factors as the choice of the host cell to be transformed, the level of expression of polypeptide desired, etc. The expression vectors described herein can be introduced into host cells to produce polypeptides, including fusion polypeptides, encoded by the polynucleotide sequences as described herein.

Expression of genes encoding polypeptides in prokaryotes, for example, *E. coli*, is most often carried out with vectors containing constitutive or inducible promoters directing the expression of either fusion or non-fusion polypeptides. Fusion vectors add a number of amino acids to a polypeptide encoded therein, usually to the amino- or carboxy-terminus of the recombinant polypeptide. Such fusion vectors typically serve one or more of the following three purposes: (1) to increase expression of the recombinant polypeptide; (2) to increase the solubility of the recombinant polypeptide; and (3) to aid in the purification of the recombinant polypeptide by acting as a ligand in affinity purification. Often, in fusion expression vectors, a proteolytic cleavage site is introduced at the junction of the fusion moiety and the recombinant polypeptide. This enables separation of the recombinant polypeptide from the fusion moiety after purification of the fusion polypeptide. In certain embodiments, a polynucleotide sequence of the disclosure is operably linked to a promoter derived from bacteriophage T5.

In certain embodiments, the host cell is a yeast cell, and the expression vector is a yeast expression vector. Examples of vectors for expression in yeast *S. cerevisiae* include pYepSecl (Baldari et al., EMBO J., 6: 229-234 (1987)), pMFa (Kurjan et al., Cell, 30: 933-943 (1982)), pJRY88 (Schultz et al., Gene, 54: 113-123 (1987)), pYES2 (Invitrogen Corp., San Diego, Calif.), and picZ (Invitrogen Corp., San Diego, Calif.).

In other embodiments, the host cell is an insect cell, and the expression vector is a baculovirus expression vector. Baculovirus vectors available for expression of proteins in cultured insect cells (e.g., Sf9 cells) include, for example, the pAc series (Smith et al., Mol. Cell Biol., 3: 2156-2165 (1983)) and the pVL series (Lucklow et al., Virology, 170: 31-39 (1989)).

In yet another embodiment, the polynucleotide sequences described herein can be expressed in mammalian cells using a mammalian expression vector. Other suitable expression systems for both prokaryotic and eukaryotic cells are well known in the art; see, e.g., Sambrook et al., "Molecular Cloning: A Laboratory Manual," second edition, Cold Spring Harbor Laboratory, (1989).

The term "corresponding wild type host cell" as referred to herein, means a cell that functions as a control cell. For example, if a polypeptide in a recombinant host cell is up-regulated, then the same polypeptide would exist at a lower level in the control cell. Conversely, if a polypeptide in a recombinant host cell is down-regulated, then the same polypeptide would exist at a higher level in the control cell. Furthermore, the "recombinant or engineered host cell" is a microorganism used to produce one or more of fatty acid derivatives including, for example, acyl-CoA, fatty acids, fatty aldehydes, short and long chain alcohols, hydrocarbons, fatty alcohols, esters (e.g., waxes, fatty acid esters, or fatty esters), terminal olefins, internal olefins, and ketones. In some embodiments, the recombinant host cell comprises one or more polynucleotides, each polynucleotide encoding a polypeptide having fatty acid biosynthetic enzyme activity.

As used herein "acyl-CoA" refers to an acyl thioester formed between the carbonyl carbon of alkyl chain and the sulfhydryl group of the 4'-phosphopantethionyl moiety of coenzyme A (CoA), which has the formula R—C(O)S-CoA, where R is any alkyl group having at least 4 carbon atoms.

As used herein "acyl-ACP" refers to an acyl thioester formed between the carbonyl carbon of alkyl chain and the sulfhydryl group of the phosphopantetheinyl moiety of an acyl carrier protein (ACP). The phosphopantetheinyl moiety is post-translationally attached to a conserved serine residue on the ACP by the action of holo-acyl carrier protein synthase (ACPS), a phosphopantetheinyl transferase. In some embodiments an acyl-ACP is an intermediate in the synthesis of fully saturated acyl-ACPs. In other embodiments an acyl-ACP is an intermediate in the synthesis of unsaturated acyl-ACPs. In some embodiments, the carbon chain will have about 5, 6, 7, 8, 9, 10, 11, 12, 13, 14, 15, 16, 17, 18, 19, 20, 21, 22, 23, 24, 25, or 26 carbons. Each of these acyl-ACPs are substrates for enzymes that convert them to fatty acid derivatives.

As used herein, the term "fatty acid derivative" means a "fatty acid" or a "fatty acid derivative", which may be referred to as a "fatty acid or derivative thereof". The term "fatty acid" means a carboxylic acid having the formula RCOOH. R represents an aliphatic group, preferably an alkyl group. R can comprise between about 4 and about 22 carbon atoms. Fatty acids can be saturated, monounsaturated, or polyunsaturated. A "fatty acid derivative" is a product made in part from the fatty acid biosynthetic pathway of the production host organism. "Fatty acid derivatives" includes products made in part from acyl-ACP or acyl-ACP derivatives. Exemplary fatty acid derivatives include, for example, acyl-CoA, fatty acids, fatty aldehydes, short and long chain alcohols, fatty alcohols, hydrocarbons, esters (e.g., waxes, fatty acid esters, or fatty esters), terminal olefins, internal olefins, and ketones.

A "fatty acid derivative composition" as referred to herein is produced by a recombinant host cell and typically comprises a mixture of fatty acid derivative. In some cases, the mixture includes more than one type of product (e.g., fatty acids and fatty alcohols, fatty acids and fatty acid esters or alkanes and olefins). In other cases, the fatty acid derivative compositions may comprise, for example, a mixture of fatty alcohols (or another fatty acid derivative) with various chain lengths and saturation or branching characteristics. In still other cases, the fatty acid derivative composition comprises a mixture of both more than one type of product and products with various chain lengths and saturation or branching characteristics.

As used herein, the term "fatty acid biosynthetic pathway" means a biosynthetic pathway that produces fatty acids and derivatives thereof. The fatty acid biosynthetic pathway may include additional enzymes or polypeptides with enzymatic activities besides the ones discussed herein to produce fatty acid derivatives having desired characteristics.

As used herein, "fatty aldehyde" means an aldehyde having the formula RCHO characterized by a carbonyl group (C═O). In some embodiments, the fatty aldehyde is any aldehyde made from a fatty alcohol. In certain embodiments, the R group is at least 5, at least 6, at least 7, at least 8, at least 9, at least 10, at least 11, at least 12, at least 13, at least 14, at least 15, at least 16, at least 17, at least 18, or at least 19, carbons in length. Alternatively, or in addition, the R group is 20 or less, 19 or less, 18 or less, 17 or less, 16 or less, 15 or less, 14 or less, 13 or less, 12 or less, 11 or less, 10 or less, 9 or less, 8 or less, 7 or less, or 6 or less carbons in length. Thus, the R group can have an R group bounded by any two of the above endpoints. For example, the R group can be 6-16 carbons in length, 10-14 carbons in length, or 12-18 carbons in length. In some embodiments, the fatty aldehyde is a C6, C7, C8, C9, C10, C11, C12, C13, C14, C15, C16, C17, C18, C19, C20, C21, C22, C23, C24, C25, or a C26 fatty aldehyde. In certain embodiments, the fatty aldehyde is a C6, C7, C8, C9, C10, C11, C12, C13, C14, C15, C16, C17, or C18 fatty aldehyde.

As used herein, "fatty alcohol" means an alcohol having the formula ROH. In some embodiments, the R group is at least 5, at least 6, at least 7, at least 8, at least 9, at least 10, at least 11, at least 12, at least 13, at least 14, at least 15, at least 16, at least 17, at least 18, or at least 19, carbons in length. Alternatively, or in addition, the R group is 20 or less, 19 or less, 18 or less, 17 or less, 16 or less, 15 or less, 14 or less, 13 or less, 12 or less, 11 or less, 10 or less, 9 or less, 8 or less, 7 or less, or 6 or less carbons in length. Thus, the R group can have an R group bounded by any two of the above endpoints. For example, the R group can be 6-16 carbons in length, 10-14 carbons in length, or 12-18 carbons in length. In some embodiments, the fatty alcohol is a C6, C7, C8, C9, C10, C11, C12, C13, C14, C15, C16, C17, C18, C19, C20, C21, C22, C23, C24, C25, or a C26 fatty alcohol. In certain embodiments, the fatty alcohol is a C6, C7, C8, C9, C10, C11, C12, C13, C14, C15, C16, C17, or C18 fatty alcohol.

The R group of a fatty acid derivative, for example a fatty alcohol, can be a straight chain or a branched chain. Branched chains may have more than one point of branching and may include cyclic branches. In some embodiments, the branched fatty acid, branched fatty aldehyde, or branched fatty alcohol is a C6, C7, C8, C9, C10, C11, C12, C13, C14, C15, C16, C17, C18, C19, C20, C21, C22, C23, C24, C25, or a C26 branched fatty acid, branched fatty aldehyde, or branched fatty alcohol. In particular embodiments, the branched fatty acid, branched fatty aldehyde, or branched fatty alcohol is a C6, C7, C8, C9, C10, C11, C12, C13, C14, C15, C16, C17, or C18 branched fatty acid, branched fatty aldehyde, or branched fatty alcohol. In certain embodiments, the hydroxyl group of the branched fatty acid, branched fatty aldehyde, or branched fatty alcohol is in the primary (C1) position.

In certain embodiments, the branched fatty acid derivative is an iso-fatty acid derivative, for example an iso-fatty aldehyde, an iso-fatty alcohol, or an antesio-fatty acid derivative, an anteiso-fatty aldehyde, or an anteiso-fatty alcohol. In exemplary embodiments, the branched fatty acid derivative is selected from iso-C7:0, iso-C8:0, iso-C9:0, iso-C10:0, iso-C11:0, iso-C12:0, iso-C13:0, iso-C14:0, iso-C15:0, iso-C16:0, iso-C17:0, iso-C18:0, iso-C19:0, anteiso-C7:0, anteiso-C8:0, anteiso-C9:0, anteiso-C10:0, anteiso-C11:0,anteiso-C12:0, anteiso-C13:0, anteiso-C14:0, anteiso-C15:0, anteiso-C16:0, anteiso-C17:0, anteiso-C18:0, and an anteiso-C19:0 branched fatty alcohol.

The R group of a branched or unbranched fatty acid derivative can be saturated or unsaturated. If unsaturated, the R group can have one or more than one point of unsaturation. In some embodiments, the unsaturated fatty acid derivative is a monounsaturated fatty acid derivative. In certain embodiments, the unsaturated fatty acid derivative is a C6:1, C7:1, C8:1, C9:1, C10:1, C11:1, C12:1, C13:1, C14:1, C15:1, C16:1, C17:1, C18:1, C19:1, C20:1, C21:1, C22:1, C23:1, C24:1, C25:1, or a C26:1 unsaturated fatty acid derivative. In certain embodiments, the unsaturated fatty acid derivative is a C10:1, C12:1, C14:1, C16:1, or C18:1 unsaturated fatty acid derivative. In other embodiments, the unsaturated fatty acid derivative is unsaturated at the omega-7 position. In certain embodiments, the unsaturated fatty acid derivative comprises a cis double bond.

As used herein, the term "clone" typically refers to a cell or group of cells descended from and essentially genetically identical to a single common ancestor, for example, the bacteria of a cloned bacterial colony arose from a single bacterial cell.

As used herein, the term "culture" typical refers to a liquid media comprising viable cells. In one embodiment, a culture comprises cells reproducing in a predetermined culture media under controlled conditions, for example, a culture of recombinant host cells grown in liquid media comprising a selected carbon source and nitrogen. "Culturing" or "cultivation" refers to growing a population of recombinant host cells under suitable conditions in a liquid or solid medium. In particular embodiments, culturing refers to the fermentative bioconversion of a substrate to an end-product. Culturing media are well known and individual components of such culture media are available from commercial sources, e.g., under the Difco™ and BBL™ trademarks. In one non-limiting example, the aqueous nutrient medium is a "rich medium" comprising complex sources of nitrogen, salts, and carbon, such as YP medium, comprising 10 g/L of peptone and 10 g/L yeast extract of such a medium. The host cell of a culture can be additionally engineered to assimilate carbon efficiently and use cellulosic materials as carbon sources according to methods described in U.S. Pat. Nos. 5,000,000; 5,028,539; 5,424,202; 5,482,846; 5,602,030; WO 2010127318. In addition, in some embodiments the host cell is engineered to express an invertase so that sucrose can be used as a carbon source.

As used herein, the term "under conditions effective to express a genetically engineered polynucleotide sequence" means any condition that allows a host cell to produce a desired fatty acid derivative. Suitable conditions include, for example, fermentation conditions.

As used herein, "modified" or an "altered level of" activity of a protein, for example an enzyme, in a recombinant host cell refers to a difference in one or more characteristics in the activity determined relative to the parent or native host cell. Typically differences in activity are determined between a recombinant host cell, having modified activity, and the corresponding wild-type host cell (e.g., comparison of a culture of a recombinant host cell relative to the corresponding wild-type host cell). Modified activities can be the result of, for example, modified amounts of protein expressed by a recombinant host cell (e.g., as the result of increased or decreased number of copies of DNA sequences encoding the protein, increased or decreased number of mRNA transcripts encoding the protein, and/or increased or decreased amounts of protein translation of the protein from mRNA); changes in the structure of the protein (e.g., changes to the primary structure, such as, changes to the protein's coding sequence that result in changes in substrate specificity, changes in observed kinetic parameters); and changes in protein stability (e.g., increased or decreased degradation of the protein). In some embodiments, the polypeptide is a mutant or a variant of any of the polypeptides described herein. In certain instances, the coding sequences for the polypeptides described herein are codon optimized for expression in a particular host cell. For example, for expression in *E. coli*, one or more codons can be optimized as described in, e.g., Grosjean et al., Gene 18:199-209 (1982).

The term "regulatory sequences" as used herein typically refers to a sequence of bases in DNA, operably-linked to DNA sequences encoding a protein that ultimately controls the expression of the protein. Examples of regulatory sequences include, but are not limited to, RNA promoter sequences, transcription factor binding sequences, transcription termination sequences, modulators of transcription (such as enhancer elements), nucleotide sequences that affect RNA stability, and translational regulatory sequences (such as, ribosome binding sites (e.g., Shine-Dalgarno sequences in prokaryotes or Kozak sequences in eukaryotes), initiation codons, termination codons).

The terms "altered level of expression" and "modified level of expression" are used interchangeably and mean that a polynucleotide, polypeptide, or hydrocarbon is present in a different concentration in an engineered host cell as compared to its concentration in a corresponding wild-type cell under the same conditions.

As used herein, the term "titer" refers to the quantity of fatty acid derivative produced per unit volume of host cell culture. In any aspect of the compositions and methods described herein, a fatty acid derivative is produced at a titer of about 25 mg/L, about 50 mg/L, about 75 mg/L, about 100 mg/L, about 125 mg/L, about 150 mg/L, about 175 mg/L, about 200 mg/L, about 225 mg/L, about 250 mg/L, about 275 mg/L, about 300 mg/L, about 325 mg/L, about 350 mg/L, about 375 mg/L, about 400 mg/L, about 425 mg/L, about 450 mg/L, about 475 mg/L, about 500 mg/L, about 525 mg/L, about 550 mg/L, about 575 mg/L, about 600 mg/L, about 625 mg/L, about 650 mg/L, about 675 mg/L, about 700 mg/L, about 725 mg/L, about 750 mg/L, about 775 mg/L, about 800 mg/L, about 825 mg/L, about 850 mg/L, about 875 mg/L, about 900 mg/L, about 925 mg/L, about 950 mg/L, about 975 mg/L, about 1000 mg/L, about 1050 mg/L, about 1075 mg/L, about 1100 mg/L, about 1125 mg/L, about 1150 mg/L, about 1175 mg/L, about 1200 mg/L, about 1225 mg/L, about 1250 mg/L, about 1275 mg/L, about 1300 mg/L, about 1325 mg/L, about 1350 mg/L, about 1375 mg/L, about 1400 mg/L, about 1425 mg/L, about 1450 mg/L, about 1475 mg/L, about 1500 mg/L, about 1525 mg/L, about 1550 mg/L, about 1575 mg/L, about 1600 mg/L, about 1625 mg/L, about 1650 mg/L, about 1675 mg/L, about 1700 mg/L, about 1725 mg/L, about 1750 mg/L, about 1775 mg/L, about 1800 mg/L, about 1825 mg/L, about 1850 mg/L, about 1875 mg/L, about 1900 mg/L, about 1925 mg/L, about 1950 mg/L, about 1975 mg/L, about 2000 mg/L (2 g/L), 3 g/L, 5 g/L, 10 g/L, 20 g/L, 30 g/L, 40 g/L, 50 g/L, 60 g/L, 70 g/L, 80 g/L, 90 g/L, 100 g/L or a range bounded by any two of the foregoing values. In other embodiments, a fatty acid derivative is produced at a titer of more than 100 g/L, more than 200 g/L, more than 300 g/L, or higher, such as 500 g/L, 700 g/L, 1000 g/L, 1200 g/L, 1500 g/L, or 2000 g/L. The preferred titer of fatty acid derivative produced by a recombinant host cell according to the methods of the disclosure is from 5 g/L to 200 g/L, 10 g/L to 150 g/L, 20 g/L to 120 g/L and 30 g/L to 100 g/L. In one embodiment, the titer of fatty acid derivative produced by a recombinant host cell according to the methods of the disclosure is about 1 g/L to about 250 g/L and more particularly, 90 g/L to about 120 g/L. The titer may refer to a particular fatty acid derivative or a combination of fatty acid derivatives produced by a given recombinant host cell culture.

As used herein, the "yield of fatty acid derivative produced by a host cell" refers to the efficiency by which an input carbon source is converted to product (i.e., fatty alcohol or fatty aldehyde) in a host cell. Host cells engineered to produce fatty acid derivatives according to the methods of the disclosure have a yield of at least 3%, at least 4%, at least 5%, at least 6%, at least 7%, at least 8%, at least 9%, at least 10%, at least 11%, at least 12%, at least 13%, at least 14%, at least 15%, at least 16%, at least 17%, at least 18%, at least 19%, at least 20%, at least 21%, at least 22%, at least 23%, at least 24%, at least 25%, at least 26%, at least 27%, at least 28%, at least 29%, or at least 30% or a range bounded by any two of the foregoing values. In other embodiments, a fatty acid derivative or derivatives is produced at a yield of more than 30%, 40%, 50%, 60%, 70%, 80%, 90% or more. Alternatively, or in addition, the yield is about 30% or less, about 27% or less, about 25% or less, or about 22% or less. Thus, the yield can be bounded by any two of the above endpoints. For example, the yield of a fatty acid derivative or derivatives produced by the recombinant host cell according to the methods of the disclosure can be 5% to 15%, 10% to 25%, 10% to 22%, 15% to 27%, 18% to 22%, 20% to 28%, or 20% to 30%. In a particular embodiment, the yield of a fatty acid derivative or derivatives produced by the recombinant host cell is about 10% to about 40%. In another particular embodiment, the yield of a fatty acid derivative or derivatives produced by the recombinant host cell is about 25%. The yield may refer to a particular fatty acid derivative or a combination of fatty acid derivatives produced by a given recombinant host cell culture.

As used herein, the term "productivity" refers to the quantity of a fatty acid derivative or derivatives produced per unit volume of host cell culture per unit time. In any aspect of the compositions and methods described herein, the productivity of a fatty acid derivative or derivatives produced by a recombinant host cell is at least 100 mg/L/hour, at least 200 mg/L/hour, at least 300 mg/L/hour, at least 400 mg/L/hour, at least 500 mg/L/hour, at least 600 mg/L/hour, at least 700 mg/L/hour, at least 800 mg/L/hour, at least 900 mg/L/hour, at least 1000 mg/L/hour, at least 1100 mg/L/hour, at least 1200 mg/L/hour, at least 1300 mg/L/hour, at least 1400 mg/L/hour, at least 1500 mg/L/hour, at least 1600 mg/L/hour, at least 1700 mg/L/hour, at least 1800 mg/L/hour, at least 1900 mg/L/hour, at least 2000 mg/L/hour, at least 2100 mg/L/hour, at least 2200 mg/L/hour, at least 2300 mg/L/hour, at least 2400 mg/L/hour, or at least 2500 mg/L/hour. For example, the productivity of a fatty acid derivative or derivatives produced by a recombinant host cell according to the methods of the may be from 500 mg/L/hour to 2500 mg/L/hour, or from 700 mg/L/hour to 2000 mg/L/hour. In one particular embodiment, the yield is about 0.7 mg/L/h to about 3 g/L/h. The productivity may refer to a particular fatty acid derivative or a combination of fatty acid derivatives produced by a given recombinant host cell culture.

As used herein, the term "total fatty species" and "total fatty acid product" may be used interchangeably herein with reference to the amount of fatty alcohols, fatty aldehydes and fatty acids, as evaluated by GC-FID as described in International Patent Application Publication WO2008/119082. The same terms may be used to mean fatty esters and free fatty acids when referring to a fatty ester analysis.

As used herein, the term "glucose utilization rate" means the amount of glucose used by the culture per unit time, reported as grams/liter/hour (g/L/hr). As used herein, the term "carbon source" refers to a substrate or compound suitable to be used as a source of carbon for prokaryotic or simple eukaryotic cell growth. Carbon sources can be in various forms, including, but not limited to polymers, carbohydrates, acids, alcohols, aldehydes, ketones, amino acids, peptides, and gases (e.g., CO and $CO_2$). Exemplary carbon sources include, but are not limited to, monosaccharides, such as glucose, fructose, mannose, galactose, xylose, and arabinose; oligosaccharides, such as fructo-oligosaccharide and galacto-oligosaccharide; polysaccharides such as starch, cellulose, pectin, and xylan; disaccharides, such as sucrose, maltose, cellobiose, and turanose; cellulosic material and variants such as hemicelluloses, methyl cellulose and sodium carboxymethyl cellulose; saturated or unsaturated fatty acids, succinate, lactate, and acetate; alcohols, such as ethanol, methanol, and glycerol, or mixtures thereof. The carbon source can also be a product of photosynthesis, such as glucose. In certain preferred embodiments, the carbon source is biomass. In other preferred embodiments, the carbon source is glucose. In other preferred embodiments the carbon source is sucrose.

As used herein, the term "biomass" refers to any biological material from which a carbon source is derived. In some embodiments, a biomass is processed into a carbon source, which is suitable for bioconversion. In other embodiments, the biomass does not require further processing into a carbon source. The carbon source can be converted into a biofuel. An exemplary source of biomass is plant matter or vegetation, such as corn, sugar cane, or switchgrass. Another exemplary source of biomass is metabolic waste products, such as animal matter (e.g., cow manure). Further exemplary sources of biomass include algae and other marine plants. Biomass also includes waste products from industry, agriculture, forestry, and households, including, but not limited to, fermentation waste, ensilage, straw, lumber, sewage, garbage, cellulosic urban waste, and food leftovers. The term "biomass" also refers to sources of carbon, such as carbohydrates (e.g., monosaccharides, disaccharides, or polysaccharides).

As used herein, the term "isolated," with respect to products (such as fatty acids and derivatives thereof) refers to products that are separated from cellular components, cell culture media, or chemical or synthetic precursors. The fatty acids and derivatives thereof produced by the methods described herein can be relatively immiscible in the fermentation broth, as well as in the cytoplasm. Therefore, the fatty acids and derivatives thereof can collect in an organic phase either intracellularly or extracellularly.

As used herein, the terms "purify," "purified," or "purification" mean the removal or isolation of a molecule from its environment by, for example, isolation or separation. "Substantially purified" molecules are at least about 60% free (e.g., at least about 70% free, at least about 75% free, at least about 85% free, at least about 90% free, at least about 95% free, at least about 97% free, at least about 99% free) from other components with which they are associated. As used herein, these terms also refer to the removal of contaminants from a sample. For example, the removal of contaminants can result in an increase in the percentage of fatty acid derivatives in a sample. For example, when a fatty acid derivative is produced in a recombinant host cell, the fatty acid derivative can be purified by the removal of host cell proteins. After purification, the percentage of fatty acid derivative in the sample is increased. The terms "purify," "purified," and "purification" are relative terms which do not require absolute purity. Thus, for example, when a fatty acid derivative is produced in recombinant host cells, a purified fatty acid derivative is a fatty acid derivative that is substantially separated from other cellular components (e.g., nucleic acids, polypeptides, lipids, carbohydrates, or other hydrocarbons).

Strain Improvements

In order generate a high titer, yield, and/or productivity of fatty acid derivatives, a number of modifications were made to the production host cells. FadR is a key regulatory factor involved in fatty acid degradation and fatty acid biosynthetic pathways (Cronan et al., *Mol. Microbiol.,* 29(4): 937-943 (1998)). The *E. coli* ACS enzyme FadD and the fatty acid transport protein FadL are components of a fatty acid uptake system. FadL mediates transport of fatty acids into the bacterial cell, and FadD mediates formation of acyl-CoA esters. When no other carbon source is available, exogenous fatty acids are taken up by bacteria and converted to acyl-CoA esters, which can bind to the transcription factor FadR and depress the expression of the fad genes that encode proteins responsible for fatty acid transport (FadL), activation (FadD), and β-oxidation (FadA, FadB, FadE, and FadH). When alternative sources of carbon are available, bacteria synthesize fatty acids as acyl-ACPs, which are used for phospholipid synthesis, but are not substrates for β-oxidation. Thus, acyl-CoA and acyl-ACP are both independent sources of fatty acids that can result in different end-products (Caviglia et al., *J. Biol. Chem.,* 279(12): 1163-1169 (2004)).

There are conflicting speculations in the art as to the factors that can limit fatty acid biosynthesis in host cells, such as *E. coli.* One suggestion is that a limitation of the main precursors for fatty acid biosynthesis, for example, acetyl-CoA and malonyl-CoA can result in decreased synthesis of fatty acid derivatives. One approach to increasing the flux through fatty acid biosynthesis is to manipulate various enzymes in the pathway (see FIGS. 1 and 2). Example 3 describes studies which show construction of fab operons that encode enzymes in the biosynthetic pathway for conversion of malonyl-CoA into acyl-ACPs and integration into the chromosome of an *E.coli* host cell. Without wanting to be bound by theory, this may increase the flux of fatty acid biosynthesis. The supply of acyl-ACPs from acetyl-CoA via the acetyl-CoA carboxylase (acc) complex and fatty acid biosynthetic (fab) pathway is another step that may limit the rate of fatty acid derivative production (see FIG. 3). Example 2 shows the effect of overexpression of an optimized version of *E. coli Corynebacterium glutamicum* accABCD (±birA) demonstrated that such genetic modifications can lead to increased production of acetyl-coA and malonyl-CoA in *E. coli.*

In another approach, mutations in the rph and ilvG genes in the *E. coli* host cell were shown to result in higher free fatty acid (FFA) production, which translated into higher production of fatty alcohol as shown in Example 4. In still another approach, transposon mutagenesis and high-throughput screening was carried out to find beneficial mutations that increase the titer or yield. As shown in Example 5, a transposon insertion in the yijP gene can improve the fatty alcohol yield in shake flask and fed-batch fermentations.

Generation of Fatty Acid Derivatives by Recombinant Host Cells

Figure 5:
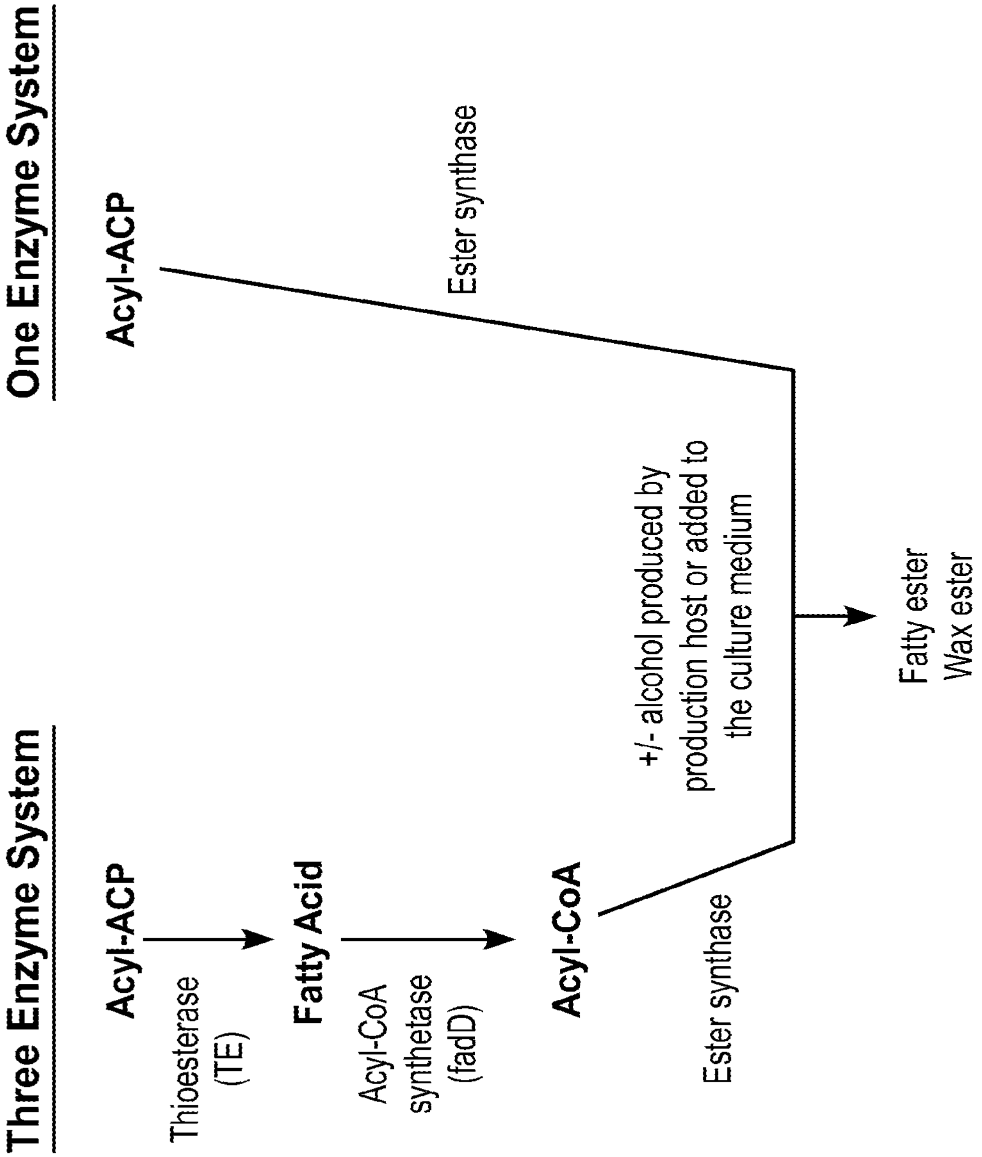
FIG. 5 presents an overview of two exemplary biosynthetic pathways for production of fatty esters starting with acyl-ACP, where the production of fatty esters is accomplished by a one-enzyme system or a three-enzyme-system.

The present disclosure provides numerous examples of polypeptides (i.e., enzymes) having activities suitable for use in the fatty acid biosynthetic pathways described herein. Such polypeptides are collectively referred to herein as "fatty acid biosynthetic polypeptides" or "fatty acid biosynthetic enzymes". Non-limiting examples of fatty acid pathway polypeptides suitable for use in recombinant host cells of the disclosure are provided herein. In some embodiments, the disclosure includes a recombinant host cell including a polynucleotide sequence which encodes a fatty acid biosynthetic polypeptide. The polynucleotide sequence, which includes an open reading frame encoding a fatty acid biosynthetic polypeptide and operably-linked regulatory sequences, can be integrated into a chromosome of the recombinant host cells, incorporated in one or more plasmid expression systems resident in the recombinant host cell, or both. In one embodiment, a fatty acid biosynthetic polynucleotide sequence encodes a polypeptide which is endogenous to the parental host cell (i.e., the control cell) of the recombinant host cell that is being engineered. Some such endogenous polypeptides are overexpressed in the recombinant host cell. In another embodiment, the fatty acid biosynthetic polynucleotide sequence encodes an exogenous or heterologous polypeptide. In other words, the polypeptide encoded by the polynucleotide is exogenous to the parental host cell. In yet another embodiment, the genetically modified host cell overexpresses a gene encoding a polypeptide (protein) that increases the rate at which the host cell produces the substrate of a fatty acid biosynthetic enzyme, i.e., a fatty acyl-thioester substrate. In certain embodiments, the enzyme encoded by the expressed gene is directly involved in fatty acid biosynthesis. Such recombinant host cells may be further engineered to include a polynucleotide sequence encoding one or more fatty acid biosynthetic polypeptides (i.e., enzymes involved in fatty acid biosynthesis). Examples of such polypeptides are polpeptides or proteins having thioesterase activity, wherein the recombinant host cell synthesizes fatty acids; or having thioesterase activity and carboxylic acid reductase (CAR) activity, wherein the recombinant host cell synthesizes fatty aldehydes and fatty alcohols; or having thioesterase activity, carboxylic acid reductase activity and alcohol dehydrogenase activity wherein the recombinant host cell synthesizes fatty alcohols; or having acyl-CoA reductase (AAR) activity wherein the recombinant host cell synthesizes fatty aldehydes and fatty alcohols; or having acyl-CoA reductase (AAR) activity and alcohol dehydrogenase activity wherein the recombinant host cell synthesizes fatty alcohols; or having fatty alcohol forming acyl-CoA reductase (FAR) activity, wherein the recombinant host cell synthesizes fatty alcohols; or having thioesterase activity, carboxylic acid reductase activity and aldehyde decarbonylase activity, wherein the recombinant host cell synthesizes alkanes; or having acyl-CoA reductase activity and aldehyde decarbonylase activity, wherein the recombinant host cell synthesizes alkanes; or having ester synthase activity wherein the recombinant host cell synthesizes fatty esters (e.g., one enzyme system; see FIG. 5); or having thioesterase activity, acyl-CoA synthase activity and ester synthase activity wherein the recombinant host cell synthesizes fatty esters (e.g., three enzyme system; see FIG. 5); or having OleA activity, wherein the recombinant host cell synthesizes aliphatic ketones; or having OleABCD activity, wherein the recombinant host cell synthesizes internal olefins; or having thioesterase activity and decarboxylase activity, wherein the recombinant host cell synthesizes terminal olefins; or combinations thereof. In some embodiments, at least one polypeptide encoded by a fatty acid biosynthetic polynucleotide is an exogenous (or heterologous) polypeptide (e.g., a polypeptide originating from an organism other than the parental host cell, or a variant of a polypeptide native to the parental microbial cell) or an endogenous polypeptide (i.e., a polypeptide native to the parental host cell) wherein the endogenous polypeptide is overexpressed in the recombinant host cell.

Table 1 below provides a listing of exemplary proteins which can be expressed in recombinant host cells to facilitate production of particular fatty acid derivatives.

TABLE 1

| Gene Designations | | | | | |
|---|---|---|---|---|---|
| Gene Designation | Source Organism | Enzyme Name | Accession No. | EC Number | Exemplary Use |
| 1. Fatty Acid Production Increase/Product Production Increase | | | | | |
| accA | *E. coli, Lactococci* | Acetyl-CoA carboxylase, subunit A (carboxyltransferase alpha) | AAC73296, NP_414727 | 6.4.1.2 | increase Malonyl-CoA production |
| accB | *E. coli, Lactococci* | Acetyl-CoA carboxylase, subunit B (BCCP: biotin carboxyl carrier protein) | NP_417721 | 6.4.1.2 | increase Malonyl-CoA production |
| accC | *E. coli, Lactococci* | Acetyl-CoA carboxylase, subunit C (biotin carboxylase) | NP_417722 | 6.4.1.2, 6.3.4.14 | increase Malonyl-CoA production |
| accD | *E. coli, Lactococci* | Acetyl-CoA carboxylase, subunit D (carboxyltransferase beta) | NP_416819 | 6.4.1.2 | increase Malonyl-CoA production |
| fadD | *E. coli* W3110 | acyl-CoA synthase | AP_002424 | 2.3.1.86, 6.2.1.3 | increase Fatty acid production |
| fabA | *E. coli* K12 | β-hydroxydecanoyl thioester dehydratase/isomerase | NP_415474 | 4.2.1.60 | increase fatty acyl-ACP/CoA production |
| fabB | *E. coli* | 3-oxoacyl-[acyl-carrier-protein] synthase I | BAA16180 | 2.3.1.41 | increase fatty acyl-ACP/CoA production |
| fabD | *E. coli* K12 | [acyl-carrier-protein] S-malonyltransferase | AAC74176 | 2.3.1.39 | increase fatty acyl-ACP/CoA production |
| fabF | *E. coli* K12 | 3-oxoacyl-[acyl-carrier-protein] synthase II | AAC74179 | 2.3.1.179 | increase fatty acyl-ACP/CoA production |
| fabG | *E. coli* K12 | 3-oxoacyl-[acyl-carrier protein] reductase | AAC74177 | 1.1.1.100 | increase fatty acyl-ACP/CoA production |
| fabH | *E. coli* K12 | 3-oxoacyl-[acyl-carrier-protein] synthase III | AAC74175 | 2.3.1.180 | increase fatty acyl-ACP/CoA production |

TABLE 1-continued

Gene Designations

| Gene Designation | Source Organism | Enzyme Name | Accession No. | EC Number | Exemplary Use |
|---|---|---|---|---|---|
| fabI | *E. coli* K12 | enoyl-[acyl-carrier-protein] reductase | NP_415804 | 1.3.1.9 | increase fatty acyl-ACP/CoA production |
| fabR | *E. coli* K12 | Transcriptional Repressor | NP_418398 | none | modulate unsaturated fatty acid production |
| fabV | *Vibrio cholerae* | enoyl-[acyl-carrier-protein] reductase | YP_001217283 | 1.3.1.9 | increase fatty acyl-ACP/CoA production |
| fabZ | *E. coli* K12 | (3R)-hydroxymyristol acyl carrier protein dehydratase | NP_414722 | 4.2.1.- | increase fatty acyl-ACP/CoA production |
| fadE | *E. coli* K13 | acyl-CoA dehydrogenase | AAC73325 | 1.3.99.3, 1.3.99.- | reduce fatty acid degradation |
| fadR | *E. coli* | transcriptional regulatory protein | NP_415705 | none | Block or reverse fatty acid degradation |
| | | 2. Chain Length Control | | | |
| tesA (with or without leader sequence) | *E. coli* | thioesterase - leader sequence is amino acids 1-26 | P0ADA1 | 3.1.2.-, 3.1.1.5 | C18 Chain Length |
| tesA (without leader sequence) | *E. coli* | thioesterase | AAC73596, NP_415027 | 3.1.2.-, 3.1.1.5 | C18:1 Chain Length |
| tesA (mutant of *E. coli* thioesterase I complexed with octanoic acid) | *E. coli* | thioesterase | L109P | 3.1.2.-, 3.1.1.5 | <C18 Chain Length |
| fatB1 | *Umbellularia californica* | thioesterase | Q41635 | 3.1.2.14 | C12:0 Chain Length |
| fatB2 | *Cuphea hookeriana* | thioesterase | AAC49269 | 3.1.2.14 | C8:0-C10:0 Chain Length |
| fatB3 | *Cuphea hookeriana* | thioesterase | AAC72881 | 3.1.2.14 | C14:0-C16:0 Chain Length |
| fatB | *Cinnamomum camphora* | thioesterase | Q39473 | 3.1.2.14 | C14:0 Chain Length |
| fatB | *Arabidopsis thaliana* | thioesterase | CAA85388 | 3.1.2.14 | C16:1 Chain Length |
| fatA1 | *Helianthus annuus* | thioesterase | AAL79361 | 3.1.2.14 | C18:1 Chain Length |
| atfata | *Arabidopsis thaliana* | thioesterase | NP_189147, NP_193041 | 3.1.2.14 | C18:1 Chain Length |
| fatA | *Brassica juncea* | thioesterase | CAC39106 | 3.1.2.14 | C18:1 Chain Length |
| fatA | *Cuphea hookeriana* | thioesterase | AAC72883 | 3.1.2.14 | C18:1 Chain Length |
| tes | *Photbacterium profundum* | thioesterase | YP_130990 | 3.1.2.14 | Chain Length |
| tesB | *E. coli* | thioesterase | NP_414986 | 3.1.2.14 | Chain Length |
| fadM | *E. coli* | thioesterase | NP_414977 | 3.1.2.14 | Chain Length |
| yciA | *E. coli* | thioesterase | NP_415769 | 3.1.2.14 | Chain Length |
| ybgC | *E. coli* | thioesterase | NP_415264 | 3.1.2.14 | Chain Length |
| | | 3. Saturation Level Control* | | | |
| Sfa | *E. coli* | Suppressor of fabA | AAN79592, AAC44390 | none | increase monounsaturated fatty acids |
| fabA | *E. coli* K12 | β-hydroxydecanoyl thioester dehydratase/isomerase | NP_415474 | 4.2.1.60 | produce unsaturated fatty acids |
| GnsA | *E. coli* | suppressors of the secG null mutation | ABD18647.1 | none | increase unsaturated fatty acid esters |
| GnsB | *E. coli* | suppressors of the secG null mutation | AAC74076.1 | none | increase unsaturated fatty acid esters |

TABLE 1-continued

| Gene Designation | Source Organism | Enzyme Name | Accession No. | EC Number | Exemplary Use |
|---|---|---|---|---|---|
| Gene Designations | | | | | |
| fabB | *E. coli* | 3-oxoacyl-[acyl-carrier-protein] synthase I | BAA16180 | 2.3.1.41 | modulate unsaturated fatty acid production |
| des | *Bacillus subtilis* | D5 fatty acyl desaturase | O34653 | 1.14.19 | modulate unsaturated fatty acid production |
| 4. Product Output: Wax Production | | | | | |
| AT3G51970 | *Arabidopsis thaliana* | long-chain-alcohol O-fatty-acyltransferase | NP_190765 | 2.3.1.26 | wax production |
| ELO1 | *Pichia angusta* | Fatty acid elongase | BAD98251 | 2.3.1.- | produce very long chain length fatty acids |
| plsC | *Saccharomyces cerevisiae* | acyltransferase | AAA16514 | 2.3.1.51 | wax production |
| DAGAT/DGAT | *Arabidopsis thaliana* | diacylglycerol acyltransferase | AAF19262 | 2.3.1.20 | wax production |
| hWS | *Homo sapiens* | acyl-CoA wax alcohol acyltransferase | AAX48018 | 2.3.1.20 | wax production |
| aft1 | *Acinetobacter* sp. ADP1 | bifunctional wax ester synthase/acyl-CoA: diacylglycerol acyltransferase | AAO17391 | 2.3.1.20 | wax production |
| ES9 | *Marinobacter hydrocarbonoclasticus* | wax ester synthase | ABO21021 | 2.3.1.20 | wax production |
| mWS | *Simmondsia chinensis* | wax ester synthase | AAD38041 | 2.3.1.- | wax production |
| 5. Product Output: Fatty Alcohol Output | | | | | |
| | | thioesterases (see above) | | | increase fatty acid/fatty alcohol production |
| BmFAR | *Bombyxmori* | FAR (fatty alcohol forming acyl-CoA reductase) | BAC79425 | 1.1.1.- | convert acyl-CoA to fatty alcohol |
| acr1 | *Acinetobacter* sp. ADP1 | acyl-CoA reductase | YP_047869 | 1.2.1.42 | reduce fatty acyl-CoA to fatty aldehydes |
| yqhD | *E. coli* W3110 | alcohol dehydrogenase | AP_003562 | 1.1.-.- | reduce fatty aldehydes to fatty alcohols; increase fatty alcohol production |
| alrA | *Acinetobacter* sp. ADP1 | alcohol dehydrogenase | CAG70252 | 1.1.-.- | reduce fatty aldehydes to fatty alcohols |
| BmFAR | *Bombyxmori* | FAR (fatty alcohol forming acyl-CoA reductase) | BAC79425 | 1.1.1.- | reduce fatty acyl-CoA to fatty alcohol |
| GTNG_1865 | *Geobacillusthermodenitrificans* NG80-2 | Long-chain aldehyde dehydrogenase | YP_001125970 | 1.2.1.3 | reduce fatty aldehydes to fatty alcohols |
| AAR | *Synechococcus elongatus* | Acyl-ACP reductase | YP_400611 | 1.2.1.42 | reduce fatty acyl-ACP/CoA to fatty aldehydes |
| carB | *Mycobacterium smegmatis* | carboxylic acid reductase protein | YP_889972 | 6.2.1.3, 1.2.1.42 | reduce fatty acids to fatty aldehyde |
| FadD | *E. coli* K12 | acyl-CoA synthetase | NP_416319 | 6.2.1.3 | activates fatty acids to fatty acyl-CoAs |
| atoB | *Erwiniacarotovora* | acetyl-CoA acetyltransferase | YP_049388 | 2.3.1.9 | production of butanol |
| hbd | *Butyrivibriofibrisolvens* | Beta-hydroxybutyryl-CoA dehydrogenase | BAD51424 | 1.1.1.157 | production of butanol |

TABLE 1-continued

| Gene Designation | Source Organism | Enzyme Name | Accession No. | EC Number | Exemplary Use |
|---|---|---|---|---|---|
| | | Gene Designations | | | |
| CPE0095 | *Clostridium perfringens* | crotonasebutyryl-CoA dehydryogenase | BAB79801 | 4.2.1.55 | production of butanol |
| bcd | *Clostridium beijerinckii* | butyryl-CoA dehydryogenase | AAM14583 | 1.3.99.2 | production of butanol |
| ALDH | *Clostridium beijerinckii* | coenzyme A-acylating aldehyde dehydrogenase | AAT66436 | 1.2.1.3 | production of butanol |
| AdhE | *E. coli* CFT073 | aldehyde-alcohol dehydrogenase | AAN80172 | 1.1.1.1 1.2.1.10 | production of butanol |
| | | 6. Fatty Alcohol Acetyl Ester Output | | | |
| | | thioesterases (see above) | | | modify output |
| acr1 | *Acinetobacter* sp. ADP1 | acyl-CoA reductase | YP_047869 | 1.2.1.42 | modify output |
| yqhD | *E. Coli* K12 | alcohol dehydrogenase | AP_003562 | 1.1.-.- | modify output |
| AAT | *Fragaria* × *ananassa* | alcohol O-acetyltransferase | AAG13130 | 2.3.1.84 | modify output |
| | | 7. Product Export | | | |
| AtMRP5 | *Arabidopsis thaliana* | *Arabidopsis thaliana* multidrug resistance-associated | NP_171908 | none | modify product export amount |
| AmiS2 | *Rhodococcus* sp. | ABC transporter AmiS2 | JC5491 | none | modify product export amount |
| AtPGP1 | *Arabidopsis thaliana* | *Arabidopsis thaliana* p glycoprotein 1 | NP_181228 | none | modify product export amount |
| AcrA | *CandidatusProtochlamydiaamoebophila* UWE25 | putative multidrug-efflux transport protein acrA | CAF23274 | none | modify product export amount |
| AcrB | *CandidatusProtochlamydiaamoebophila* UWE25 | probable multidrug-efflux transport protein, acrB | CAF23275 | none | modify product export amount |
| TolC | *Francisellatularensis* subsp. *novicida* | Outer membrane protein [Cell envelope biogenesis, | ABD59001 | none | modify product export amount |
| AcrE | *Shigellasonnei* Ss046 | transmembrane protein affects septum formation and cell membrane permeability | YP_312213 | none | modify product export amount |
| AcrF | *E. coli* | Acriflavine resistance protein F | P24181 | none | modify product export amount |
| tll1619 | *Thermosynechococcus elongatus* [BP-1] | multidrug efflux transporter | NP_682409.1 | none | modify product export amount |
| tll0139 | *Thermosynechococcus elongatus* [BP-1] | multidrug efflux transporter | NP_680930.1 | none | modify product export amount |
| | | 8. Fermentation | | | |
| replication checkpoint genes | | | | | increase output efficiency |
| umuD | *Shigellasonnei* Ss046 | DNA polymerase V, subunit | YP_310132 | 3.4.21.- | increase output efficiency |
| umuC | *E. coli* | DNA polymerase V, subunit | ABC42261 | 2.7.7.7 | increase output efficiency |
| pntA, pntB | *Shigellaflexneri* | NADH:NADPH transhydrogenase (alpha and beta subunits) | P07001, P0AB70 | 1.6.1.2 | increase output efficiency |
| | | 9. Other | | | |
| fabK | *Streptococcus pneumoniae* | trans-2-enoyl-ACP reductase II | AAF98273 | 1.3.1.9 | Contributes to fatty acid biosynthesis |
| fabL | *Bacillus licheniformis* DSM 13 | enoyl-(acyl carrier protein) reductase | AAU39821 | 1.3.1.9 | Contributes to fatty acid biosynthesis |
| fabM | *Streptococcus mutans* | trans-2,cis-3-decenoyl-ACP isomerase | DAA05501 | 4.2.1.17 | Contributes to fatty acid biosynthesis |

Production of Fatty Acids

The recombinant host cells may include one or more polynucleotide sequences that comprise an open reading frame encoding a thioesterase, e.g., having an Enzyme Commission number of EC 3.1.1.5 or EC 3.1.2.—(for example, EC 3.1.2.14), together with operably-linked regulatory sequences that facilitate expression of the protein in the recombinant host cells. In the recombinant host cells, the open reading frame coding sequences and/or the regulatory sequences are modified relative to the corresponding wild-type gene encoding the thioesterase. The activity of the thioesterase in the recombinant host cell is modified relative to the activity of the thioesterase expressed from the corresponding wild-type gene in a corresponding host cell. In some embodiments, a fatty acid derivative composition including fatty acids is produced by culturing a recombinant cell in the presence of a carbon source under conditions effective to express the thioesterase. In related embodiments, the recombinant host cell comprises a polynucleotide encoding a polypeptide having thioesterase activity, and one or more additional polynucleotides encoding polypeptides having other fatty acid biosynthetic enzyme activities. In some such instances, the fatty acid produced by the action of the thioesterase is converted by one or more enzymes having a different fatty acid biosynthetic enzyme activity to another fatty acid derivative, such as, for example, a fatty ester, fatty aldehyde, fatty alcohol, or a hydrocarbon.

The chain length of a fatty acid, or a fatty acid derivative made therefrom, can be selected for by modifying the expression of particular thioesterases. The thioesterase will influence the chain length of fatty acid derivatives produced. The chain length of a fatty acid derivative substrate can be selected for by modifying the expression of selected thioesterases (EC 3.1. 2.14 or EC 3.1.1.5). Hence, host cells can be engineered to express, overexpress, have attenuated expression, or not express one or more selected thioesterases to increase the production of a preferred fatty acid derivative substrate. For example, $C_{10}$ fatty acids can be produced by expressing a thioesterase that has a preference for producing $C_{10}$ fatty acids and attenuating thioesterases that have a preference for producing fatty acids other than $C_{10}$ fatty acids (e.g., a thioesterase which prefers to produce $C_{14}$ fatty acids). This would result in a relatively homogeneous population of fatty acids that have a carbon chain length of 10. In other instances, $C_{14}$ fatty acids can be produced by attenuating endogenous thioesterases that produce non-$C_{14}$ fatty acids and expressing the thioesterases that use $C_{14}$-ACP. In some situations, $C_{12}$ fatty acids can be produced by expressing thioesterases that use $C_{12}$-ACP and attenuating thioesterases that produce non-$C_{12}$ fatty acids. For example, C12 fatty acids can be produced by expressing a thioesterase that has a preference for producing C12 fatty acids and attenuating thioesterases that have a preference for producing fatty acids other than C12 fatty acids. This would result in a relatively homogeneous population of fatty acids that have a carbon chain length of 12. The fatty acid derivatives are recovered from the culture medium with substantially all of the fatty acid derivatives produced extracellularly. The fatty acid derivative composition produced by a recombinant host cell can be analyzed using methods known in the art, for example, GC-FID, in order to determine the distribution of particular fatty acid derivatives as well as chain lengths and degree of saturation of the components of the fatty acid derivative composition. Acetyl-CoA, malonyl-CoA, and fatty acid overproduction can be verified using methods known in the art, for example, by using radioactive precursors, HPLC, or GC-MS subsequent to cell lysis. Additional non-limiting examples of thioesterases and polynucleotides encoding them for use in the fatty acid pathway are provided in PCT Publication Application No. WO2010/075483, expressly incorporated by reference herein.

Production of Fatty Aldehydes

Figure 4:
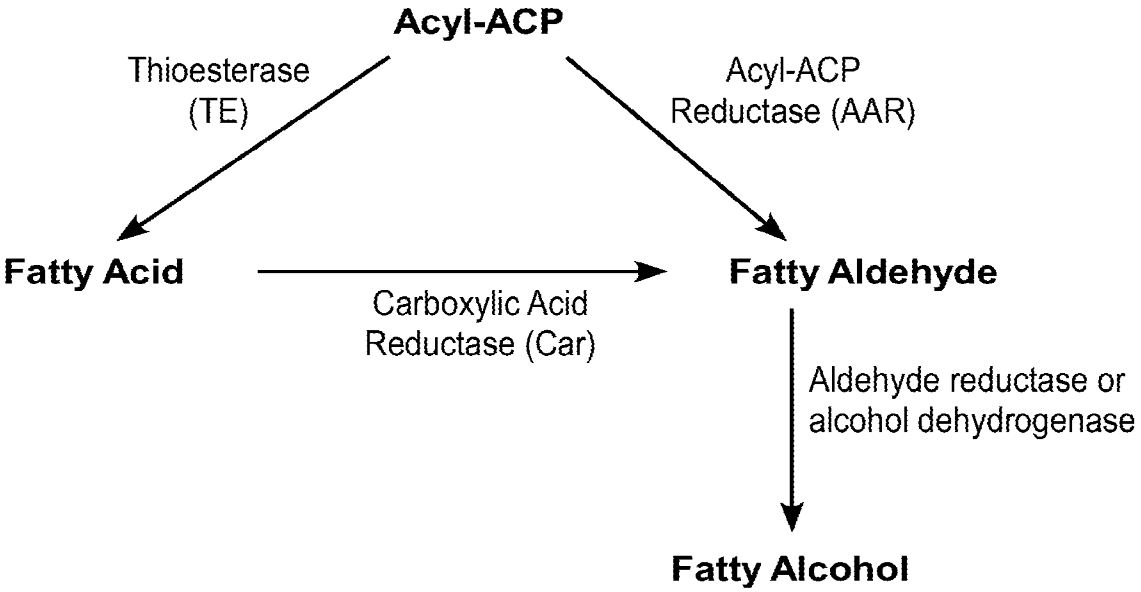
FIG. 4 presents an overview of an exemplary biosynthetic pathway for production of fatty alcohol starting with acyl-ACP, where the production of fatty aldehyde is catalyzed by the enzymatic activity of acyl-ACP reductase (AAR) or thioesterase (TE) and carboxylic acid reductase (Car). The fatty aldehyde is converted to fatty alcohol by aldehyde reductase (also referred to as alcohol dehydrogenase).

In one embodiment, the recombinant host cell produces a fatty aldehyde. In some embodiments, a fatty acid produced by the recombinant host cell is converted into a fatty aldehyde. In some embodiments, the fatty aldehyde produced by the recombinant host cell is then converted into a fatty alcohol or a hydrocarbon. In some embodiments, native (endogenous) fatty aldehyde biosynthetic polypeptides, such as aldehyde reductases, are present in the host cell (e.g., *E. coli*) and are effective to convert fatty aldehydes to fatty alcohols. In other embodiments, a native (endogenous) fatty aldehyde biosynthetic polypeptide is overexpressed. In still other embodiments, an exogenous fatty aldehyde biosynthetic polypeptide is introduced into a recombinant host cell and expressed or overexpressed. A native or recombinant host cell may comprise a polynucleotide encoding an enzyme having fatty aldehyde biosynthesis activity (e.g., a fatty aldehyde biosynthetic polypeptide or a fatty aldehyde biosynthetic polypeptide or enzyme). A fatty aldehyde is produced when the fatty aldehyde biosynthetic enzyme is expressed or overexpressed in the host cell. A recombinant host cell engineered to produce a fatty aldehyde will typically convert some of the fatty aldehyde to a fatty alcohol. In some embodiments, a fatty aldehyde is produced by expressing or overexpressing in the recombinant host cell a polynucleotide encoding a polypeptide having fatty aldehyde biosynthetic activity such as carboxylic acid reductase (CAR) activity. CarB, is an exemplary carboxylic acid reductase. In practicing the disclosure, a gene encoding a carboxylic acid reductase polypeptide may be expressed or overexpressed in the host cell. In some embodiments, the CarB polypeptide has the amino acid sequence of SEQ ID NO: 7. In other embodiments, the CarB polypeptide is a variant or mutant of SEQ ID NO: 7. Examples of carboxylic acid reductase (CAR) polypeptides and polynucleotides encoding them include, but are not limited to FadD9 (EC 6.2.1.-, UniProtKB Q50631, GenBank NP 217106, SEQ ID NO: 34), CarA (GenBank ABK75684), CarB (GenBank YP889972; SEQ ID NO: 33) and related polypeptides described in PCT Publication No. WO2010/042664 and U.S. Pat. No. 8,097,439, each of which is expressly incorporated by reference herein. In some embodiments the recombinant host cell further comprises a polynucleotide encoding a thioesterase. In some embodiments, the fatty aldehyde is produced by expressing or overexpressing in the recombinant host cell a polynucleotide encoding a fatty aldehyde biosynthetic polypeptide, such as a polypeptide having acyl-ACP reductase (AAR) activity. Expression of acyl-ACP reductase in a recombinant host cell results in the production of fatty aldehydes and fatty alcohols (see FIG. 4). Native (endogenous) aldehyde reductases present in a recombinant host cell (e.g., *E. coli*), can convert fatty aldehydes into fatty alcohols. Exemplary acyl-ACP reductase polypeptides are described in PCT Publication Nos. WO2009/140695 and WO/2009/140696, both of which are expressly incorporated by reference herein. A composition comprising fatty aldehydes (a fatty aldehyde composition) is produced by culturing a host cell in the presence of a carbon source under conditions effective to express the fatty aldehyde biosynthetic enzyme. In some embodiments, the fatty aldehyde composition comprises fatty aldehydes and fatty alcohols. Typically, the fatty aldehyde composition is recovered from the extracellular environment of the recombinant host cell, i.e., the cell culture medium.

Production of Fatty Alcohols

In some embodiments, the recombinant host cell includes a polynucleotide encoding a polypeptide (an enzyme) having fatty alcohol biosynthetic activity (a fatty alcohol biosynthetic polypeptide or a fatty alcohol biosynthetic enzyme), and a fatty alcohol is produced by the recombinant host cell. A composition comprising fatty alcohols (a fatty alcohol composition) may be produced by culturing the recombinant host cell in the presence of a carbon source under conditions effective to express a fatty alcohol biosynthetic enzyme. In some embodiments, the fatty alcohol composition comprises fatty alcohols, however, a fatty alcohol composition may comprise other fatty acid derivatives. Typically, the fatty alcohol composition is recovered from the extracellular environment of the recombinant host cell, i.e., the cell culture medium. In one approach, recombinant host cells have been engineered to produce fatty alcohols by expressing a thioesterase, which catalyzes the conversion of acyl-ACPs into free fatty acids (FFAs) and a carboxylic acid reductase (CAR), which converts free fatty acids into fatty aldehydes. Native (endogenous) aldehyde reductases present in the host cell (e.g., *E. coli*) can convert the fatty aldehydes into fatty alcohols. In some embodiments, native (endogenous) fatty aldehyde biosynthetic polypeptides, such as aldehyde reductases present in the host cell, may be sufficient to convert fatty aldehydes to fatty alcohols. However, in other embodiments, a native (endogenous) fatty aldehyde biosynthetic polypeptide is overexpressed and in still other embodiments, an exogenous fatty aldehyde biosynthetic polypeptide is introduced into a recombinant host cell and expressed or overexpressed. In some embodiments, the fatty alcohol is produced by expressing or overexpressing in the recombinant host cell a polynucleotide encoding a polypeptide having fatty alcohol biosynthetic activity which converts a fatty aldehyde to a fatty alcohol. For example, an alcohol dehydrogenase (aldehyde reductase, e.g., EC 1.1.1.1), may be used in practicing the disclosure. As used herein, an alcohol dehydrogenase refers to a polypeptide capable of catalyzing the conversion of a fatty aldehyde to an alcohol (e.g., a fatty alcohol). One of ordinary skill in the art will appreciate that certain alcohol dehydrogenases are capable of catalyzing other reactions as well, and these non-specific alcohol dehydrogenases also are encompassed by the alcohol dehydrogenase. Examples of alcohol dehydrogenase polypeptides useful in accordance with the disclosure include, but are not limited to AlrA of *Acinetobacter* sp. M-1 (SEQ ID NO: 3) or AlrA homologs such as AlrAadp1 (SEQ ID NO: 4) and endogenous *E. coli* alcohol dehydrogenases such as YjgB, (AAC77226) (SEQ ID NO: 5), DkgA (NP_417485), DkgB (NP_414743), YdjL (AAC74846), YdjJ (NP 416288), AdhP (NP_415995), YhdH (NP_417719), YahK (NP_414859), YphC (AAC75598), YqhD (446856) and YbbO [AAC73595.1]. Additional examples are described in International Patent Application Publication Nos. WO 2007/136762, WO2008/119082 and WO 2010/062480, each of which is expressly incorporated by reference herein. In certain embodiments, the fatty alcohol biosynthetic polypeptide has aldehyde reductase or alcohol dehydrogenase activity (EC 1.1.1.1).

In another approach, recombinant host cells have been engineered to produce fatty alcohols by expressing fatty alcohol forming acyl-CoA reductases or fatty acyl reductases (FARs) which convert fatty acyl-thioester substrates (e.g., fatty acyl-CoA or fatty acyl-ACP) to fatty alcohols. In some embodiments, the fatty alcohol is produced by expressing or overexpressing a polynucleotide encoding a polypeptide having fatty alcohol forming acyl-CoA reductase (FAR) activity in a recombinant host cell. Examples of FAR polypeptides useful in accordance with this embodiment are described in PCT Publication No. WO2010/062480 which is expressly incorporated by reference herein. Fatty alcohol may be produced via an acyl-CoA dependent pathway utilizing fatty acyl-ACP and fatty acyl-CoA intermediates and an acyl-CoA independent pathway utilizing fatty acyl-ACP intermediates but not a fatty acyl-CoA intermediate. In particular embodiments, the enzyme encoded by the over expressed gene is selected from a fatty acid synthase, an acyl-ACP thioesterase, a fatty acyl-CoA synthase and an acetyl-CoA carboxylase. In some embodiments, the protein encoded by the over expressed gene is endogenous to the host cell. In other embodiments, the protein encoded by the overexpressed gene is heterologous to the host cell. Fatty alcohols are also made in nature by enzymes that are able to reduce various acyl-ACP or acyl-CoA molecules to the corresponding primary alcohols. See also, U.S. Patent Publication Nos. 20100105963, and 20110206630 and U.S. Pat. No. 8,097,439, expressly incorporated by reference herein. Strategies to increase production of fatty alcohols by recombinant host cells include increased flux through the fatty acid biosynthetic pathway by overexpression of native fatty acid biosynthetic genes and/or expression of exogenous fatty acid biosynthetic genes from different organisms in the production host such that fatty alcohol biosynthesis is increased.

Production of Esters

As used herein, the term "fatty ester" may be used with reference to an ester. A fatty ester as referred to herein can be any ester made from a fatty acid, for example a fatty acid ester. In some embodiments, a fatty ester contains an A side and a B side. As used herein, an "A side" of an ester refers to the carbon chain attached to the carboxylate oxygen of the ester. As used herein, a "B side" of an ester refers to the carbon chain comprising the parent carboxylate of the ester. In embodiments where the fatty ester is derived from the fatty acid biosynthetic pathway, the A side is contributed by an alcohol, and the B side is contributed by a fatty acid. Any alcohol can be used to form the A side of the fatty esters. For example, the alcohol can be derived from the fatty acid biosynthetic pathway. Alternatively, the alcohol can be produced through non-fatty acid biosynthetic pathways. Moreover, the alcohol can be provided exogenously. For example, the alcohol can be supplied in the fermentation broth in instances where the fatty ester is produced by an organism. Alternatively, a carboxylic acid, such as a fatty acid or acetic acid, can be supplied exogenously in instances where the fatty ester is produced by an organism that can also produce alcohol. The carbon chains comprising the A side or B side can be of any length. In one embodiment, the A side of the ester is at least about 1, 2, 3, 4, 5, 6, 7, 8, 10, 12, 14, 16, or 18 carbons in length. When the fatty ester is a fatty acid methyl ester, the A side of the ester is 1 carbon in length. When the fatty ester is a fatty acid ethyl ester, the A side of the ester is 2 carbons in length. The B side of the ester can be at least about 4, 6, 8, 10, 12, 14, 16, 18, 20, 22, 24, or 26 carbons in length. The A side and/or the B side can be straight or branched chain. The branched chains can have one or more points of branching. In addition, the branched chains can include cyclic branches. Furthermore, the A side and/or B side can be saturated or unsaturated. If unsaturated, the A side and/or B side can have one or more points of unsaturation. In one embodiment, the fatty ester is produced biosynthetically. In this embodiment, first the fatty acid is activated. Non-limiting examples of "activated" fatty acids are acyl-CoA, acyl ACP, and acyl phosphate. Acyl-CoA can be a direct product of fatty acid biosynthesis or degradation. In addition, acyl-CoA can be synthesized from a free fatty acid, a CoA, and an adenosine nucleotide triphosphate (ATP). An example of an enzyme which produces acyl-CoA is acyl-CoA synthase. In some embodiments, the recombinant host cell comprises a polynucleotide encoding a polypeptide, e.g., an enzyme having ester synthase activity, (ester synthase polypeptide or an ester synthase).

A fatty ester is produced by a reaction catalyzed by the ester synthase polypeptide expressed or overexpressed in the recombinant host cell. In some embodiments, a composition comprising fatty esters fatty ester is produced by culturing the recombinant cell in the presence of a carbon source under conditions effective to express an ester synthase. In some embodiments, the fatty ester composition is recovered from the cell culture. Ester synthase polypeptides include, for example, an ester synthase polypeptide classified as EC 2.3.1.75, or any other polypeptide which catalyzes the conversion of an acyl-thioester to a fatty ester, including, without limitation, a thioesterase, an ester synthase, an acyl-CoA:alcohol transacylase, an acyltransferase, or a fatty acyl-CoA:fatty alcohol acyltransferase. For example, the polynucleotide may encode wax/dgat, a bifunctional ester synthase/acyl-CoA:diacylglycerol acyltransferase from *Simmondsia chinensis, Acinetobacter* sp. Strain ADP, *Alcanivorax borkumensis, Pseudomonas aeruginosa, Fundibacter jadensis, Arabidopsis thaliana*, or *Alkaligenes eutrophus*. In a particular embodiment, the ester synthase polypeptide is an *Acinetobacter* sp. diacylglycerol O-acyltransferase (wax-dgaT; UniProtKB Q8GGG1, GenBank AA017391) or *Simmondsia chinensis* wax synthase (UniProtKB Q9XGY6, GenBank AAD38041. In another embodiment, the ester synthase polypeptide is for example ES9 (a wax ester synthase from *Marinobacter hydrocarbonoclasticus* DSM 8798, UniProtKB A3RE51 (SEQ ID NO: 6); ES8 of *Marinobacter hydrocarbonoclasticus* DSM8789 (GenBank Accession No. AB021021; SEQ ID NO:7); GenBank AB021021, encoded by the ws2 gene; or ES376 (another wax ester synthase derived from *Marinobacter hydrocarbonoclasticus* DSM 8798, UniProtKB A3RE50, GenBank ABO21020, encoded by the ws1 gene. In a particular embodiment, the polynucleotide encoding the ester synthase polypeptide is overexpressed in the recombinant host cell. In some embodiments, a fatty acid ester is produced by a recombinant host cell engineered to express three fatty acid biosynthetic enzymes: a thioesterase enzyme, an acyl-CoA synthetase (fadD) enzyme and an ester synthase enzyme (e.g., three enzyme system; see FIG. 5). In other embodiments, a fatty acid ester is produced by a recombinant host cell engineered to express one fatty acid biosynthetic enzyme, an ester synthase enzyme (e.g., one enzyme system; see FIG. 5). Non-limiting examples of ester synthase polypeptides and polynucleotides encoding them suitable for use in these embodiments include those described in PCT Publication Nos. WO2007/136762 and WO2008/119082, and WO/2011/038134 (three enzyme system) and WO/2011/038132 (one enzyme system), each of which is expressly incorporated by reference herein. The recombinant host cell may produce a fatty ester, such as a fatty acid methyl ester, a fatty acid ethyl ester or a wax ester in the extracellular environment of the host cells.

Production of Hydrocarbons

Figure 6:
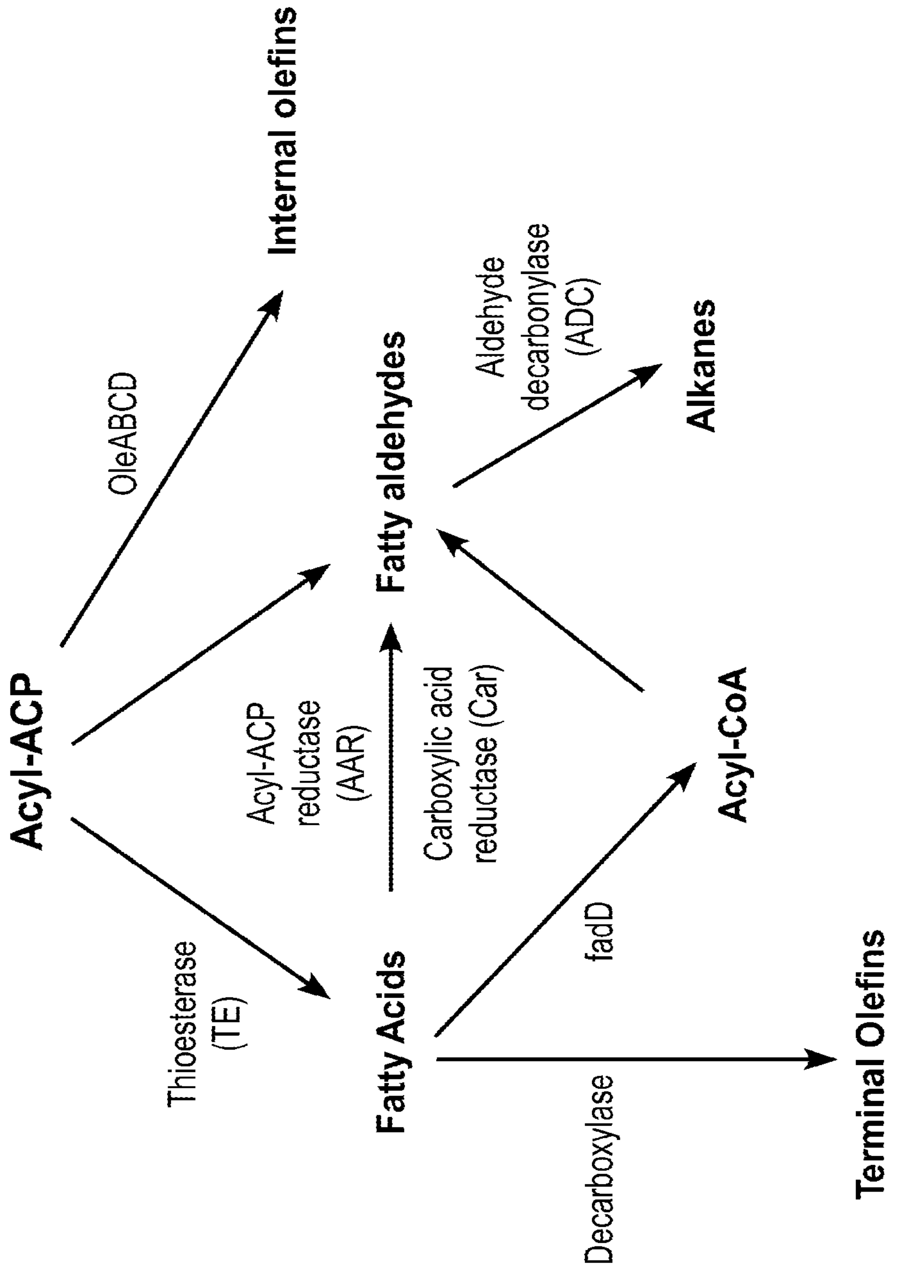
FIG. 6 presents an overview of exemplary biosynthetic pathways for production of hydrocarbons starting with acyl-ACP; the production of internal olefins is catalyzed by the enzymatic activity of OleABCD; the production of alkanes is catalyzed by the enzymatic conversion of fatty aldehydes to alkanes by way of aldehyde decarbonylase (ADC); and the production of terminal olefins is catalyzed by the enzymatic conversion of fatty acids to terminal olefins by a decarboxylase.

This aspect of the disclosure is based, at least in part, on the discovery that altering the level of expression of a fatty aldehyde biosynthetic polypeptide, for example, an acyl-ACP reductase polypeptide (EC 6.4.1.2) and a hydrocarbon biosynthetic polypeptide, e.g., a decarbonylase in a recombinant host cell facilitates enhanced production of hydrocarbons by the recombinant host cell. In one embodiment, the recombinant host cell produces a hydrocarbon, such as an alkane or an alkene (e.g., a terminal olefin or an internal olefin) or a ketone. In some embodiments, a fatty aldehyde produced by a recombinant host cell is converted by decarbonylation, removing a carbon atom to form a hydrocarbon. In other embodiments, a fatty acid produced by a recombinant host cell is converted by decarboxylation, removing a carbon atom to form a terminal olefin. In some embodiments, an acyl-ACP intermediate is converted by decarboxylation, removing a carbon atom to form an internal olefin or a ketone (see FIG. 6). In some embodiments, the recombinant host cell comprises a polynucleotide encoding a polypeptide (an enzyme) having hydrocarbon biosynthetic activity (a hydrocarbon biosynthetic polypeptide or a hydrocarbon biosynthetic enzyme), and the hydrocarbon is produced by expression or overexpression of the hydrocarbon biosynthetic enzyme in a recombinant host cell. An alkane biosynthetic pathway from cyanobacteria consisting of an acyl-acyl carrier protein reductase (AAR) and an aldehyde decarbonylase (ADC), which together convert intermediates of fatty acid metabolism to alkanes and alkenes has been used to engineer recombinant host cells for the production of hydrocarbons (FIG. 6). The second of two reactions in the pathway through which saturated acyl-ACPs are converted to alkanes in cyanobacteria entails scission of the C1-C2 bond of a fatty aldehyde intermediate by the enzyme aldehyde decarbonylase (ADC), a ferritin-like protein with a binuclear metal cofactor of unknown composition. In some embodiments, the hydrocarbon is produced by expressing or overexpressing in the recombinant host cell a polynucleotide encoding a polypeptide having hydrocarbon biosynthetic activity such as an aldehyde decarbonylase (ADC) activity (e.g., EC 4.1.99.5). Exemplary polynucleotides encoding an aldehyde decarbonylase useful in accordance with this embodiment include, but are not limited to, those described in PCT Publication Nos. WO2008/119082 and WO2009/140695 which are expressly incorporated by reference herein and those sequences presented in Table 2 below. In some embodiments the recombinant host cell further comprises a polynucleotide encoding a fatty aldehyde biosynthesis polypeptide. In some embodiments the recombinant host cell further comprises a polynucleotide encoding an acyl-ACP reductase. See, for example, Table 2 below.

TABLE 2

Exemplary Hydrocarbon Biosynthetic Polynucleotides and Polypeptides

| Protein name | Polypeptide sequence | Nucleotide sequence | Sequence |
|---|---|---|---|
| Decarbonylase (ADC) | SEQ ID NO: 35 | SEQ ID NO: 36 | *Synechococcus elongatus* PCC7942 YP.sub.--400610 (Synpcc7942.sub.--1593) |
| Acyl-ACP Reducatase (AAR) | SEQ ID NO: 37 | SEQ ID NO: 38 | *Synechococcus elongatus* PCC7942 YP_400611 (Synpcc7942_1594) |
| Decarbonylase (ADC) | SEQ ID NO: 39 | SEQ ID NO: 40 | *Prochlorococcus mariunus* CCMP1986 PMM0532 |
| Acyl-ACP Reducatase (AAR) | SEQ ID NO: 41 | SEQ ID NO: 42 | *Prochlorococcus marinus* CCMP1986 PMM0533 (NP_892651) |

In some embodiments, a composition comprising is produced by culturing the recombinant cell in the presence of a carbon source under conditions effective to express the Acyl-CoA reductase and decarbonylase polynucleotides. In some embodiments, the hydrocarbon composition comprises saturated and unsaturated hydrocarbons. However, a hydrocarbon composition may comprise other fatty acid derivatives. Typically, the hydrocarbon composition is recovered from the extracellular environment of the recombinant host cell, i.e., the cell culture medium. As used herein, an alkane refers to saturated hydrocarbons or compounds that consist only of carbon (C) and hydrogen (H), wherein these atoms are linked together by single bonds (i.e., they are saturated compounds). Olefins and alkenes refer to hydrocarbons containing at least one carbon-to-carbon double bond (i.e., they are unsaturated compounds). Terminal olefins, α-olefins, terminal alkenes, and 1-alkenes refer to the same compounds with reference to α-olefins or alkenes with a chemical formula CxH2x, distinguished from other olefins with a similar molecular formula by linearity of the hydrocarbon chain and the position of the double bond at the primary or alpha position. In some embodiments, a terminal olefin is produced by expressing or overexpressing in the recombinant host cell a polynucleotide encoding a hydrocarbon biosynthetic polypeptide, such as a polypeptide having decarboxylase activity as described, for example, in PCT Publication No. WO2009/085278 which is expressly incorporated by reference herein. In some embodiments the recombinant host cell further comprises a polynucleotide encoding a thioesterase. In other embodiments, a ketone is produced by expressing or overexpressing in the recombinant host cell a polynucleotide encoding a hydrocarbon biosynthetic polypeptide, such as a polypeptide having OleA activity as described, for example, in PCT Publication No. WO2008/147781, which is expressly incorporated by reference herein. In related embodiments, an internal olefin is produced by expressing or overexpressing in the recombinant host cell a polynucleotide encoding a hydrocarbon biosynthetic polypeptide, such as a polypeptide having OleCD or OleBCD activity together with a polypeptide having OleA activity as described, for example, in PCT Publication No. WO2008/147781, expressly incorporated by reference herein.

Recombinant Host Cells and Cell Cultures

Strategies to increase production of fatty acid derivatives by recombinant host cells include increased flux through the fatty acid biosynthetic pathway by overexpression of native fatty acid biosynthetic genes and expression of exogenous fatty acid biosynthetic genes from different organisms in the production host. As used herein, a recombinant host cell or engineered host cell refers to a host cell whose genetic makeup has been altered relative to the corresponding wild-type host cell, for example, by deliberate introduction of new genetic elements and/or deliberate modification of genetic elements naturally present in the host cell. The offspring of such recombinant host cells also contain these new and/or modified genetic elements. In any of the aspects of the disclosure described herein, the host cell can be selected from the group consisting of a plant cell, insect cell, fungus cell (e.g., a filamentous fungus, such as *Candida* sp., or a budding yeast, such as *Saccharomyces* sp.), an algal cell and a bacterial cell. In one preferred embodiment, recombinant host cells are recombinant microorganisms. Examples of host cells that are microorganisms, include but are not limited to cells from the genus *Escherichia, Bacillus, Lactobacillus, Zymomonas, Rhodococcus, Pseudomonas, Aspergillus, Trichoderma, Neurospora, Fusarium, Humicola, Rhizomucor, Kluyveromyces, Pichia, Mucor, Myceliophtora, Penicillium, Phanerochaete, Pleurotus, Trametes, Chrysosporium, Saccharomyces, Stenotrophamonas, Schizosaccharomyces, Yarrowia*, or *Streptomyces*. In some embodiments, the host cell is a Gram-positive bacterial cell. In other embodiments, the host cell is a Gram-negative bacterial cell. In some embodiments, the host cell is an *E. coli* cell. In other embodiments, the host cell is a *Bacillus lentus* cell, a *Bacillus brevis* cell, a *Bacillus stearothermophilus* cell, a *Bacillus lichenoformis* cell, a *Bacillus alkalophilus* cell, a *Bacillus coagulans* cell, a *Bacillus circulans* cell, a *Bacillus pumilis* cell, a *Bacillus thuringiensis* cell, a *Bacillus clausii* cell, a *Bacillus megaterium* cell, a *Bacillus subtilis* cell, or a *Bacillus amyloliquefaciens* cell. In other embodiments, the host cell is a *Trichoderma koningii* cell, a *Trichoderma viride* cell, a *Trichoderma reesei* cell, a *Trichoderma longibrachiatum* cell, an *Aspergillus awamori* cell, an *Aspergillus fumigates* cell, an *Aspergillus foetidus* cell, an *Aspergillus nidulans* cell, an *Aspergillus niger* cell, an *Aspergillus oryzae* cell, a *Humicola insolens* cell, a *Humicola lanuginose* cell, a *Rhodococcus opacus* cell, a *Rhizomucor miehei* cell, or a *Mucor michei* cell. In yet other embodiments, the host cell is a *Streptomyces lividans* cell or a *Streptomyces murinus* cell. In yet other embodiments, the host cell is an *Actinomycetes* cell. In some embodiments, the host cell is a *Saccharomyces cerevisiae* cell. In other embodiments, the host cell is a cell from a eukaryotic plant, algae, cyanobacterium, green-sulfur bacterium, green non-sulfur bacterium, purple sulfur bacterium, purple non-sulfur bacterium, extremophile, yeast, fungus, an engineered organism thereof, or a synthetic organism. In some embodiments, the host cell is light-dependent or fixes carbon. In some embodiments, the host cell has autotrophic activity. In some embodiments, the host cell has photoautotrophic activity, such as in the presence of light. In some embodiments, the host cell is heterotrophic or mixotrophic in the absence of light. In certain embodiments, the host cell is a cell from *Arabidopsis thaliana, Panicum virgatum, Miscanthus giganteus, Zea mays, Botryococcuse braunii, Chlamydomonas reinhardtii, Dunaliela salina, Synechococcus* Sp. PCC 7002, *Synechococcus* Sp. PCC 7942, *Synechocystis* Sp. PCC 6803, *Thermosynechococcus elongates* BP-1, *Chlorobium tepidum, Chlorojlexus auranticus, Chromatiumm vinosum, Rhodospirillum rubrum, Rhodobacter capsulatus, Rhodopseudomonas palusris, Clostridium ljungdahlii, Clostridiuthermocellum, Penicillium chrysogenum, Pichia pastoris, Saccharomyces cerevisiae, Schizosaccharomyces pombe, Pseudomonas fluorescens*, or *Zymomonas mobilis*.

Production of Fatty Acid Derivative Compositions by Recombinant Host Cells

A large variety of fatty acid derivatives can be produced by recombinant host cells comprising strain improvements as described herein, including, but not limited to, fatty acids, acyl-CoA, fatty aldehydes, short and long chain alcohols, hydrocarbons (e.g., alkanes, alkenes or olefins, such as terminal or internal olefins), fatty alcohols, esters (e.g., wax esters, fatty acid esters (e.g., methyl or ethyl esters)), and ketones. In some embodiments of the present disclosure, the higher titer of fatty acid derivatives in a particular composition is a higher titer of a particular type of fatty acid derivative (e.g., fatty alcohols, fatty acid esters, or hydrocarbons) produced by a recombinant host cell culture relative to the titer of the same fatty acid derivatives produced by a control culture of a corresponding wild-type host cell. In such cases, the fatty acid derivative compositions may comprise, for example, a mixture of the fatty alcohols with a variety of chain lengths and saturation or branching characteristics. In other embodiments of the present disclosure, the higher titer of fatty acid derivatives in a particular compositions is a higher titer of a combination of different fatty acid derivatives (for example, fatty aldehydes and alcohols, or fatty acids and esters) relative to the titer of the same fatty acid derivative produced by a control culture of a corresponding wild-type host cell.

Engineering Host Cells

In some embodiments, a polynucleotide (or gene) sequence is provided to the host cell by way of a recombinant vector, which comprises a promoter operably linked to the polynucleotide sequence. In certain embodiments, the promoter is a developmentally-regulated, an organelle-specific, a tissue-specific, an inducible, a constitutive, or a cell-specific promoter. In some embodiments, the recombinant vector includes at least one sequence including, but not limited to, (a) an expression control sequence operatively coupled to the polynucleotide sequence; (b) a selection marker operatively coupled to the polynucleotide sequence; (c) a marker sequence operatively coupled to the polynucleotide sequence; (d) a purification moiety operatively coupled to the polynucleotide sequence; (e) a secretion sequence operatively coupled to the polynucleotide sequence; and (f) a targeting sequence operatively coupled to the polynucleotide sequence. The expression vectors described herein include a polynucleotide sequence described herein in a form suitable for expression of the polynucleotide sequence in a host cell. It will be appreciated by those skilled in the art that the design of the expression vector can depend on such factors as the choice of the host cell to be transformed, the level of expression of polypeptide desired, etc. The expression vectors described herein can be introduced into host cells to produce polypeptides, including fusion polypeptides, encoded by the polynucleotide sequences as described herein. Expression of genes encoding polypeptides in prokaryotes, for example, *E. coli*, is most often carried out with vectors containing constitutive or inducible promoters directing the expression of either fusion or non-fusion polypeptides. Fusion vectors add a number of amino acids to a polypeptide encoded therein, usually to the amino- or carboxy-terminus of the recombinant polypeptide. Such fusion vectors typically serve one or more of the following three purposes (1) to increase expression of the recombinant polypeptide; (2) to increase the solubility of the recombinant polypeptide; and (3) to aid in the purification of the recombinant polypeptide by acting as a ligand in affinity purification. Often, in fusion expression vectors, a proteolytic cleavage site is introduced at the junction of the fusion moiety and the recombinant polypeptide. This enables separation of the recombinant polypeptide from the fusion moiety after purification of the fusion polypeptide. Examples of such enzymes, and their cognate recognition sequences, include Factor Xa, thrombin, and enterokinase. Exemplary fusion expression vectors include pGEX (Pharmacia Biotech, Inc., Piscataway, N.J.; Smith et al., Gene, 67: 31-40 (1988)), pMAL (New England Biolabs, Beverly, Mass.), and pRITS (Pharmacia Biotech, Inc., Piscataway, N.J.), which fuse glutathione S-transferase (GST), maltose E binding protein, or protein A, respectively, to the target recombinant polypeptide. Examples of inducible, non-fusion *E. coli* expression vectors include pTrc (Amann et al., *Gene* (1988) 69:301-315) and pET 11d (Studier et al., Gene Expression Technology: Methods in Enzymology 185, Academic Press, San Diego, Calif. (1990) 60-89). Target gene expression from the pTrc vector relies on host RNA polymerase transcription from a hybrid trp-lac fusion promoter. Target gene expression from the pET 11d vector relies on transcription from a T7 gn10-lac fusion promoter mediated by a coexpressed viral RNA polymerase (T7 gn1). This viral polymerase is supplied by host strains BL21(DE3) or HMS174 (DE3) from a resident λ prophage harboring a T7 gn1 gene under the transcriptional control of the lacUV 5 promoter. Suitable expression systems for both prokaryotic and eukaryotic cells are well known in the art; see, e.g., Sambrook et al., "Molecular Cloning: A Laboratory Manual," second edition, Cold Spring Harbor Laboratory, (1989). Examples of inducible, non-fusion *E. coli* expression vectors include pTrc (Amann et al., *Gene,* 69: 301-315 (1988)) and PET 11d (Studier et al., Gene Expression Technology: Methods in Enzymology 185, Academic Press, San Diego, Calif., pp. 60-89 (1990)). In certain embodiments, a polynucleotide sequence of the disclosure is operably linked to a promoter derived from bacteriophage T5. In one embodiment, the host cell is a yeast cell. In this embodiment, the expression vector is a yeast expression vector. Vectors can be introduced into prokaryotic or eukaryotic cells via a variety of art-recognized techniques for introducing foreign nucleic acid (e.g., DNA) into a host cell. Suitable methods for transforming or transfecting host cells can be found in, for example, Sambrook et al. (supra). For stable transformation of bacterial cells, it is known that, depending upon the expression vector and transformation technique used, only a small fraction of cells will take-up and replicate the expression vector. In order to identify and select these transformants, a gene that encodes a selectable marker (e.g., resistance to an antibiotic) can be introduced into the host cells along with the gene of interest. Selectable markers include those that confer resistance to drugs such as, but not limited to, ampicillin, kanamycin, chloramphenicol, or tetracycline. Nucleic acids encoding a selectable marker can be introduced into a host cell on the same vector as that encoding a polypeptide described herein or can be introduced on a separate vector. Cells stably transformed with the introduced nucleic acid can be identified by growth in the presence of an appropriate selection drug.

Host Cells

As used herein, an engineered or recombinant host cell is a cell used to produce a fatty acid derivative composition as further described herein. A host cell is referred to as an engineered host cell or a recombinant host cell if the expression of one or more polynucleotides or polypeptides in the host cell are altered or modified as compared to their expression in a corresponding wild-type host cell (e.g., control cell) under the same conditions. In any of the aspects of the disclosure described herein, the host cell can be selected from the group consisting of a eukaryotic plant, algae, cyanobacterium, green-sulfur bacterium, green non-sulfur bacterium, purple sulfur bacterium, purple non-sulfur bacterium, extremophile, yeast, fungus, engineered organisms thereof, or a synthetic organism. In some embodiments, the host cell is light dependent or fixes carbon. In some embodiments, the host cell has autotrophic activity. Various host cells can be used to produce fatty acid derivatives, as described herein.

Mutants or Variants

In some embodiments, the polypeptide is a mutant or a variant of any of the polypeptides described herein. The terms mutant and variant as used herein refer to a polypeptide having an amino acid sequence that differs from a wild-type polypeptide by at least one amino acid. For example, the mutant can comprise one or more of the following conservative amino acid substitutions: replacement of an aliphatic amino acid, such as alanine, valine, leucine, and isoleucine, with another aliphatic amino acid;

replacement of a serine with a threonine; replacement of a threonine with a serine; replacement of an acidic residue, such as aspartic acid and glutamic acid, with another acidic residue; replacement of a residue bearing an amide group, such as asparagine and glutamine, with another residue bearing an amide group; exchange of a basic residue, such as lysine and arginine, with another basic residue; and replacement of an aromatic residue, such as phenylalanine and tyrosine, with another aromatic residue. In some embodiments, the mutant polypeptide has about 1, 2, 3, 4, 5, 6, 7, 8, 9, 10, 15, 20, 30, 40, 50, 60, 70, 80, 90, 100, or more amino acid substitutions, additions, insertions, or deletions. Preferred fragments or mutants of a polypeptide retain some or all of the biological function (e.g., enzymatic activity) of the corresponding wild-type polypeptide. In some embodiments, the fragment or mutant retains at least 75%, at least 80%, at least 90%, at least 95%, or at least 98% or more of the biological function of the corresponding wild-type polypeptide. In other embodiments, the fragment or mutant retains about 100% of the biological function of the corresponding wild-type polypeptide. Guidance in determining which amino acid residues may be substituted, inserted, or deleted without affecting biological activity may be found using computer programs well known in the art, for example, LASERGENE™ software (DNASTAR, Inc., Madison, Wis.). In yet other embodiments, a fragment or mutant exhibits increased biological function as compared to a corresponding wild-type polypeptide. For example, a fragment or mutant may display at least a 10%, at least a 25%, at least a 50%, at least a 75%, or at least a 90% improvement in enzymatic activity as compared to the corresponding wild-type polypeptide. In other embodiments, the fragment or mutant displays at least 100% (e.g., at least 200%, or at least 500%) improvement in enzymatic activity as compared to the corresponding wild-type polypeptide. It is understood that the polypeptides described herein may have additional conservative or non-essential amino acid substitutions, which do not have a substantial effect on the polypeptide function. Whether or not a particular substitution will be tolerated (i.e., will not adversely affect desired biological function, such as carboxylic acid reductase activity) can be determined as described in Bowie et al. (Science, 247: 1306-1310 (1990)). A conservative amino acid substitution is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine), and aromatic side chains (e.g., tyrosine, phenylalanine, tryptophan, histidine).

Variants can be naturally occurring or created in vitro. In particular, such variants can be created using genetic engineering techniques, such as site directed mutagenesis, random chemical mutagenesis, Exonuclease III deletion procedures, or standard cloning techniques. Alternatively, such variants, fragments, analogs, or derivatives can be created using chemical synthesis or modification procedures. Methods of making variants are well known in the art. These include procedures in which nucleic acid sequences obtained from natural isolates are modified to generate nucleic acids that encode polypeptides having characteristics that enhance their value in industrial or laboratory applications. In such procedures, a large number of variant sequences having one or more nucleotide differences with respect to the sequence obtained from the natural isolate are generated and characterized. Typically, these nucleotide differences result in amino acid changes with respect to the polypeptides encoded by the nucleic acids from the natural isolates. For example, variants can be prepared by using random and site-directed mutagenesis. Random and site-directed mutagenesis are described in, for example, Arnold, Curr. Opin. Biotech., 4: 450-455 (1993). Random mutagenesis can be achieved using error prone PCR (see, e.g., Leung et al., Technique, 1: 11-15 (1989); and Caldwell et al., PCR Methods Applic., 2: 28-33 (1992)). In error prone PCR, PCR is performed under conditions where the copying fidelity of the DNA polymerase is low, such that a high rate of point mutations is obtained along the entire length of the PCR product. Briefly, in such procedures, nucleic acids to be mutagenized (e.g., a polynucleotide sequence encoding a carboxylic reductase enzyme) are mixed with PCR primers, reaction buffer, $MgCl_2$, $MnCl_2$, Taq polymerase, and an appropriate concentration of dNTPs for achieving a high rate of point mutation along the entire length of the PCR product. For example, the reaction can be performed using 20 fmoles of nucleic acid to be mutagenized, 30 pmole of each PCR primer, a reaction buffer comprising 50 mM KCl, 10 mM Tris HCl (pH 8.3), 0.01% gelatin, 7 mM $MgCl_2$, 0.5 mM $MnCl_2$, 5 units of Taq polymerase, 0.2 mM dGTP, 0.2 mM dATP, 1 mM dCTP, and 1 mM dTTP. PCR can be performed for 30 cycles of 94° C. for 1 min, 45° C. for 1 min, and 72° C. for 1 min. However, it will be appreciated that these parameters can be varied as appropriate. The mutagenized nucleic acids are then cloned into an appropriate vector, and the activities of the polypeptides encoded by the mutagenized nucleic acids are evaluated. Site-directed mutagenesis can be achieved using oligonucleotide-directed mutagenesis to generate site-specific mutations in any cloned DNA of interest. Oligonucleotide mutagenesis is described in, for example, Reidhaar-Olson et al., Science, 241: 53-57 (1988). Briefly, in such procedures a plurality of double stranded oligonucleotides bearing one or more mutations to be introduced into the cloned DNA are synthesized and inserted into the cloned DNA to be mutagenized (e.g., a polynucleotide sequence encoding a CAR polypeptide). Clones containing the mutagenized DNA are recovered, and the activities of the polypeptides they encode are assessed. Another method for generating variants is assembly PCR. Assembly PCR involves the assembly of a PCR product from a mixture of small DNA fragments. A large number of different PCR reactions occur in parallel in the same vial, with the products of one reaction priming the products of another reaction. Assembly PCR is described in, for example, U.S. Pat. No. 5,965,408. Still another method of generating variants is sexual PCR mutagenesis. In sexual PCR mutagenesis, forced homologous recombination occurs between DNA molecules of different, but highly related, DNA sequences in vitro as a result of random fragmentation of the DNA molecule based on sequence homology. This is followed by fixation of the crossover by primer extension in a PCR reaction. Sexual PCR mutagenesis is described in, for example, Stemmer, Proc. Natl. Acad. Sci., U.S.A., 91: 10747-10751 (1994). Variants can also be created by in vivo mutagenesis. In some embodiments, random mutations in a nucleic acid sequence are generated by propagating the sequence in a bacterial strain, such as an *E. coli* strain, which carries mutations in one or more of the DNA repair pathways. Such "mutator" strains have a higher random mutation rate than that of a wild-type strain. Propagating a DNA sequence (e.g., a polynucleotide sequence encoding a CAR polypeptide) in one of these strains will eventually generate random mutations within the DNA. Mutator strains suitable for use for in vivo mutagenesis are described in, for example, International Patent Application Publication No. WO1991/016427. Variants can also be generated using cassette mutagenesis. In cassette mutagenesis, a small region of a double-stranded DNA molecule is replaced with a synthetic oligonucleotide "cassette" that differs from the native sequence. The oligonucleotide often contains a completely and/or partially randomized native sequence. Recursive ensemble mutagenesis can also be used to generate variants. Recursive ensemble mutagenesis is an algorithm for protein engineering (i.e., protein mutagenesis) developed to produce diverse populations of phenotypically related mutants whose members differ in amino acid sequence. This method uses a feedback mechanism to control successive rounds of combinatorial cassette mutagenesis. Recursive ensemble mutagenesis is described in, for example, Arkin et al., Proc. Natl. Acad. Sci., U.S.A., 89: 7811-7815 (1992). In some embodiments, variants are created using exponential ensemble mutagenesis. Exponential ensemble mutagenesis is a process for generating combinatorial libraries with a high percentage of unique and functional mutants, wherein small groups of residues are randomized in parallel to identify, at each altered position, amino acids which lead to functional proteins. Exponential ensemble mutagenesis is described in, for example, Delegrave et al., Biotech. Res, 11: 1548-1552 (1993). In some embodiments, variants are created using shuffling procedures wherein portions of a plurality of nucleic acids that encode distinct polypeptides are fused together to create chimeric nucleic acid sequences that encode chimeric polypeptides as described in, for example, U.S. Pat. Nos. 5,965,408 and 5,939,250. Insertional mutagenesis is mutagenesis of DNA by the insertion of one or more bases. Insertional mutations can occur naturally, mediated by virus or transposon, or can be artificially created for research purposes in the lab, e.g., by transposon mutagenesis. When exogenous DNA is integrated into that of the host, the severity of any ensuing mutation depends entirely on the location within the host's genome wherein the DNA is inserted. For example, significant effects may be evident if a transposon inserts in the middle of an essential gene, in a promoter region, or into a repressor or an enhancer region. Transposon mutagenesis and high-throughput screening was done to find beneficial mutations that increase the titer or yield of a fatty acid derivative or derivatives.

Culture Recombinant Host Cells and Cell Cultures/Fermentation

As used herein, the term "fermentation" broadly refers to the conversion of organic materials into target substances by host cells, for example, the conversion of a carbon source by recombinant host cells into fatty acids or derivatives thereof by propagating a culture of the recombinant host cells in a media comprising the carbon source. As used herein, the term "conditions permissive for the production" means any conditions that allow a host cell to produce a desired product, such as a fatty acid or a fatty acid derivative. Similarly, the term "conditions in which the polynucleotide sequence of a vector is expressed" means any conditions that allow a host cell to synthesize a polypeptide. Suitable conditions include, for example, fermentation conditions. Fermentation conditions can comprise many parameters, including but not limited to temperature ranges, levels of aeration, feed rates and media composition. Each of these conditions, individually and in combination, allows the host cell to grow. Fermentation can be aerobic, anaerobic, or variations thereof (such as micro-aerobic). Exemplary culture media include broths or gels. Generally, the medium includes a carbon source that can be metabolized by a host cell directly. In addition, enzymes can be used in the medium to facilitate the mobilization (e.g., the depolymerization of starch or cellulose to fermentable sugars) and subsequent metabolism of the carbon source. For small scale production, the engineered host cells can be grown in batches of, for example, about 100 mL, 500 mL, 1 L, 2 L, 5 L, or 10 L; fermented; and induced to express a desired polynucleotide sequence, such as a polynucleotide sequence encoding a CAR polypeptide. For large scale production, the engineered host cells can be grown in batches of about 10 L, 100 L, 1000 L, 10,000 L, 100,000 L, and 1,000,000 L or larger; fermented; and induced to express a desired polynucleotide sequence. Alternatively, large scale fed-batch fermentation may be carried out. The fatty acid derivative compositions described herein are found in the extracellular environment of the recombinant host cell culture and can be readily isolated from the culture medium. A fatty acid derivative may be secreted by the recombinant host cell, transported into the extracellular environment or passively transferred into the extracellular environment of the recombinant host cell culture. The fatty acid derivative is isolated from a recombinant host cell culture using routine methods known in the art.

Products Derived from Recombinant Host Cells

As used herein, "fraction of modern carbon" or fM has the same meaning as defined by National Institute of Standards and Technology (NIST) Standard Reference Materials (SRMs4990B and 4990C, known as oxalic acids standards HOxI and HOxII, respectively. The fundamental definition relates to 0.95 times the 14C/12C isotope ratio HOxI (referenced to AD 1950). This is roughly equivalent to decay-corrected pre-Industrial Revolution wood. For the current living biosphere (plant material), fM is approximately 1.1. Bioproducts (e.g., the fatty acid derivatives produced in accordance with the present disclosure) comprising biologically produced organic compounds, and in particular, the fatty acid derivatives produced using the fatty acid biosynthetic pathway herein, have not been produced from renewable sources and, as such, are new compositions of matter. These new bioproducts can be distinguished from organic compounds derived from petrochemical carbon on the basis of dual carbon-isotopic fingerprinting or $^{14}C$ dating. Additionally, the specific source of biosourced carbon (e.g., glucose vs. glycerol) can be determined by dual carbon-isotopic fingerprinting (see, e.g., U.S. Pat. No. 7,169,588, which is herein incorporated by reference). The ability to distinguish bioproducts from petroleum based organic compounds is beneficial in tracking these materials in commerce. For example, organic compounds or chemicals comprising both biologically based and petroleum based carbon isotope profiles may be distinguished from organic compounds and chemicals made only of petroleum based materials. Hence, the bioproducts herein can be followed or tracked in commerce on the basis of their unique carbon isotope profile. Bioproducts can be distinguished from petroleum based organic compounds by comparing the stable carbon isotope ratio ($^{13}C/^{12}C$) in each sample. The $^{13}C/^{12}C$ ratio in a given bioproduct is a consequence of the $^{13}C/^{12}C$ ratio in atmospheric carbon dioxide at the time the carbon dioxide is fixed. It also reflects the precise metabolic pathway. Regional variations also occur. Petroleum, C3 plants (the broadleaf), C4 plants (the grasses), and marine carbonates all show significant differences in $^{13}C/$ $^{12}C$ and the corresponding $\delta^{13}C$ values. Furthermore, lipid matter of C3 and C4 plants analyze differently than materials derived from the carbohydrate components of the same plants as a consequence of the metabolic pathway. Within the precision of measurement, $^{13}C$ shows large variations due to isotopic fractionation effects, the most significant of which for bioproducts is the photosynthetic mechanism. The major cause of differences in the carbon isotope ratio in plants is closely associated with differences in the pathway of photosynthetic carbon metabolism in the plants, particularly the reaction occurring during the primary carboxylation (i.e., the initial fixation of atmospheric $CO_2$). Two large classes of vegetation are those that incorporate the "C3" (or Calvin-Benson) photosynthetic cycle and those that incorporate the "C4" (or Hatch-Slack) photosynthetic cycle. In C3 plants, the primary $CO_2$ fixation or carboxylation reaction involves the enzyme ribulose-1,5-diphosphate carboxylase, and the first stable product is a 3-carbon compound. C3 plants, such as hardwoods and conifers, are dominant in the temperate climate zones. In C4 plants, an additional carboxylation reaction involving another enzyme, phosphoenol-pyruvate carboxylase, is the primary carboxylation reaction. The first stable carbon compound is a 4-carbon acid that is subsequently decarboxylated. The $CO_2$ thus released is refixed by the C3 cycle. Examples of C4 plants are tropical grasses, corn, and sugar cane. Both C4 and C3 plants exhibit a range of $^{13}C/^{12}C$ isotopic ratios, but typical values are about −7 to about −13 per mil for C4 plants and about −19 to about −27 per mil for C3 plants (see, e.g., Stuiver et al., Radiocarbon 19:355 (1977)). Coal and petroleum fall generally in this latter range. The 13C measurement scale was originally defined by a zero set by Pee Dee Belemnite (PDB) limestone, where values are given in parts per thousand deviations from this material. The "δ13C" values are expressed in parts per thousand (per mil), abbreviated, ‰, and are calculated as follows:

$$\delta^{1}3C\ (‰)=[(^{13}C/^{12}C)\ \text{sample}-(^{13}C/^{12}C)\ \text{standard}]/(^{13}C/^{12}C)\ \text{standard}\times1000$$

Since the PDB reference material (RM) has been exhausted, a series of alternative RMs have been developed in cooperation with the IAEA, USGS, NIST, and other selected international isotope laboratories. Notations for the per mil deviations from PDB is $\delta^{13}C$. Measurements are made on $CO_2$ by high precision stable ratio mass spectrometry (IRMS) on molecular ions of masses 44, 45, and 46. The compositions described herein include bioproducts produced by any of the methods described herein, including, for example, fatty aldehyde and alcohol products. Specifically, the bioproduct can have a $\delta^{13}C$ of about −28 or greater, about −27 or greater, −20 or greater, −18 or greater, −15 or greater, −13 or greater, −10 or greater, or −8 or greater. For example, the bioproduct can have a $\delta^{13}C$ of about −30 to about −15, about −27 to about −19, about −25 to about −21, about −15 to about −5, about −13 to about −7, or about −13 to about −10. In other instances, the bioproduct can have a $\delta^{13}C$ of about −10, −11, −12, or −12.3. Bioproducts produced in accordance with the disclosure herein, can also be distinguished from petroleum based organic compounds by comparing the amount of $^{14}C$ in each compound. Because $^{14}C$ has a nuclear half-life of 5730 years, petroleum based fuels containing "older" carbon can be distinguished from bioproducts which contain "newer" carbon (see, e.g., Currie, "Source Apportionment of Atmospheric Particles", Characterization of Environmental Particles, J. Buffle and H. P. van Leeuwen, Eds., 1 of Vol. I of the IUPAC Environmental Analytical Chemistry Series (Lewis Publishers, Inc.) 3-74, (1992)). The basic assumption in radiocarbon dating is that the constancy of $^{14}C$ concentration in the atmosphere leads to the constancy of $^{14}C$ in living organisms. However, because of atmospheric nuclear testing since 1950 and the burning of fossil fuel since 1850, $^{14}C$ has acquired a second, geochemical time characteristic. Its concentration in atmospheric $CO_2$, and hence in the living biosphere, approximately doubled at the peak of nuclear testing, in the mid-1960s. It has since been gradually returning to the steady-state cosmogenic (atmospheric) baseline isotope rate ($^{14}C/^{12}C$) of about 1.2×10-12, with an approximate relaxation "half-life" of 7-10 years. (This latter half-life must not be taken literally; rather, one must use the detailed atmospheric nuclear input/decay function to trace the variation of atmospheric and biospheric $^{14}C$ since the onset of the nuclear age.) It is this latter biospheric $^{14}C$ time characteristic that holds out the promise of annual dating of recent biospheric carbon. $^{14}C$ can be measured by accelerator mass spectrometry (AMS), with results given in units of "fraction of modern carbon" (fM). fM is defined by National Institute of Standards and Technology (NIST) Standard Reference Materials (SRMs) 4990B and 4990C. As used herein, "fraction of modern carbon" or "fM" has the same meaning as defined by National Institute of Standards and Technology (NIST) Standard Reference Materials (SRMs) 4990B and 4990C, known as oxalic acids standards HOxI and HOxII, respectively. The fundamental definition relates to 0.95 times the $^{14}C/^{12}C$ isotope ratio HOxI (referenced to AD 1950). This is roughly equivalent to decay-corrected pre-Industrial Revolution wood. For the current living biosphere (plant material), fM is approximately 1.1. The compositions described herein include bioproducts that can have an fM $^{14}C$ of at least about 1. For example, the bioproduct of the disclosure can have an fM $^{14}C$ of at least about 1.01, an fM $^{14}C$ of about 1 to about 1.5, an fM $^{14}C$ of about 1.04 to about 1.18, or an fM $^{14}C$ of about 1.111 to about 1.124.

Another measurement of $^{14}C$ is known as the percent of modern carbon (pMC). For an archaeologist or geologist using $^{14}C$ dates, AD 1950 equals "zero years old". This also represents 100 pMC. "Bomb carbon" in the atmosphere reached almost twice the normal level in 1963 at the peak of thermo-nuclear weapons. Its distribution within the atmosphere has been approximated since its appearance, showing values that are greater than 100 pMC for plants and animals living since AD 1950. It has gradually decreased over time with today's value being near 107.5 pMC. This means that a fresh biomass material, such as corn, would give a $^{14}C$ signature near 107.5 pMC. Petroleum based compounds will have a pMC value of zero. Combining fossil carbon with present day carbon will result in a dilution of the present day pMC content. By presuming 107.5 pMC represents the $^{14}C$ content of present day biomass materials and 0 pMC represents the $^{14}C$ content of petroleum based products, the measured pMC value for that material will reflect the proportions of the two component types. For example, a material derived 100% from present day soybeans would give a radiocarbon signature near 107.5 pMC. If that material was diluted 50% with petroleum based products, it would give a radiocarbon signature of approximately 54 pMC. A biologically based carbon content is derived by assigning "100%" equal to 107.5 pMC and "0%" equal to 0 pMC. For example, a sample measuring 99 pMC will give an equivalent biologically based carbon content of 93%. This value is referred to as the mean biologically based carbon result and assumes all the components within the analyzed material originated either from present day biological material or petroleum based material. A bioproduct comprising one or more fatty acid derivatives as described herein can have a pMC of at least about 50, 60, 70, 75, 80, 85, 90, 95, 96, 97, 98, 99, or 100. In other instances, a fatty acid derivative described herein can have a pMC of between about 50 and about 100; about 60 and about 100; about 70 and about 100; about 80 and about 100; about 85 and about 100; about 87 and about 98; or about 90 and about 95. In yet other instances, a fatty acid derivative described herein can have a pMC of about 90, 91, 92, 93, 94, or 94.2.

Screening Fatty Acid Derivative Compositions Produced by Recombinant Host Cells

To determine if conditions are sufficient to allow expression, a host cell can be cultured, for example, for about 4, 8, 12, 24, 36, or 48 hours. During and/or after culturing, samples can be obtained and analyzed to determine if the conditions allow expression. For example, the host cells in the sample or the medium in which the host cells were grown can be tested for the presence of a desired product. When testing for the presence of a product, assays, such as, but not limited to, TLC, HPLC, GC/FID, GC/MS, LC/MS, MS, can be used. Recombinant host cell cultures are screened at the 96 well plate level, 1 liter and 5 liter tank level and in a 1000 L pilot plant using a GC/FID assay for "total fatty species".

Utility of Fatty Acid Derivative Compositions

A fatty acid is a carboxylic acid with a long aliphatic tail (chain), which is either saturated or unsaturated. Most naturally occurring fatty acids have a chain of an even number of carbon atoms, from 4 to 28. Fatty acids are usually derived from triglycerides. When they are not attached to other molecules, they are known as "free" fatty acids. Fatty acids are usually produced industrially by the hydrolysis of triglycerides, with the removal of glycerol. Palm, soybean, rapeseed, coconut oil and sunflower oil are currently the most common sources of fatty acids. The majority of fatty acids derived from such sources are used in human food products. Coconut oil and palm kernel oil (consist mainly of 12 and 14 carbon fatty acids). These are particularly suitable for further processing to surfactants for washing and cleansing agents as well as cosmetics. Palm, soybean, rapeseed, and sunflower oil, as well as animal fats such as tallow, contain mainly long-chain fatty acids (e.g., C18, saturated and unsaturated) which are used as raw materials for polymer applications and lubricants. Ecological and toxicological studies suggest that fatty acid-derived products based on renewable resources have more favorable properties than petrochemical-based substances. Fatty aldehydes are used to produce many specialty chemicals. For example, aldehydes are used to produce polymers, resins (e.g., Bakelite), dyes, flavorings, plasticizers, perfumes, pharmaceuticals, and other chemicals, some of which may be used as solvents, preservatives, or disinfectants. In addition, certain natural and synthetic compounds, such as vitamins and hormones, are aldehydes, and many sugars contain aldehyde groups. Fatty aldehydes can be converted to fatty alcohols by chemical or enzymatic reduction. Fatty alcohols have many commercial uses. Worldwide annual sales of fatty alcohols and their derivatives are in excess of U.S. $1 billion. The shorter chain fatty alcohols are used in the cosmetic and food industries as emulsifiers, emollients, and thickeners. Due to their amphiphilic nature, fatty alcohols behave as nonionic surfactants, which are useful in personal care and household products, such as, for example, detergents. In addition, fatty alcohols are used in waxes, gums, resins, pharmaceutical salves and lotions, lubricating oil additives, textile antistatic and finishing agents, plasticizers, cosmetics, industrial solvents, and solvents for fats. The disclosure also provides a surfactant composition or a detergent composition comprising a fatty alcohol produced by any of the methods described herein. One of ordinary skill in the art will appreciate that, depending upon the intended purpose of the surfactant or detergent composition, different fatty alcohols can be produced and used. For example, when the fatty alcohols described herein are used as a feedstock for surfactant or detergent production, one of ordinary skill in the art will appreciate that the characteristics of the fatty alcohol feedstock will affect the characteristics of the surfactant or detergent composition produced. Hence, the characteristics of the surfactant or detergent composition can be selected for by producing particular fatty alcohols for use as a feedstock. A fatty alcohol-based surfactant and/or detergent composition described herein can be mixed with other surfactants and/or detergents well known in the art. In some embodiments, the mixture can include at least about 10%, at least about 15%, at least about 20%, at least about 30%, at least about 40%, at least about 50%, at least about 60%, or a range bounded by any two of the foregoing values, by weight of the fatty alcohol. In other examples, a surfactant or detergent composition can be made that includes at least about 5%, at least about 10%, at least about 20%, at least about 30%, at least about 40%, at least about 50%, at least about 60%, at least about 70%, at least about 80%, at least about 85%, at least about 90%, at least about 95%, or a range bounded by any two of the foregoing values, by weight of a fatty alcohol that includes a carbon chain that is 8, 9, 10, 11, 12, 13, 14, 15, 16, 17, 18, 19, 20, 21, or 22 carbons in length. Such surfactant or detergent compositions also can include at least one additive, such as a microemulsion or a surfactant or detergent from non-microbial sources such as plant oils or petroleum, which can be present in the amount of at least about 5%, at least about 10%, at least about 15%, at least about 20%, at least about 30%, at least about 40%, at least about 50%, at least about 60%, at least about 70%, at least about 80%, at least about 85%, at least about 90%, at least about 95%, or a range bounded by any two of the foregoing values, by weight of the fatty alcohol. Esters have many commercial uses. For example, biodiesel, an alternative fuel, is comprised of esters (e.g., fatty acid methyl esters, fatty acid ethyl esters, etc.). Some low molecular weight esters are volatile with a pleasant odor, which makes them useful as fragrances or flavoring agents. In addition, esters are used as solvents for lacquers, paints, and varnishes. Furthermore, some naturally occurring substances, such as waxes, fats, and oils are comprised of esters. Esters are also used as softening agents in resins and plasticizers, flame retardants, and additives in gasoline and oil. In addition, esters can be used in the manufacture of polymers, films, textiles, dyes, and pharmaceuticals. Hydrocarbons have many commercial uses. For example, shorter chain alkanes are used as fuels. Longer chain alkanes (e.g., from five to sixteen carbons) are used as transportation fuels (e.g., gasoline, diesel, or aviation fuel). Alkanes having more than sixteen carbon atoms are important components of fuel oils and lubricating oils. Even longer alkanes, which are solid at room temperature, can be used, for example, as a paraffin wax. In addition, longer chain alkanes can be cracked to produce commercially valuable shorter chain hydrocarbons. Like short chain alkanes, short chain alkenes are used in transportation fuels. Longer chain alkenes are used in plastics, lubricants, and synthetic lubricants. In addition, alkenes are used as a feedstock to produce alcohols, esters, plasticizers, surfactants, tertiary amines, enhanced oil recovery agents, fatty acids, thiols, alkenylsuccinic anhydrides, epoxides, chlorinated alkanes, chlorinated alkenes, waxes, fuel additives, and drag flow reducers. Ketones are used commercially as solvents. For example, acetone is frequently used as a solvent, but it is also a raw material for making polymers. Ketones are also used in lacquers, paints, explosives, perfumes, and textile processing. In addition, ketones are used to produce alcohols, alkenes, alkanes, imines, and enamines. Lubricants are typically composed of olefins, particularly polyolefins and alpha-olefins. Lubricants can either be refined from crude petroleum or manufactured using raw materials refined from crude petroleum. Obtaining these specialty chemicals from crude petroleum requires a significant financial investment as well as a great deal of energy. It is also an inefficient process because frequently the long chain hydrocarbons in crude petroleum are cracked to produce smaller monomers. These monomers are then used as the raw material to manufacture the more complex specialty chemicals. The disclosure is further illustrated by the following examples. The examples are provided for illustrative purposes only. They are not to be construed as limiting the scope or content of the disclosure in any way.

EXAMPLES

Example 1

Production Host Modifications—Attenuation of Acyl-CoA Dehydrogenase

This example describes the construction of a genetically engineered host cell wherein the expression of a fatty acid degradation enzyme is attenuated.

The fadE gene of *Escherichia coli* MG1655 (an *E. coli* K strain) was deleted using the Lambda Red (also known as the Red-Driven Integration) system described by Datsenko et al., Proc. Natl. Acad. Sci. USA 97: 6640-6645 (2000), with the following modifications:

The following two primers were used to create the deletion of fadE:

```
Del-fadE-F
                                    (SEQ ID NO: 9)
5'-AAAAACAGCAACAATGTGAGCTTTGTTGTAATTATATTGTAAACAT
ATTGATTCCGGGGATCCGTCGACC;
and

Del-fadE-R
                                    (SEQ ID NO: 10)
5'-AAACGGAGCCTTTCGGCTCCGTTATTCATTTACGCGGCTTCAACTT
TCCTGTAGGCTGGAGCTGCTTC
```

The Del-fadE-F and Del-fadE-R primers were used to amplify the kanamycin resistance (KmR) cassette from plasmid pKD13 (described by Datsenko et al., supra) by PCR. The PCR product was then used to transform electrocompetent *E. coli* MG1655 cells containing pKD46 (described in Datsenko et al., supra) that had been previously induced with arabinose for 3-4 hours. Following a 3-hour outgrowth in a super optimal broth with catabolite repression (SOC) medium at 37° C., the cells were plated on Luria agar plates containing 50 μg/mL of Kanamycin. Resistant colonies were identified and isolated after an overnight incubation at 37° C. Disruption of the fadE gene was confirmed by PCR amplification using primers fadE-L2 and fadE-R1, which were designed to flank the *E. coli* fadE gene.

The fadE deletion confirmation primers were:

```
fadE-L2
                                    (SEQ ID NO: 11)
5'-CGGGCAGGTGCTATGACCAGGAC;
and

fadE-R1
                                    (SEQ ID NO: 12)
5'-CGCGGCGTTGACCGGCAGCCTGG
```

Figure 7:
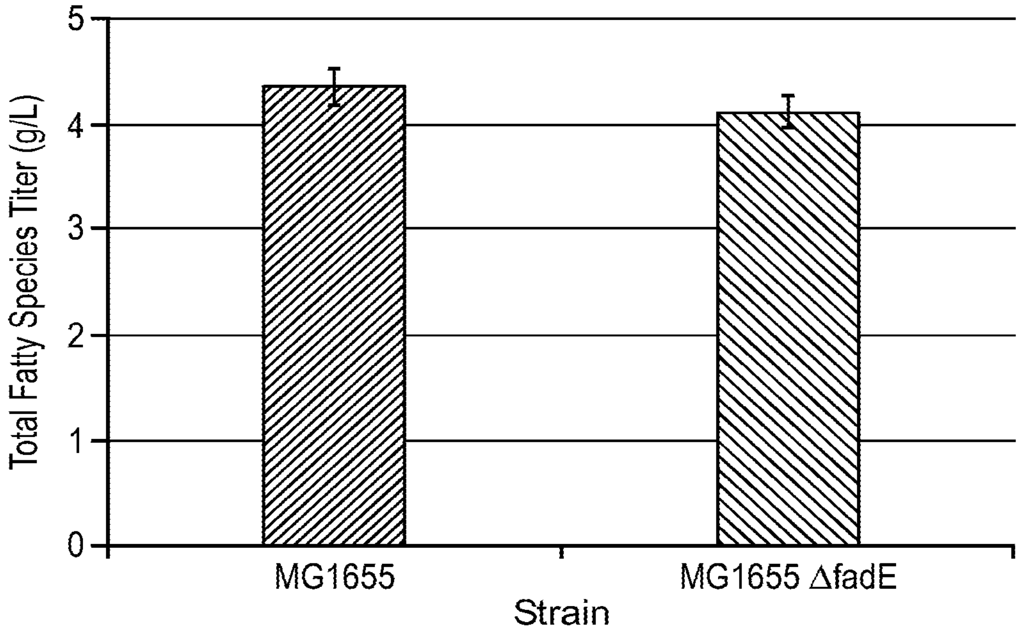
FIG. 7 illustrates fatty acid derivative (Total Fatty Species) production by the MG1655 *E. coli* strain with the fadE gene attenuated (i.e., deleted) compared to fatty acid derivative production by *E. coli* MG1655. The data presented in FIG. 7 shows that attenuation of the fadE gene did not affect fatty acid derivative production

After the fadE deletion was confirmed, a single colony was used to remove the KmR marker using the pCP20 plasmid as described by Datsenko et al., supra. The resulting MG1655 *E. coli* strain with the fadE gene deleted and the KmR marker removed was named *E. coli* MG1655 ΔfadE, or *E. coli* MG1655 D1. Fatty acid derivative (total fatty species) production by the MG1655 *E. coli* strain with the fadE gene deleted was compared to fatty acid derivative production by *E. coli* MG1655. The deletion of the fadE gene did not affect fatty acid derivative production (FIG. 7). A number of exemplary host cell strains are described herein, examples of which are described below in Table 3.

TABLE 3

Genetic Characterization of *E. coli* Strains

| Strain | Genetic Characterization |
|---|---|
| DV2 | MG1655 F−, λ−, ilvG−, rfb-50, rph-1, ΔfhuA::FRT, ΔfadE::FRT |
| DV2.1 | DV2 fabB::fabB[A329V] |
| D178 | DV2.1 entD::FRT_$P_{T5}$_entD |
| EG149 | D178 ΔinsH-11::($P_{LACUV5}$-iFAB138 |
| V642 | EG149 rph+ |
| SL313 | V642 lacIZ::$P_{A1}$_'tesA/pDG109 |
| V668 | V642 ilvG$^+$ |
| LC397 | V668 lacIZ::$P_{TRC}$_'tesA(var)_kan |
| SL571 | V668 lacIZ:: $P_{TRC}$_'tesA(var)_FRT |
| LC942 | SL571 attTn7::$P_{TRC}$_'tesA(var) |
| DG16 | LC942/pLC56 |
| V940 | LC397/pV171.1 |
| D851 | SL571 yijP::Tn5-cat/pV171.1 |
| BD64 | DV2 ΔinsH-11::$P_{LACUV5}$-iFAB138 loxP_$P_{T5}$_fadR |
| DAM1 | DV2 attTn7::$P_{TRC}$_tesA_fadD |
| Shu.002 | DV2 ΔinsH-11::$P_{T5}$-iFAB138 loxP_$P_{T5}$_fadR |

Plasmids: pDG109, pLC56 and pV171.1 both are pCL_$P_{trc}$_carB_tesA_alrA_fabB_fadR operon with variable expression of carB and tesA. iFAB138 is SEQ ID NO: 19.

Example 2

Figure 2:
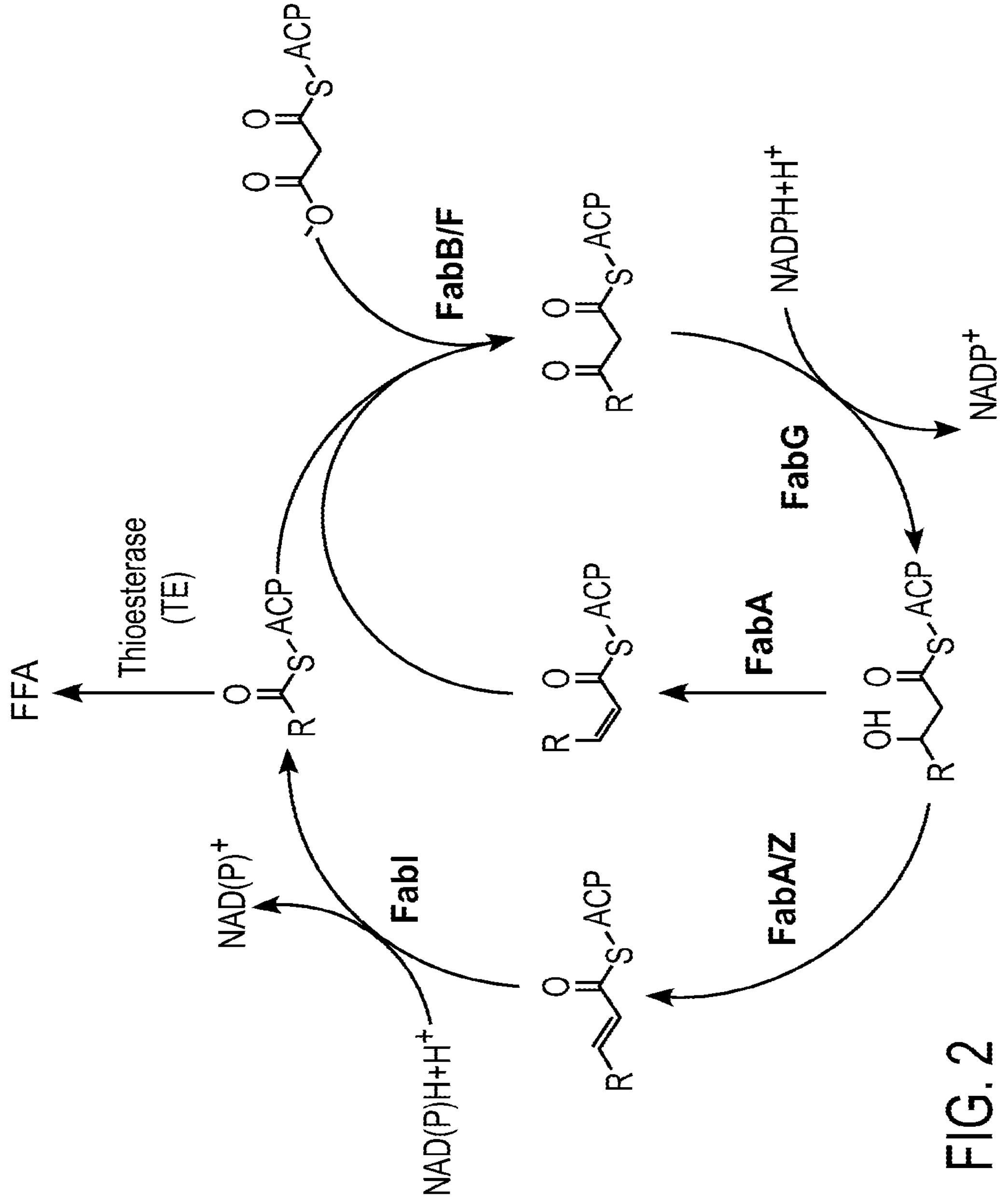
FIG. 2 presents an exemplary fatty acid biosynthetic cycle, where malonyl-ACP is produced by the transacylation of malonyl-CoA to malonyl-ACP (catalyzed by malonyl-CoA:ACP transacylase (fabD)); then β-ketoacyl-ACP synthase III (fabH) initiates condensation of malonyl-ACP with acetyl-CoA. Elongation cycles begin with the condensation of malonyl-ACP and an acyl-ACP catalyzed by β-ketoacyl-ACP synthase I (fabB) and β-ketoacyl-ACP synthase II (fabF) to produce a β-keto-acyl-ACP, then the β-keto-acyl-ACP is reduced by β-ketoacyl-ACP reductase (fabG) to produce a β-hydroxy-acyl-ACP, which is dehydrated to a trans-2-enoyl-acyl-ACP by β-hydroxyacyl-ACP dehydratase (fabA or fabZ). FabA can also isomerize trans-2-enoyl-acyl-ACP to cis-3-enoyl-acyl-ACP, which can bypass fabI and can used by fabB (typically for up to an aliphatic chain length of C16) to produce β-keto-acyl-ACP. The final step in each cycle is catalyzed by enoyl-ACP reductase (fabI) that converts trans-2-enoyl-acyl-ACP to acyl-ACP. In the methods described herein, termination of fatty acid synthesis occurs by thioesterase removal of the acyl group from acyl-ACP to release free fatty acids (FFA). Thioesterases (e.g., tesA) hydrolyze thioester bonds, which occur between acyl chains and ACP through sulfydryl bonds.
Figure 3:
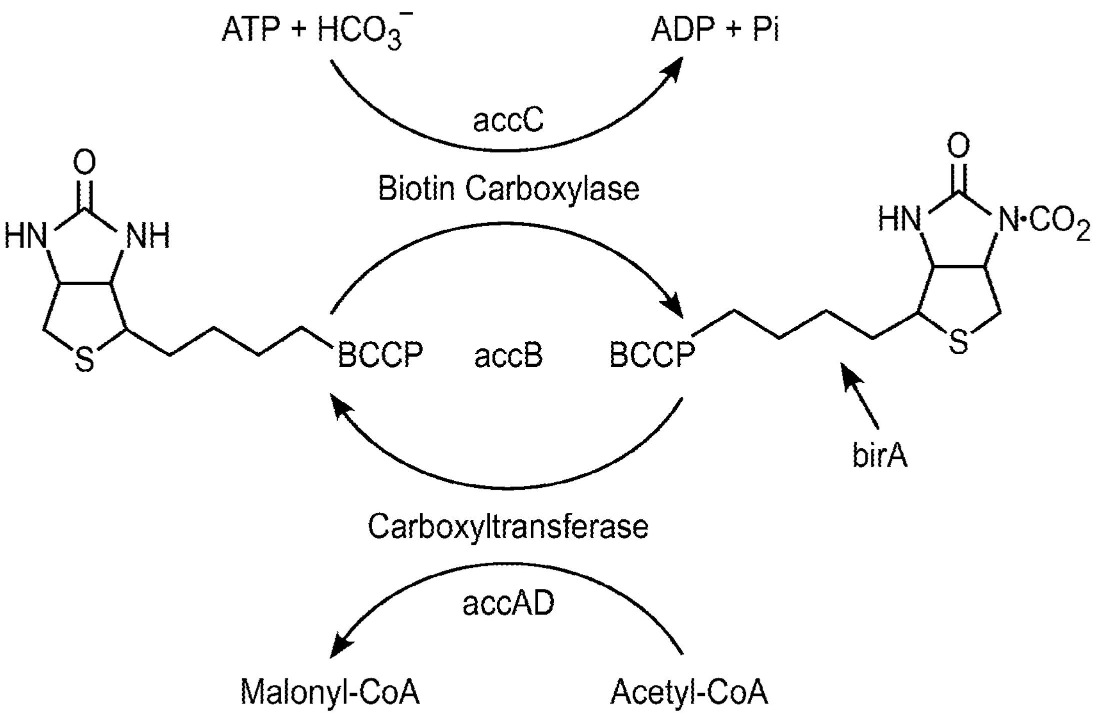
FIG. 3 illustrates the structure and function of the acetyl-CoA carboxylase (accABCD) enzyme complex. BirA biotinylates accB, the biotin carboxyl carrier protein, which is part of the acetyl-CoA carboxylase enzyme complex.

Increased Flux through the Fatty Acid Synthesis Pathway—Acetyl CoA Carboxylase Mediated Fatty Ester Production:

The main precursors for fatty acid biosynthesis are malonyl-CoA and acetyl-CoA (FIG. 1). It has been suggested that these precursors limit the rate of fatty acid biosynthesis in *E. coli*. In this example, synthetic acc operons [*Corynebacterium glutamicum* accABCD (±birA)] were overexpressed and the genetic modifications led to increased acetyl-coA and malonyl-CoA production in *E. coli*. In one approach, in order to increase malonyl-CoA levels, an acetyl-CoA carboxylase enzyme complex from *Corynebacterium glutamicum* (*C. glutamicum*) was overexpressed in *E. coli*. Acetyl-CoA carboxylase (acc) consists of four discrete subunits, accA, accB, accC and accD (FIG. 3). The advantage of *C. glutamicum* acc is that two subunits are expressed as fusion proteins, accCB and accDA, respectively, which facilitates its balanced expression. Additionally, *C. glutamicum* birA, which biotinylates the accB subunit (FIG. 3) was overexpressed. Exemplary *C. glutamicum* birA DNA sequences are presented as SEQ ID NO: 55 and SEQ ID NO: 56. A *C. glutamicum* birA protein sequence is presented as SEQ ID NO: 57.

Figure 8:
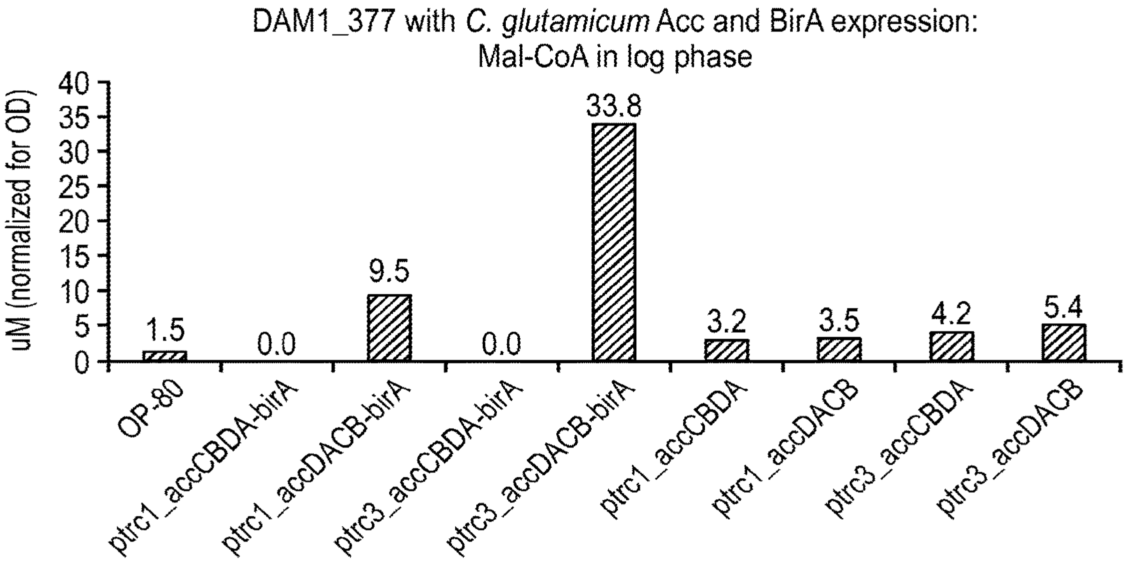
FIG. 8 shows malonyl-CoA levels in DAM1_i377 in log phase, expressing eight different *C. glutamicum* acetyl-CoA carboxylase (Acc) operon constructs.

The synthetic operons of the *C. glutamicum* acc genes were cloned in the following way in OP80 (see WO2008/119082 as incorporated-by-reference herein) Ptrc1-accDACB, Ptrc3-accDACB, Ptrc1-accCBDA and Ptrc3-CBDA. Ptrc1 and Ptrc3 are derivatives of the commonly used Ptrc promoter, which allow attenuated transcription of target genes. Note that the native sequences were amplified from the chromosomal DNA as they showed favorable codon usage (only the codon for Arg6 in accCB was changed). The *C. glutamicum* birA gene was codon optimized and obtained by gene synthesis. It was cloned downstream of the acc genes in all four operon constructs. Below we refer to the operon configuration accDACB as accD- and the operon configuration accDACB+birA as accD+. The resulting plasmids were transformed into *E. coli* DAM1_i377, which contains integrated copies (i) of leaderless thioesterease 'tesA and acyl-CoA synthetase fadD from *E. coli* and Ester synthase 9 (ES9) from *Marinobacter hydrocarbonoclasticus* (SEQ ID NO: 6). All genes are controlled by Ptrc promoters. The strains were grown in 5NBT media (described below) in shake flasks and were analyzed for malonyl-CoA using short chain-CoA assay described below. FIG. 8 shows that six of the eight *C. glutamicum* acc±birA constructs showed elevated levels of malonyl-CoA in logarithmic phase demonstrating their functionality in *E. coli*. It was noted that coexpression of birA further increased malonyl-CoA levels in the ptrc1/3_accDACB strains, in particular with the plasmid containing the Ptrc3-accDACB-birA operon configuration (plasmid pAS119.50D; SEQ ID NO: 62).

Figure 9:
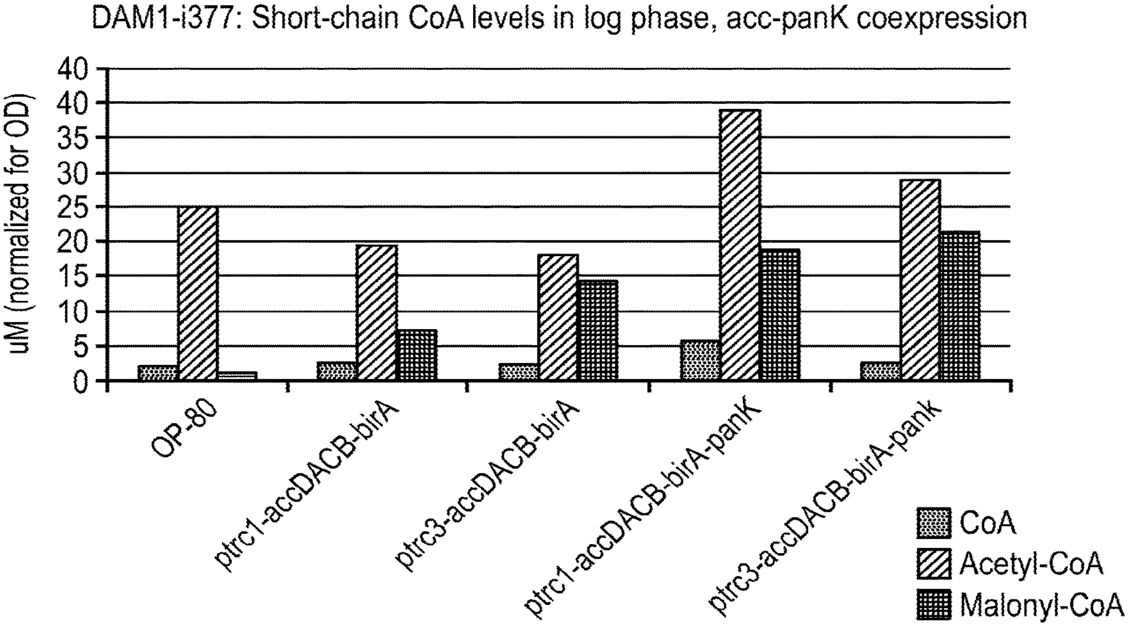
FIG. 9 shows intracellular short chain-CoA levels in *E. coli* DAM1_i377 in log phase expressing ptrc1/3_accDACB-birA±panK operon constructs. accDACB+birA is also referred to herein as accD+.

In order to test the effect of combining panK and acc-birA overexpression, the optimized panK gene was cloned downstream of birA in ptrc1/3_accDACB-birA. Pantothenate kinase panK (or CoaA) catalyzes the first step in the biosynthesis of coenzyme A, an essential cofactor that is involved in many reactions, e.g., the formation of acetyl-CoA, the substrate for acetyl-CoA carboxylase. The resulting plasmids were transformed into DAM1_i377, grown in 5NBT (+TVS1) media in shake flasks, and the strains were analyzed for short-chain-CoAs using the method described below. As shown in FIG. 9, in log phase panK coexpression further increased malonyl-CoA levels and also increased acetyl-CoA levels demonstrating that panK can further increase the malonyl-CoA levels. The impact of coexpressing an acetyl-CoA carboxylase enzyme complex on fatty ester production was evaluated by expressing ester synthase 9 (SEQ ID NO: 6) with and without acc genes in another *E. coli* production host. More specifically, plasmids OP80 (vector control), pDS57 (with ES9), pDS57-accD− (with ES9 and accDACB) or pDS57-accD+ (with ES9 and accDACB-birA; SEQ ID NO: 63) were transformed into *E. coli* strain DV2 and the corresponding transformants were selected on LB plates supplemented with 100 mg/L of spectinomycin.

Figure 10:
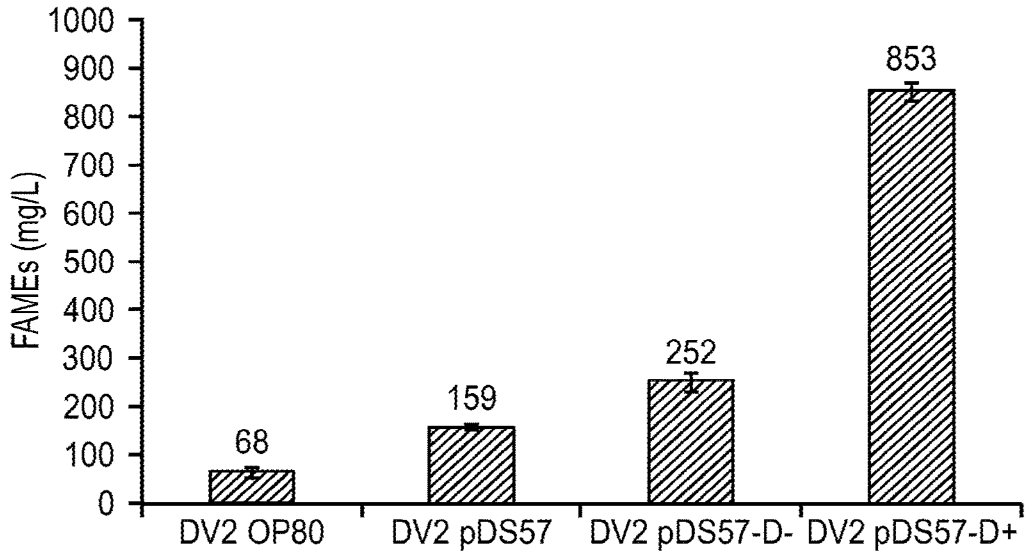
FIG. 10 shows fatty acid methyl ester (FAME) production in *E. coli* strain DV2 expressing ester synthase 9 from *M. hydrocarbonoclasticus* and components of an acetyl-CoA carboxylase complex from *C. glutamicum.*

Two transformants of each plasmid were independently inoculated into LB medium supplemented with 100 mg/L of spectinomycin and grown for 5-8 hours at 32° C. The cultures were diluted 30-fold into a minimal medium with the following composition: 0.5 g/L NaCl, 1 mM $MgSO_4 \times 7H_2O$, 0.1 mM $CaCl_2$, 2 g/L $NH_4Cl$, 3 g/L $KH_2PO_4$, 6 g/L $Na_2HPO_4$, 1 mg/L thiamine, 1× trace metal solution, 10 mg/L ferric citrate, 100 mM Bis-Tris (pH7.0), 30 g/L glucose and 100 mg/L spectinomycin. After over-night growth at 32° C., the cultures were diluted 10-fold in quadruplicate into minimal medium of the same composition except that the media contained 1 g/L instead of 2 g/L $NH_4Cl$ and was supplemented with 1 mM IPTG and 2% (v/v) methanol. The resulting cultures were then grown at 32° C. in a shaker. The production of fatty acid methyl esters (FAMEs) was analyzed by gas chromatography with flame ionization detector (GC-FID). The samples were extracted with butyl acetate in a ratio of 1:1 vol/vol. After vortexing, the samples were centrifuged, and the organic phase was analyzed by gas chromatography (GC). The analysis conditions were as follows: instrument: Trace GC Ultra, Thermo Electron Corporation with Flame ionization detector (FID) detector; column: DB-1 (1% diphenyl siloxane; 99% dimethyl siloxane) COI UFM 1/0.1/5 01 DET from Thermo Electron Corporation, phase pH 5, FT: 0.4 μm, length 5 m, id: 0.1 mm; inlet conditions: 250° C. splitless, 3.8 m 1/25 split method used depending upon sample concentration with split flow of 75 mL/m; carrier gas, flow rate: Helium, 3.0 mL/m; block temperature: 330° C.; oven temperature: 0.5 m hold at 50° C., 100° C./m to 330° C., 0.5 m hold at 330° C.; detector temperature: 300° C.; injection volume: 2 μL; run time/flow rate: 6.3 m/3.0 mL/m (splitless method), 3.8 m/1.5 mL/m (split 1/25 method), 3.04 m/1.2 mL/m (split 1/50 method). FAMEs produced are shown in FIG. 10. The expression of ES9 by itself in *E. coli* DV2 led to FAME production above the control DV2 OP80. Coexpression of the *C. glutamicum* acetyl-CoA carboxylase complex led to an approx. 1.5-fold increase in FAMEs and the additional expression of the *C. glutamicum* biotin protein ligase led to an approx. 5-fold increase in FAMEs. These results suggest that the increased supply of malonyl-CoA improves the ability of ES9 to convert intermediates of the fatty acid biosynthetic machinery to fatty acid methyl esters in *E. coli*.

Short-chain-CoA assay: 15 ml falcon tubes were prepared with 0.467 ml 10% TCA with crotonyl-CoA as internal standard and overlayed with 2 ml of silicone oil. The tubes were chilled on ice and fermentation broth equivalent to 1 ml OD600=31.2 was carefully layered on top of the silicone oil. The samples were centrifuged at 11,400 g at 4° C. for four 4 min cycles. For each sample, a 400 ml aliquots of the TCA/cellular extract was removed and placed in a fresh Eppendorf tube for neutralization with 1 ml Octylamine (in CHCl3). After vortexing, the samples were centrifuged for 30 sec at 13,000 g. 200 ml of the top layer was filtered using a 0.2 um PTFE syringe filter and then subjected to LC-MS/MS analysis.

Description of Media Used iIn Experiments:

| Media ID | | | | | | |
|---|---|---|---|---|---|---|
| 4N-BT | 5N-BT | FA2 | FA2.1 | FA2.3 | Concentration | Ingredient |
| 0.5 | 0.5 | 0.5 | 0.5 | 0.5 | g/L | NaCl |
| 2 | 2 | 2 | 2 | 2 | g/L | $NH_4Cl$ |
| 3 | 3 | 3 | 3 | 3 | g/L | $KH_2PO_4$ |
| 6 | 6 | 6 | 6 | 6 | g/L | $Na_2PO_4$ |
| 1 | 1 | 1 | 1 | 1 | mM | $MgSO_4$ |
| 0.1 | 0.1 | 0.1 | 0.1 | 0.1 | mM | $CaCl_2$ |
| 1 | 1 | 1 | 1 | 1 | mg/L | thiamine |
| 0.2 | 0.2 | 0.1 | 0.1 | 0.1 | M | Bis-Tris pH7 |
| 0.1 | 0.1 | 0.05 | 0.1 | 0.1 | % | Triton X-100 |
| 1 | 1 | 1 | 1 | 1 | x | Trace Minerals |
| 27 | 27 | 10 | 10 | 10 | mg/L | $FeCl_2 \cdot 6H_2O$ |
| 40 | 50 | 30 | 30 | 35 | g/L | glucose |

Figure 11:
FIG. 11 shows production of fatty alcohols by *E. coli* expressing the *Synechococcus elongatus* PCC7942 AAR together with the accD+ operon from *C.glutamicum* on a pCL plasmid. Triplicate samples are shown for the accD+ strains.

1000 fold concentrated Trace Vitamins Solution
0.06 g/L Riboflavin 6 g/L Niacin
5.4 g/L Pantothenic Acid
1.4 g/L Pyridoxine
0.06 g/L Biotin
0.01 g/L Folic Acid
1000 fold concentrated Trace Metal Solution
2 mL/L Concentrated hydrochloric acid
0.5 g/L boric acid
1.9 g/L cupric sulfate, pentahydrate, USP
1 g/L zinc chloride anhydrous
2 g/L sodium molybdenate dehydrate
2 g/L calcium chloride dehydrate Fatty Alcohol Production:

The impact of coexpressing an acetyl-CoA carboxylase enzyme complex on Fatty alcohol production was evaluated by expressing the Acyl-ACP reductase (AAR) from *Synechococcus elongatus* (SEQ ID NO: 38) with and without acc genes in *E. coli* DV2. The accD+ operon configuration was selected as it gave the best results when coexpressed with ester synthase (see previous example). The accDABC-birA operon was cloned downstream from the aar gene in pLS9-185 (a pCL1920 derivative) using Infusion technology (Clontech Laboratories, Inc., Mountain View, Calif.). The resulting plasmid was transformed into *E. coli* DV2 and the corresponding transformants were selected on LB plates supplemented with 100 mg/L of spectinomycin. Fatty alcohols produced are shown in FIG. 11. The coexpression of AAR and accD+ led to a ca. 1.5-fold increase in fatty alcohol titers as compared to the AAR only control (pLS9-185). The data were reproducible (triplicate samples were shown). These results demonstrate that increasing malonyl-CoA levels lead to improved fatty acid production when this acyl-ACP reductase is used. In addition, Example 3 describes co-expression of acc genes together with entire fab operons.

Example 3

Increased Flux through the Fatty Acid Synthesis Pathway—iFABs

Fatty Acid Derivative Production:

Strategies to increase the flux through the fatty acid synthesis pathway in recombinant host cells include both overexpression of native *E. coli* fatty acid biosynthesis genes and expression of exogenous fatty acid biosynthesis genes from different organisms in *E. coli*. In this study, fatty acid biosynthesis genes from different organisms were combined in the genome of *E. coli* DV2 (Table 3) under the control of the lacUV5 promoter and integrated into the IS5-11 site. Sixteen strains containing iFABs 130-145 were evaluated. The detailed structure of iFABs 130-145 is presented in Tables 4 and 5.

TABLE 4

Components from Different Species used in iFABs 130-145

| Abbreviation | Full Description |
|---|---|
| St_fabD | *Salmonella typhimurium* fabD gene |
| nSt_fabH | *Salmonella typhimurium* FabH gene with the native RBS |
| sSt_fabH | *Salmonella typhimurium* fabH gene with a synthetic RBS |
| Cac_fabF | *Clostridium acetobutylicum* (ATCC824) fabF gene |
| St_fabG | *Salmonella typhimurium* fabG gene |
| St_fabA | *Salmonella typhimurium* fabA gene |
| St_fabZ | *Salmonella typhimurium* fabZ gene |
| BS_fabI | *Bacillus subtilis* fabI gene |
| BS_fabL | *Bacillus subtilis* fabL gene |
| Vc_FabV | *Vibrio chorlerae* fabV gene |
| Ec_FabI | *Escherichia coli* fabI gene |

Each "iFAB" included various fab genes in the following order: 1) an enoyl-ACP reductase (BS_fabI, BS_FabL, Vc_FabV, or Ec_FabI); 2) a b-ketoacyl-ACP synthetase III (St_fabH); 3) a malonyl-CoA-ACP transacylase (St_fabD); 4) a b-ketoacyl-ACP reductase (St_fabG); 5) a 3-hydroxy-acyl-ACP dehydratase (St_fabA or St_fabZ); 6) a b-ketoacyl-ACP synthetase II (Cac_fabF). Note that St_fabA also has trans-2, cis-3-decenoyl-ACP isomerase activity and that Cac_fabF has b-ketoacyl-ACP synthetase II and b-ketoacyl-ACP synthetase I activities (Zhu et al., BMC Microbiology 9:119 (2009)). See Table 5, below for the specific composition of iFABs 130-145.

TABLE 5

Composition of iFABs 130-145

| ifab | BS_fabI | BS_fabL | Vc_fabV | Ec_fabI | nSt_fabH | sSt_fabH | St_fabD | St_fabG | St_fabA | St_fabZ | Cac_fabF |
|---|---|---|---|---|---|---|---|---|---|---|---|
| ifab130 | 1 | 0 | 0 | 0 | 1 | 0 | 1 | 1 | 1 | 0 | 1 |
| ifab131 | 1 | 0 | 0 | 0 | 1 | 0 | 1 | 1 | 0 | 1 | 1 |
| ifab132 | 1 | 0 | 0 | 0 | 0 | 1 | 1 | 1 | 1 | 0 | 1 |
| ifab133 | 1 | 0 | 0 | 0 | 0 | 1 | 1 | 1 | 0 | 1 | 1 |
| ifab134 | 0 | 1 | 0 | 0 | 1 | 0 | 1 | 1 | 1 | 0 | 1 |
| ifab135 | 0 | 1 | 0 | 0 | 1 | 0 | 1 | 1 | 0 | 1 | 1 |
| ifab136 | 0 | 1 | 0 | 0 | 0 | 1 | 1 | 1 | 1 | 0 | 1 |
| ifab137 | 0 | 1 | 0 | 0 | 0 | 1 | 1 | 1 | 0 | 1 | 1 |
| ifab138 | 0 | 0 | 1 | 0 | 1 | 0 | 1 | 1 | 1 | 0 | 1 |
| ifab139 | 0 | 0 | 1 | 0 | 1 | 0 | 1 | 1 | 0 | 1 | 1 |
| ifab140 | 0 | 0 | 1 | 0 | 0 | 1 | 1 | 1 | 1 | 0 | 1 |
| ifab141 | 0 | 0 | 1 | 0 | 0 | 1 | 1 | 1 | 0 | 1 | 1 |
| ifab142 | 0 | 0 | 0 | 1 | 1 | 0 | 1 | 1 | 1 | 0 | 1 |
| ifab143 | 0 | 0 | 0 | 1 | 1 | 0 | 1 | 1 | 0 | 1 | 1 |
| ifab144 | 0 | 0 | 0 | 1 | 0 | 1 | 1 | 1 | 1 | 0 | 1 |
| ifab145 | 0 | 0 | 0 | 1 | 0 | 1 | 1 | 1 | 0 | 1 | 1 |

Figure 12A:
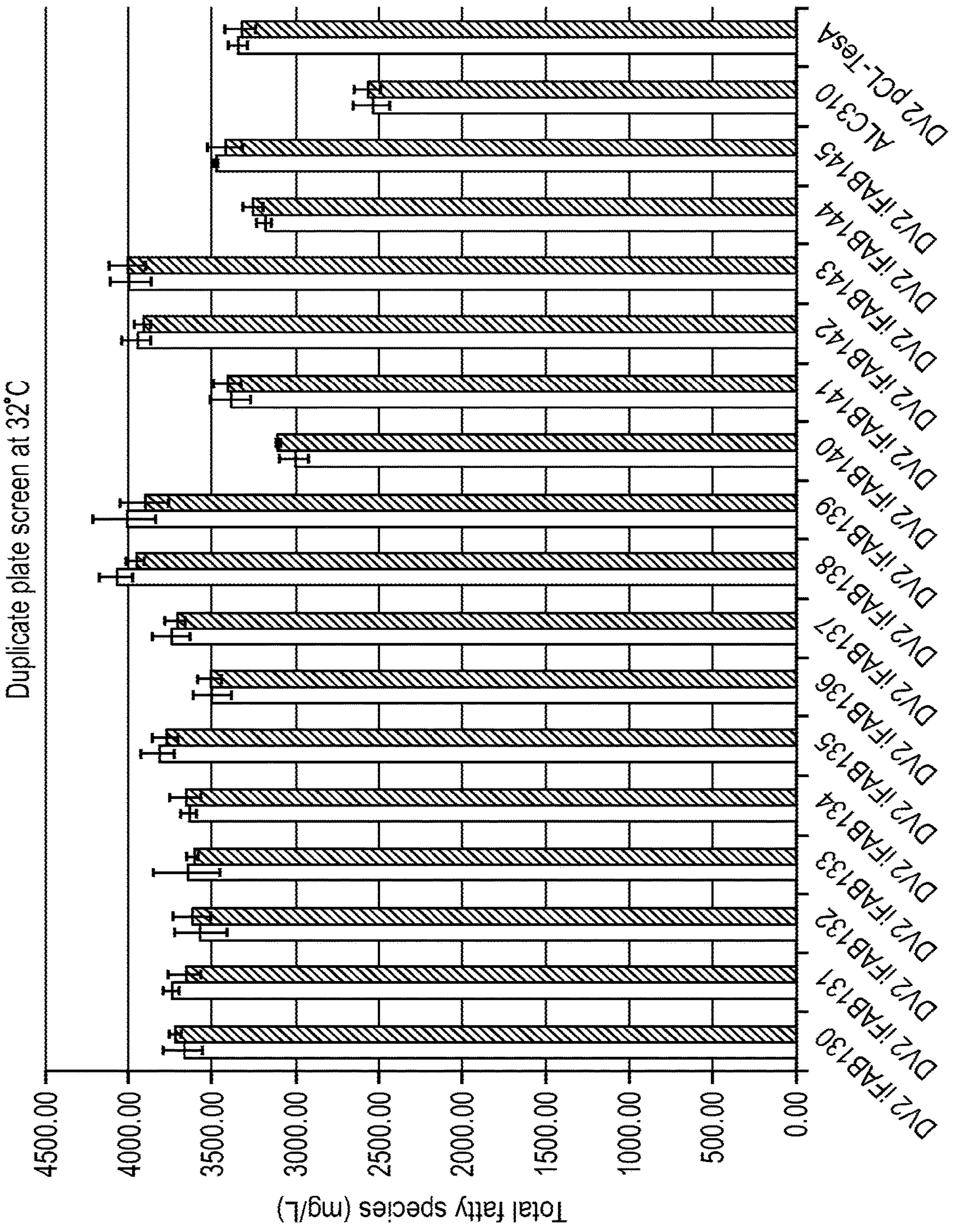
FIGS. 12A and 12B show data for production of Total Fatty Species (mg/L) from duplicate plate screens when plasmid pCL_$P_{trc}$_tesA was transformed into each of the iFAB-containing strains shown in the figures and a fermentation was run in FA2 media with 20 hours from induction to harvest at both 32° C.
Figure 12B:
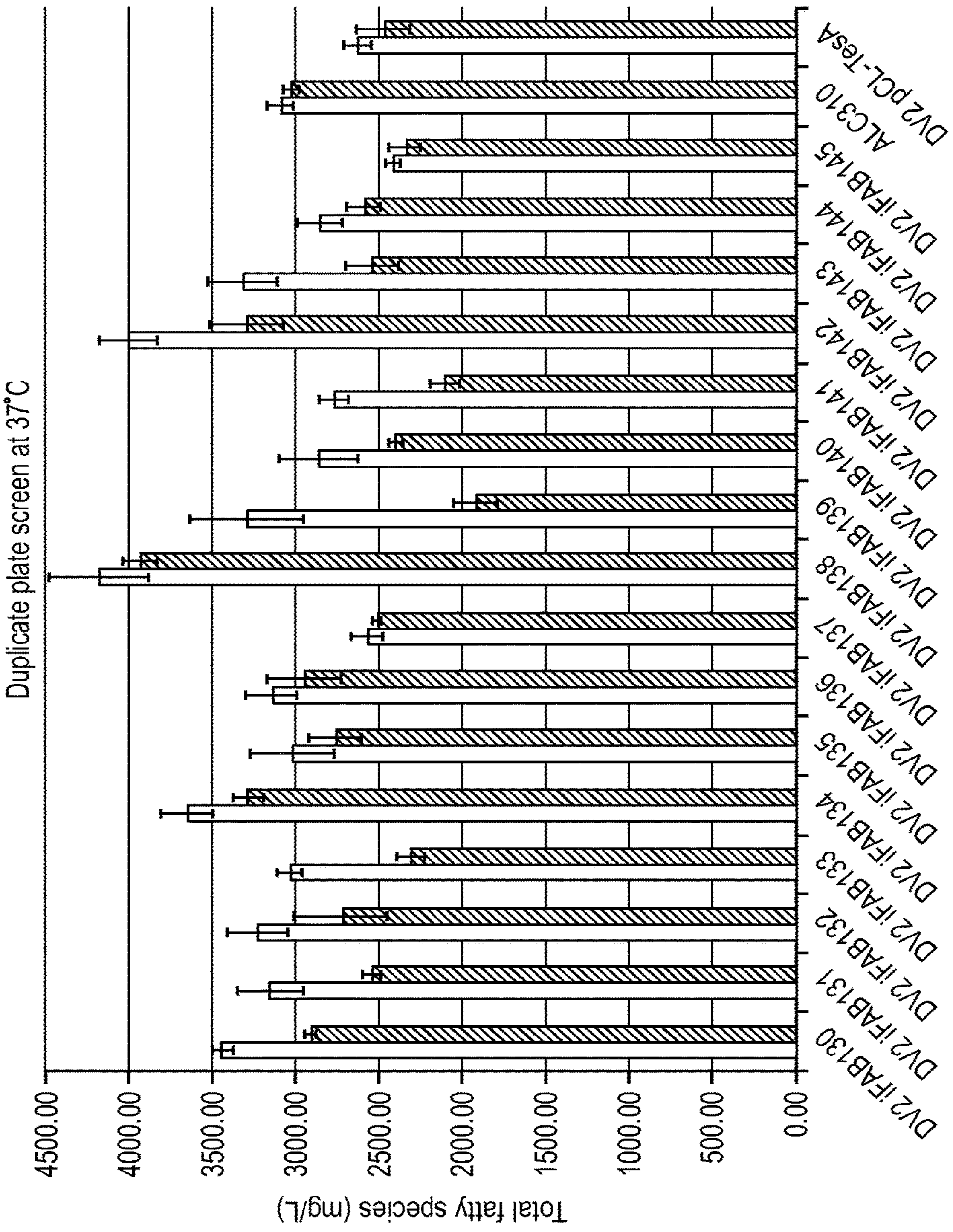

The plasmid pCL_$P_{trc}$_tesA was transformed into each of the strains and a fermentation was run in FA2 media with 20 hours from induction to harvest at both 32° C. and 37° C. Data for production of Total Fatty Species from duplicate plate screens is shown in FIGS. 12A and 12B. From this screen the best construct was determined to be DV2 with iFAB138. The sequence of iFAB138 in the genome of EG149 is presented as SEQ ID NO: 19.

Fatty Ester Production:

A full synthetic fab operon was integrated into the *E. coli* chromosome and evaluated for increased FAME production by expression in *E. coli* DAM1 pDS57. In addition, four synthetic acc operons from *Corynebaterium glutamicum* were coexpressed and evaluated for improved FAME productivity. Several strains were obtained that produced FAMES at a faster rate and higher titers. The sixteen different iFAB operons (Table 5) were put under the control of the lacUV5 promoter and integrated into the IS5-11 site of *E. coli* DAM1. These strains were named DAM1 ifab130 to 145. They were transformed either with pDS57 (containing ester synthase 377) or pDS57 co-expressing different versions of acc operons, see above) for evaluation of FAME production. Exemplary plasmids are described in Table 6.

TABLE 6

Plasmids containing Ester Synthase ES9 (from *Marinobacter hydrocarbonclasticus*) and Synthetic acc Operons (from *Corynebactrium glutamicum*)

| Plasmid | Genes |
|---|---|
| pTB.071 | pDS57-accCBDA |
| pTB.072 | pDS57-accCBDA-birA |
| pTB.073 | pDS57-accDACB |
| pTB.074 | pDS57-accDACB-birA |

pDS57 = pCL_ptrc-ES9

The DAM1 ifab strains were analyzed in 96-well plates (4NBT medium), shake flasks (5NBT medium) (see above for medium description) and in fermenters at 32° C. The best results were obtained in 96-well plates and in shake flasks, where several DAM1 ifab strains with pDS57-acc-birA plasmids showed higher FAME titers. In particular, DAM1 ifab131, ifab135, ifab137, ifab138 and ifab143 with pDS57-accDACB-birA showed 20-40% improved titers indicating that in these strains a higher flux through the fatty acid pathway was achieved, which resulted in a better product formation rate (these results were reproducible in several independent experiments).

Effect of Overexpressing fabH and fabI on Fatty Acid Methyl Ester (FAME) Production:

Strategies to increase the flux through the fatty acid synthesis pathway in recombinant host cells include both overexpression of native fatty acid biosynthesis genes and expression of heterologous fatty acid biosynthesis genes. FabH and fabI are two fatty acid biosynthetic enzymes that have been shown to be feedback inhibited (Heath and Rock, JBC 271: 1833-1836 (1996)). A study was conducted to determine if FabH and FabI might be limiting the rate of FAME production. FabH and fabI homologues (from *E. coli, B. subtilis, Acinetobacter baylyi* ADP1, *Marinobacter aquaeoli* VT8, and *Rhodococcus opacus*) were overexpressed as a synthetic operon and evaluated in *E. coli* DAM1 pDS57 (a strain observed to be a good FAME producer). In one approach, fabHfabI operons were constructed from organisms that accumulate waxes (*A. baylyi, M. aquaeoli*) or triacylglycerides (*R. opacus*) and integrated into the chromosome of *E. coli* DAM1 pDS57. In a related approach, a synthetic acc operons from *C. glutamicum* were co-expressed (as described in Example 2, above). Eleven different fabHI operons were constructed (assembled in vitro) as summarized in Table 7. The fabHI operons were put under the control of IPTG inducible lacUV5 promoter and integrated into the IS5-11 site of *E. coli* DAM1. These strains were named as shown in the table below. They were transformed either with pDS57 (containing ester synthase 377) or pDS57 coexpressing different versions of acc operons for evaluation of FAME production.

TABLE 7

Genotype of Integrated fabHI Operons

| Strain | Genotype of additional fab operon | Plasmid |
|---|---|---|
| stEP117 | DAM1 ΔinsH::$P_{LACUV5}$ (snyRBS) EcfabH (synRBS) BsfabI::kan | pDS57 |
| stEP118 | DAM1 ΔinsH::$P_{LACUV5}$ (snyRBS) EcfabH (synRBS) BsfabL::kan | pDS57 |
| stEP127 | DAM1 ΔinsH::$P_{LACUV5}$ (EcRBS) EcfabH (EcRBS) BsfabI::kan | pDS57 |
| stEP128 | DAM1 ΔinsH::$P_{LACUV5}$ (EcRBS) EcfabH (EcRBS) BsfabL::kan | pDS57 |
| stEP129 | DAM1 ΔinsH::$P_{LACUV5}$ (EcRBS) ADP1fabH (EcRBS) ADP1fabI::kan | pDS57 |
| stEP130 | DAM1 ΔinsH::$P_{LACUV5}$ (snyRBS) ADP1fabH (synRBS) ADP1fabI::kan | pDS57 |
| stEP131 | DAM1 ΔinsH::$P_{LACUV5}$ (snyRBS) VT8fabH1 (synRBS) VT8fabI::kan | pDS57 |
| stEP132 | DAM1 ΔinsH::$P_{LACUV5}$ (snyRBS) VT8fabH2 (synRBS) VT8fabI::kan | pDS57 |
| stEP133 | DAM1 ΔinsH::$P_{LACUV5}$ (EcRBS) VT8fabH1 (synRBS) VT8fabI::kan | pDS57 |
| stEP134 | DAM1 ΔinsH::$P_{LACUV5}$ (EcRBS) VT8fabH2 (synRBS) VT8fabI::kan | pDS57 |
| stEP151 | DAM1 ΔinsH::$P_{LACUV5}$ (snyRBS) RofabI (synRBS) RofabH::kan | pDS57 |
| stEP153 | DAM1 ΔinsH::$P_{LACUV5}$ (EcRBS) ADP1fabH (EcRBS) ADP1fabI::kan | pDS57-accCBDA |
| stEP154 | DAM1 ΔinsH::$P_{LACUV5}$ (EcRBS) ADP1fabH (EcRBS) ADP1fabI::kan | pDS57-accDACB |
| stEP155 | DAM1 ΔinsH::$P_{LACUV5}$ (EcRBS) ADP1fabH (EcRBS) ADP1fabI::kan | pDS57-accCBDA-birA |
| stEP156 | DAM1 ΔinsH::$P_{LACUV5}$ (EcRBS) ADP1fabH (EcRBS) ADP1fabI::kan | pDS57-accDACB-birA |
| stEP157 | DAM1 ΔinsH::$P_{LACUV5}$ (snyRBS) EcfabH (synRBS) BsfabI::kan | pDS57-accCBDA |
| stEP158 | DAM1 ΔinsH::$P_{LACUV5}$ (snyRBS) EcfabH (synRBS) BsfabI::kan | pDS57-accCBDA-birA |
| stEP159 | DAM1 ΔinsH::$P_{LACUV5}$ (EcRBS) EcfabH (synRBS) BsfabI::kan | pDS57-accCBDA |
| stEP160 | DAM1 ΔinsH::$P_{LACUV5}$ (EcRBS) EcfabH (synRBS) BsfabI::kan | pDS57-accCBDA-birA |
| stEP161 | DAM1 ΔinsH::$P_{LACUV5}$ (EcRBS) VT8fabH1 (synRBS) VT8fabI::kan | pDS57-accCBDA |
| stEP162 | DAM1 ΔinsH::$P_{LACUV5}$ (EcRBS) VT8fabH1 (synRBS) VT8fabI::kan | pDS57-accCBDA-birA |

TABLE 7-continued

| Genotype of Integrated fabHI Operons | | |
|---|---|---|
| Strain | Genotype of additional fab operon | Plasmid |
| stEP163 | DAM1 ΔinsH::$P_{LACUV5}$ (EcRBS) VT8fabH2 (synRBS) VT8fabI::kan | pDS57-accCBDA |
| stEP164 | DAM1 ΔinsH::$P_{LACUV5}$ (EcRBS) VT8fabH2 (synRBS) VT8fabI::kan | pDS57-accCBDA-birA |

Bs: *Bacillus subtilis*;
Ec: *Escherichia coli*,
ADP1: *Acinetobacter* sp. ADP1;
VT8: *Marinobacter aquaeolei* VT8;
Ro: *Rhodococcus opacus* B4

Figure 13:
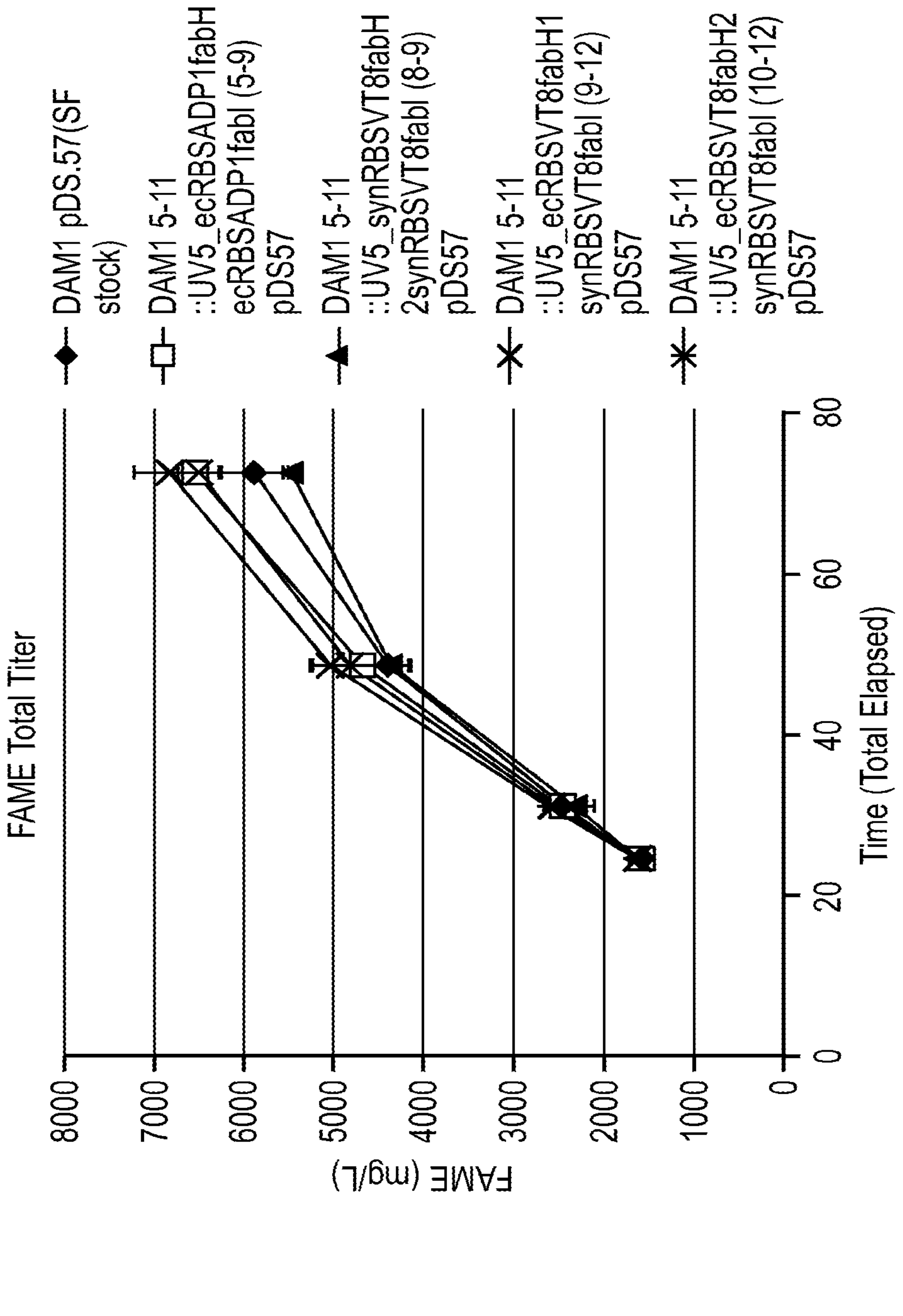
FIG. 13 shows FAME production of *E. coli* DAM1 with plasmid pDS57 and integrated fabHI operons. The fabH/I genes are from *Marinobacter aquaeoli* VT8 or from *Acinetobacter baylyi* ADP1. See Table 7 for a more details on the fabH/I operons in these strains.
Figure 14:
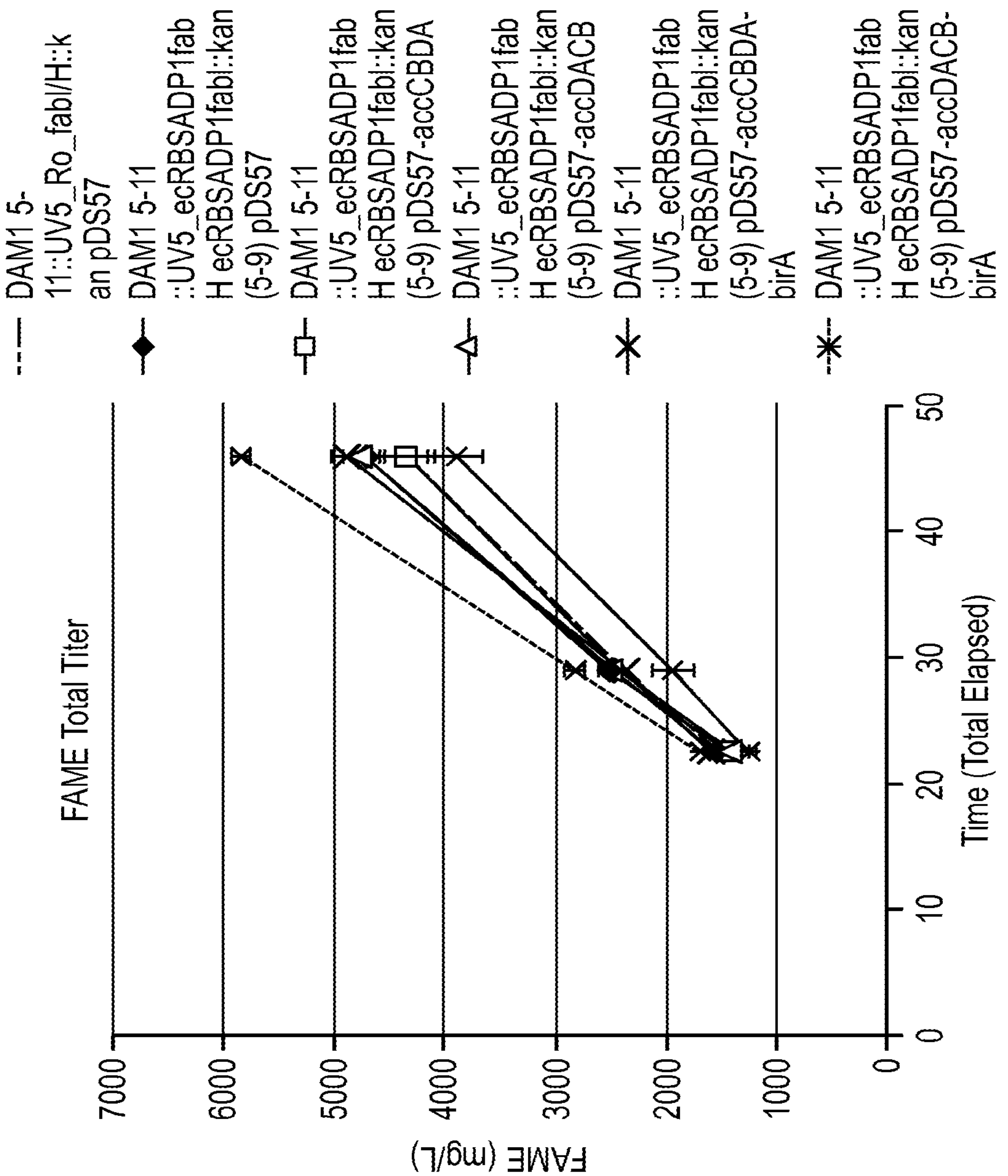
FIG. 14 shows FAME production of *E. coli* DAM1 with plasmid pDS57 and different configurations of the *C. glutamicum* acc genes as well as integrated fabHI operons. The strains contain the fabH/I genes from *Rhodococcus opacus* or *Acinetobacter baylyi* ADP1. See Table 7 for more details on the fabH/I and acc operons.

The DAM1 ifabHI strains were analyzed in 96-well plates (4NBT medium), shake flasks (5NBT medium) and in fermenters at 32° C. In a shake flask, a number of the ifabHI strains carrying pDS57 plasmid performed better than the control DAM1 pDS57strain, reaching 10 to 15% higher FAME titers (FIG. 13). Additional increase in FAME titers was obtained when ifabHI strains were transformed with pDS57-acc-birA plasmids, in particular an increase of 50% in FAME titers was observed in strain StEP156 (DAM1 IS5-11::lacUV5(ecRBS)ADP1fabH (ecRBS)ADP1fabI pDS57-accDACB-birA) (FIG. 14).

Figure 15:
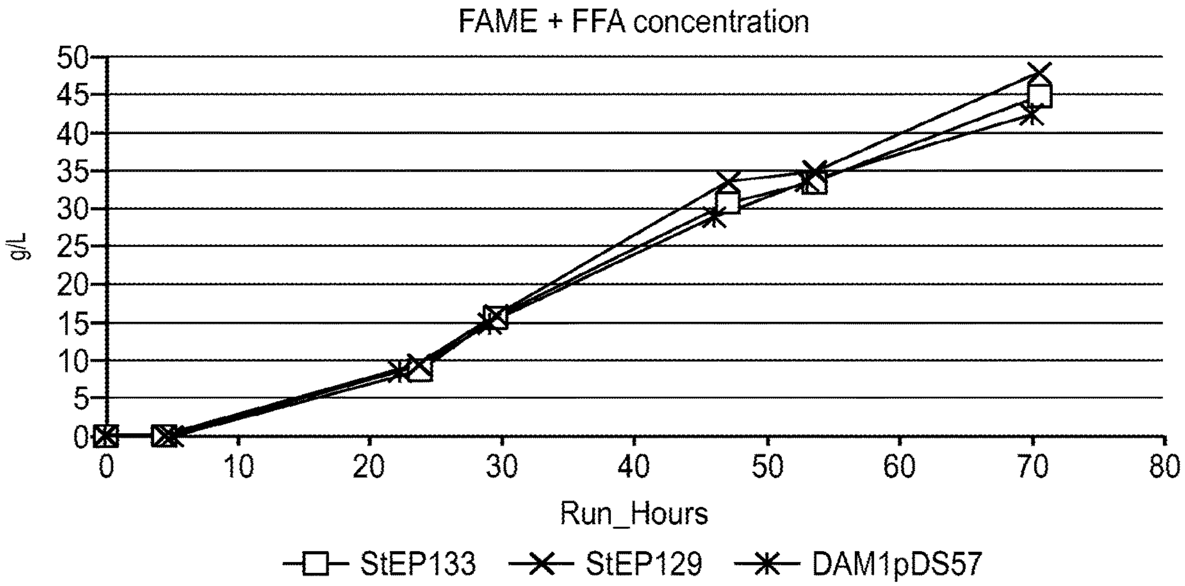
FIG. 15 shows FAME and FFA titers of two *E. coli* DAM1 pDS57 strains with integrated fabH/I genes strains selected from FIG. 13 compared to the control strain *E. coli* DAM1 pDS57.

Some of the strains with ifabHI were run in fermenters, where an increase in FAME titers, specific productivity and yield was also observed (FIG. 15), indicating that in these strains a higher flux through the fatty acid pathway was achieved, which resulted in a better product formation rate. In particular stEP129 (DAM1 5-11::UV5(ecRBS) ADP1fabH (ecRBS)ADP1fabI pDS57) showed higher FAME titers and yield in several independent fermentation runs. Other combinations of fabH and fabI may be used to achieve similar effects. Although FAME is exemplified here, this approach to alter fatty acid biosynthetic genes is a useful approach to increase production of any fatty acid derivative.

Effect of inserting a strong promoter in front of operon FAB138 on Fatty Acid Methyl Ester (FAME) production:

The lacUV5 promoter of iFAB138 was replaced by a T5 promoter (SEQ ID NO: 2) leading to higher levels of expression of iFAB138, as confirmed by mRNA analysis. The expression of iFAB138 from the T5 promoter resulted in a higher titer, yield and productivity of fatty esters. Strain shu.002 (Table 3) is isogenic to strain BD64 (Table 3) except that it contains the T5 promoter controlling expression of the iFAB138 operon (SEQ ID NO: 19).

Figure 16A:
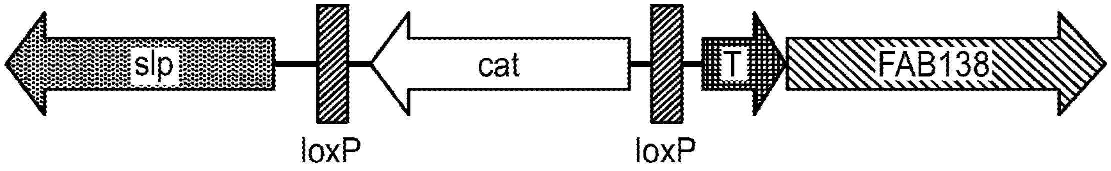
FIGS. 16A and 16B are a diagrammatic depiction of the iFAB138 locus, including a diagram of cat-loxP-$P_{T5}$ cassette integrated in front of iFAB138 (FIG. 16A); and a diagram of the $P_{T5}$_iFAB138 region (FIG. 16B).
Figure 16B:
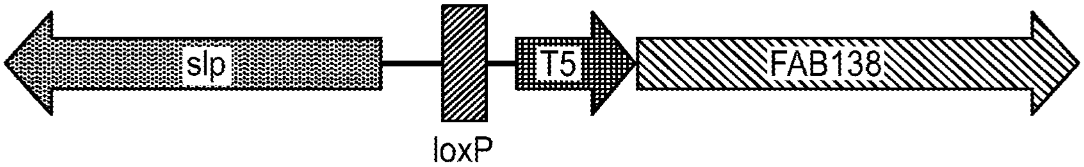

Primers DG405 and DG406 (Table 8) were used to amplify a cat-loxP and T5 promoter cassette adding 50 bp homology to each end of the PCR product, such that it could be integrated into any strain replacing the lacUV5 promoter regulating expression of the iFAB138 operon. The cat-loxP-T5 promoter was transformed into BD64/pKD46 strain. Transformants were recovered on LB+chloramphenicol plates at 37° C. overnight, patched to a fresh LB+chloramphenicol plate, and verified by colony PCR using primers DG422 and DG423. Plasmid pJW168 (Palmeros et al., *Gene* 247: 255-264 (2000)) was transformed into strain BD64 i-cat-loxP-T5_138 and selected on LB+carbenicillin plates at 32° C. In order to remove the cat marker, expression of the cre-recombinase was induced by IPTG. The plasmid pJW168 was removed by growing cultures at 42° C. Colonies were patched on LB+chloramphenicol and LB+carbenicillin to verify loss of pJW168 and removal of cat marker, respectively. The colony was also patched into LB as a positive control, all patched plates were incubated at 32° C. The removal of the cat marker was confirmed by colony PCR using primers DG422 and DG423. The resulting PCR product was verified by sequencing with primers EG744, EG749 and oTREE047, the strain was called shu.002. FIG. 16 shows the iFAB138 locus: a diagram of the cat-loxP-$P_{T5}$ cassette integrated in front of FAB138 (FIG. 16A) and a diagram of the $P_{T5}$_iFAB138 region (FIG. 16B). The sequence of the cat-loxP-T5 promoter integrated in front of iFAB138 with homology to integration site is presented as SEQ ID NO: 1 and the sequence of the iT5_FAB138 promoter region with homology to integration site is presented as SEQ ID NO: 2. There are a number of conditions that can lead to increased fatty acid flux. In this example increased fatty acid flux was achieved by altering the

TABLE 8

| Primers used to Generate iT5_138 Cassette and Verify its Insertion in New Strains | | |
|---|---|---|
| Primer Name | SEQ ID NO | Sequence |
| DG405 | 20 | TTGTCCATCTTTATATAATTTGGGGGTAGGGTGTTCTTTATGTAAAAAAAAC gtttTAGGATGCATATGGCGGCC |
| DG406 | 21 | GATAAATCCACGAATTTTAGGTTTGATGATCATTGGTCTCCTCCTGCAGGTG CGTGTTCGTCGTCATCGCAATTG |
| DG422 | 22 | ACTCACCGCATTGGTGTAGTAAGGCGCACC |
| DG423 | 23 | TGAATGTCATCACGCAGTTCCCAGTCATCC |
| EG744 | 24 | CCATCTTCTTTGTACAGACGTTGACTGAACATG |
| EG749 | 24 | GCACCATAGCCGTAATCCCACAGGTTATAG |
| oTREE047 | 26 | TGTCATTAATGGTTAATAATGTTGA |

promoter strength of operon iFAB138. The expression of iFAB138 from the T5 promoter was beneficial, nonetheless, when this promoter change was combined with the insertion of yijP::Tn5 cassette further improvements were observed in titer, yield and productivity of fatty acid esters and other fatty acid derivatives (data not shown).

Example 4

Figure 17:
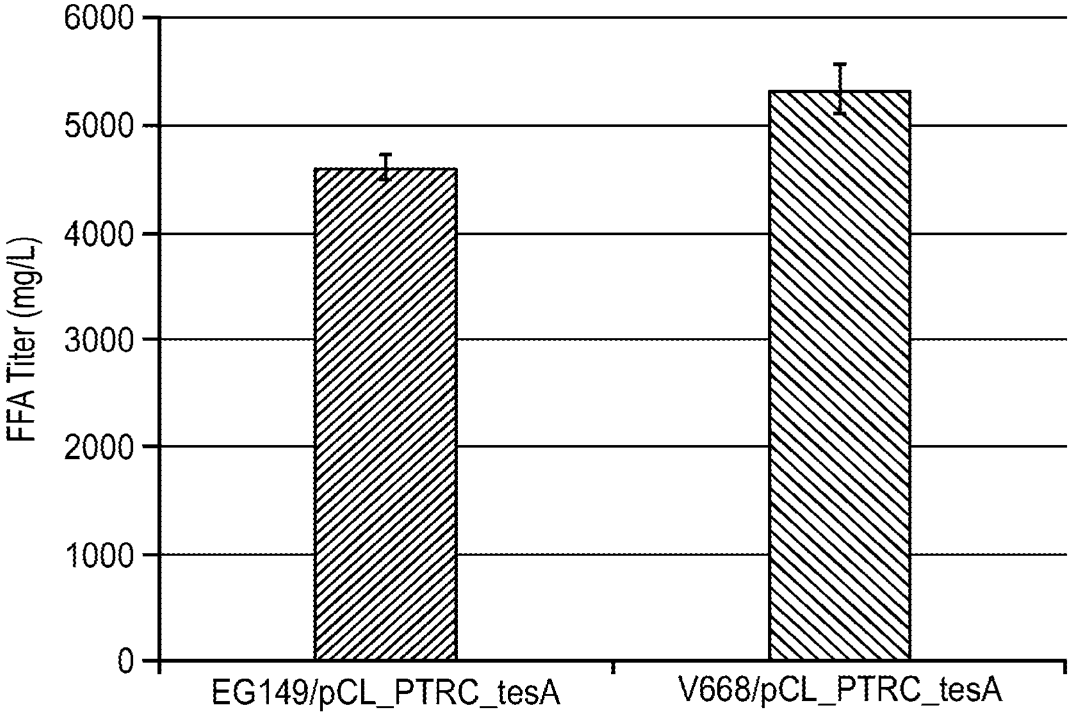
FIG. 17 shows that strain V668, which has the rph and ilvG genes repaired, produced a higher level of FFA than EG149, which has neither of the genes repaired.

Increasing the Amount of Free Fatty Acid (FFA) Product by Repairing the rph and ilvG Mutations The ilvG and rph mutations were corrected in this strain resulting in higher production of FFA. Strains EG149 and V668 (Table 3) were transformed with pCL_$P_{trc}$_tesA. Fermentation was run at 32° C. in FA2 media for 40 hours to compare the FFA production of strains EG149 and V668 with pCL_$P_{trc}$_tesA. Correcting the rph and ilvG mutations resulted in a 116% increase in the FFA production of the base strain with pCL_$P_{trc}$_tesA. As seen in FIG. 17, V668/pCL_$P_{trc}$_tesA produced more FFA than the EG149/pCL_$P_{trc}$_tesA control. Since FFA is a precursor to the LS9 products, higher FFA production is a good indicator that the new strain can produce higher levels of LS9 products.

Example 5

Increased Production of Fatty Acid Derivatives by Transposon Mutagenesis—yijP Fatty Alcohol Production:

To improve the titer, yield, productivity of fatty alcohol production by *E. coli*, transposon mutagenesis and high-throughput screening was carried out and beneficial mutations were sequenced. A transposon insertion in the yijP strain was shown to improve the strain's fatty alcohol yield in both shake flask and fed-batch fermentations. The SL313 strain produces fatty alcohols. The genotype of this strain is provided in Table 3. Transposon clones were then subjected to high-throughput screening to measure production of fatty alcohols. Briefly, colonies were picked into deep-well plates containing LB, grown overnight, inoculated into fresh LB and grown for 3 hours, inoculated into fresh FA2.1 media, grown for 16 hours, then extracted using butyl acetate. The crude extract was derivatized with BSTFA (N,O-bis[Trimethylsilyl]trifluoroacetamide) and analyzed using GC/FID. Spectinomycin (100 mg/L) was included in all media to maintain selection of the pDG109 plasmid. Hits were selected by choosing clones that produced a similar total fatty species as the control strain SL313, but that had a higher percent of fatty alcohol species and a lower percent of free fatty acids than the control. Strain 68F11 was identified as a hit and was validated in a shake flask fermentation using FA2.1 media. A comparison of transposon hit 68F11 to control strain SL313 indicated that 68F11 produces a higher percentage of fatty alcohol species than the control, while both strains produce similar titers of total fatty species. A single colony of hit 68F11, named LC535, was sequenced to identify the location of the transposon insertion. Briefly, genomic DNA was purified from a 10 mL overnight LB culture using the kit ZR Fungal/Bacterial DNA MiniPrep™ (Zymo Research Corporation, Irvine, Calif.) according to the manufacturer's instructions. The purified genomic DNA was sequenced outward from the transposon using primers internal to the transposon:

```
DG150
                                        (SEQ ID NO: 27)
5'-GCAGTTATTGGTGCCCTTAAACGCCTGGTTGCTACGCCTG-3'

DG131
                                        (SEQ ID NO: 28)
5'-GAGCCAATATGCGAGAACACCCGAGAA-3'
```

Figure 18:
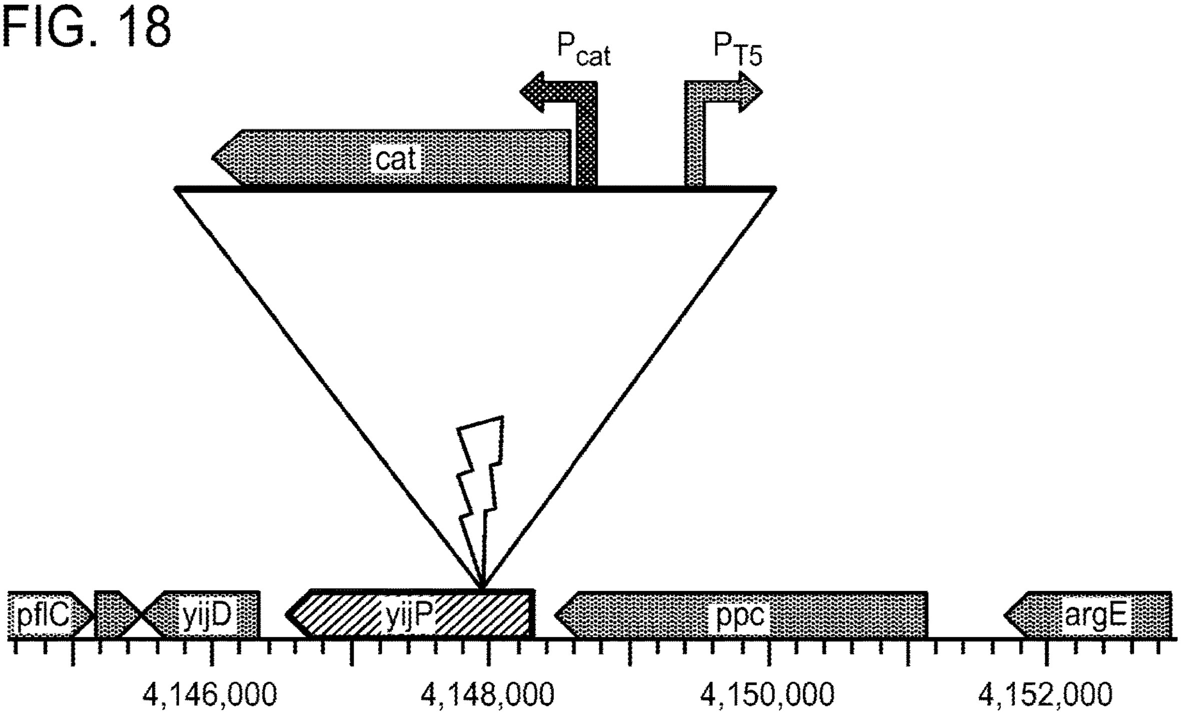
FIG. 18 is a diagrammatic depiction of a transposon cassette insertion in the yijP gene of strain LC535 (transposon hit 68F11). Promoters internal to the transposon cassette are shown, and may have effects on adjacent gene expression.

Strain LC535 was determined to have a transposon insertion in the yijP gene (FIG. 18). yijP encodes a conserved inner membrane protein whose function is unclear. The yijP gene is in an operon and co-transcribed with the ppc gene, encoding phosphoenolpyruvate carboxylase, and the yijO gene, encoding a predicted DNA-binding transcriptional regulator of unknown function. Promoters internal to the transposon likely have effects on the level and timing of transcription of yijP, ppc and yijO, and may also have effects on adjacent genes frwD, pflC, pfld, and argE. Promoters internal to the transposon cassette are shown in FIG. 18, and may have effects on adjacent gene expression. Strain LC535 was evaluated in a fed-batch fermentation on two different dates. Both fermentations demonstrated that LC535 produced fatty alcohols with a higher yield than control SL313, and the improvement was 1.3-1.9% absolute yield based on carbon input. The yijP transposon cassette was further evaluated in a different strain V940, which produces fatty alcohol at a higher yield than strain SL313. The yijP::Tn5-cat cassette was amplified from strain LC535 using primers:

```
LC277
                                        (SEQ ID NO: 29)
5'-CGCTGAACGTATTGCAGGCCGAGTTGCTGCACCGCTCCCGCCAGGC
AG-3'

LC278
                                        (SEQ ID NO: 30)
5'-GGAATTGCCACGGTGCGGCAGGCTCCATACGCGAGGCCAGGTTATC
CAACG-3'
```

This linear DNA was electroporated into strain SL571 and integrated into the chromosome using the lambda red recombination system. Colonies were screened using primers outside the transposon region:

```
DG407
                                        (SEQ ID NO: 31)
5'-AATCACCAGCACTAAAGTGCGCGGTTCGTTACCCG-3'

DG408
                                        (SEQ ID NO: 32)
5'-ATCTGCCGTGGATTGCAGAGTCTATTCAGCTACG-3'
```

A colony with the correct yijP transposon cassette was transformed with the production plasmid pV171.1 to produce strain D851. D851 was tested in a shake-flask fermentation against strain V940 that does not contain the yijP transposon cassette. The result of this fermentation showed that the yijP transposon cassette confers production of a higher percent of fatty alcohol by the D851 strain relative to the V940 strain and produces similar titers of total fatty species as the V940 control strain. Strain D851 was evaluated in a fed-batch fermentation on two different dates. Data from these fermentations is shown in Table 9 which illustrates that in 5-liter fed-batch fermentations, strains with the yijP::Tn5-cat transposon insertion had an increased total fatty species ("FAS") yield and an increase in percent fatty alcohol ("FALC"). The terms "total fatty species" and "total fatty acid product" may be used interchangeably herein with reference to the amount of fatty alcohols, fatty aldehydes and free fatty acids, as evaluated by GC-FID as described in International Patent Application Publication WO 2008/119082. The same terms may be used to mean fatty esters and free fatty acids when referring to a fatty ester analysis. As used herein, the term "fatty esters" includes beta hydroxy esters.

TABLE 9

| Effect of yijP transposon insertion on titer and yield of FAS and FALC | | | | |
|---|---|---|---|---|
| Strain | FAS Titer | FAS Yield | Percent FALC | FALC Yield |
| V940 | 68 g/L | 18.7% | 95.0% | 17.8% |
| D851 | 70 g/L | 19.4% | 96.1% | 18.6% |
| V940 | 64 g/L | 18.4% | 91.9% | 16.9% |
| D851 | 67 g/L | 19.0% | 94.0% | 17.8% |

Tank Fermentation Method:

To assess production of fatty acid and fatty acid derivatives in tank a glycerol vial of desired strain was used to inoculate 20 mL LB+spectinomycin in shake flask and incubated at 32° C. for approximately six hours. 4 mL of LB culture was used to inoculate 125 mL Low PFA Seed Media (below), which was then incubated at 32° C. shaker overnight. 50 mL of the overnight culture was used to inoculate 1 L of Tank Media. Tanks were run at pH 7.2 and 30.5° C. under pH stat conditions with a maximum feed rate of 16 g/L/hr glucose.

TABLE 10

| Low P FA Seed Media: | |
|---|---|
| Component | Concentration |
| $NH_4Cl$ | 2 g/L |
| NaCl | 0.5 g/L |
| $KH_2PO_4$ | 1 g/L |
| $MgSO_4$—$7H_2O$ | 0.25 g/L |
| $CaCl_2$—$2H_2O$ | 0.015 g/L |
| Glucose | 20 g/L |
| TM2 Trace Minerals solution | 1 mL/L |
| Ferric citrate | 10 mg/L |
| Bis Tris buffer (pH 7.0) | 100 mM |
| Spectinomycin | 115 mg/L |

TABLE 11

| Tank Media | |
|---|---|
| Component | Concentration |
| $(NH_4)_2SO_4$ | 0.5 g/L |
| $KH_2PO_4$ | 3.0 g/L |
| Ferric Citrate | 0.034 g/L |
| TM2 Trace Minerals Solution | 10 mL/L |
| Casamino acids | 5 g/L |
| Post sterile additions | |
| $MgSO_4$—$7H_2O$ | 2.2 g/L |
| Trace Vitamins Solution | 1.25 mL/L |
| Glucose | 5 g/L |
| Inoculum | 50 mL/L |

Further studies suggest that the improved titer and yield of FAS and FALC in strains with the yijP transposon insertion is due to reduction in the activity of phosphoenolpyruvate carboxylase (ppc). A ppc enzyme assay was carried out in-vitro in the following strains to evaluate this hypothesis.

1) Δppc=DG14 (LC942 Δppc::cat-sacB/pLC56)
2) wt-ppc=DG16 (LC942/pLC56)
3) yijP::Tn5=DG18 (LC942 yijP::Tn5-cat/pLC56)

Ppc activity was measured in cells grown in a shake flask fermentation using a standard shake flask protocol in FA2.3 media (described above) and harvested 12-16 hours after induction. Approximately 5 mL of cells were centrifuged and the cell paste was suspended in BugBuster Protein Extraction Reagent (Novagen) with a protease inhibitor cocktail solution. The cell suspension was incubated with gentle shaking on a shaker for 20 min. Insoluble cell debris was removed by centrifugation at 16,000×g for 20 min at 4° C. followed by transferring the supernatant to a new tube. Ppc activity in the cell lysate was determined by a coupling reaction with citrate synthase using following reaction mixture: 0.4 mM acetyl-CoA, 10 mM phosphoenolpyruvate, 0.5 mM monobromobimane, 5 mM $MgCl_2$, 10 mM $NaHCO_3$, and 10 units citrate synthase from porcine heart in 100 mM Tris-HCl (pH 8.0). The formation of CoA in the reaction with citrate synthase using oxaloacetate and acetyl-CoA was monitored photometrically using fluorescent derivatization of CoA with monobromobimane. The Ppc assay results showed that the yijP::Tn5-cat transposon cassette decreased the Ppc activity in the cell by 2.7 fold compared to wild type cells. The cells with deletion of ppc did not grow well and the activity was about 10 times lower than wild type cells. The results also indicate that the highest yield of fatty alcohol production requires a level of Ppc expression lower than the wild-type level. Proteomics data was also collected to assess the abundance of the Ppc protein in two strains with and without the yijP::Tn5-cat transposon cassette. Protein samples were collected from strains V940 and D851 grown in bioreactors under standard fatty alcohol production conditions (described above). Samples were taken at two different time points: 32 and 48 hours and prepared for analysis.

Sample collection and protein isolation was carried out as follows:

20 ml of fermentation broth were collected from each bioreactor at each time point. Samples were quenched with ice-cold PBS and harvested by centrifugation (4500 rpm/10 min) at 4° C. Cell pellet was washed with ice-cold PBS and centrifuged one more time and stored at −80° C. for further processing.

Total protein extraction was performed using a French press protocol. Briefly, cell pellets were resuspended in 7 ml of ice-cold PBS and French pressed at 2000 psi twice to ensure complete lysing of the bacteria. Samples were centrifuged for 20 min at 10000 rpm at 4° C. to separate non-lysed cells and cell debris from the protein fraction. Total protein concentration of clear lysate was determined using BCA Protein Assay Reagent. Samples were diluted to 2 mg proteins/ml concentration and frozen at −80° C.

Samples were resuspended in the appropriate buffer and trypsinized overnight at 37° C. and lyophilized. Fragmented protein samples were labeled with isotopically enriched methylpiperazine acetic acid at room temperature for 30 min. Labeled samples were separated using cation exchange liquid chromatography and subjected to mass spectroscopy analysis using an ion trap mass spectrometer. Raw data was normalized using background subtraction and bias correction.

Proteomics data showed a significant reduction in the relative abundance of Ppc protein in D851 strain when compared to V940 at 32 hours and 48 hours. D851 had about 15% of the Ppc levels of V940 at 32 hours and about 35% of the Ppc levels of V940 at 48 hours. These data show that the yijP::Tn5-cat transposon cassette results in a significant reduction in Ppc abundance in the cell. This suggests that the observed benefits to fatty alcohol production by strains harboring the yijP::Tn5-cat transposon hit is due to reducing the amount of Ppc protein.

These results suggest that altering ppc activity can improve the yield of fatty acid derivatives. There are a number of ways to alter the expression of the ppc gene, and the yijP transposon insertion is one way to accomplish this. Without wanting to be bound by theory, if the effect of reducing phosphoenolpyruvate carboxylase activity is to limit the flow of carbon through the TCA cycle, one could achieve similar results by decreasing the activity of citrate synthase (gltA) or slowing the TCA cycle by decreasing the activity of any of the enzymes involved in the TCA cycle.

Example 6

Increased Flux through the Fatty Acid Synthesis Pathway—Acyl Carrier Protein (ACP) Mediated Fatty Alcohol Production When terminal pathway enzymes from sources other than *E. coli* are expressed in *E. coli* as the heterologous host to convert fatty acyl-ACPs to products, limitations may exist in the recognition, affinity and/or turnover of the recombinant pathway enzyme towards the *E. coli* fatty acyl-ACPs. Note that although ACP proteins are conserved to some extent in all organisms, their primary sequence can differ significantly. To test this hypothesis the acp genes from several cyanobacteria were cloned downstream from the *Synechococcus elongatus* PCC7942 acyl-ACP reductase (AAR) present in pLS9-185, which is a pCL1920 derivative. In addition, the sfp gene (Accession no. X63158; SEQ ID NO: 53) from *Bacillus subtilis*, encoding a phosphopantetheinyl transferase with broad substrate specificity, was cloned downstream of the respective acp genes. This enzyme is involved in conversion of the inactive apo-ACP to the active holo-ACP. The plasmids constructed are described in Table 12.

TABLE 12

Plasmids Coexpressing Cyanobacterial ACP with and without *B. subtilis* sfp Downstream from *S. elongatus* PCC7942 AAR

| Base plasmid | ACP Source | ACP SEQ ID NO. (DNA/Polypeptide) | Without sfp | With sfp |
|---|---|---|---|---|
| pLS9-185 | *Synechococcus elongatus* 7942 | 49/50 | pDS168 | pDS168S |
| pLS9-185 | *Synechocystis* sp. 6803 | 45/46 | pDS169 | not available |
| pLS9-185 | *Prochlorococcus marinus* MED4 | 47/48 | pDS170 | pDS170S |
| pLS9-185 | *Nostoc punctiforme* 73102 | 43/44 | pDS171 | pDS171S |
| pLS9-185 | *Nostoc* sp. 7120 | 51/52 | pDS172 | pDS172S |

Figure 19:
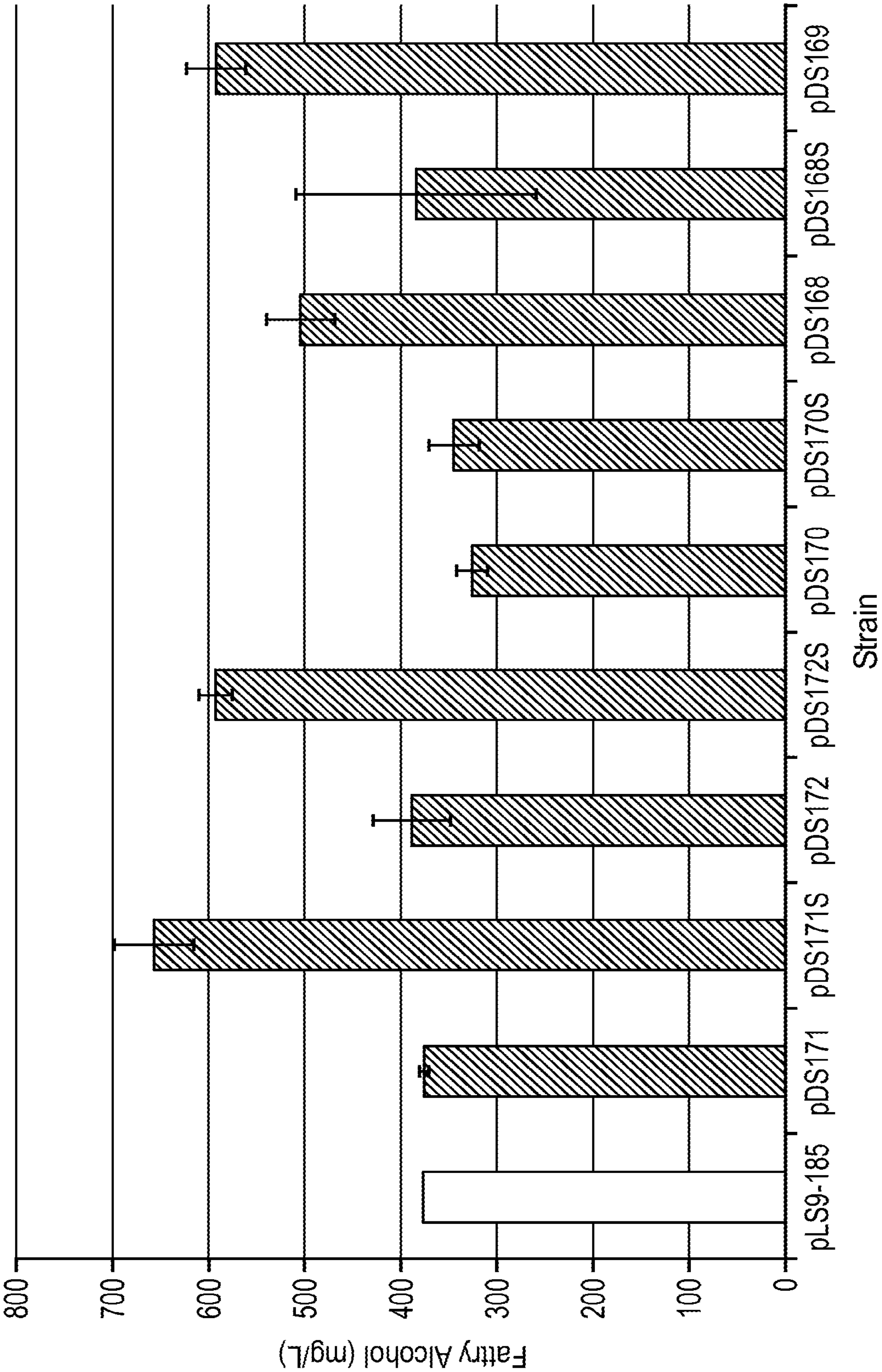
FIG. 19 illustrates fatty alcohol production in *E. coli* DV2 expressing *Synechococcus elongatus* acyl-ACP reductase (AAR) and coexpressing various cyanobacterial acyl carrier proteins (ACPs). Details regarding the source of the ACPs are provided in Table 12.

All the acp genes were cloned with a synthetic RBS into the EcoRI site immediately downstream of the aar gene in pLS9-185 using InFusion technology (Clontech Laboratories, Inc., Mountain View, Calif.). The EcoRI site was reconstructed downstream of the acp gene. Similarly, the *B. subtilis* sfp gene was InFusion cloned into this EcoRI site along with a synthetic RBS. All plasmids were transformed into *E. coli* MG1655 DV2 (Table 3). The control for these experiments was the expression of AAR alone (pLS9-185). The results from standard shake flask fermentation experiments are shown in FIG. 19. Significant improvement in fatty alcohol titers were observed in strains containing the plasmids pDS171S, pDS172S, pDS168 and pDS169 demonstrating that ACP overexpression can be beneficial for fatty alcohol production, in this case presumably by aiding in the recognition, affinity and/or turnover of acyl-ACPs by the heterologous terminal pathway enzyme. (See Table 12 for the source of the ACPs and presence or absence of sfp).

Figure 20:
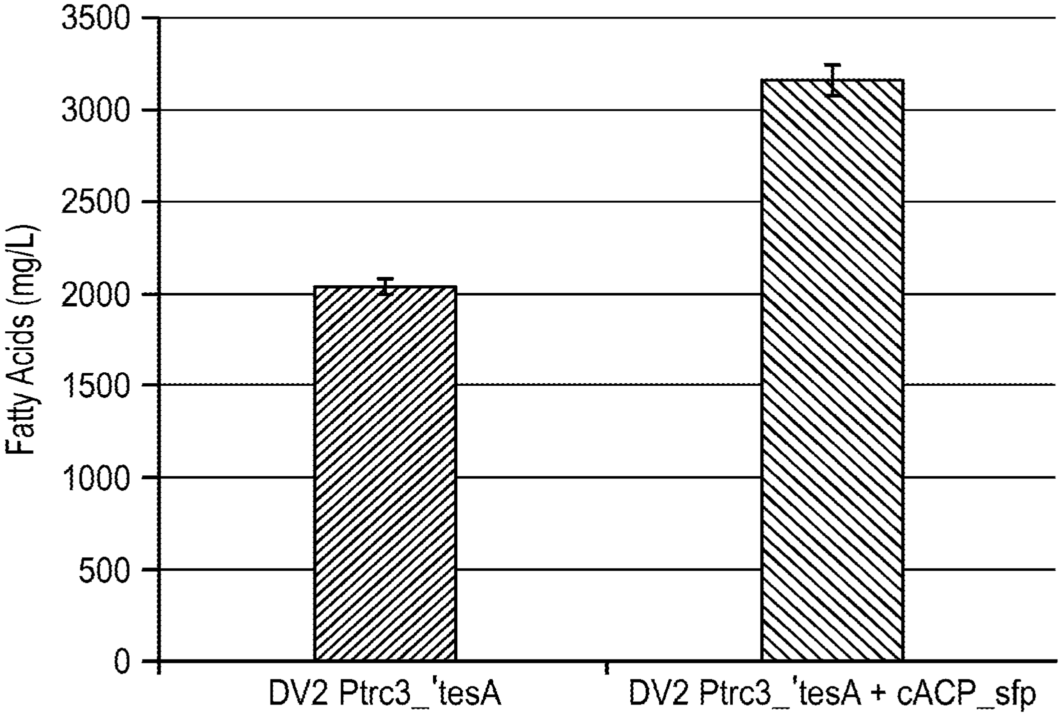
FIG. 20 illustrates fatty acid production in *E. coli* DV2 expressing leaderless *E. coli* thioesterase 'tesA and coexpressing a cyanobacterial acyl carrier protein (cACP) and *B. subtilis* sfp.

Fatty Acid Production:

In order to evaluate if the overexpression of an ACP can also increase free fatty acid production, one cyanobacterial ACP gene with sfp was amplified from pDS171s (Table 12) and cloned downstream from 'tesA into a pCL vector. The resulting operon was under the control of the Ptrc3 promoter, which provides slightly lower transcription levels than the Ptrc wildtype promoter. The construct was cloned into *E. coli* DV2 and evaluated for fatty acid production. The control strain contained the identical plasmid but without cyanobacterial ACP and *B. subtilis* sfp. The results from a standard microtiter plate fermentation experiment are shown in FIG. 20. Significant improvement in fatty acid titer was observed in the strain coexpressing the heterologous ACP demonstrating that ACP overexpression can be beneficial for fatty acid production, in this case presumably by increasing the flux through the fatty acid biosynthetic pathway.

We claim:

1. A recombinant host cell comprising a transposon insertion in a yijP gene, wherein the yijP gene is flanked by a gene encoding a phosphoenolpyruvate carboxylase (ppc) polypeptide, and wherein the transposon insertion down-regulates the ppc gene, and wherein the recombinant host cell further expresses an exogenous polynucleotide encoding a thioesterase, wherein said recombinant host cell produces a fatty acid derivative composition at a higher titer, yield or productivity than a corresponding wild type host cell when cultured in a medium containing a carbon source under conditions effective to express said ppc polypeptide.

2. A cell culture comprising the recombinant host cell according to claim 1.

3. The cell culture of claim 2, wherein the fatty acid derivative is a) a C6, C8, C10, C12, C13, C14, C15, C16, C17, or C18 fatty acid derivative, or b) a C10:1, C12:1, C14:1, C16:1, or C18:1 unsaturated fatty acid derivative.

4. The cell culture of claim 2, wherein said recombinant host cell produces a fatty acid derivative yield that is at least about 5% greater than that of said corresponding wild type host cell when cultured under the same conditions as the recombinant host cell.

5. The cell culture of claim 4, wherein said titer is from about 1 g/L to about 70 g/L.

6. The cell culture of claim 2, wherein said recombinant host cell produces a fatty acid derivative yield that is at least about 10% to about 40% greater than that of said corresponding wild type host cell when cultured under the same conditions as the recombinant host cell.

7. The cell culture of claim 2, wherein said productivity ranges from about 0.7 mg/L/hr to about 3 g/L/hr.

8. The cell culture of claim 2, wherein said cell culture comprises a fatty acid derivative composition.

9. The cell culture of claim 8, wherein the fatty acid derivative composition comprises at least one fatty acid derivative selected from the group consisting of fatty acid, a fatty ester, a fatty alcohol, a fatty aldehyde, an alkane, a terminal olefin, an internal olefin, and a ketone.

10. The cell culture of claim 8, wherein the fatty acid derivative composition comprises:

a) one or more of C8, C10, C12, C14, C16, and C18 fatty acid derivatives, b) fatty acids, c) fatty aldehydes, d) fatty alcohols, e) fatty esters, f) alkanes, g) terminal olefins, h) internal olefins, or i) ketones.

11. The cell culture of claim 8, wherein the fatty acid derivative composition comprises fatty acid derivatives having a double bond at position 7 in the carbon chain between C7 and C8 from the reduced end of a fatty alcohol.

12. The cell culture of claim 8, wherein the fatty acid derivative composition comprises unsaturated fatty acid derivatives.

13. The cell culture of claim 8, wherein the fatty acid derivative composition comprises saturated fatty acid derivatives.

14. The cell culture of claim 8, wherein the fatty acid derivative composition comprises branched chain fatty acid derivatives.

* * * * *

SEQUENCE LISTING

```
<160> NUMBER OF SEQ ID NOS: 64

<210> SEQ ID NO 1
<211> LENGTH: 1232
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 1

ttgtccatct ttatataatt tgggggtagg gtgttcttta tgtaaaaaaa acgttttagg      60

atgcatatgg cggccgcata acttcgtata gcatacatta tacgaagtta tctagagttg     120
```

catgcctgca ggtccgctta ttatcactta ttcaggcgta gcaaccaggc gtttaagggc 180
accaataact gccttaaaaa aattacgccc cgccctgcca ctcatcgcag tactgttgta 240
attcattaag cattctgccg acatggaagc catcacaaac ggcatgatga acctgaatcg 300
ccagcggcat cagcaccttg tcgccttgcg tataatattt gcccatggtg aaaacggggg 360
cgaagaagtt gtccatattg gccacgttta aatcaaaact ggtgaaactc acccagggat 420
tggctgagac gaaaaacata ttctcaataa accctttagg gaaataggcc aggttttcac 480
cgtaacacgc cacatcttgc gaatatatgt gtagaaactg ccggaaatcg tcgtggtatt 540
cactccagag cgatgaaaac gtttcagttt gctcatggaa aacggtgtaa caagggtgaa 600
cactatccca tatcaccagc tcaccgtctt tcattgccat acggaattcc ggatgagcat 660
tcatcaggcg ggcaagaatg tgaataaagg ccggataaaa cttgtgctta tttttcttta 720
cggtctttaa aaaggccgta atatccagct gaacggtctg gttataggta cattgagcaa 780
ctgactgaaa tgcctcaaaa tgttctttac gatgccattg ggatatatca acggtggtat 840
atccagtgat ttttttctcc attttagctt ccttagctcc tgaaaatctc gataactcaa 900
aaaatacgcc cggtagtgat cttatttcat tatggtgaaa gttggaacct cttacgtgcc 960
gatcaacgtc tcattttcgc caaaagttgg cccagggctt cccggtatca acagggacac 1020
caggatttat ttattctgcg aagtgatctt ccgtcacagg tatttattcg actctagata 1080
acttcgtata gcatacatta tacgaagtta tggatccagc ttatcgatac cgtcaaacaa 1140
atcataaaaa atttatttgc tttcaggaaa atttttctgt ataatagatt caattgcgat 1200
gacgacgaac acgcacctgc aggaggagac ca 1232

<210> SEQ ID NO 2
<211> LENGTH: 232
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 2
ttgtccatct ttatataatt tgggggtagg gtgttcttta tgtaaaaaaa acgttttagg 60
atgcatatgg cggccgcata acttcgtata gcatacatta tacgaagtta tggatccagc 120
ttatcgatac cgtcaaacaa atcataaaaa atttatttgc tttcaggaaa atttttctgt 180
ataatagatt caattgcgat gacgacgaac acgcacctgc aggaggagac ca 232

<210> SEQ ID NO 3
<211> LENGTH: 340
<212> TYPE: PRT
<213> ORGANISM: Acinetobacter sp.

<400> SEQUENCE: 3

Met Ser Asn His Gln Ile Arg Ala Tyr Ala Ala Met Gln Ala Gly Glu
1 5 10 15

Gln Val Val Pro Tyr Gln Phe Asp Ala Gly Glu Leu Lys Ala His Gln
20 25 30

Val Glu Val Lys Val Glu Tyr Cys Gly Leu Cys His Ser Asp Leu Ser
35 40 45

Val Ile Asn Asn Glu Trp Gln Ser Ser Val Tyr Pro Ala Val Ala Gly
50 55 60

-continued

```
His Glu Ile Ile Gly Thr Ile Ile Ala Leu Gly Ser Glu Ala Lys Gly
65                  70                  75                  80

Leu Lys Leu Gly Gln Arg Val Gly Ile Gly Trp Thr Ala Glu Thr Cys
                85                  90                  95

Gln Ala Cys Asp Pro Cys Ile Gly Gly Asn Gln Val Leu Cys Thr Gly
            100                 105                 110

Glu Lys Lys Ala Thr Ile Ile Gly His Ala Gly Gly Phe Ala Asp Lys
        115                 120                 125

Val Arg Ala Gly Trp Gln Trp Val Ile Pro Leu Pro Asp Asp Leu Asp
    130                 135                 140

Pro Glu Ser Ala Gly Pro Leu Leu Cys Gly Gly Ile Thr Val Leu Asp
145                 150                 155                 160

Pro Leu Leu Lys His Lys Ile Gln Ala Thr His His Val Gly Val Ile
                165                 170                 175

Gly Ile Gly Gly Leu Gly His Ile Ala Ile Lys Leu Leu Lys Ala Trp
            180                 185                 190

Gly Cys Glu Ile Thr Ala Phe Ser Ser Asn Pro Asp Lys Thr Glu Glu
        195                 200                 205

Leu Lys Ala Asn Gly Ala Asp Gln Val Val Asn Ser Arg Asp Ala Gln
    210                 215                 220

Ala Ile Lys Gly Thr Arg Trp Lys Leu Ile Ile Leu Ser Thr Ala Asn
225                 230                 235                 240

Gly Thr Leu Asn Val Lys Ala Tyr Leu Asn Thr Leu Ala Pro Lys Gly
                245                 250                 255

Ser Leu His Phe Leu Gly Val Thr Leu Glu Pro Ile Pro Val Ser Val
            260                 265                 270

Gly Ala Ile Met Gly Gly Ala Lys Ser Val Thr Ser Ser Pro Thr Gly
        275                 280                 285

Ser Pro Leu Ala Leu Arg Gln Leu Leu Gln Phe Ala Ala Arg Lys Asn
    290                 295                 300

Ile Ala Pro Gln Val Glu Leu Phe Pro Met Ser Gln Leu Asn Glu Ala
305                 310                 315                 320

Ile Glu Arg Leu His Ser Gly Gln Ala Arg Tyr Arg Ile Val Leu Lys
                325                 330                 335

Ala Asp Phe Asp
            340
```

<210> SEQ ID NO 4
<211> LENGTH: 314
<212> TYPE: PRT
<213> ORGANISM: Acinetobacter sp.

<400> SEQUENCE: 4

```
Met Ala Thr Thr Asn Val Ile His Ala Tyr Ala Ala Met Gln Ala Gly
1               5                   10                  15

Glu Ala Leu Val Pro Tyr Ser Phe Asp Ala Gly Glu Leu Gln Pro His
            20                  25                  30

Gln Val Glu Val Lys Val Glu Tyr Cys Gly Leu Cys His Ser Asp Val
        35                  40                  45

Ser Val Leu Asn Asn Glu Trp His Ser Ser Val Tyr Pro Val Val Ala
    50                  55                  60

Gly His Glu Val Ile Gly Thr Ile Thr Gln Leu Gly Ser Glu Ala Lys
65                  70                  75                  80

Gly Leu Lys Ile Gly Gln Arg Val Gly Ile Gly Trp Thr Ala Glu Ser
                85                  90                  95
```

```
Cys Gln Ala Cys Asp Gln Cys Ile Ser Gly Gln Gln Val Leu Cys Thr
            100                 105                 110

Gly Glu Asn Thr Ala Thr Ile Ile Gly His Ala Gly Gly Phe Ala Asp
        115                 120                 125

Lys Val Arg Ala Gly Trp Gln Trp Val Ile Pro Leu Pro Asp Glu Leu
    130                 135                 140

Asp Pro Thr Ser Ala Gly Pro Leu Leu Cys Gly Gly Ile Thr Val Phe
145                 150                 155                 160

Asp Pro Ile Leu Lys His Gln Ile Gln Ala Ile His His Val Ala Val
                165                 170                 175

Ile Gly Ile Gly Gly Leu Gly His Met Ala Ile Lys Leu Leu Lys Ala
            180                 185                 190

Trp Gly Cys Glu Ile Thr Ala Phe Ser Ser Asn Pro Asn Lys Thr Asp
        195                 200                 205

Glu Leu Lys Ala Met Gly Ala Asp His Val Val Asn Ser Arg Asp Asp
    210                 215                 220

Ala Glu Ile Lys Ser Gln Gln Gly Lys Phe Asp Leu Leu Leu Ser Thr
225                 230                 235                 240

Val Asn Val Pro Leu Asn Trp Asn Ala Tyr Leu Asn Thr Leu Ala Pro
                245                 250                 255

Asn Gly Thr Phe His Phe Leu Gly Val Val Met Glu Pro Ile Pro Val
            260                 265                 270

Pro Val Gly Ala Leu Leu Gly Gly Ala Lys Ser Leu Thr Ala Ser Pro
        275                 280                 285

Thr Gly Ser Pro Ala Ala Leu Arg Lys Leu Leu Glu Phe Ala Ala Arg
    290                 295                 300

Lys Asn Ile Ala Pro Gln Ile Glu Met Tyr
305                 310
```

<210> SEQ ID NO 5
<211> LENGTH: 1020
<212> TYPE: DNA
<213> ORGANISM: Escherichia coli

<400> SEQUENCE: 5

```
atgtcgatga taaaaagcta tgccgcaaaa gaagcgggcg gcgaactgga agtttatgag      60

tacgatcccg gtgagctgag gccacaagat gttgaagtgc aggtggatta ctgcgggatc     120

tgccattccg atctgtcgat gatcgataac gaatggggat tttcacaata tccgctggtt     180

gccgggcatg aggtgattgg gcgcgtggtg gcactcggga gcgccgcgca ggataaaggt     240

ttgcaggtcg gtcagcgtgt cgggattggc tggacggcgc gtagctgtgg tcactgcgac     300

gcctgtatta gcggtaatca gatcaactgc gagcaaggtg cggtgccgac gattatgaat     360

cgcggtggct ttgccgagaa gttgcgtgcg gactggcaat gggtgattcc actgccagaa     420

aatattgata tcgagtccgc cgggccgctg ttgtgcggcg gtatcacggt ctttaaacca     480

ctgttgatgc accatatcac tgctaccagc cgcgttgggg taattggtat tggcgggctg     540

gggcatatcg ctataaaact tctgcacgca atgggatgcg aggtgacagc ctttagttct     600

aatccggcga aagagcagga agtgctggcg atgggtgccg ataaagtggt gaatagccgc     660

gatccgcagg cactgaaagc actggcgggg cagtttgatc tcattatcaa caccgtcaac     720

gtcagcctcg actggcagcc ctattttgag gcgctgacct atggcggtaa tttccatacg     780

gtcggtgcgg ttctcacgcc gctgtctgtt ccggccttta cgttaattgc gggcgatcgc     840
```

-continued

```
agcgtctctg gttctgctac cggcacgcct tatgagctgc gtaagctgat gcgttttgcc    900

gcccgcagca aggttgcgcc gaccaccgaa ctgttcccga tgtcgaaaat taacgacgcc    960

atccagcatg tgcgcgacgg taaggcgcgt taccgcgtgg tgttgaaagc cgatttttga   1020


<210> SEQ ID NO 6
<211> LENGTH: 473
<212> TYPE: PRT
<213> ORGANISM: Marinobacter hydrocarbonoclasticus

<400> SEQUENCE: 6

Met Lys Arg Leu Gly Thr Leu Asp Ala Ser Trp Leu Ala Val Glu Ser
1               5                   10                  15

Glu Asp Thr Pro Met His Val Gly Thr Leu Gln Ile Phe Ser Leu Pro
            20                  25                  30

Glu Gly Ala Pro Glu Thr Phe Leu Arg Asp Met Val Thr Arg Met Lys
        35                  40                  45

Glu Ala Gly Asp Val Ala Pro Pro Trp Gly Tyr Lys Leu Ala Trp Ser
    50                  55                  60

Gly Phe Leu Gly Arg Val Ile Ala Pro Ala Trp Lys Val Asp Lys Asp
65                  70                  75                  80

Ile Asp Leu Asp Tyr His Val Arg His Ser Ala Leu Pro Arg Pro Gly
                85                  90                  95

Gly Glu Arg Glu Leu Gly Ile Leu Val Ser Arg Leu His Ser Asn Pro
            100                 105                 110

Leu Asp Phe Ser Arg Pro Leu Trp Glu Cys His Val Ile Glu Gly Leu
        115                 120                 125

Glu Asn Asn Arg Phe Ala Leu Tyr Thr Lys Met His His Ser Met Ile
    130                 135                 140

Asp Gly Ile Ser Gly Val Arg Leu Met Gln Arg Val Leu Thr Thr Asp
145                 150                 155                 160

Pro Glu Arg Cys Asn Met Pro Pro Pro Trp Thr Val Arg Pro His Gln
                165                 170                 175

Arg Arg Gly Ala Lys Thr Asp Lys Glu Ala Ser Val Pro Ala Ala Val
            180                 185                 190

Ser Gln Ala Met Asp Ala Leu Lys Leu Gln Ala Asp Met Ala Pro Arg
        195                 200                 205

Leu Trp Gln Ala Gly Asn Arg Leu Val His Ser Val Arg His Pro Glu
    210                 215                 220

Asp Gly Leu Thr Ala Pro Phe Thr Gly Pro Val Ser Val Leu Asn His
225                 230                 235                 240

Arg Val Thr Ala Gln Arg Arg Phe Ala Thr Gln His Tyr Gln Leu Asp
                245                 250                 255

Arg Leu Lys Asn Leu Ala His Ala Ser Gly Gly Ser Leu Asn Asp Ile
            260                 265                 270

Val Leu Tyr Leu Cys Gly Thr Ala Leu Arg Arg Phe Leu Ala Glu Gln
        275                 280                 285

Asn Asn Leu Pro Asp Thr Pro Leu Thr Ala Gly Ile Pro Val Asn Ile
    290                 295                 300

Arg Pro Ala Asp Asp Glu Gly Thr Gly Thr Gln Ile Ser Phe Met Ile
305                 310                 315                 320

Ala Ser Leu Ala Thr Asp Glu Ala Asp Pro Leu Asn Arg Leu Gln Gln
                325                 330                 335

Ile Lys Thr Ser Thr Arg Arg Ala Lys Glu His Leu Gln Lys Leu Pro
            340                 345                 350
```

Lys Ser Ala Leu Thr Gln Tyr Thr Met Leu Leu Met Ser Pro Tyr Ile
355 360 365

Leu Gln Leu Met Ser Gly Leu Gly Gly Arg Met Arg Pro Val Phe Asn
370 375 380

Val Thr Ile Ser Asn Val Pro Gly Pro Glu Gly Thr Leu Tyr Tyr Glu
385 390 395 400

Gly Ala Arg Leu Glu Ala Met Tyr Pro Val Ser Leu Ile Ala His Gly
405 410 415

Gly Ala Leu Asn Ile Thr Cys Leu Ser Tyr Ala Gly Ser Leu Asn Phe
420 425 430

Gly Phe Thr Gly Cys Arg Asp Thr Leu Pro Ser Met Gln Lys Leu Ala
435 440 445

Val Tyr Thr Gly Glu Ala Leu Asp Glu Leu Glu Ser Leu Ile Leu Pro
450 455 460

Pro Lys Lys Arg Ala Arg Thr Arg Lys
465 470

<210> SEQ ID NO 7
<211> LENGTH: 455
<212> TYPE: PRT
<213> ORGANISM: Marinobacter hydrocarbonoclasticus

<400> SEQUENCE: 7

Met Thr Pro Leu Asn Pro Thr Asp Gln Leu Phe Leu Trp Leu Glu Lys
1 5 10 15

Arg Gln Gln Pro Met His Val Gly Gly Leu Gln Leu Phe Ser Phe Pro
20 25 30

Glu Gly Ala Pro Asp Asp Tyr Val Ala Gln Leu Ala Asp Gln Leu Arg
35 40 45

Gln Lys Thr Glu Val Thr Ala Pro Phe Asn Gln Arg Leu Ser Tyr Arg
50 55 60

Leu Gly Gln Pro Val Trp Val Glu Asp Glu His Leu Asp Leu Glu His
65 70 75 80

His Phe Arg Phe Glu Ala Leu Pro Thr Pro Gly Arg Ile Arg Glu Leu
85 90 95

Leu Ser Phe Val Ser Ala Glu His Ser His Leu Met Asp Arg Glu Arg
100 105 110

Pro Met Trp Glu Val His Leu Ile Glu Gly Leu Lys Asp Arg Gln Phe
115 120 125

Ala Leu Tyr Thr Lys Val His His Ser Leu Val Asp Gly Val Ser Ala
130 135 140

Met Arg Met Ala Thr Arg Met Leu Ser Glu Asn Pro Asp Glu His Gly
145 150 155 160

Met Pro Pro Ile Trp Asp Leu Pro Cys Leu Ser Arg Asp Arg Gly Glu
165 170 175

Ser Asp Gly His Ser Leu Trp Arg Ser Val Thr His Leu Leu Gly Leu
180 185 190

Ser Asp Arg Gln Leu Gly Thr Ile Pro Thr Val Ala Lys Glu Leu Leu
195 200 205

Lys Thr Ile Asn Gln Ala Arg Lys Asp Pro Ala Tyr Asp Ser Ile Phe
210 215 220

His Ala Pro Arg Cys Met Leu Asn Gln Lys Ile Thr Gly Ser Arg Arg
225 230 235 240

Phe Ala Ala Gln Ser Trp Cys Leu Lys Arg Ile Arg Ala Val Cys Glu

-continued

```
                245                 250                 255

Ala Tyr Gly Thr Thr Val Asn Asp Val Val Thr Ala Met Cys Ala Ala
            260                 265                 270

Ala Leu Arg Thr Tyr Leu Met Asn Gln Asp Ala Leu Pro Glu Lys Pro
        275                 280                 285

Leu Val Ala Phe Val Pro Val Ser Leu Arg Arg Asp Asp Ser Ser Gly
    290                 295                 300

Gly Asn Gln Val Gly Val Ile Leu Ala Ser Leu His Thr Asp Val Gln
305                 310                 315                 320

Asp Ala Gly Glu Arg Leu Leu Lys Ile His His Gly Met Glu Glu Ala
                325                 330                 335

Lys Gln Arg Tyr Arg His Met Ser Pro Glu Glu Ile Val Asn Tyr Thr
            340                 345                 350

Ala Leu Thr Leu Ala Pro Ala Ala Phe His Leu Leu Thr Gly Leu Ala
        355                 360                 365

Pro Lys Trp Gln Thr Phe Asn Val Val Ile Ser Asn Val Pro Gly Pro
    370                 375                 380

Ser Arg Pro Leu Tyr Trp Asn Gly Ala Lys Leu Glu Gly Met Tyr Pro
385                 390                 395                 400

Val Ser Ile Asp Met Asp Arg Leu Ala Leu Asn Met Thr Leu Thr Ser
                405                 410                 415

Tyr Asn Asp Gln Val Glu Phe Gly Leu Ile Gly Cys Arg Arg Thr Leu
            420                 425                 430

Pro Ser Leu Gln Arg Met Leu Asp Tyr Leu Glu Gln Gly Leu Ala Glu
        435                 440                 445

Leu Glu Leu Asn Ala Gly Leu
    450                 455


<210> SEQ ID NO 8
<211> LENGTH: 457
<212> TYPE: PRT
<213> ORGANISM: Alcanivorax borkumensis

<400> SEQUENCE: 8

Met Lys Ala Leu Ser Pro Val Asp Gln Leu Phe Leu Trp Leu Glu Lys
1               5                   10                  15

Arg Gln Gln Pro Met His Val Gly Gly Leu Gln Leu Phe Ser Phe Pro
            20                  25                  30

Glu Gly Ala Gly Pro Lys Tyr Val Ser Glu Leu Ala Gln Gln Met Arg
        35                  40                  45

Asp Tyr Cys His Pro Val Ala Pro Phe Asn Gln Arg Leu Thr Arg Arg
    50                  55                  60

Leu Gly Gln Tyr Tyr Trp Thr Arg Asp Lys Gln Phe Asp Ile Asp His
65                  70                  75                  80

His Phe Arg His Glu Ala Leu Pro Lys Pro Gly Arg Ile Arg Glu Leu
                85                  90                  95

Leu Ser Leu Val Ser Ala Glu His Ser Asn Leu Leu Asp Arg Glu Arg
            100                 105                 110

Pro Met Trp Glu Ala His Leu Ile Glu Gly Ile Arg Gly Arg Gln Phe
        115                 120                 125

Ala Leu Tyr Tyr Lys Ile His His Ser Val Met Asp Gly Ile Ser Ala
    130                 135                 140

Met Arg Ile Ala Ser Lys Thr Leu Ser Thr Asp Pro Ser Glu Arg Glu
145                 150                 155                 160
```

-continued

```
Met Ala Pro Ala Trp Ala Phe Asn Thr Lys Lys Arg Ser Arg Ser Leu
                165                 170                 175

Pro Ser Asn Pro Val Asp Met Ala Ser Ser Met Ala Arg Leu Thr Ala
            180                 185                 190

Ser Ile Ser Lys Gln Ala Ala Thr Val Pro Gly Leu Ala Arg Glu Val
        195                 200                 205

Tyr Lys Val Thr Gln Lys Ala Lys Lys Asp Glu Asn Tyr Val Ser Ile
    210                 215                 220

Phe Gln Ala Pro Asp Thr Ile Leu Asn Asn Thr Ile Thr Gly Ser Arg
225                 230                 235                 240

Arg Phe Ala Ala Gln Ser Phe Pro Leu Pro Arg Leu Lys Val Ile Ala
                245                 250                 255

Lys Ala Tyr Asn Cys Thr Ile Asn Thr Val Val Leu Ser Met Cys Gly
            260                 265                 270

His Ala Leu Arg Glu Tyr Leu Ile Ser Gln His Ala Leu Pro Asp Glu
        275                 280                 285

Pro Leu Ile Ala Met Val Pro Met Ser Leu Arg Gln Asp Asp Ser Thr
    290                 295                 300

Gly Gly Asn Gln Ile Gly Met Ile Leu Ala Asn Leu Gly Thr His Ile
305                 310                 315                 320

Cys Asp Pro Ala Asn Arg Leu Arg Val Ile His Asp Ser Val Glu Glu
                325                 330                 335

Ala Lys Ser Arg Phe Ser Gln Met Ser Pro Glu Glu Ile Leu Asn Phe
            340                 345                 350

Thr Ala Leu Thr Met Ala Pro Thr Gly Leu Asn Leu Leu Thr Gly Leu
        355                 360                 365

Ala Pro Lys Trp Arg Ala Phe Asn Val Val Ile Ser Asn Ile Pro Gly
    370                 375                 380

Pro Lys Glu Pro Leu Tyr Trp Asn Gly Ala Gln Leu Gln Gly Val Tyr
385                 390                 395                 400

Pro Val Ser Ile Ala Leu Asp Arg Ile Ala Leu Asn Ile Thr Leu Thr
                405                 410                 415

Ser Tyr Val Asp Gln Met Glu Phe Gly Leu Ile Ala Cys Arg Arg Thr
            420                 425                 430

Leu Pro Ser Met Gln Arg Leu Leu Asp Tyr Leu Glu Gln Ser Ile Arg
        435                 440                 445

Glu Leu Glu Ile Gly Ala Gly Ile Lys
    450                 455
```

<210> SEQ ID NO 9
<211> LENGTH: 70
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 9

```
aaaaacagca acaatgtgag ctttgttgta attatattgt aaacatattg attccgggga     60

tccgtcgacc                                                            70
```

<210> SEQ ID NO 10
<211> LENGTH: 68
<212> TYPE: DNA
<213> ORGANISM: Artificial Sequence
<220> FEATURE:

<221> NAME/KEY: source
<223> OTHER INFORMATION: /note="Description of Artificial Sequence: Synthetic oligonucleotide"

<400> SEQUENCE: 10
aaacggagcc tttcggctcc gttattcatt tacgcggctt caactttcct gtaggctgga 60
gctgcttc 68

<210> SEQ ID NO 11
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 11
cgggcaggtg ctatgaccag gac 23

<210> SEQ ID NO 12
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 12
cgcggcgttg accggcagcc tgg 23

<210> SEQ ID NO 13
<211> LENGTH: 60
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 13
ccttggcatt ggcaatttga gaattcgagg aggaaaacta aatgaccatt tcctcacctt 60

<210> SEQ ID NO 14
<211> LENGTH: 60
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 14
ttttgttcgg gcccaagctt ttattgcaaa cgcagatgcg tgatttcacc cgcattcagc 60

<210> SEQ ID NO 15
<211> LENGTH: 60
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 15
cgggcccaag cttcgaattc ttattgcaaa cgcagatgcg tgatttcacc cgcattcagc 60

-continued

<210> SEQ ID NO 16
<211> LENGTH: 60
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 16
gaatagcgcc gtcgacgagg aggaaaacta aatgaccatt tcctcacctt tgattgacgt 60

<210> SEQ ID NO 17
<211> LENGTH: 60
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 17
tgatgatgat gatggtcgac ttattgcaaa cgcagatgcg tgatttcacc cgcattcagc 60

<210> SEQ ID NO 18
<211> LENGTH: 4250
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 18
atgaccattt cctcaccttt gattgacgtc gccaaccttc cagacatcaa caccactgcc 60
ggcaagatcg ccgaccttaa ggctcgccgc gcggaagccc atttccccat gggtgaaaag 120
gcagtagaga aggtccacgc tgctggacgc ctcactgccc gtgagcgctt ggattactta 180
ctcgatgagg gctccttcat cgagaccgat cagctggctc gccaccgcac caccgctttc 240
ggcctgggcg ctaagcgtcc tgcaaccgac ggcatcgtga ccggctgggg caccattgat 300
ggacgcgaag tctgcatctt ctcgcaggac ggcaccgtat tcggtggcgc gcttggtgag 360
gtgtacggcg aaaagatgat caagatcatg gagctggcaa tcgacaccgg ccgcccattg 420
atcggtcttt acgaaggcgc tggcgctcgt attcaggacg gcgctgtctc cctggacttc 480
atttcccaga ccttctacca aaacattcag gcttctggcg ttatcccaca gatctccgtc 540
atcatgggcg catgtgcagg tggcaacgct tacggcccag ctctgaccga cttcgtggtc 600
atggtggaca agacctccaa gatgttcgtt accggcccag acgtgatcaa gaccgtcacc 660
ggcgaggaaa tcacccagga agagcttggc ggagcaacca cccacatggt gaccgctggt 720
aactcccact acaccgctgc gaccgatgag gaagcactgg attgggtaca ggacctggtg 780
tccttcctcc catccaacaa tcgctcctac gcaccgatgg aagacttcga cgaggaagaa 840
ggcggcgttg aagaaaacat caccgctgac gatctgaagc tcgacgagat catcccagat 900
tccgcgaccg ttccttacga cgtccgcgat gtcatcgaat gcctcaccga cgatggcgaa 960
tacctggaaa tccaggcaga ccgcgcagaa aacgttgtta ttgcattcgg ccgcatcgaa 1020
ggccagtccg ttggctttgt tgccaaccag ccaacccagt tcgctggctg cctggacatc 1080
gactcctctg agaaggcagc tcgcttcgtc cgcacctgcg acgcgttcaa catcccaatc 1140

-continued

```
gtcatgcttg tcgacgtccc cggcttcctc ccaggcgcag gccaggagta cggtggcatt   1200
ctgcgtcgtg gcgcaaagct gctctacgca tacggcgaag caaccgttcc aaagatcacc   1260
gtcaccatgc gtaaggctta cggcggagcg tactgcgtga tgggttccaa gggcttgggc   1320
tctgacatca accttgcatg gccaaccgca cagatcgccg tcatgggcgc tgctggcgca   1380
gttggattca tctaccgcaa ggagctcatg gcagctgatg ccaagggcct cgataccgta   1440
gctctggcta agtccttcga gcgcgagtat gaagaccaca tgctcaaccc gtaccacgct   1500
gcagaacgtg gcctgatcga cgccgtgatc ctgccaagcg aaacccgcgg acagatttcc   1560
cgcaaccttc gcctgctcaa gcacaagaac gtcactcgcc ctgctcgcaa gcacggcaac   1620
atgccactgt aaggaggaaa actaaatgtc agtcgagact cgcaagatca ccaaggttct   1680
tgtcgctaac cgtggtgaga ttgcaatccg cgtgttccgt gcagctcgag atgaaggcat   1740
cggatctgtc gccgtctacg cagagccaga tgcagatgca ccattcgtgt catatgcaga   1800
cgaggctttt gccctcggtg gccaaacatc cgctgagtcc taccttgtca ttgacaagat   1860
catcgatgcg gcccgcaagt ccggcgccga cgccatccac cccggctacg gcttcctcgc   1920
agaaaacgct gacttcgcag aagcagtcat caacgaaggc ctgatctgga ttggaccttc   1980
acctgagtcc atccgctccc tcggcgacaa ggtcaccgct cgccacatcg cagataccgc   2040
caaggctcca atggctcctg gcaccaagga accagtaaaa gacgcagcag aagttgtggc   2100
tttcgctgaa gaattcggtc tcccaatcgc catcaaggca gctttcggtg gcggcggacg   2160
tggcatgaag gttgcctaca agatggaaga agtcgctgac ctcttcgagt ccgcaacccg   2220
tgaagcaacc gcagcgttcg gccgcggcga gtgcttcgtg gagcgctacc tggacaaggc   2280
acgccacgtt gaggctcagg tcatcgccga taagcacggc aacgttgttg tcgccggaac   2340
ccgtgactgc tccctgcagc gccgtttcca gaagctcgtc gaagaagcac cagcaccatt   2400
cctcaccgat gaccagcgcg agcgtctcca ctcctccgcg aaggctatct gtaaggaagc   2460
tggctactac ggtgcaggca ccgttgagta cctcgttggc tccgacggcc tgatctcctt   2520
cctcgaggtc aacacccgcc tccaggtgga acacccagtc accgaagaga ccaccggcat   2580
cgacctggtc cgcgaaatgt tccgcatcgc agaaggccac gagctctcca tcaaggaaga   2640
tccagctcca cgcggccacg cattcgagtt ccgcatcaac ggcgaagacg ctggctccaa   2700
cttcatgcct gcaccaggca agatcaccag ctaccgcgag ccacagggcc caggcgtccg   2760
catggactcc ggtgtcgttg aaggttccga aatctccgga cagttcgact ccatgctggc   2820
aaagctgatc gtttggggcg acacccgcga gcaggctctc cagcgctccc gccgtgcact   2880
tgcagagtac gttgtcgagg gcatgccaac cgttatccca ttccaccagc acatcgtgga   2940
aaacccagca ttcgtgggca acgacgaagg cttcgagatc tacaccaagt ggatcgaaga   3000
ggtttgggat aacccaatcg caccttacgt tgacgcttcc gagctcgacg aagatgagga   3060
caagacccca gcacagaagg ttgttgtgga gatcaacggc cgtcgcgttg aggttgcact   3120
cccaggcgat ctggcactcg gtggcaccgc tggtcctaag aagaaggcca agaagcgtcg   3180
cgcaggtggt gcaaaggctg gcgtatccgg cgatgcagtg gcagctccaa tgcagggcac   3240
tgtcatcaag gtcaacgtcg aagaaggcgc tgaagtcaac gaaggcgaca ccgttgttgt   3300
cctcgaggct atgaagatgg aaaaccctgt gaaggctcat aagtccggaa ccgtaaccgg   3360
ccttactgtc gctgcaggcg agggtgtcaa caagggcgtt gttctcctcg agatcaagta   3420
atctagagga ggaaaactaa atgaatgttg acattagccg ctctcgtgaa ccgttgaacg   3480
tggaactgtt gaaagaaaaa ctgctgcaga acggtgattt cggtcaagtg atctacgaga   3540
```

```
aggtcaccgg ctctaccaat gcggacctgc tggctctggc gggcagcggc gctccaaact   3600

ggaccgtcaa gactgttgaa tttcaggacc acgcccgtgg ccgtctgggt cgtccgtgga   3660

gcgcaccgga gggttcccaa accatcgtca gcgttctggt ccaactgagc attgatcagg   3720

tggaccgtat tggtacgatc ccgctggccg caggcttggc tgttatggat gcgctgaatg   3780

atctgggcgt ggagggtgca ggcctgaaat ggccgaacga tgttcagatc cacggtaaga   3840

agttgtgcgg tattctggtt gaagcaaccg gcttcgactc cactccgacc gtggttatcg   3900

gttggggtac gaatatctcg ttgacgaaag aagagctgcc ggtcccgcac gcgaccagcc   3960

tggccctgga gggtgttgaa gttgaccgta cgacgttcct gattaacatg ctgacccatc   4020

tgcatacccg tctggatcag tggcagggtc cgtctgtgga ctggctggat gactatcgcg   4080

cggtttgtag cagcattggc caagatgtgc gtgtcctgct gcctggtgac aaagagctgc   4140

tgggcgaggc gattggcgtg gcgaccggtg gtgagatccg tgtgcgcgac gccagcggca   4200

cggtccacac gctgaatgcg ggtgaaatca cgcatctgcg tttgcaataa              4250
```

```
<210> SEQ ID NO 19
<211> LENGTH: 5659
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 19

atgatcatca aacctaaaat tcgtggattt atctgtacaa caacgcaccc agtgggttgt     60

gaagcgaacg taaaagaaca aattgcctac acaaaagcac aaggtccgat caaaaacgca    120

cctaagcgcg tgttggttgt cggatcgtct agcggctatg gtctgtcatc acgcatcgct    180

gcggcgtttg gcggtggtgc ggcgacgatc ggcgtatttt tcgaaaagcc gggcactgac    240

aaaaaaccag gtactgcggg tttctacaat gcagcagcgt ttgacaagct agcgcatgaa    300

gcgggcttgt acgcaaaaag cctgaacggc gatgcgttct cgaacgaagc gaagcaaaaa    360

gcgattgagc tgattaagca agacctcggc cagattgatt tggtggttta ctcgttggct    420

tctccagtgc gtaagatgcc agacacgggt gagctagtgc gctctgcact aaaaccgatc    480

ggcgaaacgt acacctctac cgcggtagat accaataaag atgtgatcat tgaagccagt    540

gttgaacctg cgaccgagca agaaatcgct gacactgtca ccgtgatggg cggtcaagat    600

tgggaactgt ggatccaagc actggaagag gcgggtgttc ttgctgaagg ttgcaaaacc    660

gtggcgtaca gctacatcgg tactgaattg acttggccaa tttactggga tggcgcttta    720

ggccgtgcca agatggacct agatcgcgca gcgacagcgc tgaacgaaaa gctggcagcg    780

aaaggtggta ccgcgaacgt tgcagttttg aaatcagtgg tgactcaagc aagctctgcg    840

attcctgtga tgccgctcta catcgcaatg gtgttcaaga agatgcgtga acagggcgtg    900

catgaaggct gtatggagca gatctaccgc atgttcagtc aacgtctgta caaagaagat    960

ggttcagcgc cggaagtgga tgatcacaat cgtctgcgtt tggatgactg ggaactgcgt   1020

gatgacattc agcagcactg ccgtgatctg tggccacaaa tcaccacaga gaacctgcgt   1080

gagctgaccg attacgacat gtacaaagaa gagttcatca agctgtttgg ctttggcatt   1140

gaaggcattg attacgatgc tgacgtcaat ccagaagtcg aatttgatgt gattgatatc   1200

gagtaattta gtgactgagc gtacatgtat acgaagatta ttggtactgg cagctatctg   1260
```

cccgaacaag tgcggactaa cgccgatctg gaaaaaatgg ttgagacctc tgacgagtgg 1320
attgtcactc gtacaggtat tcgtaaacgc catatcgccg cgccgaatga aactgtcgcg 1380
acgatgggct ttaccgctgc gaatcgcgcg attgagatgg cggggatcga taaagaccaa 1440
attggcttga ttgtggtggc taccacatca gcaacgcatg catttccaag cgcggcatgt 1500
cagattcaaa gtatgctcgg tattaaaggt tgcccggcgt ttgatgtcgc ggcagcgtgc 1560
gcaggtttca cctacgcgtt aagcatcgcc gaccagtacg ttaaatccgg cgcggttaaa 1620
cacgcgctgg tggtcggttc cgatgtatta gcccgcactt gcgatcctgg cgatcgcggt 1680
acgatcatta ttttcggcga tggcgcaggc gcggccgtac tgagcgcttc tgaagaaccg 1740
ggtattatct ccactcatct tcatgccgat ggccgttacg gtgaattact gaccctgccg 1800
aatgccgatc gcgtaaatcc ggataacccg atttacctga caatggcggg caatgaagtc 1860
tttaaagtgg cggtcactga actggcgcat attgtcgatg agacgctggc ggctaataac 1920
ctggatcgct cagaactcga ttggctggtg ccgcatcagg ctaacctgcg tatcattagc 1980
gcgacagcga aaaaactcgg catgtcgatg gacaatgtcg tcgtcacgct ggacaggcac 2040
ggcaatacct ccgcggcttc tgtgccgtgc gcgctggatg aagccgtgcg tgacgggcga 2100
attaaagccg gtcagctggt attgcttgaa gccttcgggg gtggattcac ctggggctcc 2160
gcgctgattc gtttctagta taaggattta aacatgacgc aatttgcatt tgtgttcccc 2220
ggtcagggtt ctcagagcgt tgggatgttg gccgagatgg cggcaaatta ccctatcgta 2280
gaagaaacgt ttgctgaagc ttctgcggct ctgggatatg atctgtgggc gctcacccag 2340
caaggtccag cggaagaact gaataaaacc tggcagacgc agccggcgtt attaaccgct 2400
tccgtcgcgc tttggcgcgt ttggcagcag cagggcggta aaatgcctgc gttaatggca 2460
ggtcacagcc tgggcgaata ttccgcgctg gtttgcgctg gcgtcatcaa ctttgctgat 2520
gccgttcgtc tggtggaaat gcgcggtaaa ttcatgcagg aagcggttcc ggaaggcact 2580
ggcggcatgt ctgcgatcat cgggctggat gatgcctcta ttgctaaagc ctgtgaagaa 2640
tctgccgaag ggcaggttgt ttcgccggtt aactttaact cgccgggaca ggtggttatc 2700
gccgggcata aagaggcggt agaacgtgcg ggcgcagcct gtaaagccgc tggcgcgaaa 2760
cgcgcgctgc cgctgccggt gagcgtaccg tcgcactgcg cgctgatgaa accagcggca 2820
gataagctgg cggttgaatt agccaaaatt acctttagcg cgccaacggt gccggtagtg 2880
aacaacgttg acgtgaaatg tgaaaccgat gccgccgcta tccgcgatgc gctggttcgc 2940
cagttgtaca atccggtaca gtggacgaag agcgtggaat ttatcgcggc gcagggcgtt 3000
gaacatcttt atgaagtggg tccaggtaaa gtcctcactg gtctgacgaa acgtattgtc 3060
gacaccctga cagcgtcggc gctgaacgag ccggcggcgc tgtctgcggc acttacgcaa 3120
taaaagagga aaaccatgag ctttgaagga aagattgcgc tggtgactgg tgcaagccgt 3180
ggcataggcc gcgcaattgc agagactctc gttgcccgcg gcgcgaaagt tatcgggact 3240
gcgaccagtg aaaatggtgc gaagaacatt agcgactatt taggtgctaa cgggaaaggt 3300
ttgatgttga atgtgaccga tcctgcatct attgaatctg ttctggaaaa tattcgcgca 3360
gaatttggtg aagtggatat cctggttaat aatgccggta tcactcgtga taatctgttg 3420
atgcgaatga aagatgatga gtggaacgat attatcgaaa ccaacttatc atccgttttc 3480
cgcctgtcaa aagcggtaat gcgcgctatg atgaaaaagc gttgtggtcg cattatcact 3540
attggttctg tggttggtac catgggaaat gcaggtcagg caaactacgc tgcggcgaaa 3600
gcgggcctga tcggtttcag taaatcactg gcgcgtgaag ttgcgtcccg tggtattact 3660

-continued

```
gtcaatgttg tggctccggg ttttattgaa acggacatga cgcgtgcgct gtctgacgat   3720

cagcgtgcgg gtatcctggc gcaggtgcct gcgggtcgcc tcggcggcgc tcaggaaatc   3780

gccagtgcgg ttgcattttt agcctctgac gaagcgagtt acatcactgg tgagactctg   3840

cacgtcaacg gcggaatgta catggtttaa ttttaaggtt tacataaaac atggtagata   3900

aacgcgaatc ctatacaaaa gaagaccttc ttgcctctgg tcgtggtgaa ctgtttggcg   3960

ctaaagggcc gcaactccct gcaccgaaca tgctgatgat ggaccgcgtc gttaagatga   4020

ccgaaacggg cggcaatttc gacaaaggct atgtcgaagc cgagctggat atcaatccgg   4080

atctatggtt cttcggatgc cactttatcg gcgatccggt gatgcccggt tgtctgggtc   4140

tggatgctat gtggcaattg gtgggattct acctgggctg gttgggcggc gaaggcaaag   4200

gccgcgctct gggcgtgggc gaagtgaaat ttaccggcca ggttctgccg acagccagga   4260

aagtcaccta tcgtattcat ttcaaacgta tcgtaaaccg tcgcctgatc atgggcctgg   4320

cggacggtga ggttctggtg gatggtcgcc tgatctatac cgcacacgat ttgaaagtcg   4380

gtttgttcca ggatacttcc gcgttctaaa aggaggcaac aaaatgaatc gccgcgttgt   4440

cattacgggt attggtgcag tgacgccggt gggtaacaac gctgatagct tctggtgcag   4500

catcaaagag ggtaaatgtg gcattgacaa gatcaaagcg tttgacgcaa ccgatttcaa   4560

agttaagctg gctgccgaag tgaaggactt caccccggag gactttatcg acaagcgtga   4620

ggcgaaccgt atggaccgtt ttagccagtt tgcgatcgtt gcggcggatg aggcaatcaa   4680

ggacagcaaa ctggacctgg agtcgattga taagaatcgt ttcggcgtca ttgttggtag   4740

cggcattggc ggcatcggca ccattgagaa gcaggatgaa aagctgatta ccaaaggtcc   4800

gggtcgtgtg agccctatga ctattccgat gatcattgcg aatatggcaa gcggtaatct   4860

ggcgattcgt tatggcgcta aaggtatttg cacgaccatt gtcaccgcat gtgcgagcgc   4920

gaacaacagc attggtgagt ccttccgtaa cattaagttt ggttatagcg acgttatgat   4980

ctctggtggt agcgaagcag gtatcacccc gttgagcctg gcgggttttg cctcgatgaa   5040

ggccgtgacc aaatctgagg acccgaagcg cgccagcatc ccgttcgata aggatcgcag   5100

cggttttgtg atgggcgagg gcagcggtat cgttatcttg gaagagttgg agcacgcgct   5160

gaagcgtggt gccaaaatct atgccgagat cgttggctat ggtgcgacct gcgacgcata   5220

tcatatcacg agcccagcgc cgaatggtga aggtggtgca cgtgcaatga aactggcaat   5280

ggaagaagat aatgtccgcc cagaggacat ttcctatatc aacgcgcacg gtacgagcac   5340

ggcgtacaat gacagcttcg aaacccaagc gatcaagacg gtcctgggtg aatacgccta   5400

caaagtgccg gtgtctagca ccaagagcat gaccggccac ctgctgggcg ctggcggtgc   5460

agtcgaagcg attatctgtg ccaaagctat tgaagagggt ttcattccgc cgaccatcgg   5520

ctacaaagag gcggatccgg aatgcgacct ggattacgtt cctaacgagg gccgtaatgc   5580

agaagtcaac tacgttctgt ccaacagcct gggcttcggt ggccataatg cgactctgct   5640

gttcaaaaag tacaaatga                                                5659
```

<210> SEQ ID NO 20
<211> LENGTH: 75
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

-continued

<400> SEQUENCE: 20
ttgtccatct ttatataatt tgggggtagg gtgttcttta tgtaaaaaaa acgttttagg 60
atgcatatgg cggcc 75

<210> SEQ ID NO 21
<211> LENGTH: 75
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 21
gataaatcca cgaattttag gtttgatgat cattggtctc ctcctgcagg tgcgtgttcg 60
tcgtcatcgc aattg 75

<210> SEQ ID NO 22
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 22
actcaccgca ttggtgtagt aaggcgcacc 30

<210> SEQ ID NO 23
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 23
tgaatgtcat cacgcagttc ccagtcatcc 30

<210> SEQ ID NO 24
<211> LENGTH: 33
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 24
ccatcttctt tgtacagacg ttgactgaac atg 33

<210> SEQ ID NO 25
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 25
gcaccatagc cgtaatccca caggttatag 30

<210> SEQ ID NO 26
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 26
tgtcattaat ggttaataat gttga 25

<210> SEQ ID NO 27
<211> LENGTH: 40
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 27
gcagttattg gtgcccttaa acgcctggtt gctacgcctg 40

<210> SEQ ID NO 28
<211> LENGTH: 27
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 28
gagccaatat gcgagaacac ccgagaa 27

<210> SEQ ID NO 29
<211> LENGTH: 48
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 29
cgctgaacgt attgcaggcc gagttgctgc accgctcccg ccaggcag 48

<210> SEQ ID NO 30
<211> LENGTH: 51
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 30
ggaattgcca cggtgcggca ggctccatac gcgaggccag gttatccaac g 51

<210> SEQ ID NO 31
<211> LENGTH: 35
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

-continued

<400> SEQUENCE: 31
aatcaccagc actaaagtgc gcggttcgtt acccg 35

<210> SEQ ID NO 32
<211> LENGTH: 34
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 32
atctgccgtg gattgcagag tctattcagc tacg 34

<210> SEQ ID NO 33
<211> LENGTH: 1168
<212> TYPE: PRT
<213> ORGANISM: Mycobacterium smegmatis

<400> SEQUENCE: 33

Met Thr Ile Glu Thr Arg Glu Asp Arg Phe Asn Arg Arg Ile Asp His
1 5 10 15

Leu Phe Glu Thr Asp Pro Gln Phe Ala Ala Ala Arg Pro Asp Glu Ala
20 25 30

Ile Ser Ala Ala Ala Ala Asp Pro Glu Leu Arg Leu Pro Ala Ala Val
35 40 45

Lys Gln Ile Leu Ala Gly Tyr Ala Asp Arg Pro Ala Leu Gly Lys Arg
50 55 60

Ala Val Glu Phe Val Thr Asp Glu Glu Gly Arg Thr Thr Ala Lys Leu
65 70 75 80

Leu Pro Arg Phe Asp Thr Ile Thr Tyr Arg Gln Leu Ala Gly Arg Ile
85 90 95

Gln Ala Val Thr Asn Ala Trp His Asn His Pro Val Asn Ala Gly Asp
100 105 110

Arg Val Ala Ile Leu Gly Phe Thr Ser Val Asp Tyr Thr Thr Ile Asp
115 120 125

Ile Ala Leu Leu Glu Leu Gly Ala Val Ser Val Pro Leu Gln Thr Ser
130 135 140

Ala Pro Val Ala Gln Leu Gln Pro Ile Val Ala Glu Thr Glu Pro Lys
145 150 155 160

Val Ile Ala Ser Ser Val Asp Phe Leu Ala Asp Ala Val Ala Leu Val
165 170 175

Glu Ser Gly Pro Ala Pro Ser Arg Leu Val Val Phe Asp Tyr Ser His
180 185 190

Glu Val Asp Asp Gln Arg Glu Ala Phe Glu Ala Ala Lys Gly Lys Leu
195 200 205

Ala Gly Thr Gly Val Val Val Glu Thr Ile Thr Asp Ala Leu Asp Arg
210 215 220

Gly Arg Ser Leu Ala Asp Ala Pro Leu Tyr Val Pro Asp Glu Ala Asp
225 230 235 240

Pro Leu Thr Leu Leu Ile Tyr Thr Ser Gly Ser Thr Gly Thr Pro Lys
245 250 255

Gly Ala Met Tyr Pro Glu Ser Lys Thr Ala Thr Met Trp Gln Ala Gly
260 265 270

Ser Lys Ala Arg Trp Asp Glu Thr Leu Gly Val Met Pro Ser Ile Thr
275 280 285

-continued

```
Leu Asn Phe Met Pro Met Ser His Val Met Gly Arg Gly Ile Leu Cys
    290                 295                 300

Ser Thr Leu Ala Ser Gly Gly Thr Ala Tyr Phe Ala Ala Arg Ser Asp
305                 310                 315                 320

Leu Ser Thr Phe Leu Glu Asp Leu Ala Leu Val Arg Pro Thr Gln Leu
                325                 330                 335

Asn Phe Val Pro Arg Ile Trp Asp Met Leu Phe Gln Glu Tyr Gln Ser
            340                 345                 350

Arg Leu Asp Asn Arg Arg Ala Glu Gly Ser Glu Asp Arg Ala Glu Ala
        355                 360                 365

Ala Val Leu Glu Glu Val Arg Thr Gln Leu Leu Gly Gly Arg Phe Val
    370                 375                 380

Ser Ala Leu Thr Gly Ser Ala Pro Ile Ser Ala Glu Met Lys Ser Trp
385                 390                 395                 400

Val Glu Asp Leu Leu Asp Met His Leu Leu Glu Gly Tyr Gly Ser Thr
                405                 410                 415

Glu Ala Gly Ala Val Phe Ile Asp Gly Gln Ile Gln Arg Pro Pro Val
            420                 425                 430

Ile Asp Tyr Lys Leu Val Asp Val Pro Asp Leu Gly Tyr Phe Ala Thr
        435                 440                 445

Asp Arg Pro Tyr Pro Arg Gly Glu Leu Leu Val Lys Ser Glu Gln Met
    450                 455                 460

Phe Pro Gly Tyr Tyr Lys Arg Pro Glu Ile Thr Ala Glu Met Phe Asp
465                 470                 475                 480

Glu Asp Gly Tyr Tyr Arg Thr Gly Asp Ile Val Ala Glu Leu Gly Pro
                485                 490                 495

Asp His Leu Glu Tyr Leu Asp Arg Arg Asn Asn Val Leu Lys Leu Ser
            500                 505                 510

Gln Gly Glu Phe Val Thr Val Ser Lys Leu Glu Ala Val Phe Gly Asp
        515                 520                 525

Ser Pro Leu Val Arg Gln Ile Tyr Val Tyr Gly Asn Ser Ala Arg Ser
    530                 535                 540

Tyr Leu Leu Ala Val Val Val Pro Thr Glu Glu Ala Leu Ser Arg Trp
545                 550                 555                 560

Asp Gly Asp Glu Leu Lys Ser Arg Ile Ser Asp Ser Leu Gln Asp Ala
                565                 570                 575

Ala Arg Ala Ala Gly Leu Gln Ser Tyr Glu Ile Pro Arg Asp Phe Leu
            580                 585                 590

Val Glu Thr Thr Pro Phe Thr Leu Glu Asn Gly Leu Leu Thr Gly Ile
        595                 600                 605

Arg Lys Leu Ala Arg Pro Lys Leu Lys Ala His Tyr Gly Glu Arg Leu
    610                 615                 620

Glu Gln Leu Tyr Thr Asp Leu Ala Glu Gly Gln Ala Asn Glu Leu Arg
625                 630                 635                 640

Glu Leu Arg Arg Asn Gly Ala Asp Arg Pro Val Val Glu Thr Val Ser
                645                 650                 655

Arg Ala Ala Val Ala Leu Leu Gly Ala Ser Val Thr Asp Leu Arg Ser
            660                 665                 670

Asp Ala His Phe Thr Asp Leu Gly Gly Asp Ser Leu Ser Ala Leu Ser
        675                 680                 685

Phe Ser Asn Leu Leu His Glu Ile Phe Asp Val Asp Val Pro Val Gly
    690                 695                 700
```

-continued

Val Ile Val Ser Pro Ala Thr Asp Leu Ala Gly Val Ala Ala Tyr Ile
705 710 715 720

Glu Gly Glu Leu Arg Gly Ser Lys Arg Pro Thr Tyr Ala Ser Val His
725 730 735

Gly Arg Asp Ala Thr Glu Val Arg Ala Arg Asp Leu Ala Leu Gly Lys
740 745 750

Phe Ile Asp Ala Lys Thr Leu Ser Ala Ala Pro Gly Leu Pro Arg Ser
755 760 765

Gly Thr Glu Ile Arg Thr Val Leu Leu Thr Gly Ala Thr Gly Phe Leu
770 775 780

Gly Arg Tyr Leu Ala Leu Glu Trp Leu Glu Arg Met Asp Leu Val Asp
785 790 795 800

Gly Lys Val Ile Cys Leu Val Arg Ala Arg Ser Asp Asp Glu Ala Arg
805 810 815

Ala Arg Leu Asp Ala Thr Phe Asp Thr Gly Asp Ala Thr Leu Leu Glu
820 825 830

His Tyr Arg Ala Leu Ala Ala Asp His Leu Glu Val Ile Ala Gly Asp
835 840 845

Lys Gly Glu Ala Asp Leu Gly Leu Asp His Asp Thr Trp Gln Arg Leu
850 855 860

Ala Asp Thr Val Asp Leu Ile Val Asp Pro Ala Ala Leu Val Asn His
865 870 875 880

Val Leu Pro Tyr Ser Gln Met Phe Gly Pro Asn Ala Leu Gly Thr Ala
885 890 895

Glu Leu Ile Arg Ile Ala Leu Thr Thr Thr Ile Lys Pro Tyr Val Tyr
900 905 910

Val Ser Thr Ile Gly Val Gly Gln Gly Ile Ser Pro Glu Ala Phe Val
915 920 925

Glu Asp Ala Asp Ile Arg Glu Ile Ser Ala Thr Arg Arg Val Asp Asp
930 935 940

Ser Tyr Ala Asn Gly Tyr Gly Asn Ser Lys Trp Ala Gly Glu Val Leu
945 950 955 960

Leu Arg Glu Ala His Asp Trp Cys Gly Leu Pro Val Ser Val Phe Arg
965 970 975

Cys Asp Met Ile Leu Ala Asp Thr Thr Tyr Ser Gly Gln Leu Asn Leu
980 985 990

Pro Asp Met Phe Thr Arg Leu Met Leu Ser Leu Val Ala Thr Gly Ile
995 1000 1005

Ala Pro Gly Ser Phe Tyr Glu Leu Asp Ala Asp Gly Asn Arg Gln
1010 1015 1020

Arg Ala His Tyr Asp Gly Leu Pro Val Glu Phe Ile Ala Glu Ala
1025 1030 1035

Ile Ser Thr Ile Gly Ser Gln Val Thr Asp Gly Phe Glu Thr Phe
1040 1045 1050

His Val Met Asn Pro Tyr Asp Asp Gly Ile Gly Leu Asp Glu Tyr
1055 1060 1065

Val Asp Trp Leu Ile Glu Ala Gly Tyr Pro Val His Arg Val Asp
1070 1075 1080

Asp Tyr Ala Thr Trp Leu Ser Arg Phe Glu Thr Ala Leu Arg Ala
1085 1090 1095

Leu Pro Glu Arg Gln Arg Gln Ala Ser Leu Leu Pro Leu Leu His
1100 1105 1110

Asn Tyr Gln Gln Pro Ser Pro Pro Val Cys Gly Ala Met Ala Pro

```
    1115                1120                1125

Thr Asp  Arg Phe Arg Ala Ala  Val Gln Asp Ala Lys  Ile Gly Pro
    1130                1135                1140

Asp Lys  Asp Ile Pro His Val  Thr Ala Asp Val Ile  Val Lys Tyr
    1145                1150                1155

Ile Ser  Asn Leu Gln Met Leu  Gly Leu Leu
    1160                1165


<210> SEQ ID NO 34
<211> LENGTH: 1168
<212> TYPE: PRT
<213> ORGANISM: Mycobacterium tuberculosis

<400> SEQUENCE: 34

Met Ser Ile Asn Asp Gln Arg Leu Thr Arg Arg Val Glu Asp Leu Tyr
1               5                   10                  15

Ala Ser Asp Ala Gln Phe Ala Ala Ala Ser Pro Asn Glu Ala Ile Thr
            20                  25                  30

Gln Ala Ile Asp Gln Pro Gly Val Ala Leu Pro Gln Leu Ile Arg Met
        35                  40                  45

Val Met Glu Gly Tyr Ala Asp Arg Pro Ala Leu Gly Gln Arg Ala Leu
    50                  55                  60

Arg Phe Val Thr Asp Pro Asp Ser Gly Arg Thr Met Val Glu Leu Leu
65                  70                  75                  80

Pro Arg Phe Glu Thr Ile Thr Tyr Arg Glu Leu Trp Ala Arg Ala Gly
                85                  90                  95

Thr Leu Ala Thr Ala Leu Ser Ala Glu Pro Ala Ile Arg Pro Gly Asp
            100                 105                 110

Arg Val Cys Val Leu Gly Phe Asn Ser Val Asp Tyr Thr Thr Ile Asp
        115                 120                 125

Ile Ala Leu Ile Arg Leu Gly Ala Val Ser Val Pro Leu Gln Thr Ser
    130                 135                 140

Ala Pro Val Thr Gly Leu Arg Pro Ile Val Thr Glu Thr Glu Pro Thr
145                 150                 155                 160

Met Ile Ala Thr Ser Ile Asp Asn Leu Gly Asp Ala Val Glu Val Leu
                165                 170                 175

Ala Gly His Ala Pro Ala Arg Leu Val Val Phe Asp Tyr His Gly Lys
            180                 185                 190

Val Asp Thr His Arg Glu Ala Val Glu Ala Ala Arg Ala Arg Leu Ala
        195                 200                 205

Gly Ser Val Thr Ile Asp Thr Leu Ala Glu Leu Ile Glu Arg Gly Arg
    210                 215                 220

Ala Leu Pro Ala Thr Pro Ile Ala Asp Ser Ala Asp Asp Ala Leu Ala
225                 230                 235                 240

Leu Leu Ile Tyr Thr Ser Gly Ser Thr Gly Ala Pro Lys Gly Ala Met
                245                 250                 255

Tyr Arg Glu Ser Gln Val Met Ser Phe Trp Arg Lys Ser Ser Gly Trp
            260                 265                 270

Phe Glu Pro Ser Gly Tyr Pro Ser Ile Thr Leu Asn Phe Met Pro Met
        275                 280                 285

Ser His Val Gly Gly Arg Gln Val Leu Tyr Gly Thr Leu Ser Asn Gly
    290                 295                 300

Gly Thr Ala Tyr Phe Val Ala Lys Ser Asp Leu Ser Thr Leu Phe Glu
305                 310                 315                 320
```

-continued

```
Asp Leu Ala Leu Val Arg Pro Thr Glu Leu Cys Phe Val Pro Arg Ile
                325                 330                 335

Trp Asp Met Val Phe Ala Glu Phe His Ser Glu Val Asp Arg Arg Leu
            340                 345                 350

Val Asp Gly Ala Asp Arg Ala Ala Leu Glu Ala Gln Val Lys Ala Glu
        355                 360                 365

Leu Arg Glu Asn Val Leu Gly Gly Arg Phe Val Met Ala Leu Thr Gly
    370                 375                 380

Ser Ala Pro Ile Ser Ala Glu Met Thr Ala Trp Val Glu Ser Leu Leu
385                 390                 395                 400

Ala Asp Val His Leu Val Glu Gly Tyr Gly Ser Thr Glu Ala Gly Met
                405                 410                 415

Val Leu Asn Asp Gly Met Val Arg Arg Pro Ala Val Ile Asp Tyr Lys
            420                 425                 430

Leu Val Asp Val Pro Glu Leu Gly Tyr Phe Gly Thr Asp Gln Pro Tyr
        435                 440                 445

Pro Arg Gly Glu Leu Leu Val Lys Thr Gln Thr Met Phe Pro Gly Tyr
    450                 455                 460

Tyr Gln Arg Pro Asp Val Thr Ala Glu Val Phe Asp Pro Asp Gly Phe
465                 470                 475                 480

Tyr Arg Thr Gly Asp Ile Met Ala Lys Val Gly Pro Asp Gln Phe Val
                485                 490                 495

Tyr Leu Asp Arg Arg Asn Asn Val Leu Lys Leu Ser Gln Gly Glu Phe
            500                 505                 510

Ile Ala Val Ser Lys Leu Glu Ala Val Phe Gly Asp Ser Pro Leu Val
        515                 520                 525

Arg Gln Ile Phe Ile Tyr Gly Asn Ser Ala Arg Ala Tyr Pro Leu Ala
    530                 535                 540

Val Val Val Pro Ser Gly Asp Ala Leu Ser Arg His Gly Ile Glu Asn
545                 550                 555                 560

Leu Lys Pro Val Ile Ser Glu Ser Leu Gln Glu Val Ala Arg Ala Ala
                565                 570                 575

Gly Leu Gln Ser Tyr Glu Ile Pro Arg Asp Phe Ile Ile Glu Thr Thr
            580                 585                 590

Pro Phe Thr Leu Glu Asn Gly Leu Leu Thr Gly Ile Arg Lys Leu Ala
        595                 600                 605

Arg Pro Gln Leu Lys Lys Phe Tyr Gly Glu Arg Leu Glu Arg Leu Tyr
    610                 615                 620

Thr Glu Leu Ala Asp Ser Gln Ser Asn Glu Leu Arg Glu Leu Arg Gln
625                 630                 635                 640

Ser Gly Pro Asp Ala Pro Val Leu Pro Thr Leu Cys Arg Ala Ala Ala
                645                 650                 655

Ala Leu Leu Gly Ser Thr Ala Ala Asp Val Arg Pro Asp Ala His Phe
            660                 665                 670

Ala Asp Leu Gly Gly Asp Ser Leu Ser Ala Leu Ser Leu Ala Asn Leu
        675                 680                 685

Leu His Glu Ile Phe Gly Val Asp Val Pro Val Gly Val Ile Val Ser
    690                 695                 700

Pro Ala Ser Asp Leu Arg Ala Leu Ala Asp His Ile Glu Ala Ala Arg
705                 710                 715                 720

Thr Gly Val Arg Arg Pro Ser Phe Ala Ser Ile His Gly Arg Ser Ala
                725                 730                 735

Thr Glu Val His Ala Ser Asp Leu Thr Leu Asp Lys Phe Ile Asp Ala
```

-continued

```
            740                 745                 750

Ala Thr Leu Ala Ala Ala Pro Asn Leu Pro Ala Pro Ser Ala Gln Val
        755                 760                 765

Arg Thr Val Leu Leu Thr Gly Ala Thr Gly Phe Leu Gly Arg Tyr Leu
    770                 775                 780

Ala Leu Glu Trp Leu Asp Arg Met Asp Leu Val Asn Gly Lys Leu Ile
785                 790                 795                 800

Cys Leu Val Arg Ala Arg Ser Asp Glu Glu Ala Gln Ala Arg Leu Asp
                805                 810                 815

Ala Thr Phe Asp Ser Gly Asp Pro Tyr Leu Val Arg His Tyr Arg Glu
            820                 825                 830

Leu Gly Ala Gly Arg Leu Glu Val Leu Ala Gly Asp Lys Gly Glu Ala
        835                 840                 845

Asp Leu Gly Leu Asp Arg Val Thr Trp Gln Arg Leu Ala Asp Thr Val
    850                 855                 860

Asp Leu Ile Val Asp Pro Ala Ala Leu Val Asn His Val Leu Pro Tyr
865                 870                 875                 880

Ser Gln Leu Phe Gly Pro Asn Ala Ala Gly Thr Ala Glu Leu Leu Arg
                885                 890                 895

Leu Ala Leu Thr Gly Lys Arg Lys Pro Tyr Ile Tyr Thr Ser Thr Ile
            900                 905                 910

Ala Val Gly Glu Gln Ile Pro Pro Glu Ala Phe Thr Glu Asp Ala Asp
        915                 920                 925

Ile Arg Ala Ile Ser Pro Thr Arg Arg Ile Asp Asp Ser Tyr Ala Asn
    930                 935                 940

Gly Tyr Ala Asn Ser Lys Trp Ala Gly Glu Val Leu Leu Arg Glu Ala
945                 950                 955                 960

His Glu Gln Cys Gly Leu Pro Val Thr Val Phe Arg Cys Asp Met Ile
                965                 970                 975

Leu Ala Asp Thr Ser Tyr Thr Gly Gln Leu Asn Leu Pro Asp Met Phe
            980                 985                 990

Thr Arg Leu Met Leu Ser Leu Ala  Ala Thr Gly Ile Ala  Pro Gly Ser
        995                 1000                 1005

Phe Tyr  Glu Leu Asp Ala His  Gly Asn Arg Gln Arg  Ala His Tyr
    1010                 1015                 1020

Asp Gly  Leu Pro Val Glu Phe  Val Ala Glu Ala Ile  Cys Thr Leu
    1025                 1030                 1035

Gly Thr  His Ser Pro Asp Arg  Phe Val Thr Tyr His  Val Met Asn
    1040                 1045                 1050

Pro Tyr  Asp Asp Gly Ile Gly  Leu Asp Glu Phe Val  Asp Trp Leu
    1055                 1060                 1065

Asn Ser  Pro Thr Ser Gly Ser  Gly Cys Thr Ile Gln  Arg Ile Ala
    1070                 1075                 1080

Asp Tyr  Gly Glu Trp Leu Gln  Arg Phe Glu Thr Ser  Leu Arg Ala
    1085                 1090                 1095

Leu Pro  Asp Arg Gln Arg His  Ala Ser Leu Leu Pro  Leu Leu His
    1100                 1105                 1110

Asn Tyr  Arg Glu Pro Ala Lys  Pro Ile Cys Gly Ser  Ile Ala Pro
    1115                 1120                 1125

Thr Asp  Gln Phe Arg Ala Ala  Val Gln Glu Ala Lys  Ile Gly Pro
    1130                 1135                 1140

Asp Lys  Asp Ile Pro His Leu  Thr Ala Ala Ile Ile  Ala Lys Tyr
    1145                 1150                 1155
```

```
Ile Ser  Asn Leu Arg Leu Leu  Gly Leu Leu
    1160                 1165


<210> SEQ ID NO 35
<211> LENGTH: 696
<212> TYPE: DNA
<213> ORGANISM: Synechococcus elongatus

<400> SEQUENCE: 35

atgccgcagc ttgaagccag ccttgaactg gactttcaaa gcgagtccta caaagacgct      60

tacagccgca tcaacgcgat cgtgattgaa ggcgaacaag aggcgttcga caactacaat     120

cgccttgctg agatgctgcc cgaccagcgg gatgagcttc acaagctagc caagatggaa     180

cagcgccaca tgaaaggctt tatggcctgt ggcaaaaatc tctccgtcac tcctgacatg     240

ggttttgccc agaaattttt cgagcgcttg cacgagaact tcaaagcggc ggctgcggaa     300

ggcaaggtcg tcacctgcct actgattcaa tcgctaatca tcgagtgctt tgcgatcgcg     360

gcttacaaca tctacatccc agtggcggat gcttttgccc gcaaaatcac ggagggggtc     420

gtgcgcgacg aatacctgca ccgcaacttc ggtgaagagt ggctgaaggc gaattttgat     480

gcttccaaag ccgaactgga agaagccaat cgtcagaacc tgcccttggt ttggctaatg     540

ctcaacgaag tggccgatga tgctcgcgaa ctcgggatgg agcgtgagtc gctcgtcgag     600

gactttatga ttgcctacgg tgaagctctg gaaaacatcg gcttcacaac gcgcgaaatc     660

atgcgtatgt ccgcctatgg ccttgcggcc gtttga                               696


<210> SEQ ID NO 36
<211> LENGTH: 231
<212> TYPE: PRT
<213> ORGANISM: Synechococcus elongatus

<400> SEQUENCE: 36

Met Pro Gln Leu Glu Ala Ser Leu Glu Leu Asp Phe Gln Ser Glu Ser
1               5                   10                  15

Tyr Lys Asp Ala Tyr Ser Arg Ile Asn Ala Ile Val Ile Glu Gly Glu
            20                  25                  30

Gln Glu Ala Phe Asp Asn Tyr Asn Arg Leu Ala Glu Met Leu Pro Asp
        35                  40                  45

Gln Arg Asp Glu Leu His Lys Leu Ala Lys Met Glu Gln Arg His Met
    50                  55                  60

Lys Gly Phe Met Ala Cys Gly Lys Asn Leu Ser Val Thr Pro Asp Met
65                  70                  75                  80

Gly Phe Ala Gln Lys Phe Phe Glu Arg Leu His Glu Asn Phe Lys Ala
                85                  90                  95

Ala Ala Ala Glu Gly Lys Val Val Thr Cys Leu Leu Ile Gln Ser Leu
            100                 105                 110

Ile Ile Glu Cys Phe Ala Ile Ala Ala Tyr Asn Ile Tyr Ile Pro Val
        115                 120                 125

Ala Asp Ala Phe Ala Arg Lys Ile Thr Glu Gly Val Val Arg Asp Glu
    130                 135                 140

Tyr Leu His Arg Asn Phe Gly Glu Glu Trp Leu Lys Ala Asn Phe Asp
145                 150                 155                 160

Ala Ser Lys Ala Glu Leu Glu Glu Ala Asn Arg Gln Asn Leu Pro Leu
                165                 170                 175

Val Trp Leu Met Leu Asn Glu Val Ala Asp Asp Ala Arg Glu Leu Gly
            180                 185                 190
```

Met Glu Arg Glu Ser Leu Val Glu Asp Phe Met Ile Ala Tyr Gly Glu
195 200 205

Ala Leu Glu Asn Ile Gly Phe Thr Thr Arg Glu Ile Met Arg Met Ser
210 215 220

Ala Tyr Gly Leu Ala Ala Val
225 230

<210> SEQ ID NO 37
<211> LENGTH: 1029
<212> TYPE: DNA
<213> ORGANISM: Synechococcus elongatus

<400> SEQUENCE: 37
atggcattcg gtcttatcgg tcatctcacc agtttggagc aggcccgcga cgtttctcgc 60
aggatgggct acgacgaata cgccgatcaa ggattggagt tttggagtag cgctcctcct 120
caaatcgttg atgaaatcac agtcaccagt gccacaggca aggtgattca cggtcgctac 180
atcgaatcgt gtttcttgcc ggaaatgctg gcggcgcgcc gcttcaaaac agccacgcgc 240
aaagttctca atgccatgtc ccatgcccaa aaacacggca tcgacatctc ggccttgggg 300
ggctttacct cgattatttt cgagaatttc gatttggcca gtttgcggca agtgcgcgac 360
actaccttgg agtttgaacg gttcaccacc ggcaatactc acacggccta cgtaatctgt 420
agacaggtgg aagccgctgc taaaacgctg ggcatcgaca ttacccaagc gacagtagcg 480
gttgtcggcg cgactggcga tatcggtagc gctgtctgcc gctggctcga cctcaaactg 540
ggtgtcggtg atttgatcct gacggcgcgc aatcaggagc gtttggataa cctgcaggct 600
gaactcggcc ggggcaagat tctgcccttg gaagccgctc tgccggaagc tgactttatc 660
gtgtgggtcg ccagtatgcc tcagggcgta gtgatcgacc cagcaaccct gaagcaaccc 720
tgcgtcctaa tcgacggggg ctaccccaaa aacttgggca gcaaagtcca aggtgagggc 780
atctatgtcc tcaatggcgg ggtagttgaa cattgcttcg acatcgactg gcagatcatg 840
tccgctgcag agatggcgcg gcccgagcgc cagatgtttg cctgctttgc cgaggcgatg 900
ctcttggaat ttgaaggctg gcatactaac ttctcctggg gccgcaacca aatcacgatc 960
gagaagatgg aagcgatcgg tgaggcatcg gtgcgccacg gcttccaacc cttggcattg 1020
gcaatttga 1029

<210> SEQ ID NO 38
<211> LENGTH: 342
<212> TYPE: PRT
<213> ORGANISM: Synechococcus elongatus

<400> SEQUENCE: 38

Met Ala Phe Gly Leu Ile Gly His Leu Thr Ser Leu Glu Gln Ala Arg
1 5 10 15

Asp Val Ser Arg Arg Met Gly Tyr Asp Glu Tyr Ala Asp Gln Gly Leu
20 25 30

Glu Phe Trp Ser Ser Ala Pro Pro Gln Ile Val Asp Glu Ile Thr Val
35 40 45

Thr Ser Ala Thr Gly Lys Val Ile His Gly Arg Tyr Ile Glu Ser Cys
50 55 60

Phe Leu Pro Glu Met Leu Ala Ala Arg Arg Phe Lys Thr Ala Thr Arg
65 70 75 80

Lys Val Leu Asn Ala Met Ser His Ala Gln Lys His Gly Ile Asp Ile
85 90 95

```
Ser Ala Leu Gly Gly Phe Thr Ser Ile Ile Phe Glu Asn Phe Asp Leu
            100                 105                 110

Ala Ser Leu Arg Gln Val Arg Asp Thr Thr Leu Glu Phe Glu Arg Phe
        115                 120                 125

Thr Thr Gly Asn Thr His Thr Ala Tyr Val Ile Cys Arg Gln Val Glu
    130                 135                 140

Ala Ala Ala Lys Thr Leu Gly Ile Asp Ile Thr Gln Ala Thr Val Ala
145                 150                 155                 160

Val Val Gly Ala Thr Gly Asp Ile Gly Ser Ala Val Cys Arg Trp Leu
                165                 170                 175

Asp Leu Lys Leu Gly Val Gly Asp Leu Ile Leu Thr Ala Arg Asn Gln
            180                 185                 190

Glu Arg Leu Asp Asn Leu Gln Ala Glu Leu Gly Arg Gly Lys Ile Leu
        195                 200                 205

Pro Leu Glu Ala Ala Leu Pro Glu Ala Asp Phe Ile Val Trp Val Ala
    210                 215                 220

Ser Met Pro Gln Gly Val Val Ile Asp Pro Ala Thr Leu Lys Gln Pro
225                 230                 235                 240

Cys Val Leu Ile Asp Gly Gly Tyr Pro Lys Asn Leu Gly Ser Lys Val
                245                 250                 255

Gln Gly Glu Gly Ile Tyr Val Leu Asn Gly Gly Val Val Glu His Cys
            260                 265                 270

Phe Asp Ile Asp Trp Gln Ile Met Ser Ala Ala Glu Met Ala Arg Pro
        275                 280                 285

Glu Arg Gln Met Phe Ala Cys Phe Ala Glu Ala Met Leu Leu Glu Phe
    290                 295                 300

Glu Gly Trp His Thr Asn Phe Ser Trp Gly Arg Asn Gln Ile Thr Ile
305                 310                 315                 320

Glu Lys Met Glu Ala Ile Gly Glu Ala Ser Val Arg His Gly Phe Gln
                325                 330                 335

Pro Leu Ala Leu Ala Ile
            340
```

<210> SEQ ID NO 39
<211> LENGTH: 717
<212> TYPE: DNA
<213> ORGANISM: Prochlorococcus mariunus

<400> SEQUENCE: 39

```
atgcaaacac tcgaatctaa taaaaaaact aatctagaaa attctattga tttacccgat      60

tttactactg attcttacaa agacgcttat agcaggataa atgcaatagt tattgaaggt     120

gaacaagagg ctcatgataa ttacatttcc ttagcaacat taattcctaa cgaattagaa     180

gagttaacta aattagcgaa aatggagctt aagcacaaaa gaggctttac tgcatgtgga     240

agaaatctag gtgttcaagc tgacatgatt tttgctaaag aattcttttc caaattacat     300

ggtaattttc aggttgcgtt atctaatggc aagacaacta catgcctatt aatacaggca     360

attttaattg aagcttttgc tatatccgcg tatcacgttt acataagagt tgctgatcct     420

ttcgcgaaaa aaattaccca aggtgttgtt aaagatgaat atcttcattt aaattatgga     480

caagaatggc taaaagaaaa tttagcgact tgtaaagatg agctaatgga agcaaataag     540

gttaaccttc cattaatcaa gaagatgtta gatcaagtct cggaagatgc ttcagtacta     600

gctatggata gggaagaatt aatggaagaa ttcatgattg cctatcagga cactctcctt     660
```

-continued gaaataggtt tagataatag agaaattgca agaatggcaa tggctgctat agtttaa 717

<210> SEQ ID NO 40
<211> LENGTH: 238
<212> TYPE: PRT
<213> ORGANISM: Prochlorococcus mariunus

<400> SEQUENCE: 40

Met Gln Thr Leu Glu Ser Asn Lys Lys Thr Asn Leu Glu Asn Ser Ile
1 5 10 15

Asp Leu Pro Asp Phe Thr Thr Asp Ser Tyr Lys Asp Ala Tyr Ser Arg
20 25 30

Ile Asn Ala Ile Val Ile Glu Gly Glu Gln Glu Ala His Asp Asn Tyr
35 40 45

Ile Ser Leu Ala Thr Leu Ile Pro Asn Glu Leu Glu Glu Leu Thr Lys
50 55 60

Leu Ala Lys Met Glu Leu Lys His Lys Arg Gly Phe Thr Ala Cys Gly
65 70 75 80

Arg Asn Leu Gly Val Gln Ala Asp Met Ile Phe Ala Lys Glu Phe Phe
85 90 95

Ser Lys Leu His Gly Asn Phe Gln Val Ala Leu Ser Asn Gly Lys Thr
100 105 110

Thr Thr Cys Leu Leu Ile Gln Ala Ile Leu Ile Glu Ala Phe Ala Ile
115 120 125

Ser Ala Tyr His Val Tyr Ile Arg Val Ala Asp Pro Phe Ala Lys Lys
130 135 140

Ile Thr Gln Gly Val Val Lys Asp Glu Tyr Leu His Leu Asn Tyr Gly
145 150 155 160

Gln Glu Trp Leu Lys Glu Asn Leu Ala Thr Cys Lys Asp Glu Leu Met
165 170 175

Glu Ala Asn Lys Val Asn Leu Pro Leu Ile Lys Lys Met Leu Asp Gln
180 185 190

Val Ser Glu Asp Ala Ser Val Leu Ala Met Asp Arg Glu Glu Leu Met
195 200 205

Glu Glu Phe Met Ile Ala Tyr Gln Asp Thr Leu Leu Glu Ile Gly Leu
210 215 220

Asp Asn Arg Glu Ile Ala Arg Met Ala Met Ala Ala Ile Val
225 230 235

<210> SEQ ID NO 41
<211> LENGTH: 1044
<212> TYPE: DNA
<213> ORGANISM: Prochlorococcus mariunus

<400> SEQUENCE: 41
atggcatttg ggcttatagg tcattcaact agttttgaag atgcaaaaag aaaggcttca 60
ttattgggct ttgatcatat tgcggatggt gatttagatg tttggtgcac agctccacct 120
caactagttg aaaatgtaga ggttaaaagt gctataggta tatcaattga aggttcttat 180
attgattcat gtttcgttcc tgaaatgctt tcaagattta aaacggcaag aagaaaagta 240
ttaaatgcaa tggaattagc tcaaaaaaaa ggtattaata ttaccgcttt ggggggggttc 300 acttctatca tctttgaaaa ttttaatctc cttcaacata agcagattag aaacacttca 360
ctagagtggg aaaggtttac aactggtaat actcatactg cgtgggttat ttgcaggcaa 420
ttagagatga atgctcctaa aataggtatt gatcttaaaa gcgcaacagt tgctgtagtt 480

-continued

```
ggtgctactg gagatatagg cagtgctgtt tgtcgatggt taatcaataa aacaggtatt     540

ggggaacttc ttttggtagc taggcaaaag gaacccttgg attctttgca aaaggaatta     600

gatggtggaa ctatcaaaaa tctagatgaa gcattgcctg aagcagatat tgttgtatgg     660

gtagcaagta tgccaaagac aatggaaatc gatgctaata atcttaaaca accatgttta     720

atgattgatg gaggttatcc aaagaatcta gatgaaaaat ttcaaggaaa taatatacat     780

gttgtaaaag gaggtatagt aagattcttc aatgatatag gttggaatat gatggaacta     840

gctgaaatgc aaaatcccca gagagaaatg tttgcatgct ttgcagaagc aatgatttta     900

gaatttgaaa aatgtcatac aaactttagc tggggaagaa ataatatatc tctcgagaaa     960

atggagttta ttggagctgc ttctgtaaag catggcttct ctgcaattgg cctagataag    1020

catccaaaag tactagcagt ttga                                           1044
```

<210> SEQ ID NO 42
<211> LENGTH: 347
<212> TYPE: PRT
<213> ORGANISM: Prochlorococcus mariunus

<400> SEQUENCE: 42

```
Met Ala Phe Gly Leu Ile Gly His Ser Thr Ser Phe Glu Asp Ala Lys
1               5                   10                  15

Arg Lys Ala Ser Leu Leu Gly Phe Asp His Ile Ala Asp Gly Asp Leu
            20                  25                  30

Asp Val Trp Cys Thr Ala Pro Pro Gln Leu Val Glu Asn Val Glu Val
        35                  40                  45

Lys Ser Ala Ile Gly Ile Ser Ile Glu Gly Ser Tyr Ile Asp Ser Cys
    50                  55                  60

Phe Val Pro Glu Met Leu Ser Arg Phe Lys Thr Ala Arg Arg Lys Val
65                  70                  75                  80

Leu Asn Ala Met Glu Leu Ala Gln Lys Lys Gly Ile Asn Ile Thr Ala
                85                  90                  95

Leu Gly Gly Phe Thr Ser Ile Ile Phe Glu Asn Phe Asn Leu Leu Gln
            100                 105                 110

His Lys Gln Ile Arg Asn Thr Ser Leu Glu Trp Glu Arg Phe Thr Thr
        115                 120                 125

Gly Asn Thr His Thr Ala Trp Val Ile Cys Arg Gln Leu Glu Met Asn
    130                 135                 140

Ala Pro Lys Ile Gly Ile Asp Leu Lys Ser Ala Thr Val Ala Val Val
145                 150                 155                 160

Gly Ala Thr Gly Asp Ile Gly Ser Ala Val Cys Arg Trp Leu Ile Asn
                165                 170                 175

Lys Thr Gly Ile Gly Glu Leu Leu Leu Val Ala Arg Gln Lys Glu Pro
            180                 185                 190

Leu Asp Ser Leu Gln Lys Glu Leu Asp Gly Gly Thr Ile Lys Asn Leu
        195                 200                 205

Asp Glu Ala Leu Pro Glu Ala Asp Ile Val Val Trp Val Ala Ser Met
    210                 215                 220

Pro Lys Thr Met Glu Ile Asp Ala Asn Asn Leu Lys Gln Pro Cys Leu
225                 230                 235                 240

Met Ile Asp Gly Gly Tyr Pro Lys Asn Leu Asp Glu Lys Phe Gln Gly
                245                 250                 255

Asn Asn Ile His Val Val Lys Gly Gly Ile Val Arg Phe Phe Asn Asp
            260                 265                 270
```

Ile Gly Trp Asn Met Met Glu Leu Ala Glu Met Gln Asn Pro Gln Arg
275 280 285

Glu Met Phe Ala Cys Phe Ala Glu Ala Met Ile Leu Glu Phe Glu Lys
290 295 300

Cys His Thr Asn Phe Ser Trp Gly Arg Asn Asn Ile Ser Leu Glu Lys
305 310 315 320

Met Glu Phe Ile Gly Ala Ala Ser Val Lys His Gly Phe Ser Ala Ile
325 330 335

Gly Leu Asp Lys His Pro Lys Val Leu Ala Val
340 345

<210> SEQ ID NO 43
<211> LENGTH: 255
<212> TYPE: DNA
<213> ORGANISM: Nostoc punctiforme

<400> SEQUENCE: 43
atgagccaaa cggaactttt tgaaaaggtc aagaaaatcg tcatcgaaca actgagtgtt 60
gaagatgctt ccaaaatcac tccacaagct aagtttatgg aagatttagg agctgattcc 120
ctggatactg ttgaactcgt gatggctttg gaagaagaat ttgatatcga aattcccgac 180
gaagctgccg agcagattgt atcggttcaa gacgcagtag attacatcaa taacaaagtt 240
gctgcatcag cttaa 255

<210> SEQ ID NO 44
<211> LENGTH: 84
<212> TYPE: PRT
<213> ORGANISM: Nostoc punctiforme

<400> SEQUENCE: 44

Met Ser Gln Thr Glu Leu Phe Glu Lys Val Lys Lys Ile Val Ile Glu
1 5 10 15

Gln Leu Ser Val Glu Asp Ala Ser Lys Ile Thr Pro Gln Ala Lys Phe
20 25 30

Met Glu Asp Leu Gly Ala Asp Ser Leu Asp Thr Val Glu Leu Val Met
35 40 45

Ala Leu Glu Glu Glu Phe Asp Ile Glu Ile Pro Asp Glu Ala Ala Glu
50 55 60

Gln Ile Val Ser Val Gln Asp Ala Val Asp Tyr Ile Asn Asn Lys Val
65 70 75 80

Ala Ala Ser Ala

<210> SEQ ID NO 45
<211> LENGTH: 234
<212> TYPE: DNA
<213> ORGANISM: Synechocystis sp.

<400> SEQUENCE: 45
atgaatcagg aaatttttga aaaagtaaaa aaaatcgtcg tggaacagtt ggaagtggat 60
cctgacaaag tgacccccga tgccaccttt gccgaagatt taggggctga ttccctcgat 120
acagtggaat tggtcatggc cctggaagaa gagtttgata ttgaaattcc cgatgaagtg 180
gcggaaacca ttgataccgt gggcaaagcc gttgagcata tcgaaagtaa ataa 234

<210> SEQ ID NO 46
<211> LENGTH: 77
<212> TYPE: PRT
<213> ORGANISM: Synechocystis sp.

<400> SEQUENCE: 46

```
Met Asn Gln Glu Ile Phe Glu Lys Val Lys Lys Ile Val Val Glu Gln
1               5                   10                  15

Leu Glu Val Asp Pro Asp Lys Val Thr Pro Asp Ala Thr Phe Ala Glu
            20                  25                  30

Asp Leu Gly Ala Asp Ser Leu Asp Thr Val Glu Leu Val Met Ala Leu
        35                  40                  45

Glu Glu Glu Phe Asp Ile Glu Ile Pro Asp Glu Val Ala Glu Thr Ile
    50                  55                  60

Asp Thr Val Gly Lys Ala Val Glu His Ile Glu Ser Lys
65                  70                  75
```

<210> SEQ ID NO 47
<211> LENGTH: 243
<212> TYPE: DNA
<213> ORGANISM: Prochlorococcus marinus

<400> SEQUENCE: 47

```
atgtcacaag aagaaatcct tcaaaaagta tgctctattg tttctgagca actaagtgtt      60

gaatcagccg aagtaaaatc tgattcaaac tttcaaaatg atttaggtgc agactcccta     120

gacaccgtag agctagttat ggctcttgaa gaagcatttg atatcgagat acctgatgaa     180

gcagctgaag gtatcgcaac agtaggagat gctgttaaat tcatcgaaga aaaaaaaggt     240

taa                                                                   243
```

<210> SEQ ID NO 48
<211> LENGTH: 80
<212> TYPE: PRT
<213> ORGANISM: Prochlorococcus marinus

<400> SEQUENCE: 48

```
Met Ser Gln Glu Glu Ile Leu Gln Lys Val Cys Ser Ile Val Ser Glu
1               5                   10                  15

Gln Leu Ser Val Glu Ser Ala Glu Val Lys Ser Asp Ser Asn Phe Gln
            20                  25                  30

Asn Asp Leu Gly Ala Asp Ser Leu Asp Thr Val Glu Leu Val Met Ala
        35                  40                  45

Leu Glu Glu Ala Phe Asp Ile Glu Ile Pro Asp Glu Ala Ala Glu Gly
    50                  55                  60

Ile Ala Thr Val Gly Asp Ala Val Lys Phe Ile Glu Glu Lys Lys Gly
65                  70                  75                  80
```

<210> SEQ ID NO 49
<211> LENGTH: 243
<212> TYPE: DNA
<213> ORGANISM: Synechococcus elongatus

<400> SEQUENCE: 49

```
atgagccaag aagacatctt cagcaaagtc aaagacattg tggctgagca gctgagtgtg      60

gatgtggctg aagtcaagcc agaatccagc ttccaaaacg atctgggagc ggactcgctg     120

gacaccgtgg aactggtgat ggctctggaa gaggctttcg atatcgaaat ccccgatgaa     180

gccgctgaag gcattgcgac cgttcaagac gccgtcgatt tcatcgctag caaagctgcc     240

tag                                                                   243
```

<210> SEQ ID NO 50

-continued

<211> LENGTH: 80
<212> TYPE: PRT
<213> ORGANISM: Synechococcus elongatus

<400> SEQUENCE: 50

Met Ser Gln Glu Asp Ile Phe Ser Lys Val Lys Asp Ile Val Ala Glu
1               5                   10                  15

Gln Leu Ser Val Asp Val Ala Glu Val Lys Pro Glu Ser Ser Phe Gln
            20                  25                  30

Asn Asp Leu Gly Ala Asp Ser Leu Asp Thr Val Glu Leu Val Met Ala
        35                  40                  45

Leu Glu Glu Ala Phe Asp Ile Glu Ile Pro Asp Glu Ala Ala Glu Gly
    50                  55                  60

Ile Ala Thr Val Gln Asp Ala Val Asp Phe Ile Ala Ser Lys Ala Ala
65                  70                  75                  80

<210> SEQ ID NO 51
<211> LENGTH: 255
<212> TYPE: DNA
<213> ORGANISM: Nostoc sp.

<400> SEQUENCE: 51
atgagccaat cagaaacttt tgaaaaagtc aaaaaaattg ttatcgaaca actaagtgtg 60
gagaaccctg acacagtaac tccagaagct agttttgcca acgatttaca ggctgattcc 120
ctcgatacag tagaactagt aatggctttg gaagaagaat ttgatatcga aattcccgat 180
gaagccgcag agaaaattac cactgttcaa gaagcggtgg attacatcaa taaccaagtt 240
gccgcatcag cttaa 255

<210> SEQ ID NO 52
<211> LENGTH: 84
<212> TYPE: PRT
<213> ORGANISM: Nostoc sp.

<400> SEQUENCE: 52

Met Ser Gln Ser Glu Thr Phe Glu Lys Val Lys Lys Ile Val Ile Glu
1               5                   10                  15

Gln Leu Ser Val Glu Asn Pro Asp Thr Val Thr Pro Glu Ala Ser Phe
            20                  25                  30

Ala Asn Asp Leu Gln Ala Asp Ser Leu Asp Thr Val Glu Leu Val Met
        35                  40                  45

Ala Leu Glu Glu Glu Phe Asp Ile Glu Ile Pro Asp Glu Ala Ala Glu
    50                  55                  60

Lys Ile Thr Thr Val Gln Glu Ala Val Asp Tyr Ile Asn Asn Gln Val
65                  70                  75                  80

Ala Ala Ser Ala

<210> SEQ ID NO 53
<211> LENGTH: 675
<212> TYPE: DNA
<213> ORGANISM: Bacillus subtilis

<400> SEQUENCE: 53
atgaagattt acggaattta tatggaccgc ccgctttcac aggaagaaaa tgaacggttc 60
atgactttca tatcacctga aaaacgggag aaatgccgga gattttatca taaagaagat 120
gctcaccgca ccctgctggg agatgtgctc gttcgctcag tcataagcag gcagtatcag 180
ttggacaaat ccgatatccg ctttagcacg caggaatacg ggaagccgtg catccctgat 240

```
cttcccgacg ctcatttcaa catttctcac tccggccgct gggtcattgg tgcgtttgat    300

tcacagccga tcggcataga tatcgaaaaa acgaaaccga tcagccttga gatcgccaag    360

cgcttctttt caaaaacaga gtacagcgac cttttagcaa aagacaagga cgagcagaca    420

gactattttt atcatctatg gtcaatgaaa gaaagcttta tcaaacagga aggcaaaggc    480

ttatcgcttc cgcttgattc cttttcagtg cgcctgcatc aggacggaca agtatccatt    540

gagcttccgg acagccattc cccatgctat atcaaaacgt atgaggtcga tcccggctac    600

aaaatggctg tatgcgccgc acaccctgat ttccccgagg atatcacaat ggtctcgtac    660

gaagagcttt tataa                                                     675
```

```
<210> SEQ ID NO 54
<211> LENGTH: 224
<212> TYPE: PRT
<213> ORGANISM: Bacillus subtilis

<400> SEQUENCE: 54

Met Lys Ile Tyr Gly Ile Tyr Met Asp Arg Pro Leu Ser Gln Glu Glu
1               5                   10                  15

Asn Glu Arg Phe Met Thr Phe Ile Ser Pro Glu Lys Arg Glu Lys Cys
            20                  25                  30

Arg Arg Phe Tyr His Lys Glu Asp Ala His Arg Thr Leu Leu Gly Asp
        35                  40                  45

Val Leu Val Arg Ser Val Ile Ser Arg Gln Tyr Gln Leu Asp Lys Ser
    50                  55                  60

Asp Ile Arg Phe Ser Thr Gln Glu Tyr Gly Lys Pro Cys Ile Pro Asp
65                  70                  75                  80

Leu Pro Asp Ala His Phe Asn Ile Ser His Ser Gly Arg Trp Val Ile
                85                  90                  95

Gly Ala Phe Asp Ser Gln Pro Ile Gly Ile Asp Ile Glu Lys Thr Lys
            100                 105                 110

Pro Ile Ser Leu Glu Ile Ala Lys Arg Phe Phe Ser Lys Thr Glu Tyr
        115                 120                 125

Ser Asp Leu Leu Ala Lys Asp Lys Asp Glu Gln Thr Asp Tyr Phe Tyr
    130                 135                 140

His Leu Trp Ser Met Lys Glu Ser Phe Ile Lys Gln Glu Gly Lys Gly
145                 150                 155                 160

Leu Ser Leu Pro Leu Asp Ser Phe Ser Val Arg Leu His Gln Asp Gly
                165                 170                 175

Gln Val Ser Ile Glu Leu Pro Asp Ser His Ser Pro Cys Tyr Ile Lys
            180                 185                 190

Thr Tyr Glu Val Asp Pro Gly Tyr Lys Met Ala Val Cys Ala Ala His
        195                 200                 205

Pro Asp Phe Pro Glu Asp Ile Thr Met Val Ser Tyr Glu Glu Leu Leu
    210                 215                 220


<210> SEQ ID NO 55
<211> LENGTH: 867
<212> TYPE: DNA
<213> ORGANISM: Corynebacterium glutamicum

<400> SEQUENCE: 55

ttgggcgtgt cgcccttaaa gcgcgctttt cgacgcgacc ccactacatt ggcttccatg     60

aacgttgaca tttcacgatc cagagagccg ctaaacgttg agctcctgaa ggaaaaattg    120
```

ctccaaaacg gtgactttgg ccaggtcatt tacgaaaaag tgacaggctc cactaatgct 180
gacttgctgg cacttgcagg ttctggcgct ccaaactgga cggtgaaaac tgtcgagttt 240
caagatcatg cgcgtgggcg actcggccgc ccgtggtctg cccctgaggg ttcccaaaca 300
atcgtgtctg tgctcgttca actatctatt gatcaagtgg accggattgg cactattcca 360
ctcgcggcgg gactcgctgt catggatgcg ttgaatgacc tcggtgtgga aggtgccgga 420
ctgaaatggc ccaacgatgt tcaaatccac ggcaagaaac tctgcggcat cctggtggaa 480
gccaccggct ttgattccac cccaacagtt gtcatcggtt ggggcactaa tatcagcctg 540
actaaagagg agcttcctgt tcctcatgca acttccctcg cattggaagg tgttgaagtc 600
gacagaacca cattccttat taatatgctc acacatctgc atactcgact ggaccagtgg 660
cagggtccaa gtgtggattg gctcgatgat taccgtgcgg tatgttccag tattggccaa 720
gatgttcgag tgcttctacc tggggataaa gaactcttag gtgaagcgat cggtgtcgcg 780
actggcggag aaattcgtgt tcgcgatgct tcgggcaccg ttcacaccct caacgccggt 840
gaaattacgc accttcgcct gcagtaa 867

<210> SEQ ID NO 56
<211> LENGTH: 810
<212> TYPE: DNA
<213> ORGANISM: Corynebacterium glutamicum

<400> SEQUENCE: 56
atgaatgttg acattagccg ctctcgtgaa ccgttgaacg tggaactgtt gaaagaaaaa 60
ctgctgcaga acggtgattt cggtcaagtg atctacgaga aggtcaccgg ctctaccaat 120
gcggacctgc tggctctggc gggcagcggc gctccaaact ggaccgtcaa gactgttgaa 180
tttcaggacc acgcccgtgg ccgtctgggt cgtccgtgga gcgcaccgga gggttcccaa 240
accatcgtca gcgttctggt ccaactgagc attgatcagg tggaccgtat tggtacgatc 300
ccgctggccg caggcttggc tgttatggat gcgctgaatg atctgggcgt ggagggtgca 360
ggcctgaaat ggccgaacga tgttcagatc cacggtaaga agttgtgcgg tattctggtt 420
gaagcaaccg gcttcgactc cactccgacc gtggttatcg gttggggtac gaatatctcg 480
ttgacgaaag aagagctgcc ggtcccgcac gcgaccagcc tggccctgga gggtgttgaa 540
gttgaccgta cgacgttcct gattaacatg ctgacccatc tgcataccccg tctggatcag 600 tggcagggtc cgtctgtgga ctggctggat gactatcgcg cggtttgtag cagcattggc 660
caagatgtgc gtgtcctgct gcctggtgac aaagagctgc tgggcgaggc gattggcgtg 720
gcgaccggtg gtgagatccg tgtgcgcgac gccagcggca cggtccacac gctgaatgcg 780
ggtgaaatca cgcatctgcg tttgcaataa 810

<210> SEQ ID NO 57
<211> LENGTH: 269
<212> TYPE: PRT
<213> ORGANISM: Corynebacterium glutamicum

<400> SEQUENCE: 57

Met Asn Val Asp Ile Ser Arg Ser Arg Glu Pro Leu Asn Val Glu Leu
1 5 10 15

Leu Lys Glu Lys Leu Leu Gln Asn Gly Asp Phe Gly Gln Val Ile Tyr
20 25 30

Glu Lys Val Thr Gly Ser Thr Asn Ala Asp Leu Leu Ala Leu Ala Gly
35 40 45

-continued

```
Ser Gly Ala Pro Asn Trp Thr Val Lys Thr Val Glu Phe Gln Asp His
    50                  55                  60

Ala Arg Gly Arg Leu Gly Arg Pro Trp Ser Ala Pro Glu Gly Ser Gln
65                  70                  75                  80

Thr Ile Val Ser Val Leu Val Gln Leu Ser Ile Asp Gln Val Asp Arg
                85                  90                  95

Ile Gly Thr Ile Pro Leu Ala Ala Gly Leu Ala Val Met Asp Ala Leu
            100                 105                 110

Asn Asp Leu Gly Val Glu Gly Ala Gly Leu Lys Trp Pro Asn Asp Val
        115                 120                 125

Gln Ile His Gly Lys Lys Leu Cys Gly Ile Leu Val Glu Ala Thr Gly
    130                 135                 140

Phe Asp Ser Thr Pro Thr Val Val Ile Gly Trp Gly Thr Asn Ile Ser
145                 150                 155                 160

Leu Thr Lys Glu Glu Leu Pro Val Pro His Ala Thr Ser Leu Ala Leu
                165                 170                 175

Glu Gly Val Glu Val Asp Arg Thr Thr Phe Leu Ile Asn Met Leu Thr
            180                 185                 190

His Leu His Thr Arg Leu Asp Gln Trp Gln Gly Pro Ser Val Asp Trp
        195                 200                 205

Leu Asp Asp Tyr Arg Ala Val Cys Ser Ser Ile Gly Gln Asp Val Arg
    210                 215                 220

Val Leu Leu Pro Gly Asp Lys Glu Leu Leu Gly Glu Ala Ile Gly Val
225                 230                 235                 240

Ala Thr Gly Gly Glu Ile Arg Val Arg Asp Ala Ser Gly Thr Val His
                245                 250                 255

Thr Leu Asn Ala Gly Glu Ile Thr His Leu Arg Leu Gln
            260                 265
```

<210> SEQ ID NO 58
<211> LENGTH: 1632
<212> TYPE: DNA
<213> ORGANISM: Corynebacterium glutamicum

<400> SEQUENCE: 58

```
atgaccattt cctcaccttt gattgacgtc gccaaccttc cagacatcaa caccactgcc     60

ggcaagatcg ccgaccttaa ggctcgccgc gcggaagccc atttccccat gggtgaaaag    120

gcagtagaga aggtccacgc tgctggacgc ctcactgccc gtgagcgctt ggattactta    180

ctcgatgagg gctccttcat cgagaccgat cagctggctc gccaccgcac caccgctttc    240

ggcctgggcg ctaagcgtcc tgcaaccgac ggcatcgtga ccggctgggg caccattgat    300

ggacgcgaag tctgcatctt ctcgcaggac ggcaccgtat tcggtggcgc gcttggtgag    360

gtgtacggcg aaaagatgat caagatcatg gagctggcaa tcgacaccgg ccgcccattg    420

atcggtcttt acgaaggcgc tggcgctcgt attcaggacg gcgctgtctc cctggacttc    480

atttcccaga ccttctacca aaacattcag gcttctggcg ttatcccaca gatctccgtc    540

atcatgggcg catgtgcagg tggcaacgct tacggcccag ctctgaccga cttcgtggtc    600

atggtggaca agacctccaa gatgttcgtt accggcccag acgtgatcaa gaccgtcacc    660

ggcgaggaaa tcacccagga agagcttggc ggagcaacca cccacatggt gaccgctggt    720

aactcccact acaccgctgc gaccgatgag gaagcactgg attgggtaca ggacctggtg    780

tccttcctcc catccaacaa tcgctcctac gcaccgatgg aagacttcga cgaggaagaa    840

ggcggcgttg aagaaaacat caccgctgac gatctgaagc tcgacgagat catcccagat    900
```

```
tccgcgaccg ttccttacga cgtccgcgat gtcatcgaat gcctcaccga cgatggcgaa    960

tacctggaaa tccaggcaga ccgcgcagaa aacgttgtta ttgcattcgg ccgcatcgaa   1020

ggccagtccg ttggctttgt tgccaaccag ccaacccagt tcgctggctg cctggacatc   1080

gactcctctg agaaggcagc tcgcttcgtc cgcacctgcg acgcgttcaa catcccaatc   1140

gtcatgcttg tcgacgtccc cggcttcctc ccaggcgcag gccaggagta cggtggcatt   1200

ctgcgtcgtg gcgcaaagct gctctacgca tacggcgaag caaccgttcc aaagatcacc   1260

gtcaccatgc gtaaggctta cggcggagcg tactgcgtga tgggttccaa gggcttgggc   1320

tctgacatca accttgcatg gccaaccgca cagatcgccg tcatgggcgc tgctggcgca   1380

gttggattca tctaccgcaa ggagctcatg gcagctgatg ccaagggcct cgataccgta   1440

gctctggcta agtccttcga gcgcgagtat gaagaccaca tgctcaaccc gtaccacgct   1500

gcagaacgtg gcctgatcga cgccgtgatc ctgccaagcg aaacccgcgg acagatttcc   1560

cgcaaccttc gcctgctcaa gcacaagaac gtcactcgcc ctgctcgcaa gcacggcaac   1620

atgccactgt aa                                                       1632
```

<210> SEQ ID NO 59
<211> LENGTH: 543
<212> TYPE: PRT
<213> ORGANISM: Corynebacterium glutamicum

<400> SEQUENCE: 59

```
Met Thr Ile Ser Ser Pro Leu Ile Asp Val Ala Asn Leu Pro Asp Ile
1               5                   10                  15

Asn Thr Thr Ala Gly Lys Ile Ala Asp Leu Lys Ala Arg Arg Ala Glu
            20                  25                  30

Ala His Phe Pro Met Gly Glu Lys Ala Val Glu Lys Val His Ala Ala
        35                  40                  45

Gly Arg Leu Thr Ala Arg Glu Arg Leu Asp Tyr Leu Leu Asp Glu Gly
    50                  55                  60

Ser Phe Ile Glu Thr Asp Gln Leu Ala Arg His Arg Thr Thr Ala Phe
65                  70                  75                  80

Gly Leu Gly Ala Lys Arg Pro Ala Thr Asp Gly Ile Val Thr Gly Trp
                85                  90                  95

Gly Thr Ile Asp Gly Arg Glu Val Cys Ile Phe Ser Gln Asp Gly Thr
            100                 105                 110

Val Phe Gly Gly Ala Leu Gly Glu Val Tyr Gly Glu Lys Met Ile Lys
        115                 120                 125

Ile Met Glu Leu Ala Ile Asp Thr Gly Arg Pro Leu Ile Gly Leu Tyr
    130                 135                 140

Glu Gly Ala Gly Ala Arg Ile Gln Asp Gly Ala Val Ser Leu Asp Phe
145                 150                 155                 160

Ile Ser Gln Thr Phe Tyr Gln Asn Ile Gln Ala Ser Gly Val Ile Pro
                165                 170                 175

Gln Ile Ser Val Ile Met Gly Ala Cys Ala Gly Gly Asn Ala Tyr Gly
            180                 185                 190

Pro Ala Leu Thr Asp Phe Val Val Met Val Asp Lys Thr Ser Lys Met
        195                 200                 205

Phe Val Thr Gly Pro Asp Val Ile Lys Thr Val Thr Gly Glu Glu Ile
    210                 215                 220

Thr Gln Glu Glu Leu Gly Gly Ala Thr Thr His Met Val Thr Ala Gly
225                 230                 235                 240
```

```
Asn Ser His Tyr Thr Ala Ala Thr Asp Glu Glu Ala Leu Asp Trp Val
                245                 250                 255

Gln Asp Leu Val Ser Phe Leu Pro Ser Asn Asn Arg Ser Tyr Ala Pro
            260                 265                 270

Met Glu Asp Phe Asp Glu Glu Glu Gly Gly Val Glu Glu Asn Ile Thr
        275                 280                 285

Ala Asp Asp Leu Lys Leu Asp Glu Ile Ile Pro Asp Ser Ala Thr Val
    290                 295                 300

Pro Tyr Asp Val Arg Asp Val Ile Glu Cys Leu Thr Asp Asp Gly Glu
305                 310                 315                 320

Tyr Leu Glu Ile Gln Ala Asp Arg Ala Glu Asn Val Val Ile Ala Phe
                325                 330                 335

Gly Arg Ile Glu Gly Gln Ser Val Gly Phe Val Ala Asn Gln Pro Thr
            340                 345                 350

Gln Phe Ala Gly Cys Leu Asp Ile Asp Ser Ser Glu Lys Ala Ala Arg
        355                 360                 365

Phe Val Arg Thr Cys Asp Ala Phe Asn Ile Pro Ile Val Met Leu Val
    370                 375                 380

Asp Val Pro Gly Phe Leu Pro Gly Ala Gly Gln Glu Tyr Gly Gly Ile
385                 390                 395                 400

Leu Arg Arg Gly Ala Lys Leu Leu Tyr Ala Tyr Gly Glu Ala Thr Val
                405                 410                 415

Pro Lys Ile Thr Val Thr Met Arg Lys Ala Tyr Gly Gly Ala Tyr Cys
            420                 425                 430

Val Met Gly Ser Lys Gly Leu Gly Ser Asp Ile Asn Leu Ala Trp Pro
        435                 440                 445

Thr Ala Gln Ile Ala Val Met Gly Ala Ala Gly Ala Val Gly Phe Ile
    450                 455                 460

Tyr Arg Lys Glu Leu Met Ala Ala Asp Ala Lys Gly Leu Asp Thr Val
465                 470                 475                 480

Ala Leu Ala Lys Ser Phe Glu Arg Glu Tyr Glu Asp His Met Leu Asn
                485                 490                 495

Pro Tyr His Ala Ala Glu Arg Gly Leu Ile Asp Ala Val Ile Leu Pro
            500                 505                 510

Ser Glu Thr Arg Gly Gln Ile Ser Arg Asn Leu Arg Leu Leu Lys His
        515                 520                 525

Lys Asn Val Thr Arg Pro Ala Arg Lys His Gly Asn Met Pro Leu
    530                 535                 540
```

<210> SEQ ID NO 60
<211> LENGTH: 1776
<212> TYPE: DNA
<213> ORGANISM: Corynebacterium glutamicum

<400> SEQUENCE: 60

```
atgtcagtcg agactcgcaa gatcaccaag gttcttgtcg ctaaccgtgg tgagattgca      60

atccgcgtgt tccgtgcagc tcgagatgaa ggcatcggat ctgtcgccgt ctacgcagag     120

ccagatgcag atgcaccatt cgtgtcatat gcagacgagg cttttgccct cggtggccaa     180

acatccgctg agtcctacct tgtcattgac aagatcatcg atgcggcccg caagtccggc     240

gccgacgcca tccaccccgg ctacggcttc ctcgcagaaa acgctgactt cgcagaagca     300

gtcatcaacg aaggcctgat ctggattgga ccttcacctg agtccatccg ctccctcggc     360

gacaaggtca ccgctcgcca catcgcagat accgccaagg ctccaatggc tcctggcacc     420
```

```
aaggaaccag taaaagacgc agcagaagtt gtggctttcg ctgaagaatt cggtctccca    480

atcgccatca aggcagcttt cggtggcggc ggacgtggca tgaaggttgc ctacaagatg    540

gaagaagtcg ctgacctctt cgagtccgca acccgtgaag caaccgcagc gttcggccgc    600

ggcgagtgct tcgtggagcg ctacctggac aaggcacgcc acgttgaggc tcaggtcatc    660

gccgataagc acggcaacgt tgttgtcgcc ggaacccgtg actgctccct gcagcgccgt    720

ttccagaagc tcgtcgaaga agcaccagca ccattcctca ccgatgacca gcgcgagcgt    780

ctccactcct ccgcgaaggc tatctgtaag gaagctggct actacggtgc aggcaccgtt    840

gagtacctcg ttggctccga cggcctgatc tccttcctcg aggtcaacac ccgcctccag    900

gtggaacacc cagtcaccga agagaccacc ggcatcgacc tggtccgcga aatgttccgc    960

atcgcagaag gccacgagct ctccatcaag gaagatccag ctccacgcgg ccacgcattc   1020

gagttccgca tcaacggcga agacgctggc tccaacttca tgcctgcacc aggcaagatc   1080

accagctacc gcgagccaca gggcccaggc gtccgcatgg actccggtgt cgttgaaggt   1140

tccgaaatct ccggacagtt cgactccatg ctggcaaagc tgatcgtttg gggcgacacc   1200

cgcgagcagg ctctccagcg ctcccgccgt gcacttgcag agtacgttgt cgagggcatg   1260

ccaaccgtta tcccattcca ccagcacatc gtggaaaacc cagcattcgt gggcaacgac   1320

gaaggcttcg agatctacac caagtggatc gaagaggttt gggataaccc aatcgcacct   1380

tacgttgacg cttccgagct cgacgaagat gaggacaaga ccccagcaca gaaggttgtt   1440

gtggagatca acggccgtcg cgttgaggtt gcactcccag gcgatctggc actcggtggc   1500

accgctggtc ctaagaagaa ggccaagaag cgtcgcgcag gtggtgcaaa ggctggcgta   1560

tccggcgatg cagtggcagc tccaatgcag ggcactgtca tcaaggtcaa cgtcgaagaa   1620

ggcgctgaag tcaacgaagg cgacaccgtt gttgtcctcg aggctatgaa gatggaaaac   1680

cctgtgaagg ctcataagtc cggaaccgta accggcctta ctgtcgctgc aggcgagggt   1740

gtcaacaagg gcgttgttct cctcgagatc aagtaa                             1776
```

<210> SEQ ID NO 61
<211> LENGTH: 591
<212> TYPE: PRT
<213> ORGANISM: Corynebacterium glutamicum

<400> SEQUENCE: 61

```
Met Ser Val Glu Thr Arg Lys Ile Thr Lys Val Leu Val Ala Asn Arg
1               5                   10                  15

Gly Glu Ile Ala Ile Arg Val Phe Arg Ala Ala Arg Asp Glu Gly Ile
            20                  25                  30

Gly Ser Val Ala Val Tyr Ala Glu Pro Asp Ala Asp Ala Pro Phe Val
        35                  40                  45

Ser Tyr Ala Asp Glu Ala Phe Ala Leu Gly Gly Gln Thr Ser Ala Glu
    50                  55                  60

Ser Tyr Leu Val Ile Asp Lys Ile Ile Asp Ala Ala Arg Lys Ser Gly
65                  70                  75                  80

Ala Asp Ala Ile His Pro Gly Tyr Gly Phe Leu Ala Glu Asn Ala Asp
                85                  90                  95

Phe Ala Glu Ala Val Ile Asn Glu Gly Leu Ile Trp Ile Gly Pro Ser
            100                 105                 110

Pro Glu Ser Ile Arg Ser Leu Gly Asp Lys Val Thr Ala Arg His Ile
        115                 120                 125
```

-continued

```
Ala Asp Thr Ala Lys Ala Pro Met Ala Pro Gly Thr Lys Glu Pro Val
    130                 135                 140

Lys Asp Ala Ala Glu Val Val Ala Phe Ala Glu Glu Phe Gly Leu Pro
145                 150                 155                 160

Ile Ala Ile Lys Ala Ala Phe Gly Gly Gly Gly Arg Gly Met Lys Val
                165                 170                 175

Ala Tyr Lys Met Glu Glu Val Ala Asp Leu Phe Glu Ser Ala Thr Arg
            180                 185                 190

Glu Ala Thr Ala Ala Phe Gly Arg Gly Glu Cys Phe Val Glu Arg Tyr
        195                 200                 205

Leu Asp Lys Ala Arg His Val Glu Ala Gln Val Ile Ala Asp Lys His
    210                 215                 220

Gly Asn Val Val Val Ala Gly Thr Arg Asp Cys Ser Leu Gln Arg Arg
225                 230                 235                 240

Phe Gln Lys Leu Val Glu Glu Ala Pro Ala Pro Phe Leu Thr Asp Asp
                245                 250                 255

Gln Arg Glu Arg Leu His Ser Ser Ala Lys Ala Ile Cys Lys Glu Ala
            260                 265                 270

Gly Tyr Tyr Gly Ala Gly Thr Val Glu Tyr Leu Val Gly Ser Asp Gly
        275                 280                 285

Leu Ile Ser Phe Leu Glu Val Asn Thr Arg Leu Gln Val Glu His Pro
    290                 295                 300

Val Thr Glu Glu Thr Thr Gly Ile Asp Leu Val Arg Glu Met Phe Arg
305                 310                 315                 320

Ile Ala Glu Gly His Glu Leu Ser Ile Lys Glu Asp Pro Ala Pro Arg
                325                 330                 335

Gly His Ala Phe Glu Phe Arg Ile Asn Gly Glu Asp Ala Gly Ser Asn
            340                 345                 350

Phe Met Pro Ala Pro Gly Lys Ile Thr Ser Tyr Arg Glu Pro Gln Gly
        355                 360                 365

Pro Gly Val Arg Met Asp Ser Gly Val Val Glu Gly Ser Glu Ile Ser
    370                 375                 380

Gly Gln Phe Asp Ser Met Leu Ala Lys Leu Ile Val Trp Gly Asp Thr
385                 390                 395                 400

Arg Glu Gln Ala Leu Gln Arg Ser Arg Arg Ala Leu Ala Glu Tyr Val
                405                 410                 415

Val Glu Gly Met Pro Thr Val Ile Pro Phe His Gln His Ile Val Glu
            420                 425                 430

Asn Pro Ala Phe Val Gly Asn Asp Glu Gly Phe Glu Ile Tyr Thr Lys
        435                 440                 445

Trp Ile Glu Glu Val Trp Asp Asn Pro Ile Ala Pro Tyr Val Asp Ala
    450                 455                 460

Ser Glu Leu Asp Glu Asp Glu Asp Lys Thr Pro Ala Gln Lys Val Val
465                 470                 475                 480

Val Glu Ile Asn Gly Arg Arg Val Glu Val Ala Leu Pro Gly Asp Leu
                485                 490                 495

Ala Leu Gly Gly Thr Ala Gly Pro Lys Lys Lys Ala Lys Lys Arg Arg
            500                 505                 510

Ala Gly Gly Ala Lys Ala Gly Val Ser Gly Asp Ala Val Ala Ala Pro
        515                 520                 525

Met Gln Gly Thr Val Ile Lys Val Asn Val Glu Glu Gly Ala Glu Val
    530                 535                 540

Asn Glu Gly Asp Thr Val Val Val Leu Glu Ala Met Lys Met Glu Asn
```

545 550 555 560

Pro Val Lys Ala His Lys Ser Gly Thr Val Thr Gly Leu Thr Val Ala
565 570 575

Ala Gly Glu Gly Val Asn Lys Gly Val Val Leu Leu Glu Ile Lys
580 585 590

<210> SEQ ID NO 62
<211> LENGTH: 10025
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 62
cactatacca attgagatgg gctagtcaat gataattact agtccttttc ctttgagttg 60
tgggtatctg taaattctgc tagacctttg ctggaaaact tgtaaattct gctagaccct 120
ctgtaaattc cgctagacct ttgtgtgttt tttttgttta tattcaagtg gttataattt 180
atagaataaa gaaagaataa aaaaagataa aaagaataga tcccagccct gtgtataact 240
cactacttta gtcagttccg cagtattaca aaaggatgtc gcaaacgctg tttgctcctc 300
tacaaaacag accttaaaac cctaaaggcg tcggcatccg cttacagaca agctgtgacc 360
gtctccggga gctgcatgtg tcagaggttt tcaccgtcat caccgaaacg cgcgaggcag 420
cagatcaatt cgcgcgcgaa ggcgaagcgg catgcattta cgttgacacc atcgaatggt 480
gcaaaacctt tcgcggtatg gcatgatagc gcccggaaga gagtcaattc agggtggtga 540
atgtgaaacc agtaacgtta tacgatgtcg cagagtatgc cggtgtctct tatcagaccg 600
tttcccgcgt ggtgaaccag gccagccacg tttctgcgaa aacgcgggaa aaagtggaag 660
cggcgatggc ggagctgaat tacattccca accgcgtggc acaacaactg gcgggcaaac 720
agtcgttgct gattggcgtt gccacctcca gtctggccct gcacgcgccg tcgcaaattg 780
tcgcggcgat taaatctcgc gccgatcaac tgggtgccag cgtggtggtg tcgatggtag 840
aacgaagcgg cgtcgaagcc tgtaaagcgg cggtgcacaa tcttctcgcg caacgcgtca 900
gtgggctgat cattaactat ccgctggatg accaggatgc cattgctgtg gaagctgcct 960
gcactaatgt tccggcgtta tttcttgatg tctctgacca gacacccatc aacagtatta 1020
ttttctccca tgaagacggt acgcgactgg gcgtggagca tctggtcgca ttgggtcacc 1080
agcaaatcgc gctgttagcg ggcccattaa gttctgtctc ggcgcgtctg cgtctggctg 1140
gctggcataa atatctcact cgcaatcaaa ttcagccgat agcggaacgg gaaggcgact 1200
ggagtgccat gtccggtttt caacaaacca tgcaaatgct gaatgagggc atcgttccca 1260
ctgcgatgct ggttgccaac gatcagatgg cgctgggcgc aatgcgcgcc attaccgagt 1320
ccgggctgcg cgttggtgcg gatatctcgg tagtgggata cgacgatacc gaagacagct 1380
catgttatat cccgccgtta accaccatca aacaggattt tcgcctgctg gggcaaacca 1440
gcgtggaccg cttgctgcaa ctctctcagg gccaggcggt gaagggcaat cagctgttgc 1500
ccgtctcact ggtgaaaaga aaaaccaccc tggcgcccaa tacgcaaacc gcctctcccc 1560
gcgcgttggc cgattcatta atgcagctgg cacgacaggt ttcccgactg gaaagcgggc 1620
agtgagcgca acgcaattaa tgtaagttag cgcgaattga tctggtttga cagcttatca 1680
tcgactgcac ggtgcaccaa tgcttctggc gtcaggcagc catcggaagc tgtggtatgg 1740
ctgtgcaggt cgtaaatcac tgcataattc gtgtcgctca aggcgcactc ccgttctgga 1800

-continued

```
taatgttttt tgcgccgaca tcataacggt tctggcaaat attctgttga caattaatca   1860
tccggctcgt ataaagtgtg gaattgtgag cggataacaa tttcacacag gaaacagcgc   1920
cgctgagaaa aagcgaagcg gcactgctct ttaacaattt atcagacaat ctgtgtgggc   1980
actcgaccgg aattatcgat taactttatt attaaaaatt aaagaggtat atattaatgt   2040
atcgattaaa taaggaggaa taaaccatga ccatttcctc acctttgatt gacgtcgcca   2100
accttccaga catcaacacc actgccggca agatcgccga ccttaaggct cgccgcgcgg   2160
aagcccattt ccccatgggt gaaaaggcag tagagaaggt ccacgctgct ggacgcctca   2220
ctgcccgtga gcgcttggat tacttactcg atgagggctc cttcatcgag accgatcagc   2280
tggctcgcca ccgcaccacc gctttcggcc tgggcgctaa gcgtcctgca accgacggca   2340
tcgtgaccgg ctggggcacc attgatggac gcgaagtctg catcttctcg caggacggca   2400
ccgtattcgg tggcgcgctt ggtgaggtgt acggcgaaaa gatgatcaag atcatggagc   2460
tggcaatcga caccggccgc ccattgatcg gtctttacga aggcgctggc gctcgtattc   2520
aggacggcgc tgtctccctg gacttcattt cccagacctt ctaccaaaac attcaggctt   2580
ctggcgttat cccacagatc tccgtcatca tgggcgcatg tgcaggtggc aacgcttacg   2640
gcccagctct gaccgacttc gtggtcatgg tggacaagac ctccaagatg ttcgttaccg   2700
gcccagacgt gatcaagacc gtcaccggcg aggaaatcac ccaggaagag cttggcggag   2760
caaccaccca catggtgacc gctggtaact cccactacac cgctgcgacc gatgaggaag   2820
cactggattg ggtacaggac ctggtgtcct tcctcccatc caacaatcgc tcctacgcac   2880
cgatggaaga cttcgacgag gaagaaggcg gcgttgaaga aaacatcacc gctgacgatc   2940
tgaagctcga cgagatcatc ccagattccg cgaccgttcc ttacgacgtc cgcgatgtca   3000
tcgaatgcct caccgacgat ggcgaatacc tggaaatcca ggcagaccgc gcagaaaacg   3060
ttgttattgc attcggccgc atcgaaggcc agtccgttgg ctttgttgcc aaccagccaa   3120
cccagttcgc tggctgcctg gacatcgact cctctgagaa ggcagctcgc ttcgtccgca   3180
cctgcgacgc gttcaacatc ccaatcgtca tgcttgtcga cgtccccggc ttcctcccag   3240
gcgcaggcca ggagtacggt ggcattctgc gtcgtggcgc aaagctgctc tacgcatacg   3300
gcgaagcaac cgttccaaag atcaccgtca ccatgcgtaa ggcttacggc ggagcgtact   3360
gcgtgatggg ttccaagggc ttgggctctg acatcaacct tgcatggcca accgcacaga   3420
tcgccgtcat gggcgctgct ggcgcagttg gattcatcta ccgcaaggag ctcatggcag   3480
ctgatgccaa gggcctcgat accgtagctc tggctaagtc cttcgagcgc gagtatgaag   3540
accacatgct caacccgtac cacgctgcag aacgtggcct gatcgacgcc gtgatcctgc   3600
caagcgaaac ccgcggacag atttcccgca accttcgcct gctcaagcac aagaacgtca   3660
ctcgccctgc tcgcaagcac ggcaacatgc cactgtaagg aggaaaacta aatgtcagtc   3720
gagactcgca agatcaccaa ggttcttgtc gctaaccgtg gtgagattgc aatccgcgtg   3780
ttccgtgcag ctcgagatga aggcatcgga tctgtcgccg tctacgcaga gccagatgca   3840
gatgcaccat tcgtgtcata tgcagacgag gcttttgccc tcggtggcca aacatccgct   3900
gagtcctacc ttgtcattga caagatcatc gatgcggccc gcaagtccgg cgccgacgcc   3960
atccaccccg gctacggctt cctcgcagaa aacgctgact tcgcagaagc agtcatcaac   4020
gaaggcctga tctggattgg accttcacct gagtccatcc gctccctcgg cgacaaggtc   4080
accgctcgcc acatcgcaga taccgccaag gctccaatgg ctcctggcac caaggaacca   4140
```

-continued gtaaaagacg cagcagaagt tgtggctttc gctgaagaat tcggtctccc aatcgccatc 4200
aaggcagctt tcggtggcgg cggacgtggc atgaaggttg cctacaagat ggaagaagtc 4260
gctgacctct tcgagtccgc aacccgtgaa gcaaccgcag cgttcggccg cggcgagtgc 4320
ttcgtggagc gctacctgga caaggcacgc cacgttgagg ctcaggtcat cgccgataag 4380
cacggcaacg ttgttgtcgc cggaacccgt gactgctccc tgcagcgccg tttccagaag 4440
ctcgtcgaag aagcaccagc accattcctc accgatgacc agcgcgagcg tctccactcc 4500
tccgcgaagg ctatctgtaa ggaagctggc tactacggtg caggcaccgt tgagtacctc 4560
gttggctccg acggcctgat ctccttcctc gaggtcaaca cccgcctcca ggtggaacac 4620
ccagtcaccg aagagaccac cggcatcgac ctggtccgcg aaatgttccg catcgcagaa 4680
ggccacgagc tctccatcaa ggaagatcca gctccacgcg gccacgcatt cgagttccgc 4740
atcaacggcg aagacgctgg ctccaacttc atgcctgcac caggcaagat caccagctac 4800
cgcgagccac agggcccagg cgtccgcatg gactccggtg tcgttgaagg ttccgaaatc 4860
tccggacagt tcgactccat gctggcaaag ctgatcgttt ggggcgacac ccgcgagcag 4920
gctctccagc gctcccgccg tgcacttgca gagtacgttg tcgagggcat gccaaccgtt 4980
atcccattcc accagcacat cgtggaaaac ccagcattcg tgggcaacga cgaaggcttc 5040
gagatctaca ccaagtggat cgaagaggtt tgggataacc caatcgcacc ttacgttgac 5100
gcttccgagc tcgacgaaga tgaggacaag accccagcac agaaggttgt tgtggagatc 5160
aacggccgtc gcgttgaggt tgcactccca ggcgatctgg cactcggtgg caccgctggt 5220
cctaagaaga aggccaagaa gcgtcgcgca ggtggtgcaa aggctggcgt atccggcgat 5280
gcagtggcag ctccaatgca gggcactgtc atcaaggtca acgtcgaaga aggcgctgaa 5340
gtcaacgaag gcgacaccgt tgttgtcctc gaggctatga agatggaaaa ccctgtgaag 5400
gctcataagt ccggaaccgt aaccggcctt actgtcgctg caggcgaggg tgtcaacaag 5460
ggcgttgttc tcctcgagat caagtaatct agaggaggaa aactaaatga atgttgacat 5520
tagccgctct cgtgaaccgt tgaacgtgga actgttgaaa gaaaaactgc tgcagaacgg 5580
tgatttcggt caagtgatct acgagaaggt caccggctct accaatgcgg acctgctggc 5640
tctggcgggc agcggcgctc caaactggac cgtcaagact gttgaatttc aggaccacgc 5700
ccgtggccgt ctgggtcgtc cgtggagcgc accggagggt tcccaaacca tcgtcagcgt 5760
tctggtccaa ctgagcattg atcaggtgga ccgtattggt acgatcccgc tggccgcagg 5820
cttggctgtt atggatgcgc tgaatgatct gggcgtggag ggtgcaggcc tgaaatggcc 5880
gaacgatgtt cagatccacg gtaagaagtt gtgcggtatt ctggttgaag caaccggctt 5940
cgactccact ccgaccgtgg ttatcggttg ggggtacgaat atctcgttga cgaaagaaga 6000
gctgccggtc ccgcacgcga ccagcctggc cctggagggt gttgaagttg accgtacgac 6060
gttcctgatt aacatgctga cccatctgca tacccgtctg gatcagtggc agggtccgtc 6120
tgtggactgg ctggatgact atcgcgcggt ttgtagcagc attggccaag atgtgcgtgt 6180
cctgctgcct ggtgacaaag agctgctggg cgaggcgatt ggcgtggcga ccggtggtga 6240
gatccgtgtg cgcgacgcca gcggcacggt ccacacgctg aatgcgggtg aaatcacgca 6300
tctgcgtttg caataaaagc ttgtttaaac ggtctccagc ttggctgttt tggcggatga 6360
gagaagattt tcagcctgat acagattaaa tcagaacgca gaagcggtct gataaaacag 6420
aatttgcctg gcggcagtag cgcggtggtc ccacctgacc ccatgccgaa ctcagaagtg 6480
aaacgccgta gcgccgatgg tagtgtgggg tctccccatg cgagagtagg gaactgccag 6540

-continued

```
gcatcaaata aaacgaaagg ctcagtcgaa agactgggcc tttcgtttta tctgttgttt   6600
gtcggtgaac gctctcctga cgcctgatgc ggtattttct ccttacgcat ctgtgcggta   6660
tttcacaccg catatggtgc actctcagta caatctgctc tgatgccgca tagttaagcc   6720
agccccgaca cccgccaaca cccgctgacg agcttagtaa agccctcgct agattttaat   6780
gcggatgttg cgattacttc gccaactatt gcgataacaa gaaaaagcca gcctttcatg   6840
atatatctcc caatttgtgt agggcttatt atgcacgctt aaaaataata aaagcagact   6900
tgacctgata gtttggctgt gagcaattat gtgcttagtg catctaacgc ttgagttaag   6960
ccgcgccgcg aagcggcgtc ggcttgaacg aattgttaga cattatttgc cgactacctt   7020
ggtgatctcg cctttcacgt agtggacaaa ttcttccaac tgatctgcgc gcgaggccaa   7080
gcgatcttct tcttgtccaa gataagcctg tctagcttca agtatgacgg gctgatactg   7140
ggccggcagg cgctccattg cccagtcggc agcgacatcc ttcggcgcga ttttgccggt   7200
tactgcgctg taccaaatgc gggacaacgt aagcactaca tttcgctcat cgccagccca   7260
gtcgggcggc gagttccata gcgttaaggt ttcatttagc gcctcaaata gatcctgttc   7320
aggaaccgga tcaaagagtt cctccgccgc tggacctacc aaggcaacgc tatgttctct   7380
tgcttttgtc agcaagatag ccagatcaat gtcgatcgtg gctggctcga agatacctgc   7440
aagaatgtca ttgcgctgcc attctccaaa ttgcagttcg cgcttagctg gataacgcca   7500
cggaatgatg tcgtcgtgca caacaatggt gacttctaca gcgcggagaa tctcgctctc   7560
tccaggggaa gccgaagttt ccaaaaggtc gttgatcaaa gctcgccgcg ttgtttcatc   7620
aagccttacg gtcaccgtaa ccagcaaatc aatatcactg tgtggcttca ggccgccatc   7680
cactgcggag ccgtacaaat gtacggccag caacgtcggt tcgagatggc gctcgatgac   7740
gccaactacc tctgatagtt gagtcgatac ttcggcgatc accgcttccc tcatgatgtt   7800
taactttgtt ttagggcgac tgccctgctg cgtaacatcg ttgctgctcc ataacatcaa   7860
acatcgaccc acggcgtaac gcgcttgctg cttggatgcc cgaggcatag actgtacccc   7920
aaaaaaacag tcataacaag ccatgaaaac cgccactgcg ccgttaccac cgctgcgttc   7980
ggtcaaggtt ctggaccagt tgcgtgagcg catacgctac ttgcattaca gcttacgaac   8040
cgaacaggct tatgtccact gggttcgtgc cttcatccgt ttccacggtg tgcgtcaccc   8100
ggcaaccttg ggcagcagcg aagtcgaggc atttctgtcc tggctggcga acgagcgcaa   8160
ggtttcggtc tccacgcatc gtcaggcatt ggcggccttg ctgttcttct acggcaaggt   8220
gctgtgcacg gatctgccct ggcttcagga gatcggaaga cctcggccgt cgcggcgctt   8280
gccggtggtg ctgaccccgg atgaagtggt tcgcatcctc ggttttctgg aaggcgagca   8340
tcgtttgttc gcccagcttc tgtatggaac gggcatgcgg atcagtgagg gtttgcaact   8400
gcgggtcaag gatctggatt tcgatcacgg cacgatcatc gtgcgggagg gcaagggctc   8460
caaggatcgg gccttgatgt tacccgagag cttggcaccc agcctgcgcg agcaggggaa   8520
ttaattccca cgggttttgc tgcccgcaaa cgggctgttc tggtgttgct agtttgttat   8580
cagaatcgca gatccggctt cagccggttt gccggctgaa agcgctattt cttccagaat   8640
tgccatgatt ttttccccac gggaggcgtc actggctccc gtgttgtcgg cagctttgat   8700
tcgataagca gcatcgcctg tttcaggctg tctatgtgtg actgttgagc tgtaacaagt   8760
tgtctcaggt gttcaatttc atgttctagt tgctttgttt tactggtttc acctgttcta   8820
ttaggtgtta catgctgttc atctgttaca ttgtcgatct gttcatggtg aacagctttg   8880
```

aatgcaccaa aaactcgtaa aagctctgat gtatctatct tttttacacc gttttcatct 8940
gtgcatatgg acagttttcc ctttgatatg taacggtgaa cagttgttct acttttgttt 9000
gttagtcttg atgcttcact gatagataca agagccataa gaacctcaga tccttccgta 9060
tttagccagt atgttctcta gtgtggttcg ttgtttttgc gtgagccatg agaacgaacc 9120
attgagatca tacttacttt gcatgtcact caaaaatttt gcctcaaaac tggtgagctg 9180
aatttttgca gttaaagcat cgtgtagtgt ttttcttagt ccgttatgta ggtaggaatc 9240
tgatgtaatg gttgttggta ttttgtcacc attcattttt atctggttgt tctcaagttc 9300
ggttacgaga tccatttgtc tatctagttc aacttggaaa atcaacgtat cagtcgggcg 9360
gcctcgctta tcaaccacca atttcatatt gctgtaagtg tttaaatctt tacttattgg 9420
tttcaaaacc cattggttaa gccttttaaa ctcatggtag ttattttcaa gcattaacat 9480
gaacttaaat tcatcaaggc taatctctat atttgccttg tgagttttct tttgtgttag 9540
ttcttttaat aaccactcat aaatcctcat agagtatttg ttttcaaaag acttaacatg 9600
ttccagatta tattttatga attttttaa ctggaaaaga taaggcaata tctcttcact 9660
aaaaactaat tctaattttt cgcttgagaa cttggcatag tttgtccact ggaaaatctc 9720
aaagccttta accaaaggat tcctgatttc cacagttctc gtcatcagct ctctggttgc 9780
tttagctaat acaccataag cattttccct actgatgttc atcatctgag cgtattggtt 9840
ataagtgaac gataccgtcc gttctttcct tgtagggttt tcaatcgtgg ggttgagtag 9900
tgccacacag cataaaatta gcttggtttc atgctccgtt aagtcatagc gactaatcgc 9960
tagttcattt gctttgaaaa caactaattc agacatacat ctcaattggt ctaggtgatt 10020
ttaat 10025

<210> SEQ ID NO 63
<211> LENGTH: 11469
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 63
cactatacca attgagatgg gctagtcaat gataattact agtccttttc ctttgagttg 60
tgggtatctg taaattctgc tagacctttg ctggaaaact tgtaaattct gctagaccct 120
ctgtaaattc cgctagacct ttgtgtgttt tttttgttta tattcaagtg gttataattt 180
atagaataaa gaaagaataa aaaaagataa aaagaataga tcccagccct gtgtataact 240
cactacttta gtcagttccg cagtattaca aaaggatgtc gcaaacgctg tttgctcctc 300
tacaaaacag accttaaaac cctaaaggcg tcggcatccg cttacagaca agctgtgacc 360
gtctccggga gctgcatgtg tcagaggttt tcaccgtcat caccgaaacg cgcgaggcag 420
cagatcaatt cgcgcgcgaa ggcgaagcgg catgcattta cgttgacacc atcgaatggt 480
gcaaaacctt tcgcggtatg gcatgatagc gcccggaaga gagtcaattc agggtggtga 540
atgtgaaacc agtaacgtta tacgatgtcg cagagtatgc cggtgtctct tatcagaccg 600
tttcccgcgt ggtgaaccag gccagccacg tttctgcgaa aacgcgggaa aaagtggaag 660
cggcgatggc ggagctgaat tacattccca accgcgtggc acaacaactg gcgggcaaac 720
agtcgttgct gattggcgtt gccacctcca gtctggccct gcacgcgccg tcgcaaattg 780
tcgcggcgat taaatctcgc gccgatcaac tgggtgccag cgtggtggtg tcgatggtag 840

-continued aacgaagcgg cgtcgaagcc tgtaaagcgg cggtgcacaa tcttctcgcg caacgcgtca 900
gtgggctgat cattaactat ccgctggatg accaggatgc cattgctgtg gaagctgcct 960
gcactaatgt tccggcgtta tttcttgatg tctctgacca gacacccatc aacagtatta 1020
ttttctccca tgaagacggt acgcgactgg gcgtggagca tctggtcgca ttgggtcacc 1080
agcaaatcgc gctgttagcg ggcccattaa gttctgtctc ggcgcgtctg cgtctggctg 1140
gctggcataa atatctcact cgcaatcaaa ttcagccgat agcggaacgg gaaggcgact 1200
ggagtgccat gtccggtttt caacaaacca tgcaaatgct gaatgagggc atcgttccca 1260
ctgcgatgct ggttgccaac gatcagatgg cgctgggcgc aatgcgcgcc attaccgagt 1320
ccgggctgcg cgttggtgcg gatatctcgg tagtgggata cgacgatacc gaagacagct 1380
catgttatat cccgccgtta accaccatca aacaggattt tcgcctgctg gggcaaacca 1440
gcgtggaccg cttgctgcaa ctctctcagg gccaggcggt gaagggcaat cagctgttgc 1500
ccgtctcact ggtgaaaaga aaaaccaccc tggcgcccaa tacgcaaacc gcctctcccc 1560
gcgcgttggc cgattcatta atgcagctgg cacgacaggt ttcccgactg gaaagcgggc 1620
agtgagcgca acgcaattaa tgtaagttag cgcgaattga tctggtttga cagcttatca 1680
tcgactgcac ggtgcaccaa tgcttctggc gtcaggcagc catcggaagc tgtggtatgg 1740
ctgtgcaggt cgtaaatcac tgcataattc gtgtcgctca aggcgcactc ccgttctgga 1800
taatgttttt tgcgccgaca tcataacggt tctggcaaat attctgaaat gagctgttga 1860
caattaatca tccggctcgt ataatgtgtg gaattgtgag cggataacaa tttcacacag 1920
gaaacagcgc cgctgagaaa aagcgaagcg gcactgctct ttaacaattt atcagacaat 1980
ctgtgtgggc actcgaccgg aattatcgat taactttatt attaaaaatt aaagaggtat 2040
atattaatgt atcgattaaa taaggaggaa taaaccatga aacgtctcgg aaccctggac 2100
gcctcctggc tggcggttga atctgaagac accccgatgc atgtgggtac gcttcagatt 2160
ttctcactgc cggaaggcgc accagaaacc ttcctgcgtg acatggtcac tcgaatgaaa 2220
gaggccggcg atgtggcacc accctgggga tacaaactgg cctggtctgg tttcctcggg 2280
cgcgtgatcg ccccggcctg gaaagtcgat aaggatatcg atctggatta tcacgtccgg 2340
cactcagccc tgcctcgccc cggcggggag cgcgaactgg gtattctggt atcccgactg 2400
cactctaacc ccctggattt ttcccgccct ctttgggaat gccacgttat tgaaggcctg 2460
gagaataacc gttttgccct ttacaccaaa atgcaccact cgatgattga cggcatcagc 2520
ggcgtgcgac tgatgcagag ggtgctcacc accgatcccg aacgctgcaa tatgccaccg 2580
ccctggacgg tacgcccaca ccaacgccgt ggtgcaaaaa ccgacaaaga ggccagcgtg 2640
cccgcagcgg tttcccaggc aatggacgcc ctgaagctcc aggcagacat ggcccccagg 2700
ctgtggcagg ccggcaatcg cctggtgcat tcggttcgac acccggaaga cggactgacc 2760
gcgcccttca ctggaccggt ttcggtgctc aatcaccggg ttaccgcgca gcgacgtttt 2820
gccacccagc attatcaact ggaccggctg aaaaacctgg cccatgcttc cggcggttcc 2880
ttgaacgaca tcgtgcttta cctgtgtggc accgcattgc ggcgctttct ggctgagcag 2940
aacaatctgc cagacacccc gctgacggct ggtataccgg tgaatatccg gccggcagac 3000
gacgagggta cgggcaccca gatcagtttt atgattgcct cgctggccac cgacgaagct 3060
gatccgttga accgcctgca acagatcaaa acctcgaccc gacgggccaa ggagcacctg 3120
cagaaacttc caaaaagtgc cctgacccag tacaccatgc tgctgatgtc accctacatt 3180
ctgcaattga tgtcaggtct cggggggagg atgcgaccag tcttcaacgt gaccatttcc 3240
aacgtgcccg gcccggaagg cacgctgtat tatgaaggag cccggcttga ggccatgtat 3300
ccggtatcgc taatcgctca cggcggcgcc ctgaacatca cctgcctgag ctatgccgga 3360
tcgctgaatt tcggttttac cggctgtcgg gatacgctgc cgagcatgca gaaactggcg 3420
gtttataccg gtgaagctct ggatgagctg gaatcgctga ttctgccacc caagaagcgc 3480
gcccgaaccc gcaagtaact cgaggaggaa aactaaatga ccatttcctc acctttgatt 3540
gacgtcgcca accttccaga catcaacacc actgccggca agatcgccga ccttaaggct 3600
cgccgcgcgg aagcccattt ccccatgggt gaaaaggcag tagagaaggt ccacgctgct 3660
ggacgcctca ctgcccgtga gcgcttggat tacttactcg atgagggctc cttcatcgag 3720
accgatcagc tggctcgcca ccgcaccacc gctttcggcc tgggcgctaa gcgtcctgca 3780
accgacggca tcgtgaccgg ctggggcacc attgatggac gcgaagtctg catcttctcg 3840
caggacggca ccgtattcgg tggcgcgctt ggtgaggtgt acggcgaaaa gatgatcaag 3900
atcatggagc tggcaatcga caccggccgc ccattgatcg gtctttacga aggcgctggc 3960
gctcgtattc aggacggcgc tgtctccctg gacttcattt cccagacctt ctaccaaaac 4020
attcaggctt ctggcgttat cccacagatc tccgtcatca tgggcgcatg tgcaggtggc 4080
aacgcttacg gcccagctct gaccgacttc gtggtcatgg tggacaagac ctccaagatg 4140
ttcgttaccg gcccagacgt gatcaagacc gtcaccggcg aggaaatcac ccaggaagag 4200
cttggcggag caaccaccca catggtgacc gctggtaact ccccactacac cgctgcgacc 4260 gatgaggaag cactggattg ggtacaggac ctggtgtcct tcctcccatc caacaatcgc 4320
tcctacgcac cgatggaaga cttcgacgag gaagaaggcg gcgttgaaga aaacatcacc 4380
gctgacgatc tgaagctcga cgagatcatc ccagattccg cgaccgttcc ttacgacgtc 4440
cgcgatgtca tcgaatgcct caccgacgat ggcgaatacc tggaaatcca ggcagaccgc 4500
gcagaaaacg ttgttattgc attcggccgc atcgaaggcc agtccgttgg ctttgttgcc 4560
aaccagccaa cccagttcgc tggctgcctg gacatcgact cctctgagaa ggcagctcgc 4620
ttcgtccgca cctgcgacgc gttcaacatc ccaatcgtca tgcttgtcga cgtccccggc 4680
ttcctcccag gcgcaggcca ggagtacggt ggcattctgc gtcgtggcgc aaagctgctc 4740
tacgcatacg gcgaagcaac cgttccaaag atcaccgtca ccatgcgtaa ggcttacggc 4800
ggagcgtact gcgtgatggg ttccaagggc ttgggctctg acatcaacct tgcatggcca 4860
accgcacaga tcgccgtcat gggcgctgct ggcgcagttg gattcatcta ccgcaaggag 4920
ctcatggcag ctgatgccaa gggcctcgat accgtagctc tggctaagtc cttcgagcgc 4980
gagtatgaag accacatgct caacccgtac cacgctgcag aacgtggcct gatcgacgcc 5040
gtgatcctgc caagcgaaac ccgcggacag atttcccgca accttcgcct gctcaagcac 5100
aagaacgtca ctcgccctgc tcgcaagcac ggcaacatgc cactgtaagg aggaaaacta 5160
aatgtcagtc gagactcgca agatcaccaa ggttcttgtc gctaaccgtg gtgagattgc 5220
aatccgcgtg ttccgtgcag ctcgagatga aggcatcgga tctgtcgccg tctacgcaga 5280
gccagatgca gatgcaccat tcgtgtcata tgcagacgag gcttttgccc tcggtggcca 5340
aacatccgct gagtcctacc ttgtcattga caagatcatc gatgcggccc gcaagtccgg 5400
cgccgacgcc atccaccccg gctacggctt cctcgcagaa aacgctgact tcgcagaagc 5460
agtcatcaac gaaggcctga tctggattgg accttcacct gagtccatcc gctccctcgg 5520
cgacaaggtc accgctcgcc acatcgcaga taccgccaag gctccaatgg ctcctggcac 5580
caaggaacca gtaaaagacg cagcagaagt tgtggctttc gctgaagaat tcggtctccc 5640
aatcgccatc aaggcagctt tcggtggcgg cggacgtggc atgaaggttg cctacaagat 5700
ggaagaagtc gctgacctct tcgagtccgc aacccgtgaa gcaaccgcag cgttcggccg 5760
cggcgagtgc ttcgtggagc gctacctgga caaggcacgc cacgttgagg ctcaggtcat 5820
cgccgataag cacggcaacg ttgttgtcgc cggaacccgt gactgctccc tgcagcgccg 5880
tttccagaag ctcgtcgaag aagcaccagc accattcctc accgatgacc agcgcgagcg 5940
tctccactcc tccgcgaagg ctatctgtaa ggaagctggc tactacggtg caggcaccgt 6000
tgagtacctc gttggctccg acggcctgat ctccttcctc gaggtcaaca cccgcctcca 6060
ggtggaacac ccagtcaccg aagagaccac cggcatcgac ctggtccgcg aaatgttccg 6120
catcgcagaa ggccacgagc tctccatcaa ggaagatcca gctccacgcg gccacgcatt 6180
cgagttccgc atcaacggcg aagacgctgg ctccaacttc atgcctgcac caggcaagat 6240
caccagctac cgcgagccac agggcccagg cgtccgcatg gactccggtg tcgttgaagg 6300
ttccgaaatc tccggacagt tcgactccat gctggcaaag ctgatcgttt ggggcgacac 6360
ccgcgagcag gctctccagc gctcccgccg tgcacttgca gagtacgttg tcgagggcat 6420
gccaaccgtt atcccattcc accagcacat cgtggaaaac ccagcattcg tgggcaacga 6480
cgaaggcttc gagatctaca ccaagtggat cgaagaggtt tgggataacc caatcgcacc 6540
ttacgttgac gcttccgagc tcgacgaaga tgaggacaag accccagcac agaaggttgt 6600
tgtggagatc aacggccgtc gcgttgaggt tgcactccca ggcgatctgg cactcggtgg 6660
caccgctggt cctaagaaga aggccaagaa gcgtcgcgca ggtggtgcaa aggctggcgt 6720
atccggcgat gcagtggcag ctccaatgca gggcactgtc atcaaggtca acgtcgaaga 6780
aggcgctgaa gtcaacgaag gcgacaccgt tgttgtcctc gaggctatga agatggaaaa 6840
ccctgtgaag gctcataagt ccggaaccgt aaccggcctt actgtcgctg caggcgaggg 6900
tgtcaacaag ggcgttgttc tcctcgagat caagtaatct agaggaggaa aactaaatga 6960
atgttgacat tagccgctct cgtgaaccgt tgaacgtgga actgttgaaa gaaaaactgc 7020
tgcagaacgg tgatttcggt caagtgatct acgagaaggt caccggctct accaatgcgg 7080
acctgctggc tctggcgggc agcggcgctc caaactggac cgtcaagact gttgaatttc 7140
aggaccacgc ccgtggccgt ctgggtcgtc cgtggagcgc accggagggt tcccaaacca 7200
tcgtcagcgt tctggtccaa ctgagcattg atcaggtgga ccgtattggt acgatcccgc 7260
tggccgcagg cttggctgtt atggatgcgc tgaatgatct gggcgtggag ggtgcaggcc 7320
tgaaatggcc gaacgatgtt cagatccacg gtaagaagtt gtgcggtatt ctggttgaag 7380
caaccggctt cgactccact ccgaccgtgg ttatcggttg ggtacgaat atctcgttga 7440
cgaaagaaga gctgccggtc ccgcacgcga ccagcctggc cctggagggt gttgaagttg 7500
accgtacgac gttcctgatt aacatgctga cccatctgca tacccgtctg gatcagtggc 7560
agggtccgtc tgtggactgg ctggatgact atcgcgcggt ttgtagcagc attggccaag 7620
atgtgcgtgt cctgctgcct ggtgacaaag agctgctggg cgaggcgatt ggcgtggcga 7680
ccggtggtga gatccgtgtg cgcgacgcca gcggcacggt ccacacgctg aatgcgggtg 7740
aaatcacgca tctgcgtttg caataagttt aaacggtctc cagcttggct gttttggcgg 7800
atgagagaag attttcagcc tgatacagat taaatcagaa cgcagaagcg gtctgataaa 7860
acagaatttg cctggcggca gtagcgcggt ggtcccacct gaccccatgc cgaactcaga 7920

-continued

```
agtgaaacgc cgtagcgccg atggtagtgt ggggtctccc catgcgagag tagggaactg   7980
ccaggcatca aataaaacga aaggctcagt cgaaagactg ggcctttcgt tttatctgtt   8040
gtttgtcggt gaacgctctc ctgacgcctg atgcggtatt ttctccttac gcatctgtgc   8100
ggtatttcac accgcatatg gtgcactctc agtacaatct gctctgatgc cgcatagtta   8160
agccagcccc gacacccgcc aacacccgct gacgagctta gtaaagccct cgctagattt   8220
taatgcggat gttgcgatta cttcgccaac tattgcgata acaagaaaaa gccagccttt   8280
catgatatat ctcccaattt gtgtagggct tattatgcac gcttaaaaat aataaaagca   8340
gacttgacct gatagtttgg ctgtgagcaa ttatgtgctt agtgcatcta acgcttgagt   8400
taagccgcgc cgcgaagcgg cgtcggcttg aacgaattgt tagacattat ttgccgacta   8460
ccttggtgat ctcgcctttc acgtagtgga caaattcttc caactgatct gcgcgcgagg   8520
ccaagcgatc ttcttcttgt ccaagataag cctgtctagc ttcaagtatg acgggctgat   8580
actgggccgg caggcgctcc attgcccagt cggcagcgac atccttcggc gcgattttgc   8640
cggttactgc gctgtaccaa atgcgggaca acgtaagcac tacatttcgc tcatcgccag   8700
cccagtcggg cggcgagttc catagcgtta aggtttcatt tagcgcctca aatagatcct   8760
gttcaggaac cggatcaaag agttcctccg ccgctggacc taccaaggca acgctatgtt   8820
ctcttgcttt tgtcagcaag atagccagat caatgtcgat cgtggctggc tcgaagatac   8880
ctgcaagaat gtcattgcgc tgccattctc caaattgcag ttcgcgctta gctggataac   8940
gccacggaat gatgtcgtcg tgcacaacaa tggtgacttc tacagcgcgg agaatctcgc   9000
tctctccagg ggaagccgaa gtttccaaaa ggtcgttgat caaagctcgc cgcgttgttt   9060
catcaagcct tacggtcacc gtaaccagca aatcaatatc actgtgtggc ttcaggccgc   9120
catccactgc ggagccgtac aaatgtacgg ccagcaacgt cggttcgaga tggcgctcga   9180
tgacgccaac tacctctgat agttgagtcg atacttcggc gatcaccgct tccctcatga   9240
tgtttaactt tgttttaggg cgactgccct gctgcgtaac atcgttgctg ctccataaca   9300
tcaaacatcg acccacggcg taacgcgctt gctgcttgga tgcccgaggc atagactgta   9360
ccccaaaaaa acagtcataa caagccatga aaaccgccac tgcgccgtta ccaccgctgc   9420
gttcggtcaa ggttctggac cagttgcgtg agcgcatacg ctacttgcat tacagcttac   9480
gaaccgaaca ggcttatgtc cactgggttc gtgccttcat ccgtttccac ggtgtgcgtc   9540
acccggcaac cttgggcagc agcgaagtcg aggcatttct gtcctggctg gcgaacgagc   9600
gcaaggtttc ggtctccacg catcgtcagg cattggcggc cttgctgttc ttctacggca   9660
aggtgctgtg cacggatctg ccctggcttc aggagatcgg aagacctcgg ccgtcgcggc   9720
gcttgccggt ggtgctgacc ccggatgaag tggttcgcat cctcggtttt ctggaaggcg   9780
agcatcgttt gttcgcccag cttctgtatg gaacgggcat gcggatcagt gagggtttgc   9840
aactgcgggt caaggatctg gatttcgatc acggcacgat catcgtgcgg gagggcaagg   9900
gctccaagga tcgggccttg atgttacccg agagcttggc acccagcctg cgcgagcagg   9960
ggaattaatt cccacgggtt ttgctgcccg caaacgggct gttctggtgt tgctagtttg  10020
ttatcagaat cgcagatccg gcttcagccg gtttgccggc tgaaagcgct atttcttcca  10080
gaattgccat gatttttttcc ccacgggagg cgtcactggc tcccgtgttg tcggcagctt  10140
tgattcgata agcagcatcg cctgtttcag gctgtctatg tgtgactgtt gagctgtaac  10200
aagttgtctc aggtgttcaa tttcatgttc tagttgcttt gttttactgg tttcacctgt  10260
tctattaggt gttacatgct gttcatctgt tacattgtcg atctgttcat ggtgaacagc  10320
```

-continued

```
tttgaatgca ccaaaaactc gtaaaagctc tgatgtatct atcttttta caccgttttc  10380

atctgtgcat atggacagtt ttccctttga tatgtaacgg tgaacagttg ttctactttt  10440

gtttgttagt cttgatgctt cactgataga tacaagagcc ataagaacct cagatccttc  10500

cgtatttagc cagtatgttc tctagtgtgg ttcgttgttt ttgcgtgagc catgagaacg  10560

aaccattgag atcatactta ctttgcatgt cactcaaaaa ttttgcctca aaactggtga  10620

gctgaatttt tgcagttaaa gcatcgtgta gtgtttttct tagtccgtta tgtaggtagg  10680

aatctgatgt aatggttgtt ggtattttgt caccattcat ttttatctgg ttgttctcaa  10740

gttcggttac gagatccatt tgtctatcta gttcaacttg gaaaatcaac gtatcagtcg  10800

ggcggcctcg cttatcaacc accaatttca tattgctgta agtgtttaaa tctttactta  10860

ttggtttcaa aacccattgg ttaagccttt taaactcatg gtagttattt tcaagcatta  10920

acatgaactt aaattcatca aggctaatct ctatatttgc cttgtgagtt ttcttttgtg  10980

ttagttcttt taataaccac tcataaatcc tcatagagta tttgttttca aaagacttaa  11040

catgttccag attatatttt atgaattttt ttaactggaa aagataaggc aatatctctt  11100

cactaaaaac taattctaat ttttcgcttg agaacttggc atagtttgtc cactggaaaa  11160

tctcaaagcc tttaaccaaa ggattcctga tttccacagt tctcgtcatc agctctctgg  11220

ttgctttagc taatacacca taagcatttt ccctactgat gttcatcatc tgagcgtatt  11280

ggttataagt gaacgatacc gtccgttctt tccttgtagg gttttcaatc gtggggttga  11340

gtagtgccac acagcataaa attagcttgg tttcatgctc cgttaagtca tagcgactaa  11400

tcgctagttc atttgctttg aaaacaacta attcagacat acatctcaat tggtctaggt  11460

gattttaat                                                          11469
```

<210> SEQ ID NO 64
<211> LENGTH: 1173
<212> TYPE: PRT
<213> ORGANISM: Mycobacterium smegmatis

<400> SEQUENCE: 64

```
Met Thr Ser Asp Val His Asp Ala Thr Asp Gly Val Thr Glu Thr Ala
1               5                   10                  15

Leu Asp Asp Glu Gln Ser Thr Arg Arg Ile Ala Glu Leu Tyr Ala Thr
            20                  25                  30

Asp Pro Glu Phe Ala Ala Ala Ala Pro Leu Pro Ala Val Val Asp Ala
        35                  40                  45

Ala His Lys Pro Gly Leu Arg Leu Ala Glu Ile Leu Gln Thr Leu Phe
    50                  55                  60

Thr Gly Tyr Gly Asp Arg Pro Ala Leu Gly Tyr Arg Ala Arg Glu Leu
65                  70                  75                  80

Ala Thr Asp Glu Gly Gly Arg Thr Val Thr Arg Leu Leu Pro Arg Phe
                85                  90                  95

Asp Thr Leu Thr Tyr Ala Gln Val Trp Ser Arg Val Gln Ala Val Ala
            100                 105                 110

Ala Ala Leu Arg His Asn Phe Ala Gln Pro Ile Tyr Pro Gly Asp Ala
        115                 120                 125

Val Ala Thr Ile Gly Phe Ala Ser Pro Asp Tyr Leu Thr Leu Asp Leu
    130                 135                 140

Val Cys Ala Tyr Leu Gly Leu Val Ser Val Pro Leu Gln His Asn Ala
145                 150                 155                 160
```

-continued

```
Pro Val Ser Arg Leu Ala Pro Ile Leu Ala Glu Val Glu Pro Arg Ile
                165                 170                 175

Leu Thr Val Ser Ala Glu Tyr Leu Asp Leu Ala Val Glu Ser Val Arg
            180                 185                 190

Asp Val Asn Ser Val Ser Gln Leu Val Val Phe Asp His His Pro Glu
        195                 200                 205

Val Asp Asp His Arg Asp Ala Leu Ala Arg Ala Arg Glu Gln Leu Ala
    210                 215                 220

Gly Lys Gly Ile Ala Val Thr Thr Leu Asp Ala Ile Ala Asp Glu Gly
225                 230                 235                 240

Ala Gly Leu Pro Ala Glu Pro Ile Tyr Thr Ala Asp His Asp Gln Arg
                245                 250                 255

Leu Ala Met Ile Leu Tyr Thr Ser Gly Ser Thr Gly Ala Pro Lys Gly
            260                 265                 270

Ala Met Tyr Thr Glu Ala Met Val Ala Arg Leu Trp Thr Met Ser Phe
        275                 280                 285

Ile Thr Gly Asp Pro Thr Pro Val Ile Asn Val Asn Phe Met Pro Leu
    290                 295                 300

Asn His Leu Gly Gly Arg Ile Pro Ile Ser Thr Ala Val Gln Asn Gly
305                 310                 315                 320

Gly Thr Ser Tyr Phe Val Pro Glu Ser Asp Met Ser Thr Leu Phe Glu
                325                 330                 335

Asp Leu Ala Leu Val Arg Pro Thr Glu Leu Gly Leu Val Pro Arg Val
            340                 345                 350

Ala Asp Met Leu Tyr Gln His His Leu Ala Thr Val Asp Arg Leu Val
        355                 360                 365

Thr Gln Gly Ala Asp Glu Leu Thr Ala Glu Lys Gln Ala Gly Ala Glu
    370                 375                 380

Leu Arg Glu Gln Val Leu Gly Gly Arg Val Ile Thr Gly Phe Val Ser
385                 390                 395                 400

Thr Ala Pro Leu Ala Ala Glu Met Arg Ala Phe Leu Asp Ile Thr Leu
                405                 410                 415

Gly Ala His Ile Val Asp Gly Tyr Gly Leu Thr Glu Thr Gly Ala Val
            420                 425                 430

Thr Arg Asp Gly Val Ile Val Arg Pro Pro Val Ile Asp Tyr Lys Leu
        435                 440                 445

Ile Asp Val Pro Glu Leu Gly Tyr Phe Ser Thr Asp Lys Pro Tyr Pro
    450                 455                 460

Arg Gly Glu Leu Leu Val Arg Ser Gln Thr Leu Thr Pro Gly Tyr Tyr
465                 470                 475                 480

Lys Arg Pro Glu Val Thr Ala Ser Val Phe Asp Arg Asp Gly Tyr Tyr
                485                 490                 495

His Thr Gly Asp Val Met Ala Glu Thr Ala Pro Asp His Leu Val Tyr
            500                 505                 510

Val Asp Arg Arg Asn Asn Val Leu Lys Leu Ala Gln Gly Glu Phe Val
        515                 520                 525

Ala Val Ala Asn Leu Glu Ala Val Phe Ser Gly Ala Ala Leu Val Arg
    530                 535                 540

Gln Ile Phe Val Tyr Gly Asn Ser Glu Arg Ser Phe Leu Leu Ala Val
545                 550                 555                 560

Val Val Pro Thr Pro Glu Ala Leu Glu Gln Tyr Asp Pro Ala Ala Leu
                565                 570                 575

Lys Ala Ala Leu Ala Asp Ser Leu Gln Arg Thr Ala Arg Asp Ala Glu
```

-continued

```
            580                 585                 590

Leu Gln Ser Tyr Glu Val Pro Ala Asp Phe Ile Val Glu Thr Glu Pro
        595                 600                 605

Phe Ser Ala Ala Asn Gly Leu Leu Ser Gly Val Gly Lys Leu Leu Arg
    610                 615                 620

Pro Asn Leu Lys Asp Arg Tyr Gly Gln Arg Leu Glu Gln Met Tyr Ala
625                 630                 635                 640

Asp Ile Ala Ala Thr Gln Ala Asn Gln Leu Arg Glu Leu Arg Arg Ala
                645                 650                 655

Ala Ala Thr Gln Pro Val Ile Asp Thr Leu Thr Gln Ala Ala Ala Thr
            660                 665                 670

Ile Leu Gly Thr Gly Ser Glu Val Ala Ser Asp Ala His Phe Thr Asp
        675                 680                 685

Leu Gly Gly Asp Ser Leu Ser Ala Leu Thr Leu Ser Asn Leu Leu Ser
    690                 695                 700

Asp Phe Phe Gly Phe Glu Val Pro Val Gly Thr Ile Val Asn Pro Ala
705                 710                 715                 720

Thr Asn Leu Ala Gln Leu Ala Gln His Ile Glu Ala Gln Arg Thr Ala
                725                 730                 735

Gly Asp Arg Arg Pro Ser Phe Thr Thr Val His Gly Ala Asp Ala Thr
            740                 745                 750

Glu Ile Arg Ala Ser Glu Leu Thr Leu Asp Lys Phe Ile Asp Ala Glu
        755                 760                 765

Thr Leu Arg Ala Ala Pro Gly Leu Pro Lys Val Thr Thr Glu Pro Arg
    770                 775                 780

Thr Val Leu Leu Ser Gly Ala Asn Gly Trp Leu Gly Arg Phe Leu Thr
785                 790                 795                 800

Leu Gln Trp Leu Glu Arg Leu Ala Pro Val Gly Gly Thr Leu Ile Thr
                805                 810                 815

Ile Val Arg Gly Arg Asp Asp Ala Ala Ala Arg Ala Arg Leu Thr Gln
            820                 825                 830

Ala Tyr Asp Thr Asp Pro Glu Leu Ser Arg Arg Phe Ala Glu Leu Ala
        835                 840                 845

Asp Arg His Leu Arg Val Val Ala Gly Asp Ile Gly Asp Pro Asn Leu
    850                 855                 860

Gly Leu Thr Pro Glu Ile Trp His Arg Leu Ala Ala Glu Val Asp Leu
865                 870                 875                 880

Val Val His Pro Ala Ala Leu Val Asn His Val Leu Pro Tyr Arg Gln
                885                 890                 895

Leu Phe Gly Pro Asn Val Val Gly Thr Ala Glu Val Ile Lys Leu Ala
            900                 905                 910

Leu Thr Glu Arg Ile Lys Pro Val Thr Tyr Leu Ser Thr Val Ser Val
        915                 920                 925

Ala Met Gly Ile Pro Asp Phe Glu Glu Asp Gly Asp Ile Arg Thr Val
    930                 935                 940

Ser Pro Val Arg Pro Leu Asp Gly Gly Tyr Ala Asn Gly Tyr Gly Asn
945                 950                 955                 960

Ser Lys Trp Ala Gly Glu Val Leu Leu Arg Glu Ala His Asp Leu Cys
                965                 970                 975

Gly Leu Pro Val Ala Thr Phe Arg Ser Asp Met Ile Leu Ala His Pro
            980                 985                 990

Arg Tyr Arg Gly Gln Val Asn Val  Pro Asp Met Phe Thr  Arg Leu Leu
        995                 1000                1005
```

-continued

```
Leu Ser  Leu Leu Ile Thr Gly  Val Ala Pro Arg Ser  Phe Tyr Ile
    1010                 1015                 1020

Gly Asp  Gly Glu Arg Pro Arg  Ala His Tyr Pro Gly  Leu Thr Val
    1025                 1030                 1035

Asp Phe  Val Ala Glu Ala Val  Thr Thr Leu Gly Ala  Gln Gln Arg
    1040                 1045                 1050

Glu Gly  Tyr Val Ser Tyr Asp  Val Met Asn Pro His  Asp Asp Gly
    1055                 1060                 1065

Ile Ser  Leu Asp Val Phe Val  Asp Trp Leu Ile Arg  Ala Gly His
    1070                 1075                 1080

Pro Ile  Asp Arg Val Asp Asp  Tyr Asp Asp Trp Val  Arg Arg Phe
    1085                 1090                 1095

Glu Thr  Ala Leu Thr Ala Leu  Pro Glu Lys Arg Arg  Ala Gln Thr
    1100                 1105                 1110

Val Leu  Pro Leu Leu His Ala  Phe Arg Ala Pro Gln  Ala Pro Leu
    1115                 1120                 1125

Arg Gly  Ala Pro Glu Pro Thr  Glu Val Phe His Ala  Ala Val Arg
    1130                 1135                 1140

Thr Ala  Lys Val Gly Pro Gly  Asp Ile Pro His Leu  Asp Glu Ala
    1145                 1150                 1155

Leu Ile  Asp Lys Tyr Ile Arg  Asp Leu Arg Glu Phe  Gly Leu Ile
    1160                 1165                 1170
```